US 10,583,188 B2

(12) United States Patent
Garcia-Sastre et al.

(10) Patent No.: US 10,583,188 B2
(45) Date of Patent: *Mar. 10, 2020

(54) INFLUENZA VIRUS VACCINES AND USES THEREOF

(71) Applicant: ICAHN SCHOOL OF MEDICINE AT MOUNT SINAI, New York, NY (US)

(72) Inventors: Adolfo Garcia-Sastre, New York, NY (US); Peter Palese, New York, NY (US); Florian Krammer, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,503

(22) Filed: Oct. 16, 2018

(65) Prior Publication Data

US 2019/0099484 A1    Apr. 4, 2019

Related U.S. Application Data

(60) Continuation of application No. 15/158,785, filed on May 19, 2016, now Pat. No. 10,137,189, which is a division of application No. 14/109,358, filed on Dec. 17, 2013, now Pat. No. 9,371,366.

(60) Provisional application No. 61/840,899, filed on Jun. 28, 2013, provisional application No. 61/738,672, filed on Dec. 18, 2012.

(51) Int. Cl.
| | | |
|---|---|---|
| *A61K 39/145* | (2006.01) | |
| *C12N 7/00* | (2006.01) | |
| *C07K 14/005* | (2006.01) | |
| *A61K 39/12* | (2006.01) | |
| *A61K 39/00* | (2006.01) | |

(52) U.S. Cl.
CPC ............ *A61K 39/145* (2013.01); *A61K 39/12* (2013.01); *C07K 14/005* (2013.01); *C12N 7/00* (2013.01); *A61K 2039/521* (2013.01); *A61K 2039/5252* (2013.01); *A61K 2039/54* (2013.01); *A61K 2039/543* (2013.01); *A61K 2039/545* (2013.01); *A61K 2039/55* (2013.01); *A61K 2039/70* (2013.01); *C12N 2760/16123* (2013.01); *C12N 2760/16134* (2013.01); *C12N 2760/16223* (2013.01); *C12N 2760/16234* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,522,811 A | 6/1985 | Eppstein et al. |
| 4,603,112 A | 7/1986 | Paoletti et al. |
| 4,693,981 A | 9/1987 | Wiesehahn et al. |
| 4,716,111 A | 12/1987 | Osband et al. |
| 4,722,848 A | 2/1988 | Paoletti et al. |
| 4,769,330 A | 9/1988 | Paoletti et al. |
| 5,057,540 A | 10/1991 | Kensil et al. |
| 5,106,619 A | 4/1992 | Wiesehahn et al. |
| 5,110,587 A | 5/1992 | Paoletti et al. |
| 5,166,057 A | 11/1992 | Palese et al. |
| 5,174,993 A | 12/1992 | Paoletti |
| 5,182,192 A | 1/1993 | Steplewski et al. |
| 5,413,923 A | 5/1995 | Kucherlapati et al. |
| 5,484,719 A | 1/1996 | Lam et al. |
| 5,545,806 A | 8/1996 | Lonberg et al. |
| 5,569,825 A | 10/1996 | Lonberg et al. |
| 5,571,709 A | 11/1996 | Devauchelle et al. |
| 5,573,916 A | 11/1996 | Cheronis et al. |
| 5,589,174 A | 12/1996 | Okuno et al. |
| 5,612,487 A | 3/1997 | Lam et al. |
| 5,625,126 A | 4/1997 | Lonberg et al. |
| 5,631,350 A | 5/1997 | Okuno et al. |
| 5,633,425 A | 5/1997 | Lonberg et al. |
| 5,643,576 A | 7/1997 | Johnston et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,891,705 A | 4/1999 | Budowsky et al. |
| 5,916,771 A | 6/1999 | Hori et al. |
| 5,929,304 A | 7/1999 | Radin et al. |
| 6,001,634 A | 12/1999 | Palese et al. |
| 6,034,298 A | 3/2000 | Lam et al. |
| 6,136,320 A | 10/2000 | Arntzen et al. |
| 6,146,642 A | 11/2000 | Garcia-Sastre et al. |
| 6,165,476 A | 12/2000 | Strom et al. |
| 6,265,189 B1 | 7/2001 | Paoletti et al. |
| 6,337,070 B1 | 1/2002 | Okuno et al. |
| 6,468,544 B1 | 10/2002 | Egorov et al. |
| 6,544,785 B1 | 4/2003 | Palese et al. |
| 6,551,820 B1 | 4/2003 | Mason et al. |
| 6,573,079 B1 | 6/2003 | Palese et al. |
| 6,635,246 B1 | 10/2003 | Barrett et al. |
| 6,649,372 B1 | 11/2003 | Palese et al. |
| 6,669,943 B1 | 12/2003 | Palese et al. |

(Continued)

FOREIGN PATENT DOCUMENTS

| | | |
|---|---|---|
| CA | 2121559 A1 | 10/1994 |
| CA | 2718923 A1 | 9/2009 |

(Continued)

OTHER PUBLICATIONS

Tan et al. (Journal of Virology, Jun. 2012, vol. 86, p. 6179-6188 in IDS on Dec. 20, 2018).*

(Continued)

*Primary Examiner* — Agnieszka Boesen
(74) *Attorney, Agent, or Firm* — Jones Day

(57) ABSTRACT

Provided herein are chimeric influenza hemagglutinin (HA) polypeptides, compositions comprising the same, vaccines comprising the same, and methods of their use.

Figure 2:
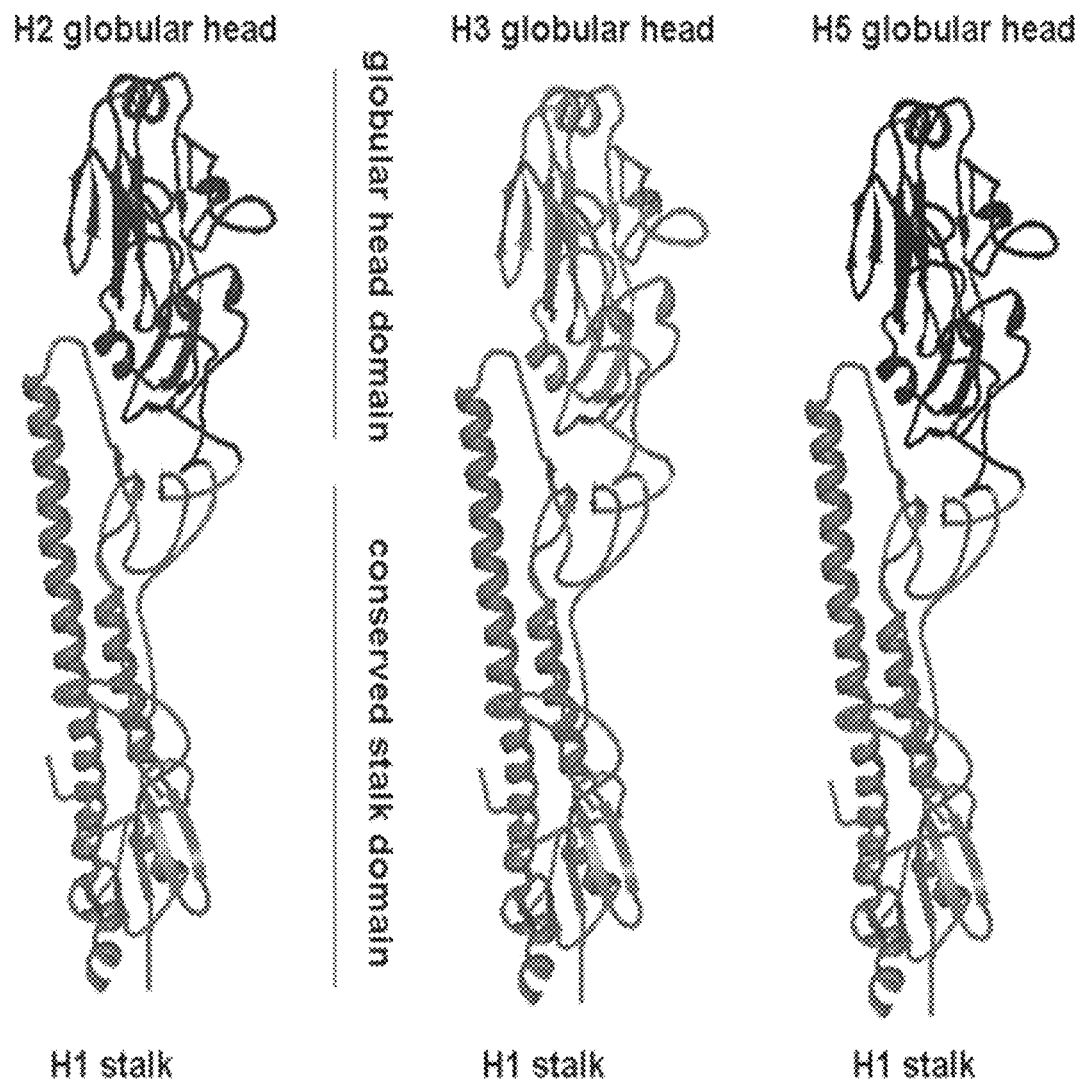

33 Claims, 56 Drawing Sheets
Specification includes a Sequence Listing.

(56) References Cited

U.S. PATENT DOCUMENTS

| | | | |
|---|---|---|---|
| 6,720,409 B2 | 4/2004 | Okuno et al. | |
| 6,770,799 B2 | 8/2004 | Mor et al. | |
| 6,852,522 B1 | 2/2005 | Palese et al. | |
| 6,867,293 B2 | 3/2005 | Andrews et al. | |
| 6,887,699 B1 | 5/2005 | Palese et al. | |
| 6,942,861 B2 | 9/2005 | McKee et al. | |
| 6,951,754 B2 | 10/2005 | Hoffmann | |
| 7,312,064 B2 | 12/2007 | Hoffmann | |
| 7,384,774 B2 | 6/2008 | Palese et al. | |
| 7,442,379 B2 | 10/2008 | Garcia-Sastre et al. | |
| 7,494,808 B2 | 2/2009 | Palese et al. | |
| 7,504,560 B2 | 3/2009 | Amtzen et al. | |
| 7,566,458 B2 | 7/2009 | Yang et al. | |
| 8,367,077 B2 | 2/2013 | Zurbriggen et al. | |
| 8,603,467 B2 | 12/2013 | Chen et al. | |
| 8,673,314 B2 | 3/2014 | Garcia Sastre et al. | |
| 8,828,406 B2 | 9/2014 | Garcia-Sastre et al. | |
| 9,051,359 B2 | 6/2015 | Garcia-Sastre et al. | |
| 9,175,069 B2 | 11/2015 | Garcia-Sastre et al. | |
| 9,371,366 B2 | 6/2016 | Garcia-Sastre et al. | |
| 9,452,211 B2 | 9/2016 | Meijberg et al. | |
| 9,701,723 B2 | 7/2017 | Garcia-Sastre et al. | |
| 9,707,288 B2 | 7/2017 | Schrader | |
| 9,708,373 B2 | 7/2017 | Garcia-Sastre et al. | |
| 9,849,172 B2 | 12/2017 | Garcia-Sastre et al. | |
| 9,908,930 B2 | 3/2018 | Palese et al. | |
| 9,968,670 B2 | 5/2018 | Garcia-Sastre et al. | |
| 10,131,695 B2 | 11/2018 | Garcia-Sastre et al. | |
| 10,137,189 B2 * | 11/2018 | Garcia-Sastre | A61K 39/145 |
| 10,179,806 B2 | 1/2019 | Garcia-Sastre et al. | |
| 2002/0164770 A1 | 11/2002 | Hoffman | |
| 2003/0134338 A1 | 7/2003 | Makarocskiy | |
| 2004/0002061 A1 | 1/2004 | Kawaoka | |
| 2004/0073011 A1 | 4/2004 | Hagay et al. | |
| 2005/0009008 A1 | 1/2005 | Robinson et al. | |
| 2005/0042229 A1 | 2/2005 | Yang et al. | |
| 2005/0048074 A1 | 3/2005 | Cardineau et al. | |
| 2005/0064391 A1 | 3/2005 | Segal et al. | |
| 2005/0106178 A1 | 5/2005 | O'hagan et al. | |
| 2005/0201946 A1 | 9/2005 | Friede et al. | |
| 2006/0008473 A1 | 1/2006 | Yana et al. | |
| 2006/0204487 A1 | 9/2006 | Shaaltiel et al. | |
| 2006/0217338 A1 | 9/2006 | Lu et al. | |
| 2006/0280754 A1 | 12/2006 | Garry et al. | |
| 2007/0020238 A1 | 1/2007 | Baltimore et al. | |
| 2007/0036809 A1 | 2/2007 | Michl et al. | |
| 2007/0207171 A1 | 9/2007 | Dubensky et al. | |
| 2007/0275014 A1 | 11/2007 | Yusibov et al. | |
| 2008/0019998 A1 | 1/2008 | Wang et al. | |
| 2008/0032921 A1 | 2/2008 | Alexander et al. | |
| 2008/0038232 A1 | 2/2008 | Shaaltiel et al. | |
| 2008/0152657 A1 | 6/2008 | Horowitz et al. | |
| 2008/0176247 A1 | 7/2008 | Chou et al. | |
| 2008/0193455 A1 | 8/2008 | Stassen et al. | |
| 2008/0248066 A1 | 10/2008 | Dubensky et al. | |
| 2009/0053762 A1 | 2/2009 | Shaaltiel | |
| 2009/0068221 A1 | 3/2009 | Morrison | |
| 2009/0081255 A1 | 3/2009 | Bublot et al. | |
| 2009/0082548 A1 | 3/2009 | Shaaltiel et al. | |
| 2009/0169547 A1 | 7/2009 | Sahin et al. | |
| 2009/0208477 A1 | 8/2009 | Shaaltiel et al. | |
| 2009/0291472 A1 | 11/2009 | Lu et al. | |
| 2009/0304730 A1 | 12/2009 | Amon et al. | |
| 2009/0304739 A1 | 12/2009 | Rappouli et al. | |
| 2009/0311265 A1 | 12/2009 | Van Den Brink et al. | |
| 2009/0311669 A1 | 12/2009 | Kawaoka | |
| 2010/0184192 A1 | 7/2010 | Smith et al. | |
| 2010/0297165 A1 | 11/2010 | Berzofsky et al. | |
| 2010/0297174 A1 | 11/2010 | Garcia-Sastre et al. | |
| 2011/0027270 A1 | 2/2011 | Garcia-Sastre et al. | |
| 2011/0111494 A1 | 5/2011 | Hill et al. | |
| 2011/0182938 A1 | 7/2011 | Weiner et al. | |
| 2012/0039898 A1 | 2/2012 | Throsby et al. | |
| 2012/0122185 A1 | 5/2012 | Palese et al. | |
| 2012/0189658 A1 | 7/2012 | Couture et al. | |
| 2012/0244183 A1 | 9/2012 | Garcia-Sastre et al. | |
| 2013/0129747 A1 | 5/2013 | Schrader | |
| 2013/0129761 A1 | 5/2013 | Garcia-Sastre et al. | |
| 2013/0209499 A1 | 8/2013 | Garcia-Sastre et al. | |
| 2013/0224187 A1 | 8/2013 | Rother et al. | |
| 2014/0170163 A1 | 6/2014 | Garcia Sastre et al. | |
| 2014/0193484 A1 | 7/2014 | Bertholet Girardin et al. | |
| 2014/0328875 A1 | 11/2014 | Garcia Sastre et al. | |
| 2015/0132330 A1 | 5/2015 | Garcia-Sastre et al. | |
| 2015/0239960 A1 | 8/2015 | Garcia-Sastre et al. | |
| 2015/0252103 A1 | 9/2015 | Sahin et al. | |
| 2015/0266951 A1 | 9/2015 | Song | |
| 2015/0297712 A1 | 10/2015 | Garcia-Sastre et al. | |
| 2015/0299270 A1 | 10/2015 | Galarza et al. | |
| 2015/0335729 A1 | 11/2015 | Garcia-Sastre et al. | |
| 2016/0015828 A1 | 1/2016 | Torgov et al. | |
| 2016/0017025 A1 | 1/2016 | Samira et al. | |
| 2016/0022806 A1 | 1/2016 | Weiner et al. | |
| 2016/0038585 A1 | 2/2016 | Dormitzer et al. | |
| 2016/0137721 A1 | 5/2016 | Palese et al. | |
| 2016/0185860 A1 | 6/2016 | Sahin et al. | |
| 2016/0355553 A1 | 12/2016 | Meijberg et al. | |
| 2016/0355590 A1 | 12/2016 | Epstein | |
| 2016/0361408 A1 | 12/2016 | Garcia-Sastre et al. | |
| 2016/0362455 A1 | 12/2016 | Meijberg et al. | |
| 2016/0376347 A1 | 12/2016 | Saelens et al. | |
| 2017/0327565 A1 | 11/2017 | Schrader | |
| 2018/0002385 A1 | 1/2018 | Garcia-Sastre et al. | |
| 2018/0008696 A1 | 1/2018 | Palese et al. | |
| 2018/0265573 A1 | 9/2018 | Palese et al. | |
| 2018/0333479 A1 | 11/2018 | Garcia-Sastre et al. | |
| 2019/0106461 A1 | 4/2019 | Garcia-Sastre et al. | |
| 2019/0125859 A1 | 5/2019 | Palese et al. | |

FOREIGN PATENT DOCUMENTS

| | | |
|---|---|---|
| CN | 1196788 C | 4/2005 |
| CN | 103665155 A | 3/2014 |
| EP | 0621339 A2 | 10/1994 |
| EP | 0702085 A1 | 3/1996 |
| EP | 0780475 A1 | 6/1997 |
| EP | 2540312 A1 | 1/2013 |
| JP | H 789992 A | 4/1995 |
| JP | H 10-502168 A | 2/1998 |
| JP | 2004258814 A | 9/2004 |
| JP | 2006347922 A | 12/2006 |
| JP | 2008249712 A | 10/2008 |
| JP | 2009022186 A | 2/2009 |
| JP | 2009131237 A | 6/2009 |
| JP | 2012521786 A | 10/2010 |
| JP | 2011057653 A | 3/2011 |
| JP | 2012530499 A | 12/2012 |
| WO | WO 1984000687 A1 | 3/1984 |
| WO | WO 1991010741 A1 | 7/1991 |
| WO | WO 1992001047 A1 | 1/1992 |
| WO | WO 1994009136 A1 | 4/1994 |
| WO | WO 1994012629 A1 | 6/1994 |
| WO | WO 1994016109 A1 | 7/1994 |
| WO | WO 1994017826 A1 | 8/1994 |
| WO | WO 1995034324 A1 | 12/1995 |
| WO | WO 1996011279 A2 | 4/1996 |
| WO | WO 1996033735 A1 | 10/1996 |
| WO | WO 1996034096 A1 | 10/1996 |
| WO | WO 1996034625 A1 | 11/1996 |
| WO | WO 1997006270 A1 | 2/1997 |
| WO | WO 1997012032 A1 | 4/1997 |
| WO | WO 1997040161 A1 | 10/1997 |
| WO | WO 1997040177 A1 | 10/1997 |
| WO | WO 1998002530 A1 | 1/1998 |
| WO | WO 1998013501 A2 | 4/1998 |
| WO | WO 1998016654 A1 | 4/1998 |
| WO | WO 1998024893 A2 | 6/1998 |
| WO | WO 1998046645 A2 | 10/1998 |
| WO | WO 1998050433 A2 | 11/1998 |
| WO | WO 1998053078 A1 | 11/1998 |
| WO | WO 1999002657 A1 | 1/1999 |
| WO | WO 1999015672 A1 | 4/1999 |
| WO | WO 2001004333 A1 | 1/2001 |

(56) References Cited

FOREIGN PATENT DOCUMENTS

| WO | WO 2002000885 A2 | 1/2002 |
|---|---|---|
| WO | WO 2005000901 A2 | 1/2005 |
| WO | WO 2007045674 A1 | 4/2007 |
| WO | WO 2007064802 A1 | 6/2007 |
| WO | WO 2007103322 A2 | 9/2007 |
| WO | WO 2007109812 A2 | 9/2007 |
| WO | WO 2007109813 A1 | 9/2007 |
| WO | WO 2007110776 A1 | 10/2007 |
| WO | WO 2007134237 A2 | 11/2007 |
| WO | WO 2007134327 A2 | 11/2007 |
| WO | WO 2008005777 A2 | 1/2008 |
| WO | WO 2008028946 A2 | 3/2008 |
| WO | WO 2008032219 A2 | 3/2008 |
| WO | WO 2009001217 A2 | 12/2008 |
| WO | WO 2009009876 A1 | 1/2009 |
| WO | WO 2009012489 A1 | 1/2009 |
| WO | WO 2009025770 A2 | 2/2009 |
| WO | WO 2009036157 A1 | 3/2009 |
| WO | WO 2009068992 A1 | 6/2009 |
| WO | WO 2009076778 A1 | 6/2009 |
| WO | WO 2009079259 A2 | 6/2009 |
| WO | WO 2009092038 A1 | 7/2009 |
| WO | WO 2009121004 A2 | 10/2009 |
| WO | WO 2009150532 A1 | 12/2009 |
| WO | WO 2009156405 A1 | 12/2009 |
| WO | WO 2010003235 A1 | 1/2010 |
| WO | WO 2010036170 A1 | 4/2010 |
| WO | WO 2010036948 A2 | 4/2010 |
| WO | WO 2010117786 A1 | 10/2010 |
| WO | WO 2010130636 A1 | 11/2010 |
| WO | WO 2010138564 A1 | 12/2010 |
| WO | WO 2010148511 A1 | 12/2010 |
| WO | WO 2011014645 A1 | 2/2011 |
| WO | WO 2011044152 A1 | 4/2011 |
| WO | WO 2011087092 A1 | 7/2011 |
| WO | WO 2011103453 A2 | 8/2011 |
| WO | WO 2011111966 A2 | 9/2011 |
| WO | WO 2011123495 A1 | 10/2011 |
| WO | WO 2011126370 A1 | 10/2011 |
| WO | WO 2012009790 A1 | 1/2012 |
| WO | WO 2013043729 A1 | 3/2013 |
| WO | WO 2013079473 A1 | 6/2013 |
| WO | WO 2014159960 A1 | 1/2014 |
| WO | WO 2014099931 A1 | 6/2014 |
| WO | WO 2014152841 A1 | 9/2014 |
| WO | WO 2015199564 A1 | 12/2015 |
| WO | WO 2016005480 A1 | 1/2016 |
| WO | WO 2016005482 A1 | 1/2016 |
| WO | WO 2016118937 A1 | 7/2016 |
| WO | WO 2016205347 A1 | 12/2016 |
| WO | WO 2017021893 A1 | 2/2017 |
| WO | WO 2017035479 A1 | 3/2017 |
| WO | WO 2017210445 A1 | 12/2017 |
| WO | WO 2017218624 A1 | 12/2017 |
| WO | WO 2018187706 A2 | 10/2018 |
| WO | WO 2019032463 A1 | 2/2019 |

OTHER PUBLICATIONS

Wang et al. (PNAS, 2010, vol. 107, p. 18979-18984 in IDS on Dec. 20, 2018).*
Krause et al. Journal of Virology, Oct. 2011, p. 10905-10908 in IDS on Dec. 20, 2018).*
Hai et al. (Journal of Virology, Mar. 2012, p. 5774-5781 in IDS on Dec. 20, 2018).*
Babai et al., "A novel liposomal influenza vaccine (Influsome-VAC) containing hemagglutinin-neuraminidase and IL-2 or GM-CSF induces protective anti-neuraminidase antibodies cross-reacting with a wide spectrum of influenza A viral strains," Vaccine 20(3-4):505-515 (2001).
Babu et al., "Live attenuated H7N7 influenza vaccine primes for a vigorous antibody response to inactivated H7N7 influenza vaccine," Vaccine 32:6798-6804 (2014).

Berry, "Cross-reactive MAb to the binding domain of botulinum neurotoxin A, B, and E developed using a sequential immunization strategy: anti-botulinum neurotoxin," Hybridoma 26(6) (2007).

Bianchi et al., "Universal influenza B vaccine based on the maturational cleavage site of the hemagglutinin precursor," J. Virol. 79(12):7380-7388 (2005).

Bommakanti et al., "Design of an HA2-based *Escherichia coli* expressed influenza immunogen that protects mice from pathogenic challenge," Proc. Natl. Acad. Sci. USA 107:13701-13706 (2010).

Bommakanti et al., "Design of *Eschericia coli*-Expressed Stalk Domain Immunogens of H1N1 Hemagglutinin That Protect Mice from Lethal Challenge," J. Virol. 86(24):13434-13444 (2012).

Boni et al., "Guidelines for identifying homologous recombination events in influenza A virus," PLoS One 5(5):e10434 (2010).

Boni et al., "No evidence for intra-segment recombination of 2009 H1N1 influenza virus in swine," Gene 494(2):242-245 (2012).

Bowie et al., "Deciphering the Message in Protein Sequences: Tolerance to Amino Acid Substitutions," Science 247:1306-1310 (1990).

Bullough et al., "Structure of influenza haemagglutinin at the pH of membrane fusion," Nature 371:37-43 (1994).

Casali et al., "Site-directed mutagenesis of the hinge peptide from the hemagglutinin protein: enhancement of the pH-responsive conformational change," Protein Eng. Des. Sel. 21(6):395-404 (2008).

Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf(2007).

Chen et al., "Generation of Live Attenuated Novel Influenza Virus A/California/7/09 (H1N1) Vaccines with High Yield in Embryonated Chicken Eggs," J. Virol. 84(1):44-51 (2010).

Chen et al., "Influenza Virus Hemagglutinin and Neuraminidase, but Not the Matrix Protein, Are Required for Assembly and Budding if Plasmid-Derived Virus-Like Particles," J. Virol. 81(13):7111-7123 (2007).

Chen et al., "N- and C-terminal residues combine in the fusion-pH influenza hemagglutinin $HA_2$ subunit to form an N cap that terminateds the triple-stranded coiled coil," Proc. Natl. Acad. Sci. 96(16):8967-8972 (1999).

Chen et al., "Vaccine design of hemagglutinin glycoprotein against influenza," Trends Biotechnol. 29(9):426-434 (2011).

Chen et al., 2016, "Influenza A viruses expressing intra- or inter-group chimeric hemagglutinins," 90:3789-3793, doi:10.1128/JVI.03060-15.

Clementi et al., "A Human Monoclonal Antibody with Neutralizing Activity against Highly Divergent Influenza Subtypes," PLoS One 6(12):e28001 (2001).

Copeland et al., "Functional chimeras of human immunodeficiency virus type 1 Gp120 and influenza A virus (H3) hemagglutinin," J Virol. 79:6459-6471 (2005).

Corti et al., "A neutralizing antibody selected from plasma cells that binds to group 1 and group 2 influenza A hemagglutinins," Science 333(6044):850-856 (2011).

Cotter et al., "A Single Amino Acid in the Stalk Region of the H1N1pdm Influenza Virus HA Protein Affects Viral Fusion, Stability and Infectivity," PLoS Pathogens 10(1):e1003831 (2014).

Cox and Fukuda, "Influenza," Infect. Dis. Clin. North Am. 12(1):27-38 (1998).

Crotty et al., "Tracking human antigen-specific memory B cells: a sensitive and generalized ELISPOT system," J. Immunol. Methods 286 (1-2):111-122 (2004).

D'Aoust et al., "Influenza virus-like particles produced by transient expression in Nicotiana benthaminana induce a protective immune response against a lethal viral challenge in mice," J. Plant Biotechnol. 6(9):930-940 (2008).

D'Aoust et al., "The production of hemagglutinin-based virus-like particles in plants: a rapid, efficient and safe response to pandemic influenza," Plant Biotechnol. 8(5):607-619 (2010).

Das et al., "Glycosylation Focuses Sequence Variation in the Influenza A Virus H1 Hemagglutinin Globular Domain," PLoS Pathogens 6(11):e1001211 (2010).

(56) References Cited

OTHER PUBLICATIONS

Database Geneseq "Influenza A virus hemagglutinin protein, H1PR8", Accession No. AJG95109, dated Nov. 15, 2007.
Database GenPept "Hemagglutinin precursor [Contains: Hemagglutinin HA1 chain; Hemagglutinin HA2 chain]", Accession No. P03437, dated Jul. 21, 1986.
Dillon et al., "Induction of protective class I MHC-restricted CTL in mice by a recombinant influenza vaccine in aluminum hydroxide adjuvant," Vaccine 10(5):309-318 (1992).
Doms RW & Moore JP, "HIV-1 Membrane Fusion: Targets of Opportunity," JCB, 151(2): F9-F13 (2000).
Doyle et al., "Analysis of Progressive Deletions of the Transmembrane and Cytoplasmic Domains of Influenza Hemagglutinin," JCB 103:1193-1204 (1986).
Dunand et al., "Both Neutralizing and Non-Neutralizing Human H7N9 Influenza Vaccine-Induced Monoclonal Antibodies Confer Protection," Cell Host & Microbe 19:1-14 (2016).
Eda et al., "Sequential immunization with V3 peptides from primary human immunodeficiency virus type 1 produces cross-neutralizing antibodies against primary isolates with a matching narrow-neutralization sequence motif," J. Virol. 80(11):5552-5562 (2006).
Ekiert et al., "Cross-neutralization of influenza A viruses mediated by a single antibody loop," Nature 489:526-532 (2012).
Ekiert et al., 2009, "Antibody recognition of a highly conserved influenza virus epitope", Science; 324(5924):246-251.
Ekiert et al., 2011, "A highly conserved neutralizing epitope on group 2 influenza A viruses", Science 333:843-850.
EMA Guideline on the exposure to medicinal products during pregnancy: need for post-authorization data (Doc. Ref. EMEA/CHMP/313666/2005 ) adopted at Community level in May 2006); http://www.ema.europa.eu/docs/en_GB/document_library/Regulatory_and_procedural_guideline/2009/11/WC500011303.pdf.
Ermler et al., "Chimeric Hemagglutinin Constructs Induce Broad Protection against Influenza B Virus Challenge in the Mouse Model," J. Virol. 91(12): e00286-17 (2017).
Extended European Search Report for European Application No. 11763347.9, dated Feb. 2, 2015.
Flandorfer et al., "Chimeric Influenza A Viruses with a Functional Influenza B Virus Neuraminidase or Hemagglutinin," J. Virol. 77(17):9116-9123 (2003).
Fluzone®, 2009-2010 Fluzone Seasonal influenza vaccine package insert, 2009.
Fodor et al., 1999, "Rescue of influenza A virus from recombinant DNA," J. Virol. 73:9679-9682 (1999).
Fujii et al., "Selective incorporation of influenza virus RNA segments into virions," Proc. Natl. Acad. Sci. USA 100:2002-2007 (2002).
Gao & Palese, "Rewiring the RNAs of influenza virus to prevent reassortment," Proc. Natl. Acad. Sci. USA 106:15891-15896 (2009).
Gao et al., "Human infection with a novel avian-origin influenza A(H7N9) virus," N. Engl. J. Med. 368:1888-1897 (2013).
García-Sastre et al., "Use of a mammalian internal ribosomal entry site element for expression of a foreign protein by a transfectant influenza virus," J. Virol. 68:6254-6261 (1994).
García-Sastre et al., "Introduction of foreign sequences into the genome of influenza A virus," Dev. Biol. Stand 82:237-246 (1994).
Gauger et al., "Enhanced pneumonia and disease in pigs vaccinated with an inactivated human-like (δ-cluster) H1N2 vaccine and challenged with pandemic 2009 H1N1 influenza virus," Vaccine 29(15):2712-2719 (2011).
Genbank, NCBI Reference Sequence: YP_163736.1, HA2 [Influenza A virus (A/Puerto Rico/8/1934(H1N1))].
Gerhard et al., "Prospects for universal influenza virus vaccine," Emerging Infectious Diseases; 12(4):569-574 (2006).
Gibbs et al., "Recombination in the hemagglutinin gene of the 1918 Spanish Flu," Science 293(5536):1842-1845 (2001).
Giddings et al., "Transgenic plants as factories for biopharmaceuticals," Nat. Biotechnol. 18:1151-1155 (2000).
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Goff et al., 2013, "Induction of cross-reactive antibodies to novel H7N9 influenza virus by recombinant Newcastle disease virus expressing a North American lineage H7 subtype hemagglutinin," J. Virol., 87 (14): 8235-40.
Goff et al., 2013, "Adjuvants and immunization strategies to induce influenza virus hemagglutinin stalk antibodies", PLoS One 8:e79194.
Gomord et al., 2005, "Biopharmaceutical production in plants: problems, solutions and opportunities." Trends in Biotechnology, 23(11):559-565.
Gould et al., 1987, "Mouse H-2k-Restricted Cytotoxic T Cells Recognize Antigenic Determinants in Both The HA1 and HA2 Subunits of the Influenza A/PR/8/34 Hemagglutinin," J. Exp. Med., 166:693-701.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Graves et al., "Preparation of influenza virus subviral particles lacking the HA1 subunit of hemagglutinin: unmasking of cross-reactive HA2 determinants," Virology 126(1):106-116 (1983).
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Hallily et al., 2015, "High-Affinity H7 Head and Stalk Domain-Specific Antibody Response to an Inactivated Influenza H7N7 Vaccine After Priming With Attenuated Influenza Vaccine," Journal of Infectious Diseases, 212: 1270-1278.
Haynes, 2009, "Influenza virus-like particle vaccines", Expert Rev. Vaccines, 8(4): 435-445.
Heaton et al., "In Vivo Bioluminescent Imaging of Influenza A Virus Infection and Characterization of Novel Cross-Protective Monoclonal Antibodies," J. Virol. 87(15):8272-8281 (2013).
Hong et al., "Antibody recognition of the pandemic H1N1 Influenza virus hemagglutinin receptor binding site," J. Virol. 87(22):12471-12480 (2013) (Epub Sep. 11, 2013).
Horimoto et al., 2003, "Generation of influenza A viruses with chimeric (type A/B) hemagglutinins." J Virol. 77(14):8031-8038.
Horimoto et al., 2004, "Influenza A viruses possessing type B hemagglutinin and neuraminidase: potential as vaccine components." Microbes and Infection, 6(6): 579-583.
Horvath et al., 1998, "Hemagglutinin-based multipeptide construct elicits enhanced protective immune response in mice against influenza A virus infection", Immunology Letters; 60(2/03):127-136.
Igarashi et al.: 2008, "Genetically destined potentials for N-linked glycosylation of influenza virus hemagglutinin" Virology, 376:323-329.
International Search Report dated Feb. 19, 2013 or PCT Application No. PCT/US2012/056122, Published as WO 2013/043729.
International Search Report dated Apr. 28, 2014 of PCT Application No. PCT/US2013/075697, Published as WO 2014/099931.
International Search Report dated Jun. 26, 2014 for PCT Application No. PCT/US2014/025526, Published as WO 2014/159960.
International Search Report dated Jul. 13, 2011 of PCT Application No. PCT/US2011/030441, Published as WO 2011/123495.
International Search Report dated Aug. 24, 2010 or PCT Application No. PCT/US2010/029202, Published as WO 2010/117786.
International Search Report of International Application No. PCT/US2010/036170, dated Aug. 17, 2010.
International Search Report of International Application No. PCT/US2011/025467, dated Oct. 19, 2011.
International Search Report of International Application No. PCT/US2016/014640, dated Jun. 3, 2016.
International Search Report of International Application No. PCT/US2016/037595, dated Sep. 15, 2016.

(56) References Cited

OTHER PUBLICATIONS

International Search Report of International Application No. PCT/US2017/035479, dated Oct. 25, 2017.
International Search Report of International Application No. PCT/US2017/037384, dated Nov. 3, 2017.
Izurieta et al., 2000, "Influenza and the rates of hospitalization for respiratory disease among infants and young children," NEJM 342(4):232-239.
Kanekiyo et al., 2013, "Self-assembling influenza nanoparticle vaccines elicit broadly neutralizing H1N1 antibodies." Nature, 499(7456):102-6.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes are Reflected in Their Antigenic Architecture: Analysis of H9 Escape Mutants", Journal of Virology, 78(1):240-249.
Khurana et al., 2013, "DNA Priming Prior to Inactivated Influenza A(H5N1) Vaccination Expands the Antibody Epitope Repertoire and Increases Affinity Maturation in a Boost-Interval—Dependent Manner in Adults," Journal of Infectious Disease, 208:413-417.
Kistner et al., 2007, "Cell culture (Vero) derived whole virus (H5N1) vaccine based on wild-type virus strain induces cross-protective immune responses," Vaccine 25(32):6028-6036.
Krammer and Palese, 2013, "Influenza virus hemagglutinin stalk-based antibodies and vaccines," Curr. Opin. Virol., 3, 521-530.
Krammer et al., 2010. "Trichoplusia ni cells (High Five) are highly efficient for the production of influenza A virus-like particles: a comparison of two insect cell lines as production platforms for influenza vaccines," Mol Biotechnol., 45(3):226-234.
Krammer et al., 2012, "A carboxy-terminal trimerization domain stabilizes conformational epitopes on the stalk domain of soluble recombinant hemagglutinin substrates," PLoS One. 7:e43603. doi:10.1371/journal.pone.0043603.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2013, "Chimeric hemagglutinin influenza virus vaccine constructs elicit broadly protective stalk-specific antibodies", J Virol. 87:6542-6550.
Krammer et al., 2014, "Assessment of influenza virus hemagglutinin stalk-based immunity in ferrets," J. Virol., 88:3432-3442.
Krammer et al., 2014, "H3 stalk-based chimeric hemagglutinin influenza virus constructs protect mice from H7N9 challenge", J Virol, 88:2340-2343.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Krause et al., 2012, "Human monoclonal antibodies to pandemic 1957 H2N2 and pandemic 1968 H3N2 influenza viruses", J. Virol. 86:6334-6340.
Landry et al., 2008, "Three-dimensional structure determines the pattern of CD4+ T-cell epitope dominance in influenza virus hemagglutinin", Journal of Virology; 82(3):1238-1248.
Landry et al., 2010, "Preclinical and Clinical Development of Plant-Made Virus-Like Particle Vaccine against Avian H5N1 Influenza", PLoS One, 5(12): e15559.
Lebendiker M. "Purification Protocols." The Wolfson Centre for Applied Structural Biology, http://wolfson.huji.ac.il/purification/Purification_Protocols.html. Apr. 5, 2006.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.

Lee et al. 2012, "Heterosubtypic antibody recognition of the influenza virus hemagglutinin receptor binding site enhanced by avidity", Proc. Natl. Acad. Sci. U.S.A. 109:17040-17045.
Leroux-Roels, et al. 2008. "Broad Glade 2 cross-reactive immunity induced by an adjuvanted Glade 1 rH5N1 pandemic influenza vaccine", PLOS One; 3(2):e1665.
Li et al., 1992, "Influenza A virus transfectants with chimaeric haemagglutinins containing epitopes from different subtypes", Journal of Virology, 67:399-404.
Lorieau et al., "The complete influenza hemagglutinin fusion domain adopts a tight helical hairpin arrangement at the lipid:water interface," PNAS, 107(25):11341-11346 (2010).
Lowen et al., "Blocking interhost transmission of influenza virus by vaccination in the guinea pig model," J. Virol. 83(7):2803-2818 (2009).
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Mallajosyula et al., 2014, "Influenza hemagglutinin stem-fragment immunogen elicits broadly neutralizing antibodies and confers heterologous protection." PNAS, 111(25):E2514-23.
Marasco et al.. 2007, "The growth and potential of human antiviral monoclonal antibody therapeutics", Nat. Biotechnol: 25(12):1421-1434.
Margine et al., 2013, "H3N2 influenza virus infection induces broadly reactive hemagglutinin stalk antibodies in humans and mice", J. Virol. 87:4728-4737.
Margine et al., 2013, "Hemagglutinin stalk-based universal vaccine constructs protect against group 2 influenza A viruses", J Virol, 10435-10446.
Mbawuike et al., 1994, "Influenza A subtype cross-protection after immunization of outbred mice with purified chimeric NS1/HA2 influenza virus protein", Vaccine, 1994: 12(25):1340-1348.
Mett et al., 2008, "A plant-produced influenza subunit vaccine protects ferrets against virus challenge", Influenza and Other Respiratory Viruses, 2(1):33-40.
Miller et al., 2013, "1976 and 2009 H1N1 influenza virus vaccines boost anti-hemagglutinin stalk antibodies in humans", J. Infect. Dis. 207:98-105.
Mo et al., 2003. "Coexpression of complementary fragments of CIC-5 and restoration of chloride channel function in a Dent's disease mutation", Am J Physiol Cell Physiol; 286:C79-C89.
Mok et al., 2008, "Enhancement of the CD8<+> T cell response to a subdominant epitope respiratory syncytial virus by deletion of an immunodominant epitope", Vaccine: 26(37):4775-4782.
Montgomery et al., "Heterologous and homologous protection against influenza A by DNA vaccination: optimization of DNA vectors," DNA Cell Biol. 12(9):777-783 (1993).
Montplaisir et al., 2009, "Risk of narcolepsy associated with inactivated adjuvanted (AS03) A/H1N1 (2009) pandemic influenza vaccine in Quebec," PLoS One 9 (9): e108489.
Nachbagauer et al., "A chimeric haemagglutinin-based influenza split virion vaccine aduvanted with AS03 induces protective stalk-reactive antibodies in mice," Npj Vaccines 1:16015 (2016).
Nachbagauer et al., 2014, "Induction of broadly reactive anti-hemagglutinin stalk antibodies by an H5N1 vaccine in humans," J. Virol. 88 (22): 13260-13268.
Nachbagauer et al., 2015, "Hemagglutinin stalk immunity reduces influenza virus replication and transmission in ferrets", J. Virol., doi:10.1128/JVI.02481-15.
NCT01676402, Clinical Trial, "Seasonal Influenza HA DNA With Trivalent Inactivated Vaccine (TIV) Administered ID or IM in Healthy Adults 18-70 Years," (last updated Jul. 17, 2014).
Neumann et al., 1999, "Generation of influenza A viruses entirely from cloned cDNAs", PNAS 96:9345-9350.
Ni et al, "Structural basis for the divergent evolution of influenza B virus hemagglutinin," Virology 446(1-2):112-122 (2013) (Epub Aug. 27, 2013).

(56) References Cited

OTHER PUBLICATIONS

O'Brien MA, Uyeki TM, Shay DK, Thompson WW, Kleinman K, McAdam A, Yu XJ, Platt R, Lieu TA. Incidence of outpatient visits and hospitalizations related to influenza in infrants and young children. *Pediatrics*. 2004; 113: 585-593.
Ohkura et al., "Epitope mapping of neutralizing monoclonal antibody in avian influenza A H5N1 virus hemagglutinin," Biochem. Biophys. Res. Commun. 418(1):38-43 (2012) (Epub Dec. 27, 2011).
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among Ell and H2 strains," J. Virol., 68(1):517-520.
Oshima et al., 2011, "Naturally Occurring Antibodies in Humans Can Neutralize a Variety of Influenza Virus Strains, Including H, H1, H2, and H5". Journal of Virology, 85(21):11048-11057.
Ott et al., 2000. The Adjuvant MF59: A 10-Year Perspective, p. 211-228. In O'Hagan DT (ed.), Vaccine Adjuvants, vol. 42. Springer.
Palese P & Shaw M (2007). Orthomyxoviridae: The Viruses and Their Replication. In D.M. Knipe, & P.M. Howley (Eds.), Fields Virology (pp. 1647-1689). Philadelphia, PA: Wolters Kluwer Lippincott Williams & Wilkins.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Perricone et al., 2013, "Autoimmune/inflammatory syndrome induced by adjuvants (ASIA) 2013: Unveiling the pathogenic, clinical and diagnostic aspects," *J Autoimmun.*, 47:1-16.
Pica et al., "Hemagglutinin stalk antibodies elicited by the 2009 pandemic influenza virus as a mechanism for the extinction or seasonal H1N1 viruses." Proc Nat Acad Sci U S A. 2012; 109(7):2573-2578.
Pleschka et al., 1996, "A plasmid-based reverse genetics system for influenza A virus", J Virol 70:4188-92.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Q0PZR5, UniProtKB Accession No. QPZR5, Oct. 29, 2014 [online]. [Retrieved on Sep. 2, 2016]. Retrieved from the internet <URL: http://www.uniprot.org/uniprot/Q0PZR5.txt?version=53> Entire document.
Reid et al., Hemagglutinin [Influenza A virus (A/South Carolina/1/1918(H1N1))]. GenBank Acc. No. AAD17229.1. Dep. Oct. 11, 2000.
Rivera et al., "Probing the structure of influenza B hemagglutinin using site-directed mutagenesis," Virology 206(2):787-795 (1995).
Roberts el al., 1993, "Role of conserved glycosylation sites in maturation and transport of influenza A virus hemagglutinin " J Virol, 67(6):3048-60.
Robertson, 1987, "Sequence Analysis of the Haemagglutinin of A/Taiwan/1/86, a New Variant of Human Influenza A(H1/N1) Virus," J. Gen. Virol., 68:1205-1208.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Rudikoff et al., 1982, "Single amino acid substitution altering antigen-binding specificity." Proc Nat Acad Sci U S A., 79(6):1979-1983.
Ryder et al., 2016, "Vaccination with VSV-vectored chimeric hemagglutinins protects mice against divergent influenza virus challenge strains", J. Virol., 90(5):2544-2550.
Sagawa et al., 1996, "The immunological activity of a deletion mutant of influenza virus haemagglutinin lacking the globular region", J Gen Virol; 77:1483-1487.
Salem, 2000, "In vivo acute depletion of CD8(+) T cells before murine cytomegalovirus infection upregulated innate antiviral activity of natural killer cells", Int. J. Immunopharmacol. 22:707-718.
Santak, M., "Old and new ways to combat human influenza virus." Periodicus Biologorum, 2012; 114(2):221-234.
Schneeman et al., 2012, "A Virus-Like Particle That Elicits Cross-Reactive Antibodies to the Conserved Stem of Influenza Virus Hemagglutinin," J. Virol., 86(21): 11686-22697.
Schulze, 1997, "Effects of Glycosylation on the Properites and Functions of Influenza Virus Hemagglutinin", The Journal of Infectious Diseases, 176(S1):S24-S28.
Shoji et al., 2008, "Plant-expressed HA as a seasonal influenza vaccine candidate", Vaccine, 26(23):2930-2934.
Simmons et al., 2007. "Prophylactic and therapeutic efficacy of human monoclonal antibodies against H5N1 Influenza", PLOS Medicine; 4(5):928-936.
Song et al., 2007, "Influenza A Virus Hemagglutinin Protein, H1PR8," GENESEQ, XP002595511.
Sparrow et al., 2016, "Passive immunization for influenza through antibody therapies, a review of the pipeline, challenges, and potential applications." Vaccine, 34: 5442-5448.
Stech et al., 2005, "A new approach to an influenza live vaccine: modification of the cleavage site of hemagglutinin", Nat. Med. 11(6):683-689.
Steel et al., "Influenza Virus Vaccine Based on the Conserved Hemagglutinin Stalk Domain," mBIO 1(1). pii: e00018-10 (9 pages).
Stephenson et al., 2005, "Cross-reactivity to highly pathogenic avian influenza H5N1 viruses alter vaccination with nonadjuvantcd and MF59-adjuvanted influenza A/Duck/Singapore/97 (H5N3) vaccine: a potential priming strategy." J Infect Dis., 191(8):1210-1215.
Stevens et al., 2006, "Structure and Receptor Specificity of the Hemagglutinin from an H5N1 Influenza Virus" Science, 312:404-409.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Sui et al.. 2009, "Structural and functional bases for broad-spectrum neutralization of avian and human influenza A viruses", Nat Struct Mol Biol; 16(3):265-273.
Sui et al.. 2009, "Structural and functional bases for broad-spectrum neutralization of avian and human influenza A viruses", Nat Struct Mol Biol; 16(3):265-273; Supplementary Information.
Sun et al., 2011, "Glycosylation Site Alteration in the Evolution of Influenza A (H1N1) Viruses." PLoS Pathogens, 6(7):e22844.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tamura et al., 1998, "Definition of amino acid residues on the epitope responsible for recognition by influenza a virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacyin vivo", J. Virol. 86:6179-6188.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 18(4):1884-1894.
Tete et al., 2016, "Dissecting the hemagglutinin head and stalk-specific IgG antibody response in healthcare workers following pandemic H1N1 vaccination," *Nature Partner Journals (NPJ) Vaccine*, Article No. 16001 doi:10.1038/npjvaccines.2016.1.
Thoennes et al., 2008, "Analysis of residues near the fusion peptide in the influenza hemagglutinin structure for roles in triggering membrane fusion", Virology; 370(2):403-414.

(56) References Cited

OTHER PUBLICATIONS

Thomson et al., 2012, "Pandemic H1N1 Influenza Infection and Vaccination in Humans Induces Cross-Protective Antibodies that Target the Hemagglutinin Stem", Front. Immunol. 3:87.
Throsby et al., 2008, "Heterosubtypic neutralizing monoclonal antibodies cross-protective against H5N1 and H1N1 recovered from human IgM-memory B cells", PLoS ONE; 3(12):e3942.
Tong et al., 2013. "New world bats harbor diverse influenza A viruses," PLoS Pathog. 9: e1003657.
Tran et al., 2016, "Cryo-electron microscopy structures of chimeric hemagglutinin displayed on a universal influenza vaccine candidate", MBio, 7(2): e00257-16.
Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Vanlandschoot et al., 1995. "A fairly conserved epitope on the hemagglutinin of influenza A (H3N2) virus with variable accessibility to neutralizing antibody." Virology, 212(2)526-34.
Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.
Vareckova et al., 2008, "HA2-specific monoclonal antibodies as tools for differential recognition of influenza A virus antigenic subtypes," Virus Research, 132:181-186.
Vigerust et al., 2007, "N-Linked Glycosylation Attenuates H3N2 Influenza Viruses", Journal of Virology, 81(16): 8593-8600.
Vincent et al., 2008, "Failure of protection and enhanced pneumonia with a US H1N2 swine influenza virus in pigs vaccinated with an inactivated classical swine H1N1 vaccine," Vet Microbiol., 126 (4): 310-23.
Wang et al., "Crystal structure of unliganded influenza B virus hemagglutinin," J Virol. 82(6):3011-3020 (2008) (Epub Jan. 9, 2008).
Wang et al., 2007, "Incorporation of High Levels of Chimeric Human Immunodeficiency Virus Envelope Glycoproteins into Virus-Like Particles", J. Virol., 81(20):10869-10878.
Wang et al., 2008, "Simplified recombinational approach for influenza A virus reverse genetics", J. Virol. Methods 151:74-78.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Wang et al., 2009, "Glycans on influenza hemagglutinin affect receptor binding and immune response." PNAS, 106(43): 18137-18142.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):1-9.
Wang et al., 2010, "Vaccination with a synthetic peptide from the influenza virus hemagglutinin provides protection against distinct viral subtypes". PNAS. 107(44):18979-18984.
Wang et al., 2012, "Generation of recombinant pandemic H1N1 influenza virus with the HA cleavable by bromelain and identification of the residues influencing HA bromelain cleavage." Vaccine, 30(4):872-8.
Webby et al., 2010, Hemagglutinin [Influenza A virus (A/Brisbane/59/2007(H1N1))]. GenBank Acc. No. ADE28750.1. Dep. Mar. 29, 2010.
Wei et al., 2010, "Induction of Broadly Neutralizing H1N1 Influenza Antibodies by Vaccination," Science; 329: 1060- 1064.
Weis and Brunger, 1990, "Refinement of the Influenza Virus Hemagglutinin by Simulated Annealing." J. Mol. Biol. 212:737-761.
Weis et al. 1988, "Structure of the influenza virus haemagglutinin complexed with its receptor, sialic acid." Nature, 333:426-431.
Weldon et al., 2010, "Enhanced immunogenicity of stabilized trimeric soluble influenza hemagglutinin", PLoSONE 5(9): e12466.
WHO World Health Organization Factsheet No. 211. Influenza Nov. 2016. https://www.who.int/mediacentre/factsheets/fs211/en.
Wiley and Skehel, 1983, "The three-dimensional structure and antigenic variation of the influenza virus haemagglutinin" Division of Virology, 107-111.
Wiley, 1987, "The Structure and Function of the Hemagglutinin Membrane Glycoprotein of Influenza Virus." Ann. Rev. Biochem., 56:365-94.
Wilson et al., 1981, "Structure of the haemagglutinin membrane glycoprotein of influenza virus at 3 A resolution." Nature, 289:366-373.
Winter et al., 1981, "Nucleotide Sequence of the Haemagglutinin Gene of a Human Influenza Virus H1 Subtype" Nature, 292:72-75.
Wohlbold et al., "In the Shadow of Hemagglutinin: A Growing Interest in Influenza Viral Neuraminidase and Its Role as a Vaccine Antigen," Viruses 6(6):2465-2494 (2014).
Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Worobey et al., 2002, "Questioning the Evidence for Genetic Recombination in the 1918 "Spanish Flu" Virus", Science, 296(5566): 211a.
Wrammert et al., 2011, "Broadly cross-reactive antibodies dominate the human B cell response against 2009 pandemic H1N1 influenza virus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jun. 26, 2014 for PCT Application No. PCT/US2014/025526, Published as WO 2014/159960.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.
Written Opinion of International application No. PCT/US2010/036170, dated Aug. 17, 2010.
Written Opinion of International application No. PCT/US2011/025467, dated Oct. 19, 2011.
Written Opinion of the International Searching Authority for International Application No. PCT/US2016/014640, dated Jun. 3, 2016.
Written Opinion of the International Searching Authority for International Application No. PCT/US2016/037595, dated Sep. 15, 2016.
Written Opinion of the International Searching Authority for International Application No. PCT/US2017/035479, dated Oct. 25, 2017.
Written Opinion of the International Searching Authority for International Application No. PCT/US2017/037384, dated Nov. 3, 2017.
Yang et al., 2006, "Targeting lentiviral vectors to specific cell types in vivo", PNAS 103: 11479-11484.
Yang et al. 2007, "Immunization by Avian H5 Influenza Hemagglutinin Mutants with Altered Receptor Binding Specificity", Science, 317(5839):825-828.
Yang et al., 2014, "Structural stability of influenza A(H1N1)pdm09 virus hemagglutinins." J. Virol., 88(9):4828-4838.
Yassine et al., 2015, "Hemagglutinin-stem nanoparticles generate heterosubtypic influenza protection." Nat. Med. 21(9):1065-1070.
Yasugi et al., 2013, "Human monoclonal antibodies broadly neutralizing against influenza B virus", PLoS Pathog. 9(2): e1003150.
Yoshida et al., A. "Cross-protective potential of a novel monoclonal antibody directed against antigenic site B of the hemagglutinin of influenza A viruses." PLoS Pathog. 2009; 5(3);e1000350.
Zamarin et al., 2006, "Influenza A virus PB1-F2 protein contributes to viral pathogenesis in mice". J Virol. 80(16):7976-7983.

(56) References Cited

OTHER PUBLICATIONS

Zhang et al., "Crystal structure of the swine-origin A (H1N1)-2009 influenza A virus hemagglutinin (HA) reveals similar antigenicity to that of the 1918 pandemic virus," Protein Cell 1(5):459-467 (2010) (Epub Jun. 4, 2010).
Zhang et al., "Determination of serum neutralization antibodies against seasonal influenza A strain H3N2 and the emerging strains 2009 H1N1 and avian H5N1," Scand. J. Infect. Dis. 43(3):216-220 (2011).
Zheng, et al., 1996, "Nonconserved nucleotides at the 3' and 5' ends of an influenza A virus RNA play an important role in viral RNA replication", Virology 217:242-251.
Air, "Influenza virus antigenicity and broadly neutralizing epitopes," Curr. Opin. Virol. 11:113-121 (2015).
Anonymous, "alignment" IBIS—Integrated Biotechnological Information, European Patent Office, retreived from ibis.internal.epo.org/exam/jobResult?id=285344, on Sep. 26, 2014 (1 page).
Anonymous, "Amino Acids Reference Chart—Sigma-Aldrich" retreived from www.sigmaaldrich.com/life-science/metabolomics/learning-center/amino-acid-reference-chart.html, on Jul. 17, 2015 (3 pages).
Doyle et al., "A monoclonal antibody targeting a highly conserved epitope in influenza B neuraminidase provides protection against drug resistant strains," Biochem. Biophys. Res. Commun. 441(1):226-229 (2013).
Fleury, et al., 2007, GenBank Acc. No. P03437, Updated Apr. 3, 2007.
GenBank Accession No. ACS71642, haemagglutinin [Influenza A virus (A/Perth/16/2009(H3N2))], 2009.
GenBank Accession No. BAF48478-2007, haemagglutinin [Influenza A virus (A/duck/Czech/1956(H4N6))], 2007.
Georgiev et al. 2018, "Two-Component Ferritin Nanoparticles for Multimerization of Diverse Trimeric Antigens," ACS Infect Dis., 4(5):788-796.
Gravel et al., "Qualitative and quantitative analyses of virtually all subtypes of influenza A and B viral neuraminidases using antibodies targeting the universally conserved sequences," Vaccine 28(36):5774-5784 (2010).
Harvey et al. 2011, "Improved antigen yield in pandemic H1N1 (2009) candidate vaccine viruses with chimeric hemagglutinin molecules," J Virol., 85(12):6086-6090.
Hu et al., "Fully human broadly neutralizing monoclonal antibodies against influenza A viruses generated from the memory B cells of 2009 pandemic H1N1 influenza vaccine recipient," Virology 435(2):320-328 (2013) (Epub Oct. 16, 2012).
Impagliazzo et al., 2015, "A stable trimeric influenza hemagglutinin stem as a broadly protective immunogen." Science, 349(6254):1301-1306 and supplemental materials.
International Preliminary Report on Patentability of International application No. PCT/US2011/030441, dated Oct. 2, 2012.
International Search Report of International Application No. PCT/US2018/026489, dated Aug. 27, 2018.
International Search Report of International Application No. PCT/US2018/045399, dated Nov. 29, 2018.
Krammer, 2017, "Annex I: Sequence comparison of the J&J, VRC and MSSM headless HA constructs (tentative H3 numbering included)" (3 pages).
Nelson et al., 2008, "Lehninger Principles of Biochemistry—Fifth Edition," Chapter 4.3, p. 123, W.H. Freeman and Company.
Singleton et al., 1995, "Dictionary of Microbiology and Molecular Biology—Second Edition." A Wiley-Interscience Publication (3 pages).
Van Der Lubbe, 2018, "Mini-HA Is Superior to Full Length Hemagglutinin Immunization in Inducing Stem-Specific Antibodies and Protection Against Group 1 Influenza Virus Challenges in Mice," Front Immunol., 9:2350.
Wohlbold et al., "Broadly protective murine monoclonal antibodies against influenza B virus target highly conserved neuraminidase epitopes," Nat. Microbiol. 2(10):1415-1424 (2017).

Written Opinion of the International Searching Authority for International Application No. PCT/US2018/026489, dated Aug. 27, 2018.
Written Opinion of the International Searching Authority for International Application No. PCT/US2018/045399, dated Nov. 29, 2018.
Anthony et al., 2012, "Emergence of fatal avian influenza in New England harbor seals," MBio., 3(4):e00166-12.
Arzey et al., 2012, "Influenza virus A (H10N7) in chickens and poultry abattoir workers, Australia," Emerg Infect Dis., 18(5):814-816.
Baker et al., 1976, "Effect of Ca++ on the stability of influenza virus neuraminidase," Arch Virol., 52(1-2):7-18.
Baker et al., 2013, "Protection against lethal influenza with a viral mimic," J Virol., 87(15):8591-8605.
Baz et al., 2013, "Replication and immunogenicity of swine, equine, and avian h3 subtype influenza viruses in mice and ferrets," J Virol., 87(12):6901-6910.
Belshe, 2007, "Translational research on vaccines: influenza as an example," Clin Pharmacol Ther., 82(6):745-749.
Bright et al., 2007, "Influenza virus-like particles elicit broader immune responses than whole virion inactivated influenza virus or recombinant hemagglutinin," Vaccine, 25(19):3871-3878.
Broecker et al., 2018, "Immunodominance of Antigenic Site B in the Hemagglutinin of the Current H3N2 Influenza Virus in Humans and Mice," J Virol., 92(20):e01100-18.
Carter et al., 2016, "Design and Characterization of a Computationally Optimized Broadly Reactive Hemagglutinin Vaccine for H1N1 Influenza Viruses," J Virol., 90(9):4720-4734.
Centers for Disease Control and Prevention (CDC), 2009, "Swine influenza A (H1N1) infection in two children—Southern California, Mar.-Apr. 2009," MMWR Morb Mortal Wkly Rep., 58(15):400-402.
Centers for Disease Control and Prevention (CDC), 2009, "Update on influenza A (H1N1) 2009 monovalent vaccines," MMWR Morb Mortal Wkly Rep., 58(39):1100-1101.
Centers for Disease Control and Prevention (CDC), 2010, "Estimates of deaths associated with seasonal influenza—United States, 1976-2007," MMWR Morb Mortal Wkly Rep., 59(33):1057-1062.
Centers for Disease Control and Prevention (CDC), 2012, "Notes from the field: Highly pathogenic avian influenza A (H7N3) virus infection in two poultry workers—Jalisco, Mexico, Jul. 2012," MMWR Morb Mortal Wkly Rep., 61(36):726-727.
Centers for Disease Control and Prevention (CDC), 2012, "Notes from the field: Outbreak of influenza A (H3N2) virus among persons and swine at a county fair—Indiana, Jul. 2012," MMWR Morb Mortal Wkly Rep., 61(29):561.
Chen et al., 2009, "Evaluation of live attenuated influenza a virus h6 vaccines in mice and ferrets," J Virol., 83(1):65-72.
Claas et al., 1998, "Human influenza A H5N1 virus related to a highly pathogenic avian influenza virus," Lancet, 351(9101):472-477.
Corti et al., 2010, "Heterosubtypic neutralizing antibodies are produced by individuals immunized with a seasonal influenza vaccine," J Clin Invest., 120(5):1663-1673.
De Jong et al., 2000, "Mismatch between the 1997/1998 influenza vaccine and the major epidemic A(H3N2) virus strain as the cause of an inadequate vaccine-induced antibody response to this strain in the elderly," J Med Virol., 61(1):94-99.
Desselberger et al., 1978, "Biochemical evidence that "new" influenza virus strains in nature may arise by recombination (reassortment)," Proc Natl Acad Sci USA, 75(7):3341-3345.
Dowdle et al., 1973, "Inactivated influenza vaccines. 2. Laboratory indices of protection," Postgrad Med J., 49(569):159-163.
Dreyfus et al., 2012, "Highly conserved protective epitopes on influenza B viruses," Science, 337(6100):1343-1348.
Easterbrook et al., 2012, "Protection against a lethal H5N1 influenza challenge by intranasal immunization with virus-like particles containing 2009 pandemic H1N1 neuraminidase in mice," Virology, 432(1):39-44.
Ekiert et al., 2012, "Broadly neutralizing antibodies against influenza virus and prospects for universal therapies," Curr Opin Virol., 2(2):134-141.

(56) References Cited

OTHER PUBLICATIONS

Ellebedy et al., 2014, "Induction of broadly cross-reactive antibody responses to the influenza HA stem region following H5N1 vaccination in humans," Proc Natl Acad Sci USA, 111(36):13133-13138.
Eriksson et al., 2007, "Local and systemic cytokine and chemokine responses after parenteral influenza vaccination," Influenza Other Respir Viruses, 1(4):139-146.
Fouchier et al., 2004, "Avian influenza A virus (H7N7) associated with human conjunctivitis and fatal case of acute respiratory distress sydrome," Proc Natl Acad Sci USA, 101(5):1356-1361.
Garcon et al., 2012, "Development and evaluation of AS03, an Adjuvant System containing α-tocopherol and squalene in oil-in-water emulsion," Exptert Rev Vaccines, 11(3):349-366.
GenBank Accession No. DQ017504.1, Influenza A virus (A/mallard/Alberta/24/01(H7N3)) from Canada segment 4, complete sequence, 2005.
Gerdil, 2003, "The annual production cycle for influenza vaccine," Vaccine, 21(16):1776-1779.
Gerhard et al., 1981, "Antigenic structure of influenza virus haemagglutinin defined by hybridoma antibodies," Nature, 290(5808):713-717.
Giles et al., 2012, "Computationally optimized antigens to overcome influenza viral diversity," Expert Rev Vaccines, 11(3):267-269.
Hamilton et al., 2016, "Club cells surviving influenza A virus infection induce temporary nonspecific antiviral immunity," Proc Natl Acad Sci USA, 113(14):3861-3866.
Harris et al., 2006, "Influenza virus pleiomorphy characterized by cryoelectron tomography," Proc Natl Acad Sci USA, 103(50):19123-19127.
Heaton et al., 2013, "Genome-wide mutagenesis of influenza virus reveals unique plasticity of the hemagglutinin and NS1 proteins," Proc Natl Acad Sci USA, 110(50):20248-20253.
Hobson et al., 1972, "The role of serum haemagglutination-inhibiting antibody in protection against challenge infection with influenza A2 and B viruses," J Hyg (Lond), 70(4):767-777.
Hoffmann et al., 2000, "A DNA transfection system for generation of influenza A virus from eight plasmids," Proc Natl Acad Sci USA, 97(11):6108-6113.
Isakova-Sivak et al., 2011, "Genetic bases of the temperature-sensitive phenotype of a master donor virus used in live attenuated influenza vaccines: A/Leningrad/134/17/57 (H2N2)," Virology, 412(2):297-305.
Isakova-Sivak et al., 2015, "Safety, immunogenicity and infectivity of new live attenuated influenza vaccines," Expert Rev Vaccines, 14(10):1313-1329.
Jayasundara et al., 2014, "Natural attack rate of influenza in unvaccinated children and adults: a meta-regression analysis," BMC Infect Dis., 14:670.
Jin et al., 2003, "Multiple amino acid residues confer temperature sensitivity to human influenza virus vaccine strains (FluMist) derived from cold-adapted A/Ann Arbor/6/60," Viroglogy, 306(1):18-24.
Joh Hira et al., 2004, "Production of monoclonal antibodies against a conserved region of Hemagglutinin of Influenza A virus and enzymatic activity of the light chain," Lectures in the Chemical Society of Japan, 84(2):1156, 2 J6-15 in Japanese with English translation of Abstract (4 pages).
Johansson et al., 1987, "Antigen-presenting B cells and helper T cells cooperatively mediate intravirionic antigenic competition between influenza A virus surface glycoproteins," Proc Natl Acad Sci USA, 84(19):6869-6873.
Johansson et al., 1993, "Dissociation of influenza virus hemagglutinin and neuraminidase eliminates their intravirionic antigenic competition," J Virol., 67(10):5721-5723.
Johnson et al., 2002, "Updating the accounts: global mortality of the 1918-1920 "Spanish" influenza pandemic," Bull Hist Med., 76(1):105-115.
Joseph et al 2007, "Evaluation of replication and pathogenicity of avian influenza a H7 subtype viruses in a mouse model," J Virol., 81(19):10558-10566.

Kayali et al., 2011, "Evidence of infection with H4 and H11 avian influenza viruses among Lebanese chicken growers," PLoS One, 6(10):e26818.
Khurana et al., 2013, "Vaccine-induced anti-HA2 antibodies promote virus fusion and enhance influenza virus respiratory disease," Sci Transl Med., 5(200):200ra114.
Kilbourne et al., 1987, "Immunologic response to the influenza virus neuraminidase is influenced by prior experience with the associated viral hemagglutinin. I. Studies in human vaccinees," J Immunol., 138(9):3010-3013.
Krammer et al., 2014, "An H7N1 influenza virus vaccine induces broadly reactive antibody responses against H7N9 in humans," Clin Vaccine Immunol., 21(8):1153-1163.
Krammer et al., 2015, "Advances in the development of influenza virus vaccines," Nat Rev Drug Discov., 14(3):167-182.
Ledgerwood et al., 2011, "DNA priming and influenza vaccine immunogenicity: two phase 1 open label randomised clinical trials," Lancet Infect Dis., 11(12):916-924.
Li et al., 1999, "Recombinant influenza A virus vaccines for the pathogenic human A/Hong Kong/97 (H5N1) viruses," J Infect Dis., 179(5):1132-1138.
Li et al., 2012, "Pandemic H1N1 influenza vaccine induces a recall response in humans that favors broadly cross-reactive memory B cells," Proc Natl Acad Sci USA, 109(23):9047-9052.
Liang et al., 1994, "Heterosubtypic immunity to influenza type A virus in mice. Effector mechanisms and their longevity," J Immunol., 152(4):1653-1661.
Lowen et al., 2006, "The guinea pig as a transmission model for human influenza viruses," Proc. Natl Acad Sci USA, 103(26):9988-9992.
Margine et al., 2013, "Expression of functional recombinant hemagglutinin and neuraminidase proteins from the novel H7N9 influenza virus using the baculovirus expression system," J Vis Exp., 6(81):e51112.
Martinez-Romero et al., 2013, "Substitutions T200A and E227A in the hemagglutinin of pandemic 2009 influenza A virus increase lethality but decrease transmission," J Virol., 87(11):6507-6511.
Monto et al., 2015, "Antibody to Influenza Virus Neuraminidase. An Independent Correlate of Protection," J Infect Dis., 212(8):1191-1199.
Moody et al., 2011, "H3N2 influenza infection elicits more cross-reactive and less clonally expanded anti-hemagglutinin antibodies than influenza vaccination," PLoS One, 6(10):e25797.
Morel et al., 2011, "Adjuvant System AS03 containing α-tocopherol modulates innate immune response and leads to improved adaptive immunity," Vaccine, 29(13):2461-2473.
Nachbagauer et al., 2016, "Age Dependence and Isotype Specificity of Influenza Virus Hemagglutinin Stalk-Reactive Antibodies in Humans," MBio., 7(1):e01996-15.
Ohmit et al., 2011, "Influenza hemagglutination-inhibition antibody titer as a correlate of vaccine-induced protection," J Infect Dis., 204(12):1879-1885.
Oxford, 2013, "Towards a universal influenza vaccine: volunteer virus challenge studies in quarantine to speed the development and subsequent licensing," Br J Clin Pharmacol., 76(2):210-216.
Palese, 2004, "Influenza: old and new threats," Nat Med., 10(12 Suppl):S82-87.
Park et al., 2006, "Engineered viral vaccine constructs with dual specificity: avian influenza and Newcastle disease," Proc Natl Acad Sci USA, 103(21):8203-8208.
Pearson et al., 1988, "Improved tools for biological sequence comparison," Proc Natl Acad Sci USA, 85(8):2444-2448.
Ridenour et al., 2015, "Development of influenza A(H7N9) candidate vaccine viruses with improved hemagglutinin antigen yield in eggs," Influenza Other Respir Viruses, 9(5):263-270.
Rolfes et al., 2014, "Update: influenza activity—United States, Sep. 28-Dec. 6, 2014," MMWR Morb Mortal Wkly Rep., 63(50):1189-1194.
Runstadler et al., 2013, "Connecting the study of wild influenza with the potential for pandemic disease," Infect Genet Evol., 17:162-187.
Scheiffele et al., 1997, "Interaction of influenza virus haemagglutinin with sphingolipid-cholesterol membrane domains via its transmembrane domain," EMBO J., 16(18):5501-5508.

(56) References Cited

OTHER PUBLICATIONS

Schuind et al., 2015, "Immunogenicity and Safety of an EB66 Cell-Culture-Derived Influenza A/Indonesia/5/2005(H5N1) AS03-Adjuvanted Vaccine: A Phase 1 Randomized Trial," J Infect Dis., 212(4):531-541.
Schulman et al., 1968, "Protective effects of specific immunity to viral neuraminidase on influenza virus infection of mice," J Virol., 2(8):778-786.
Seibert et al., 2010, "Oseltamivir-resistant variants of the 2009 pandemic H1N1 influenza A virus are not attenuated in the guinea pig and ferret transmission models," J Virol., 84(21):11219-11226.
Seibert et al., 2013, "Recombinant IgA is sufficient to prevent influenza virus transmission in guinea pigs," J Virol., 87(14):7793-7804.
Steel et al., 2009, "Live attenuated influenza viruses containing NS1 truncations as vaccine candidates against H5N1 highly pathogenic avian influenza," J Virol., 83(4):1742-1753.
Subbarao et al., 2013, "The prospects and challenges of universal vaccines for influenza," Trends Microbiol., 21(7):350-358.
Sui et al., 2011, "Wide prevalence of heterosubtypic broadly neutralizing human anti-influenza A antibodies," Clin Infect Dis., 52(8):1003-1009.
Swkowronski et al., 2013, "Virus-host interactions and the unusual age and sex distribution of human cases of influenza A(H7N9) in China, Apr. 2013," Euro Surveill., 18(17):20465.
Thompson et al., 2003, "Mortality associated with influenza and respiratory syncytial virus in the United States," JAMA, 289(2):179-186.
Treanor et al., 2007, "Safety and immunogenicity of a baculovirus-expressed hemagglutinin influenza vaccine: a randomized controlled trial," JAMA, 297(14):1577-1582.
Tricco et al., 2013, "Comparing influenza vaccine efficacy against mismatched and matched strains: a systematic review and meta-analysis," BMC Med., 11:153.
Tweed et al., 2004, "Human illness from avian influenza H7N3, British Columbia," Emerg Infect. Dis., 10(12):2196-2199.
Van Der Brand et al., 2011, "Efficacy of vaccination with different combinations of MF59-adjuvanted and nonadjuvanted seasonal and pandemic influenza vaccines against pandemic H1N1 (2009) influenza virus infection in ferrets," J Virol., 85(6):2851-2858.
Van Der Most et al., 2014, "Seeking help: B cells adapting to flu variability," Sci Transl Med., 6(246):246ps8.
Van Reeth et al., 2009, "Prior infection with an H1N1 swine influenza virus partially protects pigs against a low pathogenic H5N1 avian influenza virus," Vaccine, 27(45):6330-6339.
Wan et al., 2013, "Molecular basis for broad neuraminidase immunity: conserved epitopes in seasonal and pandemic H1N1 as well as H5N1 influenza viruses," J Virol., 87(16):9290-9300.
Wang et al., 2006, "Hemagglutinin (HA) proteins from H1 and H3 serotypes of influenza A viruses require different antigen designs for the induction of optimal protective antibody responses as studied by codon-optimized HA DNA vaccines," J Virol., 80(23):11628-11637.
Wang et al., 2010, "Broadly protective monoclonal antibodies against H3 influenza viruses following sequential immunization with different hemagglutinins," PLoS Pathog., 6(2):e1000796.
Wang et al., 2011, "Biochemistry. Catching a moving target," Science, 333(6044):834-835.
Weir et al., 2016, "An overview of the regulation of influenza vaccines in the United States," Influenza Other Respir Viruses, 10(5):354-360.
Wrammert et al., 2008, "Rapid cloning of high-affinity human monoclonal antibodies against against influenza virus," Nature, 453(7195):667-671.
Yewdell., 2013, "To dream the impossible dream: universal influenza vaccination," Curr Opin Virol., 3(3):316-321.
Yoshida et al., 2007, "Preparation of monoclonal antibodies against common region of influenza A virus hemagglutinin (HA)," Lectures in the Chemical Society of Japan, 87(2):1307, 2 J3-02 in Japanese with English translation of Abstract (4 pages).

* cited by examiner

```
                                  ▼(Mature residue 1)
    H1    -MKANLLVLLCALA--AAD--------ADTICIGYHANNSTDTVDTVLEKNVTVTHSVNL
    H2    ----MAIIYLILLFT--AVR--------GDQICIGYHSNNSTEKVDTILERNVTVTHAQNI
    H3    --MKTIIALSYIFCLALGQDLPGNDNSTATLCLGHHAVPNGTLVKTITDDQIEVTNATEL
    H4    --MLSIVILFLLIAENS-----SQNYTGNPVICMGHHAVANGTMVKTLADDQVEVVTAQEL
    H5    --MERIVLLLAIVS--LVK--------SDQICIGYHANKSTKQVDTIMEKNVTVTHAQDI
    H6    ---MIAIIVVAILAT---AGR-------SDKICIGYHANNSTTQIDTILEKNVTVTHSVEL
    H7    --MNTQILVFALVAVIPTN---------ADKICLGHHAVSNGTKVNTLTERGVEVVNATET
    H8    ---MEKFIAIAT-LASTNA----------YDRICIGYQSMNSTDTVNTLIEQNVPVTQMEL
    H9    --METKAIIAALLMVTAAN--------ADKICIGYQSTNSTETVDTLTESNVPVTHTKEL
    H10   --MYKVVVIIALLGAVKG---------LDRICLGHHAVANGTIVKTLTNEQEEVTNATET
    H11   --MEKTLLFAAIFL--CVK--------ADEICIGYLSNNSTDKVDTIIEKNNVTVTSSVEL
    H12   --MEKFIILSTVLAASFA---------YDKICIGYQTNNSTETVNTLSEQNVPVTQVEEL
    H13   -MALNVIATLTLIS-VCVH--------ADRICVGYLSTNSSERVDTLLENGVPVTSSIDL
    H14   ---MIALILVALALSHTAYSQITNGTTGNPIICLGHHAVENGTSVKTLTDNHVEVVSAKEL
    H15   --MNTQIIVILVLGLSMVK--------SDKICLGHHAVANGTKVNTLTERGVEVVNATET
    H16   -MMIKVLYFLIIVLGRYSK--------ADKICIGYLSNNSSDTVDTLTENGVPVTSSVDL
    H17   MELIVLLILLNPYT--FVL--------GDRICIGYQANQNNQTVNTLLEQNVPVTGAQEI
                                  ▲(Mature residue 1)
                ▼(Residue Ap)                        (Residue Cp)▼
    H1    LEDSHNGKLCRLKGIAPLQLGKCNIAGWLLGNPECDPLLPVRSWSYIVETPNSENGICYP
    H2    LEKTHNGKLCKLNGIPPLELGDCSIAGWLLGNPECDRLLTVPEWSYIMEKENPRNGLCYP
    H3    VQSSSTGKICNN-PHRILDGIDCTLIDALLGDPHCDVFQNET-WDLFVERSKAFS-NCYP
    H4    VESQNLPELCPS-PLRLVDGQTCDIINGALGSPGCDHLNGAE-WDVFIERPNAVD-TCYP
    H5    LERTHNGKLCSLNGVKPLILRDCSVAGWLLGNPMCDEFLNLPEWLYIVEKDNPINSLCYP
    H6    LENQKEERFCKILEKAPLDLKGCTIEGWILGNPQCDLLLGDQSWSYIVERPTAQNGICYP
    H7    VERTNIPKICSK-GKRTTDLGQCGLLGTITGPPQCDQFLEFS-ADLIIERPEGND--VCYP
    H8    VETEKHPAYCNTDLGAPLELRDCKIEAVIYGNPKCDIHLKDQGWSYIVERPSAPEGMCYP
    H9    LHTEHNGMLCATDLGHPLILDTCTIEGLIYGNPSCDILLGGKEWSYIVERSSAVNGMCYP
    H10   VESTNLNKLCMK-GRSYKDLGNCHPVGMLIGTPVCDPHLTGT-WDTLIEPENAIA-HCYP
    H11   VETEHTGSFCSINGKQPISLGDCSFAGWILGNPMCDELIGKTSWSYIVEKPNPTNGICYP
    H12   VHRGIDPILCGTELGSPLVLDDCSLEGLILGNPKCDLYINGREWSYIVERPKEMEGVCYP
    H13   IETNHTGTYCSLNGVSPVHLGDCSFEGNIVGNPACTSNFGIREWSYLIEDPAAPHGLCYP
    H14   VETNHTDELCPS-PLKLVDGQDCHLINGALGSPGCDRLQDTT-WDVFIERPTAVD-TCYP
    H15   VEITGIDKVCTK-GKKAVDLGSCGILGTIIGPPQCDHLEFK-ADLIIERRNSSD-ICYP
    H16   VETNHTGTYCSLNGISPIHLGDCSFEGWIVGNPSCATNINIREWSYLIEDPNAPNKFCYP
    H17   LETNHNGKLCSLNGVPPLDLQSCTLAGWLLGNPNCDSLLEAEEWSYIKINESAFDDLCFP
                ▲(Residue Ap)                        (Residue Cp)▲

H1    GDFIDYEELREQLSSVSSFERFEIFPKESSWPNHNTNGVTAACSHE-GKSSFYRNLLWLT
    H2    GSFNDYEELKHLLSSVTHFEKVKILPKDRWTQHTTTGG-SRACAVS-GNPSFFRNMVWLT
    H3    YDVPDYASLRSLVASSGTLE--FITEGFTW-TGVTQNCGSNACKRG-PGNGFFSRLNWLT
    H4    PDVPEYQSLRSILANNGKFE--FIAEEFQW-NTVKQNGKSGACKRA-NVDDPFNRLNWLV
    H5    GDFNDYEELKYLLSSTNHFEKIRIIPRSSWSNHDASSGVSSACPYI-GRSSFLRNVVWLI
    H6    GVLNEVEELKALIGSSGERVERFEMFPKSTWTGVDTSSGVTRACPYN-SGSSFYRNLLWII
    H7    GKFVNEEALRQILRGSGGID--KETMGFTY-SGIRTNGTTSACRRS-G-SSFYAEMEWLL
    H8    GSVENLEELRFVFSSAASYKRIRLFDYSRWNVTRS-GTSKACNASTGGQSFYSINWLT
    H9    GNVENLEELRSLFSSAKSYKRIQIFPDKTWNVTYS--GTSRACSN-----SFYRSMRWLT
    H10   GATINEEALRQKIMESGGIS--KMSTGPTYGSSITSAGTTKACMRN-GGDSFYAELKWLV
    H11   GTLESEEELRLKFSGVLEFNKPEVFTSNGWGAVNSGVGVTAACKPG-GSNSFFRNMVWLI
    H12   GSIENQEELRSLFSSIKKYERVKMFDFTKWNVTYT--GTSKACNNTSNQGSFYPSMPWLT
    H13   GELNNNGELRHLFSGIRSFSKTELIPPTSWGEVLD---GTTSACRDNTGTNSFYRNLVWFI
    H14   FDVPDYQSLRSILASSGSLE--FIAEQFTW-NGVKVDGSSSACLRG-GRNSFFSRLNWLT
    H15   GRFTNEEALRQIIRESGGID--KESMGFRY-SGIRTDGATSACKRT-V-SSFYSEMKWLS
    H16   GELDNNGELRHLFSGVNSFSRTELINPSKWGNVLD--GVTASCLDR-GASSFYRNLVWIV
    H17   GNFENLQDLLLEMSGVQNFTKVKLFNPQSMTG-VTTNNVDQTCPFE-GKPSFYRNLNWIQ

H1    E-K-EGSYPKLKNSYVNKKGKEVLVLWGIHHPPNSKEQQNLYQNENAYVSVVTSNYNRRF
    H2    K-K-GSNYPIAKGSYNNTSGEQMLIIWGVHHPNDETEQRTLYQNVGTYVSIGTSTLNKRS
    H3    KS---GSTYPVLNVTMPNNDNFDKLYIWGVHHPSTNQEQTSLVVQESGRVTVSTRRSQQSI
    H4    KSD-GNAYPLQNLTKINNGDYARLYIWGVHHPSTSTEQTNLYKNNPGRVTVSTKTSQFSV
    H5    K-K-NNTYPTIKRSYNNTNQEDLLILWGIHHPNDAAEQTKLYQNPTTYVSVGTSTLNQRS
    H6    KTK-SAAYSVIKGAYNNTGNQPILYFWGVHHPPDTNEQNTLYGSGDRYVRMGTESMNFAK
    H7    SNTDNASFPQMTKSYKNTRRESALIVWGIHHSGSTTEQTKLYGSGNKLITVGGSSKYHQSF
    H8    KKE-PDTYDPNEGAYVNNEDGDIIFLWGIHHPPDTKEQTTLYKNANTLSSVTTNTINRSF
    H9    HK--SNSYPFQNAHYTNNERENILFMWGIHHPPTDTEQTDLYKNADTTTSVTTEDINRTF
    H10   SKTKGQNFPQTTNTYRNTDTAEHLIIWGIHHPSSTQEKNDLYGTQSLSISVESSTYQNNF
    H11   H-Q-SGTYPVIKRFPNNTKGRDVLIVWGIHHPATLTEHQDLYKEDSSYVAVGSETYNRRF
    H12   LK--SGQFPVQTDEYKNTRDSDIVFTWAIHHPFTSDEQVKLYKNPDTLSSVTTVEINRSF
    H13   K-K-NTRYPVISKTYNNTTGRDVLVLWGIHHPVSVDETKTLYVNSDPYTLVSTKSWSEKY
    H14   KAT-NGNYGPINVTKENTGSYVRLYIWGVHHPSSDNEQTDLYKVATGRVTVSTRSDQISI
    H15   SSMNNQVFPQLNQTYRNTRKEPALIVWGVHHSSSLDEQNKLYGTGNKLITVGSSKYQQSF
    H16   K-K-DEKYPVIKGDYNNTGRDVLVLWGIHHPDTETTATNLYVNKNPYTLVSTKEWSKRY
    H17   G-----NSGLPFNIEIKNPTSNPLLLWGIHNTKDAAQQRNLYGNDYSYTIFNFGEKSEEF
```

FIG. 1A

FIG. 1B

```
H1   HDSNVKNLYEKVKSQLKNNAKEIGNGCFEFYHKCDNECMESVRNGTYDYPKYSEESKLNR
H2   HDSNVKNLYDRVRMQLRDNAKELGNGCFEFYHKCDDECMNSVKNGTYDYPKYEEESKLNR
H3   TDSEMNKLFEKTRRQLRENAEDMGNGCFKIYHKCDNACIESIRNGTYDHDVYRDEALNNR
H4   TDSEMNKLFERVRRQLRENAEDKGNGCFEIFHKCDNNCIESIRNGTYDHDIYRDEAINNR
H5   HDSNVNNLYDKVRLQLKDNARELGNGCFEFYHKCDNECMESVRNGTYDYPQYSEEARLNR
H6   HDANVKNLYERVKSQLRDNAMILGNGCFEFWHKCDDECMESVKNGTYDYPQYQDESKLNR
H7   ADSEMNRLYERVRKQLRENAEEDGTGCFEIFHKCDDDCMASIRNNTYDKSKYREEAMQNR
H8   HDSNVKNLFDEVKPRLSANAIDAGNGCFDILHKCDNECMETIKNGTYDHKEYEEEAKLER
H9   HDANVNNLYNKVKPALGSNAVEDGNGCFELYHKCDDQCMETIRNGTYDRQKYQEESRLER
H10  ADSEMLNLYERVRKQLRQNAEEDGKGCFEIYHTCDDSCMESIRNNTYDHSQYREEALLNR
H11  HDSNVRNLHEKVPRRMLKDNAKDEGNGCFTFYHKCDNKCIERVRNGTYDHKEPEEESKINR
H12  HDANVRNLHDRVPRVLRENAIDTGDGCFEILHKCDNNCMDTIRNGTYNHKEYEEESKIER
H13  HDANVKNLHEQVPRELKDNAIDEGNGCFELLHKCNDSCMETIRNGTYDHTEYAEESKLKR
H14  TDSEMNKLFERVRRQLRENAEDQGNGCFEIFHQCDNNCIESIRNGTYDHNIYRDEAINNR
H15  ADSEMNKLYERVRRQLRENAEEDGTGCFEIFHRCDDQCMESIRNNTYNHTEYRQEALQNR
H16  HDANVRNLHDQVKRALKSNAIDEGDGCFNLLHKCNDSCMETIRNGTYNHEDYREESQLKR
H17  HDANVKNLFEKVKAQLKDNAIDEGNGCPLLLHKCNNSCMDDIKNGTYKYMDYREESHIEK

H1   EKVDGVKLESMG-IYQILAIYSTVASSLVLLVSLGAISFWMCSNGSLQCRICI
H2   NEIKGVKLSNMG-VYQILAIYATVAGSLSLAIMIAGISLWMCSNGSLQCRICI
H3   FQIKGVELKSGY---KDWILWISFAISCFLLCVVLLGFIMWACQRGNIRCNICI
H4   FQIQGVKLTQGY---KDIILWISFSISCFLLVALLLAFILWACQNGNIRCQICI
H5   EEISGVKLESMG-VYQILSIYSTVASSLALAIMIAGLSFWMCSNGSLQCRICI
H6   QEIESVKLESLG-VYQILAIYSTVSSSLVLVGLIIAVGLWMCSNGSMQCRICI
H7   IQIDPVKLSSGY--KDVILWPSFGASCFLLLAIAMGLVFICVKNGNMRCTICI
H8   SKINGVKLEENT-TYKILSIYSTVAASLCLAILIAGGLILGMQNGSCRCMFCI
H9   QKIEGVKLESEG-TYKILTIYSTVASSLVLAMGPAAPLFWAMSNGSCRCNICI
H10  LNINPVKLSSGY--KDIILWFSFGESCFVLLAVVMGLVFFCLKNGNMRCTICI
H11  QEIEGVKLDSSGNVYKILSIYSCIASSLVLAALIMGPMFWACSNGSCRCTICI
H12  QKVNGVKLEENS-TYKILSIYSSVASSLVLLLMIIGGFIFGCQNGNVRCTFCI
H13  QEIDGIKLKSEDNVYKALSIYSCIASSVVLVGLILSFIMWACSSGNCRFNVCI
H14  IKINPVTLTMGY---KDIILWISFSMSCFVPVALILGFVLWACQNGNIRCQICI
H15  IMINPVKLSSGY---KDVILWPSFGASCVMLLAIAMGLIFMCVKNGNLRCTICI
H16  QEIEGIKLKTEDNVYKVLSIYSCIASSIVLVGLILAFIMWACSNGSCRFNVCI
H17  QKIDGVKLTDYS-RYYIMTLYSTIASSVVLGSLIIAAPLWGCQKGSIQCKICI
```

FIG. 1C

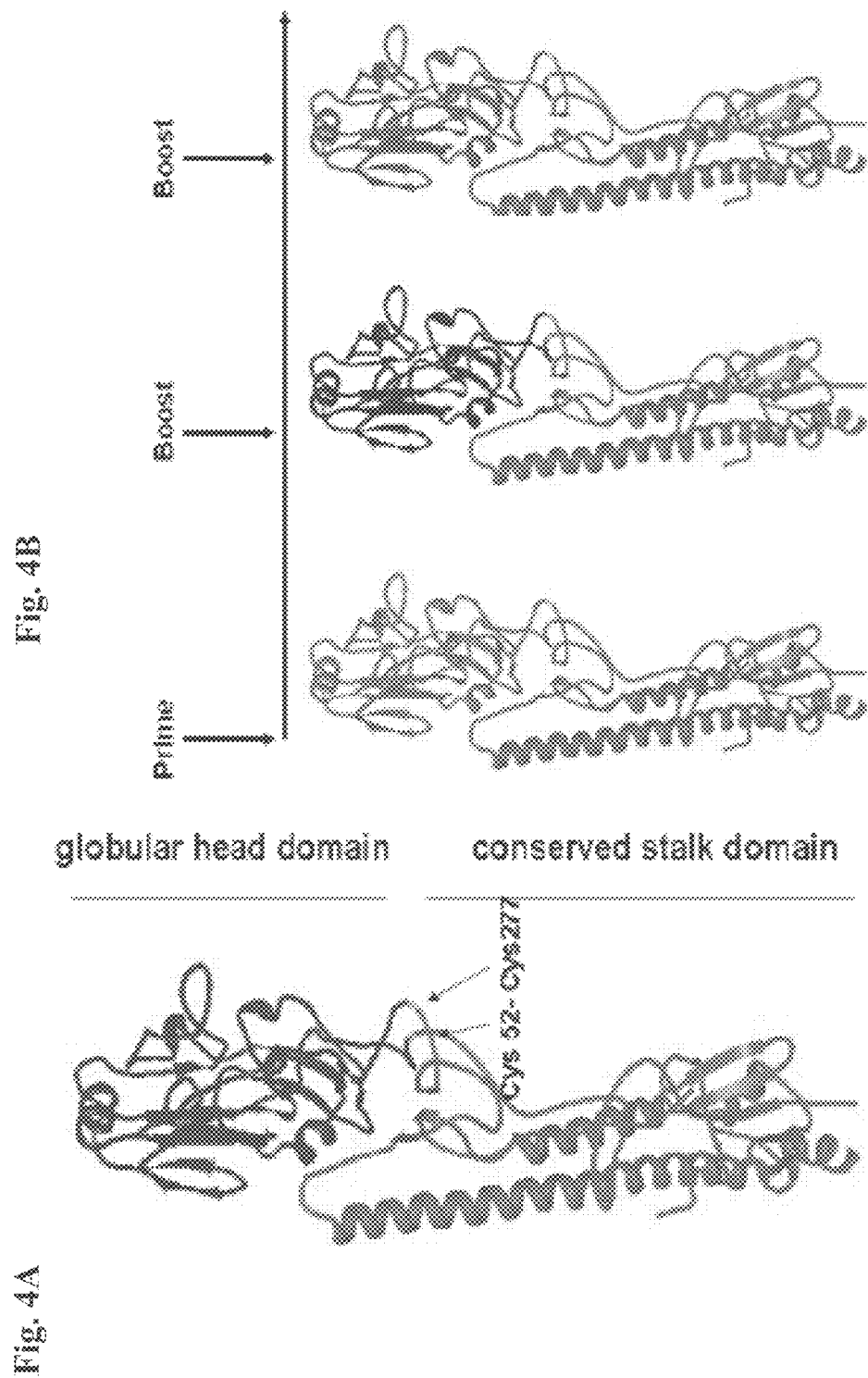

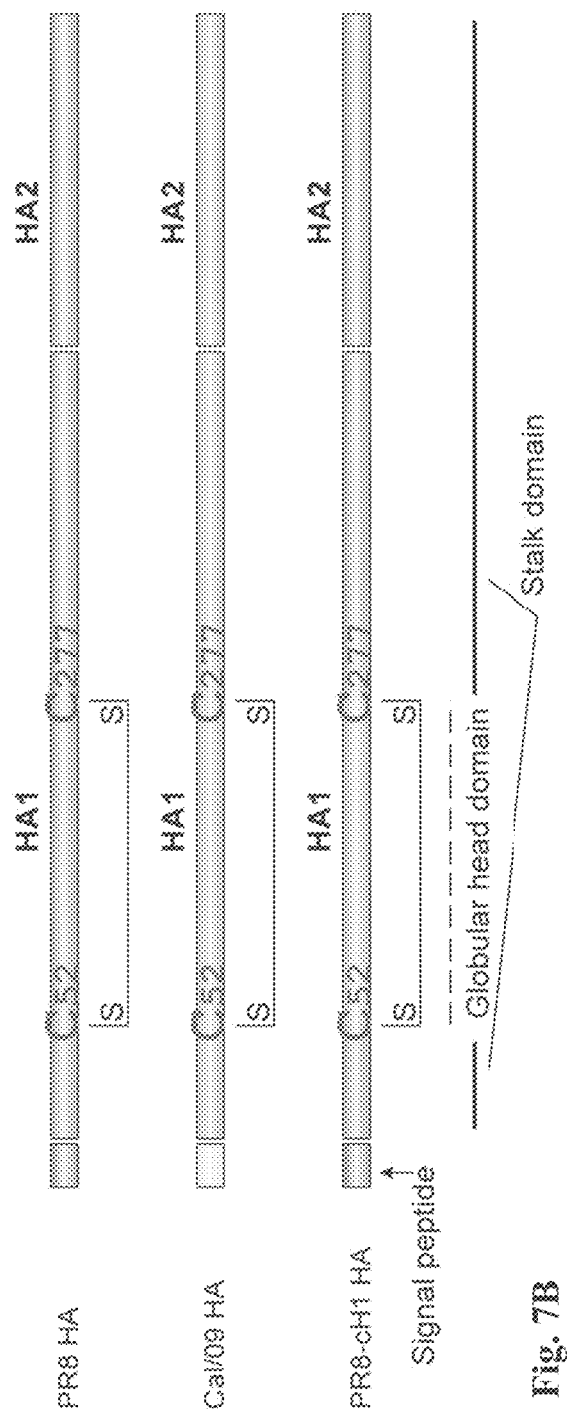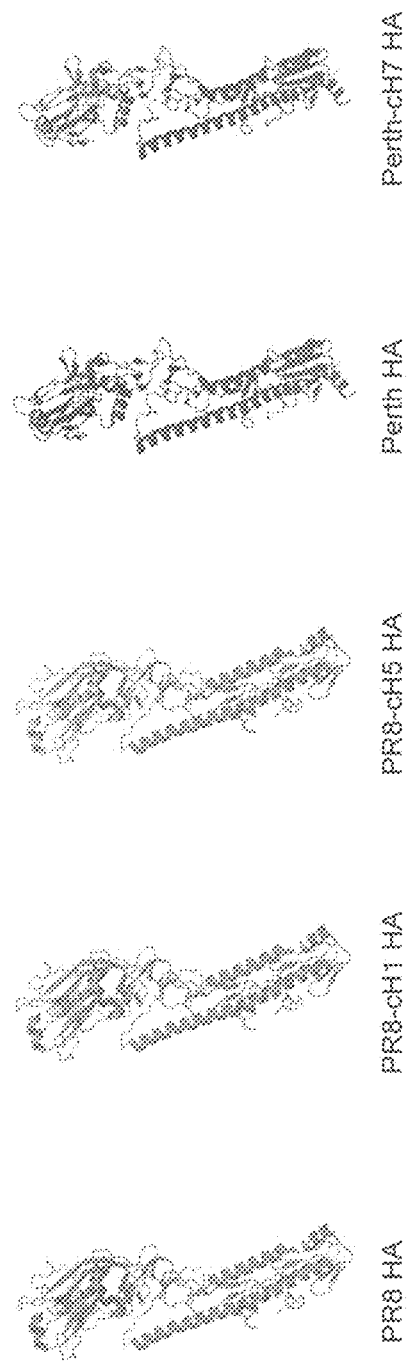
Fig. 7A
Fig. 7B

Hemagglutinin

FIG. 8A

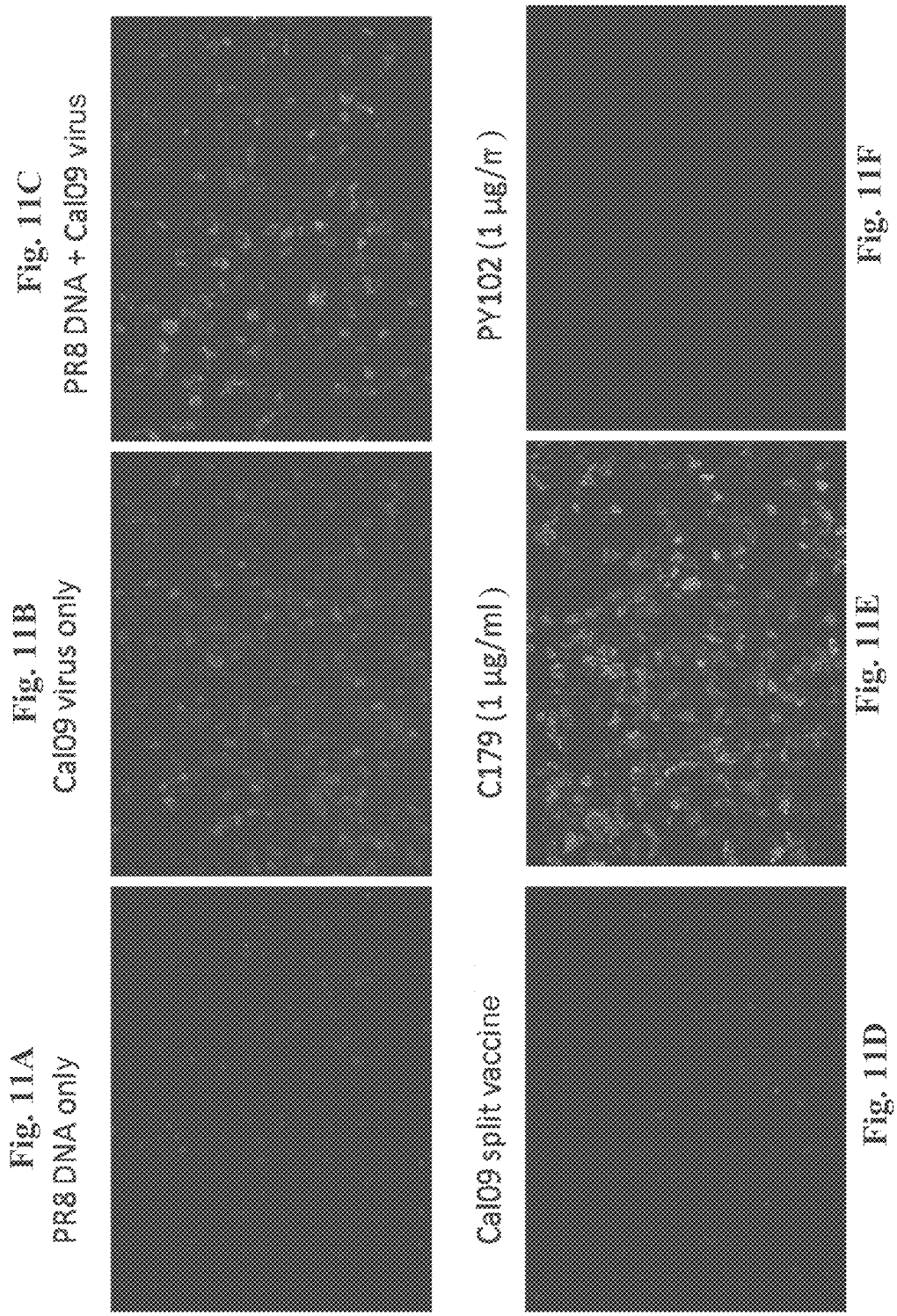

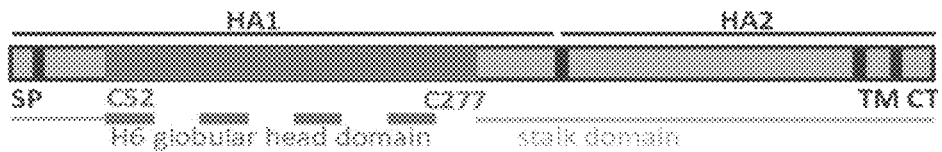
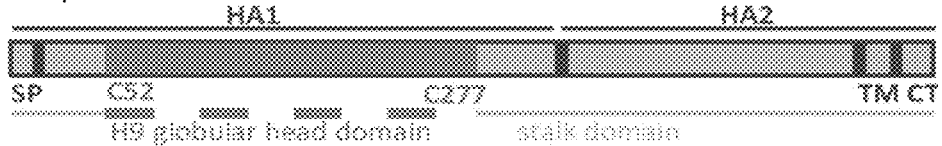
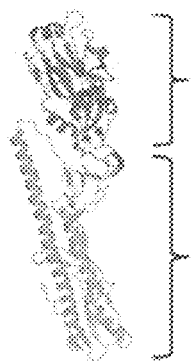
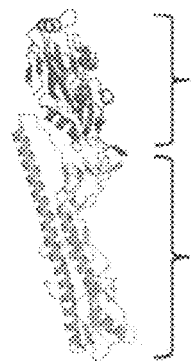
cH6/1          cH9/1          Fig. 14A
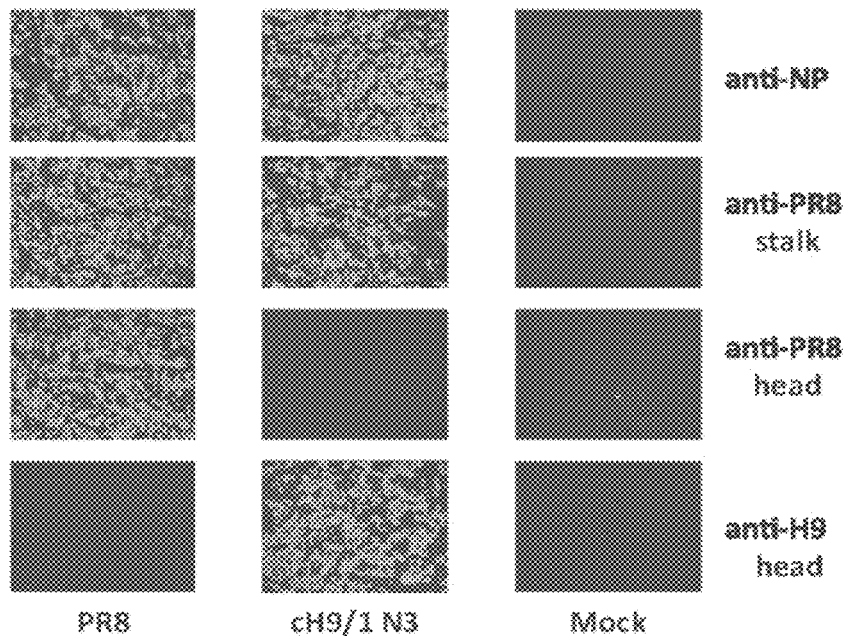
Fig. 14B Fig. 16A  Plaque Reduction Assay
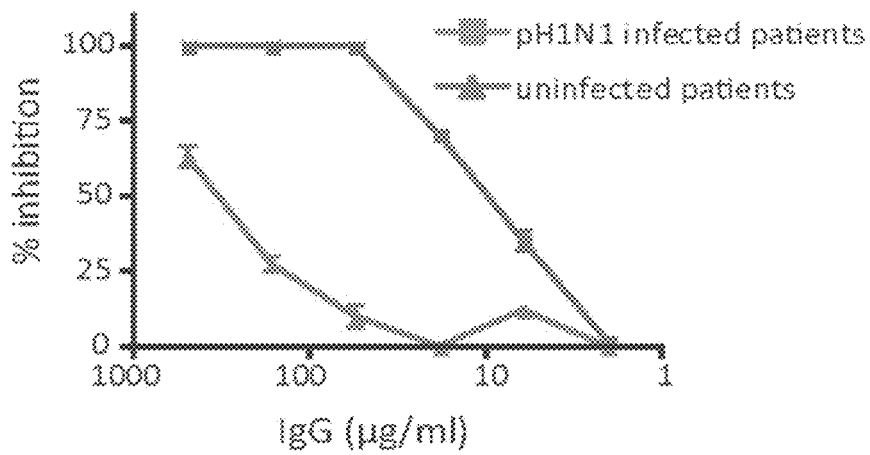
Fig. 16B
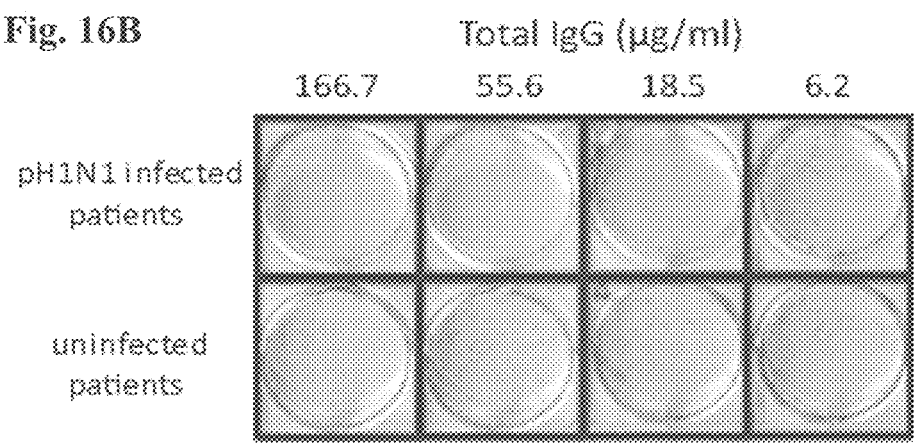
Fig. 16C  Pseudotype Particle Inhibition Assay
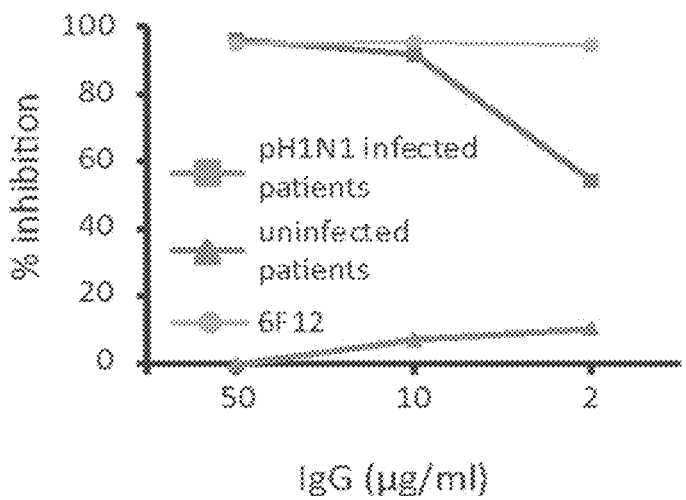

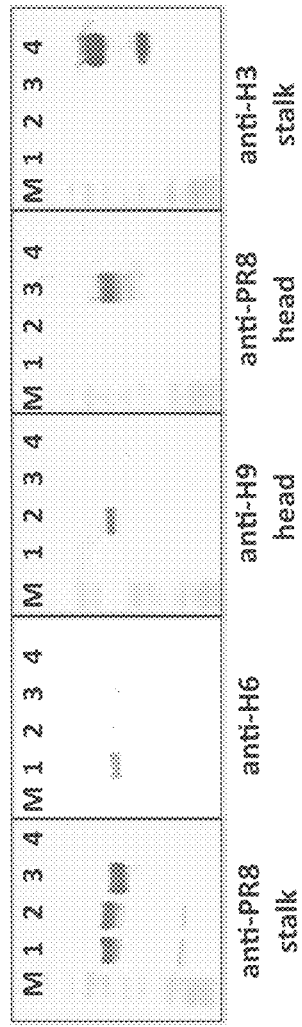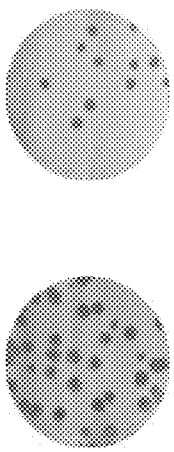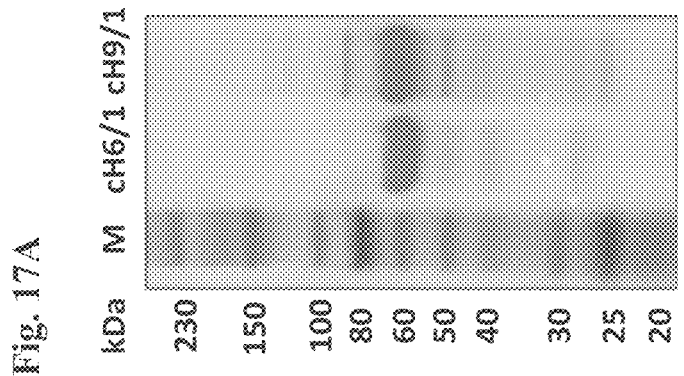

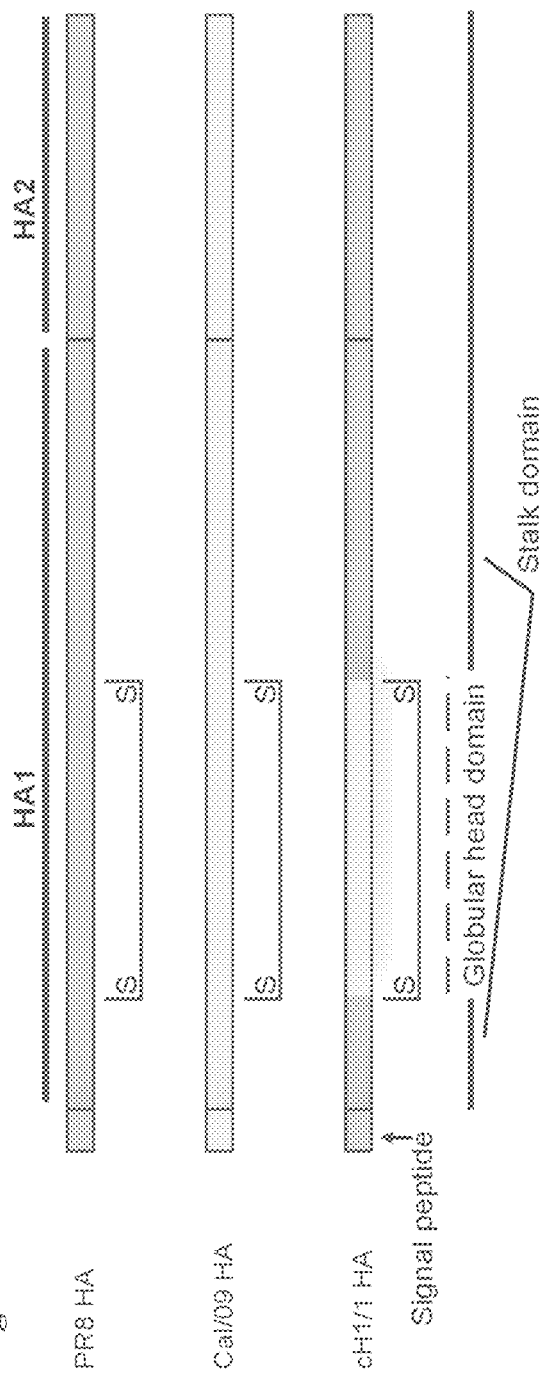
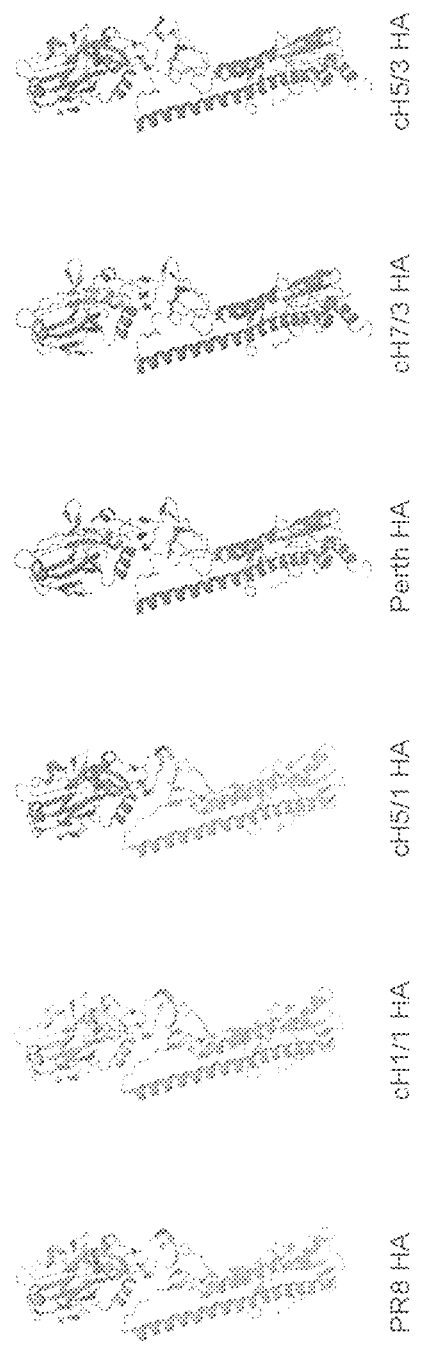
Fig. 19A
Fig. 19B

Percent amino acid identity in the globular head domain

| | A/PR/8/34 (H1) | A/Cal/4/09 (H1) | A/VN/1203/04 (H5) | A/Perth/16/09 (H3) | A/mallard/Alb/24/01 (H7) |
|---|---|---|---|---|---|
| A/PR/8/34 (H1) | | 70 | 50 | 31 | 32 |
| A/Cal/4/09 (H1) | | | 46 | 31 | 27 |
| A/VN/1203/04 (H5) | | | | 34 | 31 |
| A/Perth/16/09 (H3) | | | | | 30 |
| A/mallard/Alb/24/01 (H7) | | | | | |

Percent amino acid identity in the stalk domain

| | A/PR/8/34 (H1) | A/Cal/4/09 (H1) | A/VN/1203/04 (H5) | A/Perth/16/09 (H3) | A/mallard/Alb/24/01 (H7) |
|---|---|---|---|---|---|
| A/PR/8/34 (H1) | | 90 | 77 | 47 | 47 |
| A/Cal/4/09 (H1) | | | 78 | 50 | 48 |
| A/VN/1203/04 (H5) | | | | 46 | 49 |
| A/Perth/16/09 (H3) | | | | | 61 |
| A/mallard/Alb/24/01 (H7) | | | | | |

Percent amino acid identity of the full length hemagglutinin

| | A/PR/8/34 (H1) | A/Cal/4/09 (H1) | A/VN/1203/04 (H5) | A/Perth/16/09 (H3) | A/mallard/Alb/24/01 (H7) |
|---|---|---|---|---|---|
| A/PR/8/34 (H1) | | 82 | 65 | 40 | 42 |
| A/Cal/4/09 (H1) | | | 65 | 42 | 40 |
| A/VN/1203/04 (H5) | | | | 41 | 42 |
| A/Perth/16/09 (H3) | | | | | 49 |
| A/mallard/Alb/24/01 (H7) | | | | | |

FIG. 20

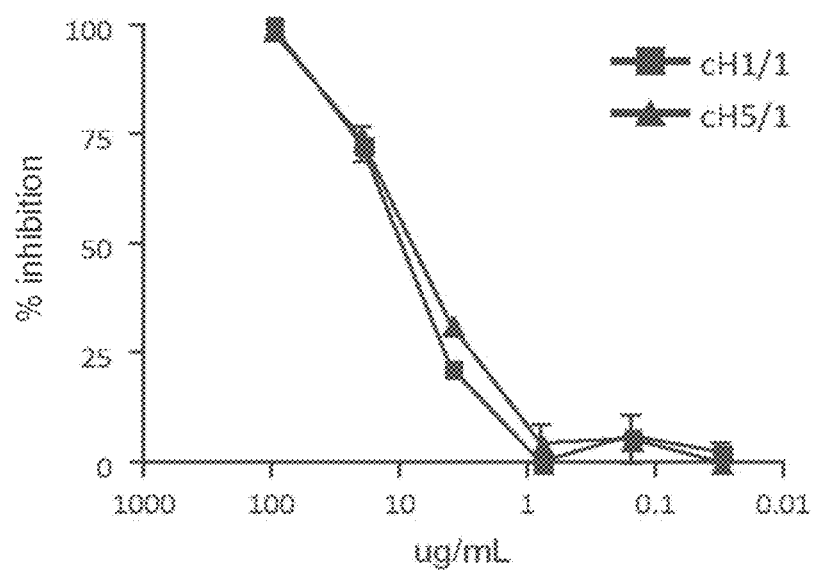
Fig. 26A Plaque reduction assay
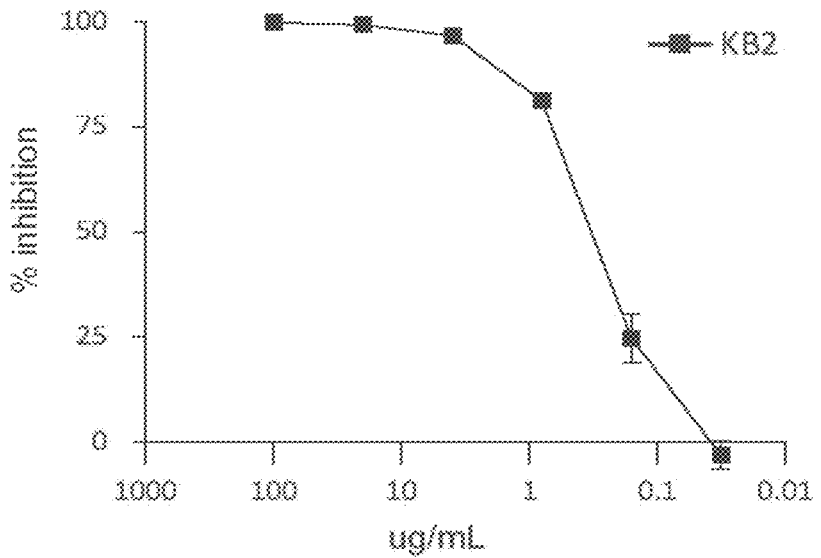
Fig. 26B Psuedotype particle inhibition assay

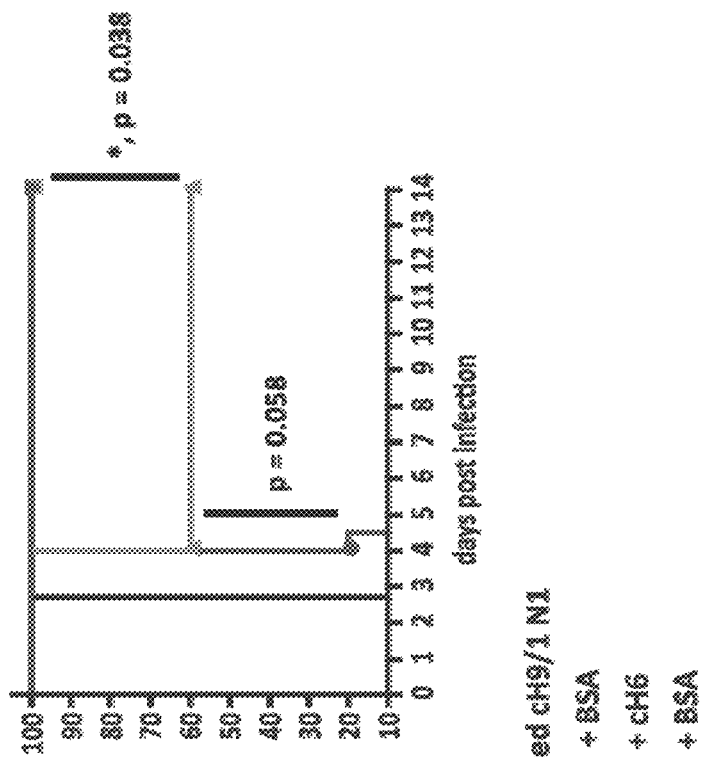
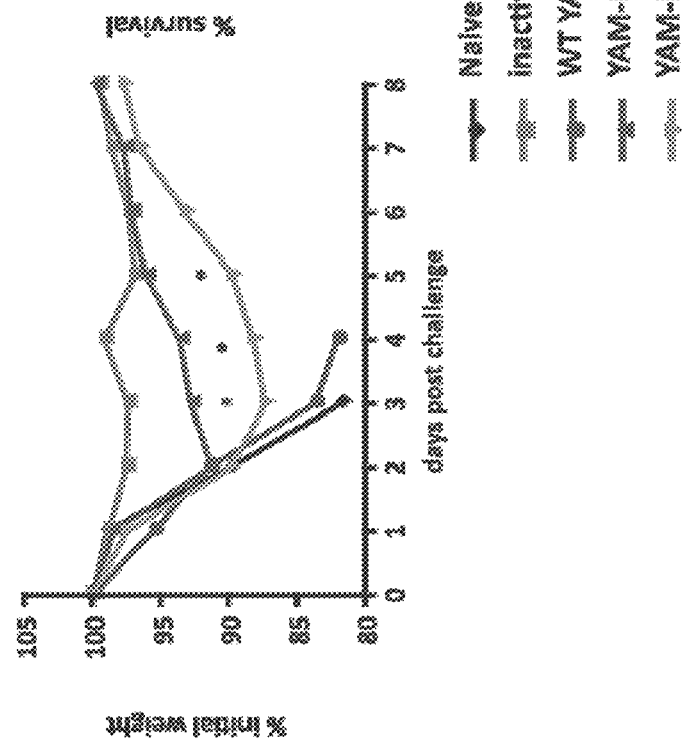
Fig. 28A
Fig. 28B

FIG. 28D

- CR6261 (pos. contr.)
- WT Yam + BSA (neg. contr.)
- Yam-H1 +cH6/1
- Yam-H1 + BSA
- Yam-H1 + BSA

FIG. 28E

FIG. 29A

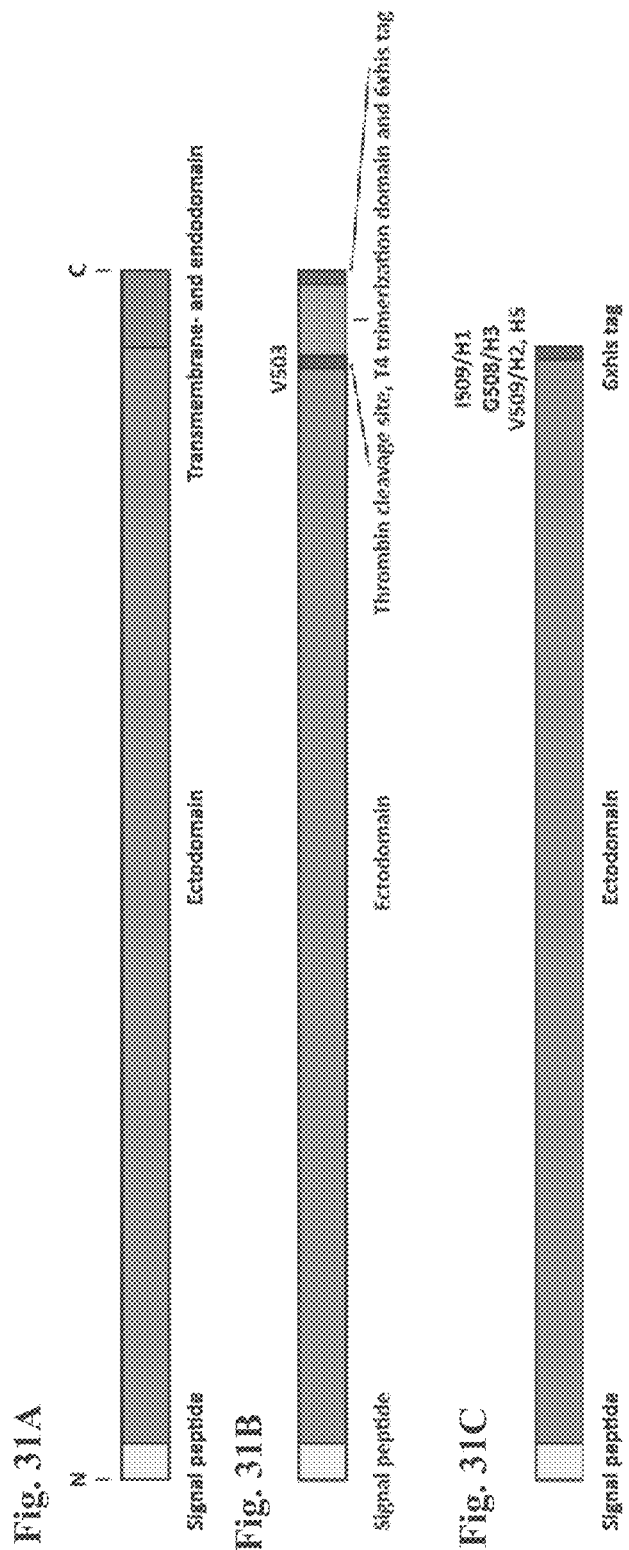

**MKAIIVLLMVVTSNADRICTGITSSNSPHVVKTATQGEVNVTG
VIPLTTTPTKSYFA**$C$*DLDGVKPLILRDCSVAGWLLGNPMCDEFINV
PEWSYIVEKANPVNDLCYPGDFNDYEELKHLLSRINHFEKIQIIPKSSW
SSHEASLGVSSACPYQGKSSFFRNVVWLIKKNSTYPTIKRSYNNTNQED
LLVLWGIHHPNDAAEQTKLYQNPTTYISVGTSTLNQRLVPRIATRSKVN
GQSGRMEFFWTILKPNDAINFESNGNFIAPEYAYKIVKKGDSTIMKSE
LEYGN*$C$**ADCLHEKYGGLNKSKPYYTGEHAKAIGNCPIWVKTP
LKLANGTKYRPPAKLLKERGFFGAIAGFLEGGWEGMIAGWH
GYTSHGAHGVAVAADLKSTQEAINKITKNLNSLSELEVKNLQ
RLSGAMDELHNEILELDEKVDDLRADTISSQIELAVLLSNEGII
NSEDEHLLALERKLKKMLGPSAVEIGNGCFETKHKCNQTCLD
RIAAGTFNAGEFSLPTFDSLNITAASLNDDGLDNHTILLYYSTA
ASSLAVTLMLAIFIVYMVSRDNVSCSICL**

Bold Text: B/Florida/4/2006 stalk domain

Italicized Text: A/Vietnam/1203/2004 H5 globular head domain

Enlarged Text: Cysteines from H5 globular head domain which may guide insertion location of the globular head domain

FIG. 36 er. No. 15/158,785, filed May 19, 2016 (now U.S. Pat. No. 10,137,189), which is a divisional of U.S. patent application Ser. No. 14/109,358, filed Dec. 17, 2013 (now U.S. Pat. No. 9,371,366), which claims priority to U.S. Provisional Patent Application No. 61/738,672, filed Dec. 18, 2012, and U.S. Provisional Patent Application No. 61/840,899, filed Jun. 28, 2013, the disclosure of each of which is incorporated herein by reference in its entirety.

INFLUENZA VIRUS VACCINES AND USES THEREOF

This application is a continuation of U.S. patent application Ser. No. 15/158,785, filed May 19, 2016 (now U.S. Pat. No. 10,137,189), which is a divisional of U.S. patent application Ser. No. 14/109,358, filed Dec. 17, 2013 (now U.S. Pat. No. 9,371,366), which claims priority to U.S. Provisional Patent Application No. 61/738,672, filed Dec. 18, 2012, and U.S. Provisional Patent Application No. 61/840,899, filed Jun. 28, 2013, the disclosure of each of which is incorporated herein by reference in its entirety.

This invention was made with government support under Grant Nos. AI070469, AI086061 and HHSN266200700010C awarded by the National Institutes of Health. The government has certain rights in the invention.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 06923-291-999_SEQ_LISTING.txt, was created on Oct. 15, 2018, and is 106,300 bytes in size.

1. INTRODUCTION

Provided herein are chimeric influenza virus hemagglutinin polypeptides and compositions comprising the same, vaccines comprising the same, and methods of their use.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza A viruses are mainly avians, but influenza A viruses (including those of avian origin) also can infect and cause illness in humans and other animal hosts (bats, canines, pigs, horses, sea mammals, and mustelids). For example, the H5N1 avian influenza A virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; March 2003). In the United States, influenza viruses infect an estimated 10-15% of the population (Glezen and Couch R B (1978) Interpandemic influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957, 1968, and 2009. Due to the lack of pre-formed immunity against the major viral antigen, hemagglutinin (HA), pandemic influenza can affect greater than 50% of the population in a single year and often causes more severe disease than epidemic influenza. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human influenza A H5N1 virus related to a highly pathogenic avian influenza virus. Lancet 351: 472-7), there have been concerns that it may be the next pandemic virus. Further, H7 and H9 strains are candidates for new pandemics since these strains infect humans on occasion.

An effective way to protect against influenza virus infection is through vaccination; however, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine.

3. SUMMARY

In one aspect, provided herein are chimeric influenza hemagglutinin (HA) polypeptides that induce a cross-protective immune response against the conserved HA stem domain of influenza viruses. The chimeric influenza HA polypeptides provided herein comprise a stable (e.g., properly formed) HA stem domain and a globular HA head domain that is heterologous to the stem domain (i.e. the head and stem domains are derived from different strains and/or subtypes of influenza virus).

In certain embodiments, a chimeric influenza hemagglutinin (HA) polypeptide provided herein comprises (i) the stem domain of the hemagglutinin from an influenza virus of the H1 subtype and (ii) the globular head domain of the hemagglutinin from an influenza virus of the H5 subtype (sometimes referred to herein as a "cH5/1 chimeric influenza hemagglutinin polypeptide"). In a specific embodiment, the stem domain of a cH5/1 chimeric influenza hemagglutinin polypeptide is the stem domain of A/California/4/2009 (H1N1) HA (or the stem domain of an A/California/4/2009-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA). In specific embodiments, the stem domain of the hemagglutinin from an influenza virus of the H1 subtype of a cH5/1 chimeric influenza hemagglutinin polypeptide provided herein is from an H1 subtype that the majority of the population is naive to. In certain embodiments, the stem domain of the hemagglutinin from an influenza virus of the H1 subtype of a cH5/1 chimeric influenza hemagglutinin polypeptide provided herein is from an upcoming H1N1 vaccine strain, e.g., the H1N1 vaccine strain in use in the year 2013, 2014, 2015, 2016, 2017, 2018, 2019, 2020, 2021, 2022, 2023, 2024, 2025, 2026, 2027, 2028, 2029, 2030, 2031, 2032, 2032, 2033, 2034, or 2035.

In a specific embodiment, a cH5/1 chimeric influenza hemagglutinin polypeptide does not comprise the stem domain of A/Puerto Rico/8/34 ("PR8") HA and does not comprise the globular head domain of A/Vietnam/1203/2004 (H5) HA.

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H5 subtype (sometimes referred to herein as a "cH5/3 chimeric influenza hemagglutinin polypeptide"). In a specific embodiment, the stem domain of a cH5/3 chimeric influenza hemagglutinin polypeptide is the stem domain of A/Victoria/361/2011 (H3N2) HA (or the stem domain of an A/Victoria/361/2011 (H3N2)-like influenza virus HA). In another specific embodiment, the stem domain of a cH5/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH5/3 chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/3 chimeric influenza hemagglutinin polypeptide is the stem domain of A/Victoria/361/2011 (H3N2) (or the stem domain of an A/Victoria/361/2011 (H3N2)-like influenza virus HA) HA and the globular head domain of the cH5/3 chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH5/3 chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH5/3 chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH5/3 chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH5/3 chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In another specific embodiment, the stem domain of a cH5/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA). In another specific embodiment, the stem domain of a cH5/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH5/3 chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH5/3 chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH5/3 chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH5/3 chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/3 chimeric influenza hemagglutinin polypeptide is the stem domain of A/harbor seal/Massachusetts/1/2011 (H3N8) (or the stem domain of an A/harbor seal/Massachusetts/1/2011 (H3N8)-like influenza virus HA) HA and the globular head domain of the cH5/3 chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH5/3 chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In another specific embodiment, the stem domain of a cH5/3 chimeric influenza hemagglutinin polypeptide is the stem domain of A/Indiana/10/2011 (H3N2) HA (or the stem domain of an A/Indiana/10/2011 (H3N2)-like influenza virus HA). In another specific embodiment, the stem domain of a cH5/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH5/3 chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH5/3 chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/3 chimeric influenza hemagglutinin polypeptide is the stem domain of A/Indiana/10/2011 (H3N2) (or the stem domain of an A/Indiana/10/2011 (H3N2)-like influenza virus HA) HA and the globular head domain of the cH5/3 chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH5/3 chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH5/3 chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH5/3 chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA). In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH5/3 chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH5/3 chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH5/3 chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH5/3 chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH5/3 chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH5/3 chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In specific embodiments, the stem domain of the hemagglutinin from an influenza virus of the H3 subtype of a cH5/3 chimeric influenza hemagglutinin polypeptide provided herein is from an H3 subtype that the majority of the population is naive to. In certain embodiments, the stem domain of the hemagglutinin from an influenza virus of the H3 subtype of a cH5/3 chimeric influenza hemagglutinin polypeptide provided herein is from an upcoming H3N2 vaccine strain, e.g., the H3N2 vaccine strain in use in the year 2013, 2014, 2015, 2016, 2017, 2018, 2019, 2020, 2021, 2022, 2023, 2024, 2025, 2026, 2027, 2028, 2029, 2030, 2031, 2032, 2032, 2033, 2034, or 2035.

In a specific embodiment, a cH5/3 chimeric influenza hemagglutinin polypeptide provided herein does not comprise the globular head domain of A/Vietnam/1203/2004 (H5) HA and does not comprise the stem domain of A/Perth/16/2009 (H3) HA.

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H7 subtype (sometimes referred to herein as a "cH7/3 chimeric influenza hemagglutinin polypeptide").

In a specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/3 chimeric influenza hemagglutinin polypeptide is the stem domain of A/Victoria/361/2011 (H3N2) HA (or the stem domain of an A/Victoria/361/2011 (H3N2)-like influenza virus HA) and the globular head domain of the cH7/3 chimeric influenza hemagglutinin polypeptide is the globular head domain of A/mallard/Netherlands/12/2000 (H7) HA (or the globular head domain of an A/mallard/Netherlands/12/2000 (H7)-like influenza virus HA).

In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/

Massachusetts/1/2011 (H3N8)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/3 chimeric influenza hemagglutinin polypeptide is the stem domain of A/harbor seal/Massachusetts/1/2011 (H3N8) HA (or the stem domain of an A/harbor seal/Massachusetts/1/2011 (H3N8)-like influenza virus HA) and the globular head domain of the cH7/3 chimeric influenza hemagglutinin polypeptide is the globular head domain of A/mallard/Netherlands/12/2000 (H7) HA (or the globular head domain of an A/mallard/Netherlands/12/2000 (H7)-like influenza virus HA).

In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/3 chimeric influenza hemagglutinin polypeptide is the stem domain of A/Indiana/10/2011 (H3N2) HA (or the stem domain of an A/Indiana/10/2011 (H3N2)-like influenza virus HA) and the globular head domain of the cH7/3 chimeric influenza hemagglutinin polypeptide is the globular head domain of A/mallard/Netherlands/12/2000 (H7) HA (or the globular head domain of an A/mallard/Netherlands/12/2000 (H7)-like influenza virus HA).

In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/3 chimeric influenza hemagglutinin polypeptide is the stem domain of A/Perth/16/2009 (H3N2) HA (or the stem domain of an A/Perth/16/2009 (H3N2)-like influenza virus HA) and the globular head domain of the cH7/3 chimeric influenza hemagglutinin polypeptide is the globular head domain of A/mallard/Netherlands/12/2000 (H7) HA (or the globular head domain of an A/mallard/Netherlands/12/2000 (H7)-like influenza virus HA).

In specific embodiments, the stem domain of the hemagglutinin from an influenza virus of the H3 subtype of a cH7/3 chimeric influenza hemagglutinin polypeptide provided herein is from an H3 subtype that the majority of the population is naive to. In certain embodiments, the stem domain of the hemagglutinin from an influenza virus of the H3 subtype of a cH7/3 chimeric influenza hemagglutinin polypeptide provided herein is from an upcoming H3N2 vaccine strain, e.g., the H3N2 vaccine strain in use in the year 2013, 2014, 2015, 2016, 2017, 2018, 2019, 2020, 2021, 2022, 2023, 2024, 2025, 2026, 2027, 2028, 2029, 2030, 2031, 2032, 2032, 2033, 2034, or 2035.

In a specific embodiment, a cH7/3 chimeric influenza hemagglutinin polypeptide does not comprise the globular head domain of A/mallard/Alberta/24/2001 (H7). In another specific embodiment, a cH7/3 chimeric influenza hemagglutinin polypeptide does not comprise the stem domain of A/Perth/16/2009 (H3).

In certain embodiments, a chimeric influenza hemagglutinin (HA) polypeptide provided herein comprises (i) the stem domain of the hemagglutinin from an influenza B virus and (ii) the globular head domain of the hemagglutinin from an influenza virus of the H5 subtype (sometimes referred to herein as a "cH5/B chimeric influenza hemagglutinin polypeptide").

In a specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA). In another specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA) and the globular head domain of the cH5/B chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA) and the globular head domain of the cH5/B chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA) and the globular head domain of the cH5/B chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA) and the globular head domain of the cH5/B chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA) and the globular head domain of the cH5/B chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/B chimeric influenza hemagglutinin polypeptide is the stem domain of B/Malaysia/2506/2004 HA (or the stem domain of an B/Malaysia/2506/2004-like influenza virus HA) and the globular head domain of the cH5/B chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In another specific embodiment, the stem domain of a cH5/B chimeric influenza hemagglutinin polypeptide is the stem domain of B/Florida/4/2006 HA (or the stem domain of an B/Florida/4/2006-like influenza virus HA). In another specific embodiment, the stem domain of a cH5/B chimeric influenza hemagglutinin polypeptide is the stem domain of B/Florida/4/2006 HA (or the stem domain of an B/Florida/4/2006-like influenza virus HA) and the globular head domain of the cH5/B chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/B chimeric influenza hemagglutinin polypeptide is the stem domain of B/Florida/4/2006 HA (or the stem domain of an B/Florida/4/2006-like influenza virus HA) and the globular head domain of the cH5/B chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/B chimeric influenza hemagglutinin polypeptide is the stem domain of B/Florida/4/2006 HA (or the stem domain of an B/Florida/4/2006-like influenza virus HA) and the globular head domain of the cH5/B chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/B chimeric influenza hemagglutinin polypeptide is the stem domain of B/Florida/4/2006 HA (or the stem domain of an B/Florida/4/2006-like influenza virus HA) and the globular head domain of the cH5/B chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/B chimeric influenza hemagglutinin polypeptide is the stem domain of B/Florida/4/2006 HA (or the stem domain of an B/Florida/4/2006-like influenza virus HA) and the globular head domain of the cH5/B chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/B chimeric influenza hemagglutinin polypeptide is the stem domain of B/Florida/4/2006 HA (or the stem domain of an B/Florida/4/2006-like influenza virus HA) and the globular head domain of the cH5/B chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA). In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA) and the globular head domain of the cH5/B chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA) and the globular head domain of the cH5/B chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA) and the globular head domain of the cH5/B chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA) and the globular head domain of the cH5/B chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA) and the globular head domain of the cH5/B chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/B chimeric influenza hemagglutinin polypeptide is the stem domain of B/Wisconsin/1/2010 HA (or the stem domain of an B/Wisconsin/1/2010-like influenza virus HA) and the globular head domain of the cH5/B chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA). In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA) and the globular head domain of the cH5/B chimeric influenza hemagglutinin polypeptide is the globular head domain of A/Vietnam/1203/2004 (H5) HA (or the globular head domain of an A/Vietnam/1203/2004 (H5)-like influenza virus HA). In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA) and the globular head domain of the cH5/B chimeric influenza hemagglutinin polypeptide is the globular head domain of A/Indonesia/5/2005 (H5) HA (or the globular head domain of an A/Indonesia/5/2005 (H5)-like influenza virus HA). In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA) and the globular head domain of the cH5/B chimeric influenza hemagglutinin polypeptide is the globular head domain of A/Anhui/1/2005 (H5) HA (or the globular head domain of an A/Anhui/1/2005 (H5)-like influenza virus HA). In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA) and the globular head domain of the cH5/B chimeric influenza hemagglutinin polypeptide is the globular head domain of A/Bar headed goose/Quinghai/1A/2005 (H5) HA (or the globular head domain of an A/Bar headed goose/Quinghai/1A/2005 (H5)-like influenza virus HA). In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA) and the globular head domain of the cH5/B chimeric influenza hemagglutinin polypeptide is the globular head domain of A/turkey/Turkey/1/2005 (H5) HA (or the globular head domain of an A/turkey/Turkey/1/2005 (H5)-like influenza virus HA). In another specific embodiment, the stem domain of a cH5/B chimeric influenza hemagglutinin polypeptide is the stem domain of B/Brisbane/60/2008 HA (or the stem domain of an B/Brisbane/60/2008-like influenza virus HA) and the globular head domain of the cH5/B chimeric influenza hemagglutinin polypeptide is the globular head domain of A/Whooperswan/Mongolia/244/2005 (H5) HA (or the globular head domain of an A/Whooperswan/Mongolia/244/2005 (H5)-like influenza virus HA).

In certain embodiments, a chimeric influenza hemagglutinin (HA) polypeptide provided herein comprises (i) the stem domain of the hemagglutinin from an influenza B virus and (ii) the globular head domain of the hemagglutinin from an influenza virus of the H7 subtype (sometimes referred to herein as a "cH7/B chimeric influenza hemagglutinin polypeptide").

In a specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/B chimeric influenza hemagglutinin polypeptide is the stem domain of B/Malaysia/2506/2004 HA (or the stem domain of an B/Malaysia/2506/2004-like influenza virus HA) and the globular head domain of the cH7/B chimeric influenza hemagglutinin polypeptide is the globular head domain of A/mallard/Massachusetts/12/2000 (H7) HA (or the globular head domain of an A/mallard/Massachusetts/12/2000 (H7)-like influenza virus HA).

In another specific embodiment, the stem domain of a cH7/B chimeric influenza hemagglutinin polypeptide is the stem domain of B/Florida/4/2006 HA (or the stem domain of an B/Florida/4/2006-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/B chimeric influenza hemagglutinin polypeptide is the stem domain of B/Florida/4/2006 HA (or the stem domain of an B/Florida/4/2006-like influenza virus HA) and the globular head domain of the cH7/B chimeric influenza hemagglutinin polypeptide is the globular head domain of A/mallard/Massachusetts/12/2000 (H7) HA (or the globular head domain of an A/mallard/Massachusetts/12/2000 (H7)-like influenza virus HA).

In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/B chimeric influenza hemagglutinin polypeptide is the stem domain of B/Wisconsin/1/2010 HA (or the stem domain of an B/Wisconsin/1/2010-like influenza virus HA) and the globular head domain of the cH7/B chimeric influenza hemagglutinin polypeptide is the globular head domain of A/mallard/Massachusetts/12/2000 (H7) HA (or the globular head domain of an A/mallard/Massachusetts/12/2000 (H7)-like influenza virus HA).

In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/Netherlands/219/03 (H7) HA (or the globular head domain of an A/Netherlands/219/03 (H7)-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/Canada/504/04 (H7) HA (or the globular head domain of an A/Canada/504/04 (H7)-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/Canada/444/04 (H7) HA (or the globular head domain of an A/Canada/444/04 (H7)-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/chicken/Jalisco/CPA1/2012 (H7) HA (or the globular head domain of an A/chicken/Jalisco/CPA1/2012 (H7)-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/mallard/Alberta/24/2001 (H7) HA (or the globular head domain of an A/mallard/Alberta/24/2001 (H7)-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/Rhea/NC/39482/93 (H7) HA (or the globular head domain of an A/Rhea/NC/39482/93 (H7)-like influenza virus HA). In another specific embodiment, the stem domain of a cH7/B chimeric influenza hemagglutinin polypeptide is the stem domain of B/Brisbane/60/2008 HA (or the stem domain of an B/Brisbane/60/2008-like influenza virus HA) and the globular head domain of the cH7/B chimeric influenza hemagglutinin polypeptide is the globular head domain of A/mallard/Massachusetts/12/2000 (H7) HA (or the globular head domain of an A/mallard/Massachusetts/12/2000 (H7)-like influenza virus HA).

In certain embodiments, a chimeric influenza hemagglutinin (HA) polypeptide provided herein comprises (i) the stem domain of the hemagglutinin from an influenza B virus and (ii) the globular head domain of the hemagglutinin from a different influenza B virus strain (sometimes referred to herein as a "cB/B chimeric influenza hemagglutinin polypeptide").

In a specific embodiment, the stem domain of a cB/B chimeric influenza hemagglutinin polypeptide is the stem domain of B/Malaysia/2506/2004 HA (or the stem domain of an B/Malaysia/2506/2004-like influenza virus HA). In another specific embodiment, the stem domain of a cB/B chimeric influenza hemagglutinin polypeptide is the stem domain of B/Malaysia/2506/2004 HA (or the stem domain of an B/Malaysia/2506/2004-like influenza virus HA) and the globular head domain of the cB/B chimeric influenza hemagglutinin polypeptide is the globular head domain of B/Lee/1940 HA (or the globular head domain of an B/Lee/1940-like influenza virus HA). In another specific embodiment, the stem domain of a cB/B chimeric influenza hemagglutinin polypeptide is the stem domain of B/Malaysia/2506/2004 HA (or the stem domain of an B/Malaysia/2506/2004-like influenza virus HA) and the globular head domain of the cB/B chimeric influenza hemagglutinin polypeptide is the globular head domain of B/seal/Netherlands/1/99 HA (or the globular head domain of a B/seal/Netherlands/1/99-like influenza virus).

In another specific embodiment, the stem domain of a cB/B chimeric influenza hemagglutinin polypeptide is the stem domain of B/Florida/4/2006 HA (or the stem domain of an B/Florida/4/2006-like influenza virus HA). In another specific embodiment, the stem domain of a cB/B chimeric influenza hemagglutinin polypeptide is the stem domain of B/Florida/4/2006 HA (or the stem domain of an B/Florida/4/2006-like influenza virus HA) and the globular head domain of the cB/B chimeric influenza hemagglutinin polypeptide is the globular head domain of B/Lee/1940 HA (or the globular head domain of a B/Lee/1940-like influenza virus). In another specific embodiment, the stem domain of a cB/B chimeric influenza hemagglutinin polypeptide is the stem domain of B/Florida/4/2006 HA (or the stem domain of an B/Florida/4/2006-like influenza virus HA) and the globular head domain of the cB/B chimeric influenza hemagglutinin polypeptide is the globular head domain of B/seal/Netherlands/1/99 HA (or the globular head domain of a B/seal/Netherlands/1/99-like influenza virus).

In another specific embodiment, the stem domain of a cB/B chimeric influenza hemagglutinin polypeptide is the stem domain of B/Wisconsin/1/2010 HA (or the stem domain of an B/Wisconsin/1/2010-like influenza virus HA). In another specific embodiment, the stem domain of a cB/B chimeric influenza hemagglutinin polypeptide is the stem domain of B/Wisconsin/1/2010 HA (or the stem domain of an B/Wisconsin/1/2010-like influenza virus HA) and the globular head domain of the cB/B chimeric influenza hemagglutinin polypeptide is the globular head domain of B/Lee/1940 HA (or the globular head domain of a B/Lee/1940-like influenza virus). In another specific embodiment, the stem domain of a cB/B chimeric influenza hemagglutinin polypeptide is the stem domain of B/Wisconsin/1/2010 HA (or the stem domain of an B/Wisconsin/1/2010-like influenza virus HA) and the globular head domain of the cB/B chimeric influenza hemagglutinin polypeptide is the globular head domain of B/seal/Netherlands/1/99 HA (or the globular head domain of a B/seal/Netherlands/1/99-like influenza virus).

In another specific embodiment, the stem domain of a cB/B chimeric influenza hemagglutinin polypeptide is the stem domain of B/Brisbane/60/2008 HA (or the stem domain of an B/Brisbane/60/2008-like influenza virus HA). In another specific embodiment, the stem domain of a cB/B chimeric influenza hemagglutinin polypeptide is the stem domain of B/Brisbane/60/2008 HA (or the stem domain of an B/Brisbane/60/2008-like influenza virus HA) and the globular head domain of the cB/B chimeric influenza hemagglutinin polypeptide is the globular head domain of B/Lee/1940 HA (or the globular head domain of a B/Lee/1940-like influenza virus). In another specific embodiment, the stem domain of a cB/B chimeric influenza hemagglutinin polypeptide is the stem domain of B/Brisbane/60/2008 HA (or the stem domain of an B/Brisbane/60/2008-like influenza virus HA) and the globular head domain of the cB/B chimeric influenza hemagglutinin polypeptide is the globular head domain of B/seal/Netherlands/1/99 HA (or the globular head domain of a B/seal/Netherlands/1/99-like influenza virus).

In specific embodiments, the chimeric influenza hemagglutinin polypeptides described herein are soluble, e.g., are soluble in compositions, e.g., the compositions described herein. Exemplary methods for generating soluble chimeric influenza hemagglutinin polypeptides are described in Section 6.6.1.2, infra.

When designing the foregoing chimeric influenza HA polypeptides, care should be taken to maintain the stability of the resulting protein. In this regard, in certain embodiments, it is recommended that for chimeric influenza hemagglutinin polypeptides comprising stem domains from influenza A viruses, the cysteine residues identified as Ap and Aq in FIG. 1 be maintained since they contribute to the stability of the HA stalk as discussed in more detail in Section 5.1 infra. For example, for the best stability, it is preferred to "swap" the HA globular domain as a whole (between the Ap and Aq cysteine residues as shown in FIG. 1) since the resulting conformation would be closest to the native structure. Similarly, chimeric influenza hemagglutinin polypeptides comprising the stem domains of influenza B viruses may utilize cysteines present in the globular head domains of the influenza A virus from which the globular head domain of the chimeric influenza hemagglutinin polypeptide is obtained (see, e.g., FIG. 36).

In another aspect, provided herein are immunogenic compositions (e.g., vaccine formulations) comprising one, two, or more of the chimeric influenza hemagglutinin polypeptides described herein. In certain embodiments, the immunogenic compositions (e.g., vaccine formulations) provided herein may comprise chimeric influenza hemagglutinin polypeptide(s) described herein, influenza viruses (e.g., live or killed virus) that comprise a chimeric influenza hemagglutinin polypeptide(s) described herein or a genome engineered to encode chimeric influenza hemagglutinin polypeptide(s) described herein; or vectors or cells that comprise a chimeric influenza hemagglutinin polypeptide(s) described herein or a genome engineered to encode chimeric influenza hemagglutinin polypeptide(s) described herein. In certain embodiments, the immunogenic compositions provided herein may comprise (i) a cH5/1 chimeric influenza hemagglutinin polypeptide described herein, a cH5/3 chimeric influenza hemagglutinin polypeptide described herein, a cH7/3 chimeric influenza hemagglutinin polypeptide described herein, a cH5/B chimeric influenza hemagglutinin polypeptide described herein, a cH7/B chimeric influenza hemagglutinin polypeptide described herein, or a cHB/B chimeric influenza hemagglutinin polypeptide described herein; (ii) a combination of a cH5/1 chimeric influenza hemagglutinin polypeptide described herein and a cH5/3 chimeric influenza hemagglutinin polypeptide described herein; or a combination of a cH5/1 chimeric influenza hemagglutinin polypeptide described herein and a cH7/3 chimeric influenza hemagglutinin polypeptide described herein; (iii) a combination of a cH5/1 chimeric influenza hemagglutinin polypeptide described herein and a cH5/3 chimeric influenza hemagglutinin polypeptide described herein and either of a cH5/B, a cH7/B, or a cB/B chimeric influenza hemagglutinin polypeptide described herein; or (iv) a combination of a cH5/1 chimeric influenza hemagglutinin polypeptide described herein and a cH7/3 chimeric influenza hemagglutinin polypeptide described herein and either of a cH5/B, a cH7/B, or a cB/B chimeric influenza hemagglutinin polypeptide described herein.

In a specific embodiment, provided herein are vaccine formulations comprising one or more of the chimeric influenza hemagglutinin polypeptides described herein. In a specific embodiment, provided herein is a monovalent vaccine comprising one of the chimeric influenza hemagglutinin polypeptides described herein. In another specific embodiment, provided herein is a bivalent vaccine comprising two of the chimeric influenza hemagglutinin polypeptides described herein (i.e., two distinct chimeric influenza hemagglutinin polypeptides). In another specific embodiment, provided herein is a trivalent vaccine comprising three of the chimeric influenza hemagglutinin polypeptides described herein (i.e., three distinct chimeric influenza hemagglutinin polypeptides).

The vaccine formulations provided herein may comprise the chimeric influenza hemagglutinin polypeptides described herein in any form. For example, the vaccine formulations provided herein may comprise subunit vaccines comprising one or more of the chimeric influenza hemagglutinin polypeptides described herein (e.g., compositions comprising chimeric influenza hemagglutinin polypeptides, e.g., soluble chimeric influenza hemagglutinin polypeptides); live influenza viruses (e.g., live attenuated influenza viruses) that express one or more of the chimeric influenza hemagglutinin polypeptides described herein; live influenza viruses (e.g., live attenuated influenza viruses) comprising a genome that encodes one or more of the chimeric influenza hemagglutinin polypeptides described herein; killed influenza viruses that comprise one or more of the chimeric influenza hemagglutinin polypeptides described herein; killed influenza viruses comprising a genome that encodes one or more of the chimeric influenza hemagglutinin polypeptides described herein; virus/viral-like particles ("VLPs") that contain one or more of the chimeric influenza hemagglutinin polypeptides described herein; split virus vaccines, wherein said virus expresses one or more of the chimeric influenza hemagglutinin polypeptides described herein and/or comprises a genome that encodes one or more of the chimeric influenza hemagglutinin polypeptides described herein; viral expression vectors (e.g., non-influenza virus expression vectors) that express one or more of the chimeric influenza hemagglutinin polypeptides described herein; and bacterial expression vectors that express one or more of the chimeric influenza hemagglutinin polypeptides described herein.

The vaccine formulations described herein can elicit highly potent and broadly neutralizing antibodies against the HA stem domain of the chimeric influenza hemagglutinin polypeptides. Such "universal" vaccines can be used to induce and/or boost cross-protective immune responses across influenza virus subtypes.

In another aspect, provided herein are methods of immunizing a subject against an influenza virus disease or infection comprising administering to the subject a composition comprising one or more of the chimeric influenza hemagglutinin (HA) polypeptides described herein or a vaccine formulation described herein. In certain embodiments, a subject is primed with a first composition comprising one or more of the chimeric influenza hemagglutinin (HA) polypeptides described herein or a vaccine formulation described herein, and later boosted with the same or a different composition (e.g., a composition comprising a different chimeric influenza hemagglutinin (HA) polypeptide; a composition comprising the same chimeric influenza hemagglutinin (HA) polypeptide but in a different context (e.g., the first composition comprises a subunit vaccine comprising a chimeric influenza hemagglutinin (HA) polypeptide and the different composition comprises a viral vector that comprises the same chimeric influenza hemagglutinin (HA) polypeptide), or a composition comprising a different chimeric influenza hemagglutinin (HA) polypeptide in a different context) comprising one or more of the chimeric influenza hemagglutinin (HA) polypeptides described herein or a vaccine formulation described herein. The subject may be boosted once, or more than once with a composition comprising one or more of the chimeric influenza hemagglutinin (HA) polypeptides described herein or a vaccine formulation described herein. In certain embodiments, when the subject is boosted more than once, the first and the second boosts are with different compositions comprising one or more of the chimeric influenza hemagglutinin (HA) polypeptides described herein or a vaccine formulation described herein, and each boost comprises a different composition than the composition comprising one or more of the chimeric influenza hemagglutinin (HA) polypeptides described herein or a vaccine formulation described herein used to prime the subject.

In a specific embodiment, provided herein is a method of immunizing a subject (e.g., a human subject) against influenza virus comprising administering to the subject a first dose of an effective amount of a chimeric influenza hemagglutinin (HA) polypeptide described herein, a vector described herein, an immunogenic composition described herein, or a vaccine formulation described herein and administering to the subject a second dose of an effective amount of a chimeric influenza hemagglutinin (HA) polypeptide described herein, a vector described herein, an immunogenic composition described herein, or a vaccine formulation described herein 30 days to 6 months after the subject has received the first dose, wherein (i) the chimeric influenza hemagglutinin (HA) polypeptide or the chimeric influenza hemagglutinin (HA) polypeptide of the vector, the immunogenic composition, or vaccine formulation in the first and second doses are the same or different (e.g., the globular head of the chimeric influenza hemagglutinin (HA) polypeptide administered in the first dose is different than the globular head of the chimeric influenza hemagglutinin (HA) polypeptide administered in the second dose); and/or (ii) the type of immunogenic composition or vector or vaccine formulation administered in both doses are the same or different. In certain embodiments, the method comprises administering to the subject a third dose of an effective amount of a chimeric influenza hemagglutinin (HA) polypeptide described herein, a vector described herein, an immunogenic composition described herein, or a vaccine formulation described herein 30 days to 6 months after the subject has received the second dose, wherein (i) the chimeric influenza hemagglutinin (HA) polypeptide or the chimeric influenza hemagglutinin (HA) polypeptide of the vector, the immunogenic composition, or vaccine formulation is the same or different than the chimeric influenza hemagglutinin (HA) polypeptide in the first and/or second dose; and (ii) the type of immunogenic composition or vector or vaccine formulation administered in both doses are the same or different. In certain embodiments, two, three, or more chimeric influenza hemagglutinin (HA) polypeptides are administered as part of the first, second, and/or third doses, wherein each chimeric HA polypeptide in a dose is different from each other. In some embodiments, the first, second, and/or third dose of the vector, the immunogenic composition, or vaccine formulation comprises two, three, or more chimeric influenza hemagglutinin (HA) polypeptides, wherein each chimeric influenza hemagglutinin (HA) polypeptide in the vector, the immunogenic composition, or vaccine formulation administered in a dose is different from each other (e.g., the globular head of the chimeric influenza hemagglutinin (HA) polypeptide administered in the first dose is different than the globular head of the chimeric influenza hemagglutinin (HA) polypeptide administered in the second dose, etc.).

In another specific embodiment, provided herein is a method of immunizing a 1-5 year old human subject against influenza virus comprising administering to the subject a first dose of an effective amount a chimeric influenza hemagglutinin (HA) polypeptide described herein, a vector described herein, an immunogenic composition described herein, or a vaccine formulation described herein and administering to the subject a second dose of an effective amount of a chimeric influenza hemagglutinin (HA) polypeptide described herein, a vector described herein, an immunogenic composition described herein, or a vaccine formulation described herein 30 days to 6 months after the subject has received the first dose, wherein (i) the chimeric influenza hemagglutinin (HA) polypeptide or the chimeric influenza hemagglutinin (HA) polypeptide of the vector, the immunogenic composition, or vaccine formulation in the first and second doses are the same or different (e.g., the globular head of the chimeric influenza hemagglutinin (HA) polypeptide administered in the first dose is different than the globular head of the chimeric influenza hemagglutinin (HA) polypeptide administered in the second dose); and/or (ii) the type of immunogenic composition or vector or vaccine formulation administered in both doses are the same or different. In certain embodiments, the method comprises administering to the subject a third dose of an effective amount of a chimeric influenza hemagglutinin (HA) polypeptide described herein, a vector described herein, an immunogenic composition described herein, or a vaccine formulation described herein 30 days to 6 months after the subject has received the second dose, wherein (i) the chimeric influenza hemagglutinin (HA) polypeptide or the chimeric influenza hemagglutinin (HA) polypeptide of the vector, the immunogenic composition, or vaccine formulation in the first and second doses are the same or different (e.g., the globular head of the chimeric influenza hemagglutinin (HA) polypeptide administered in the first dose is different than the globular head of the chimeric influenza hemagglutinin (HA) polypeptide administered in the second dose); and/or (ii) the type of immunogenic composition or vector or vaccine formulation administered in both doses are the same or different. In certain embodiments, two, three, or more chimeric influenza hemagglutinin (HA) polypeptides are administered as part of the first, second, and/or third doses, wherein each chimeric HA polypeptide in a dose is different from each other. In some embodiments, the first, second, and/or third dose of the vector, the immunogenic composition, or vaccine formulation comprises two, three, or more chimeric influenza hemagglutinin (HA) polypeptides, wherein each chimeric influenza hemagglutinin (HA) polypeptide in the vector, the immunogenic composition, or vaccine formulation administered in a dose is different from each other (e.g., the globular head of the chimeric influenza hemagglutinin (HA) polypeptide administered in the first dose is different than the globular head of the chimeric influenza hemagglutinin (HA) polypeptide administered in the second dose, etc.).

In another aspect, provided herein are kits comprising one or more of the chimeric influenza hemagglutinin (HA) polypeptides described herein or a vaccine formulation described herein. The kits provided herein may further comprise one or more additional components, e.g., an antibody that specifically binds one or more of the chimeric influenza hemagglutinin (HA) polypeptides provided in the kit.

The working Examples (e.g., Section 6, Examples) demonstrate, inter alia, the production of constructs encoding chimeric influenza HA polypeptides comprising an HA stem domain and displaying a heterologous HA globular head domain, and the production of stable chimeric HA polypeptides from these constructs which are cross-reactive with antibodies to both the stem domain and the head domain. The working Examples also illustrate the use of such constructs in the generation of a protective immune response in subjects against multiple different strains and subtypes of influenza virus, i.e., the Examples demonstrate that the chimeric influenza HA polypeptides described herein can be used as a universal influenza vaccine.

3.1 Terminology

The terms "about" or "approximate," when used in reference to an amino acid position refer to the particular amino acid position in a sequence or any amino acid that is within five, four, three, two, or one residues of that amino acid position, either in an N-terminal direction or a C-terminal direction.

As used herein, the term "about" or "approximately" when used in conjunction with a number refers to any number within 1, 5 or 10% of the referenced number. In certain embodiments, the term "about" encompasses the exact number recited.

As used herein, the term "fragment" in the context of a nucleic acid sequence refers to a nucleotide sequence comprising a portion of consecutive nucleotides from a parent sequence. In a specific embodiment, the term refers to a nucleotide sequence of 5 to 15, 5 to 25, 10 to 30, 15 to 30, 10 to 60, 25 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence.

As used herein, the term "fragment" in the context of an amino acid sequence refers to an amino acid sequence comprising a portion of consecutive amino acid residues from a parent sequence. In a specific embodiment, the term refers to an amino acid sequence of 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, or 200 consecutive amino acid residues of a parent sequence.

As used herein, the terms "disease" and "disorder" are used interchangeably to refer to a condition in a subject. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (ix) prevent or reduce the spread of an influenza virus from one subject to another subject; (x) reduce organ failure associated with an influenza virus infection; (xi) reduce hospitalization of a subject; (xii) reduce hospitalization length; (xiii) increase the survival of a subject with an influenza virus infection or disease associated therewith; (xiv) eliminate an influenza virus infection or disease associated therewith; (xv) inhibit or reduce influenza virus replication; (xvi) inhibit or reduce the entry of an influenza virus into a host cell(s); (xviii) inhibit or reduce replication of the influenza virus genome; (xix) inhibit or reduce synthesis of influenza virus proteins; (xx) inhibit or reduce assembly of influenza virus particles; (xxi) inhibit or reduce release of influenza virus particles from a host cell(s); (xxii) reduce influenza virus titer; and/or (xxiii) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, the effective amount results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

"Hemagglutinin" and "HA" refer to any hemagglutinin known to those of skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g. HA1 and HA2. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

As used herein, the terms "chimeric influenza virus hemagglutinin polypeptide," "chimeric influenza virus HA polypeptide," "chimeric hemagglutinin polypeptide" and "chimeric influenza hemagglutinin polypeptide" refer to an influenza hemagglutinin that comprises an influenza virus hemagglutinin stem domain and an influenza virus hemagglutinin globular head domain, wherein the influenza virus hemagglutinin head domain is heterologous to the influenza virus hemagglutinin stem domain (i.e., the globular head domain of the chimeric influenza virus hemagglutinin polypeptide is from a different strain or subtype of influenza virus than the stem domain of the chimeric influenza virus hemagglutinin polypeptide).

"HA1 N-terminal stem segment" refers to a polypeptide segment that corresponds to the amino-terminal portion of the stem domain of an influenza hemagglutinin HA1 polypeptide. In certain embodiments, an HA1 N-terminal stem segment consists of amino acid residues corresponding approximately to amino acids $HA1_{N-term}$ through $A_p$ of an HA1 domain. $HA1_{N-term}$ is the N-terminal amino acid of HA1 as recognized by those of skill in the art. $A_p$ is the cysteine residue in the HA1 N-terminal stem segment that forms or is capable of forming a disulfide bond with a cysteine residue in an HA1 C-terminal stem segment. Residue $A_p$ is identified in influenza A hemagglutinin polypeptides in FIG. 1. Exemplary HA1 N-terminal stem segments are described herein. In certain embodiments, an HA1 N-terminal stem segment consists of amino acid residues corresponding approximately to amino acids 1-52 of HA1 from an H3 hemagglutinin. Note that, in this numbering system, 1 refers to the N-terminal amino acid of the mature HA0 protein, from which the signal peptide has been removed. Those of skill in the art will readily be able recognize the amino acid residues that correspond to the HA1 N-terminal stem segment of other influenza HA polypeptides, e.g., the amino acid residues that correspond to the HA1 N-terminal stem segment of HA1 from an H1 hemagglutinin (see, e.g., FIG. 1).

"HA1 C-terminal stem segment" refers to a polypeptide segment that corresponds to the carboxy-terminal portion of the stem domain of an influenza hemagglutinin HA1 polypeptide. In certain embodiments, an HA1 C-terminal stem segment consists of amino acid residues corresponding approximately to amino acids $A_q$ through $HA1_{C-term}$ of an HA1 domain. $HA1_{C-term}$ is the C-terminal amino acid of the HA1 domain as recognized by those of skill in the art. Residue $A_q$ is identified in influenza A hemagglutinin polypeptides in FIG. 1. Exemplary HA1 C-terminal stem segments are described herein. In certain embodiments, an HA1 C-terminal stem segment consists of amino acid residues corresponding approximately to amino acids 277-329 of HA1 from an H3 hemagglutinin. Note that, in this numbering system, 1 refers to the N-terminal amino acid of the mature HA0 protein, from which the signal peptide has been removed. Those of skill in the art will readily be able recognize the amino acid residues that correspond to the HA1 C-terminal stem segment of other influenza HA polypeptides, e.g., the amino acid residues that correspond to the HA1 C-terminal stem segment of HA1 from an H1 hemagglutinin (see, e.g., FIG. 1).

"HA2" refers to a polypeptide domain that corresponds to the HA2 domain of an influenza hemagglutinin polypeptide known to those of skill in the art. In certain embodiments, an HA2 consists of a stem domain, a luminal domain, a transmembrane domain and a cytoplasmic domain (see, e.g., Scheiffle et al., 2007, *EMBO J.* 16(18):5501-5508, the contents of which are incorporated by reference in their entirety). In certain embodiments, an HA2 consists of a stem domain, a luminal domain and a transmembrane domain. In certain embodiments, an HA2 consists of a stem domain and a luminal domain; in such embodiments, the HA2 might be soluble. In certain embodiments, an HA2 consists of a stem domain; in such embodiments, the HA2 might be soluble.

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a "heterologous polypeptide" may refer to a polypeptide derived from a different virus, e.g., a different influenza strain or subtype, or an unrelated virus or different species. In specific embodiments, when used in the context of a globular head domain of a chimeric influenza virus hemagglutinin described herein, the term heterologous refers to an influenza HA globular head domain that is associated with an influenza HA stem domain that it would not normally be found associated with (e.g., the head and stem domains of the HA would not be found together in nature).

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating.

As used herein, the term "influenza virus disease" refers to the pathological state resulting from the presence of an influenza virus (e.g., influenza A or B virus) in a cell or subject or the invasion of a cell or subject by an influenza virus. In specific embodiments, the term refers to a respiratory illness caused by an influenza virus.

As used herein, the phrases "IFN deficient system" or "IFN-deficient substrate" refer to systems, e.g., cells, cell lines and animals, such as pigs, mice, chickens, turkeys, rabbits, rats, etc., which do not produce IFN or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the term "like," when used in the context of an "influenza-like virus," refers an influenza virus that represents a different isolate of the referenced influenza virus, wherein the amino acid sequence of said different isolate, or of the amino acid sequence of the HA of said different isolate, is identical to, or nearly identical to, the amino acid sequence of the referenced influenza virus or the amino acid sequence of the HA of the referenced influenza virus; and/or the immune response against said different isolate confers full protection against the referenced influenza virus, and vice versa. In certain embodiments, an influenza virus isolate that has an amino acid sequence that is nearly identical to the amino acid sequence of a referenced influenza virus has an amino acid sequence that is at least 90%, 91%, 92%, 93%, 94%, 95%, 96%, 97%, 98%, 99%, or 99.5% identical to the amino acid sequence of the referenced influenza virus. In certain embodiments, an influenza virus isolate that represents an "influenza-like virus" comprises an HA that has an amino acid sequence that is nearly identical to the amino acid sequence of the HA of a referenced influenza virus, e.g., the HA of the influenza-like virus has an amino acid sequence that is at least 90%, 91%, 92%, 93%, 94%, 95%, 96%, 97%, 98%, 99%, or 99.5% identical to the amino acid sequence of the HA of the referenced influenza virus.

As used herein, the numeric term "log" refers to $\log_{10}$.

As used herein, the phrase "majority of the population is naive to," in reference to a strain or subtype (e.g., an H1 subtype) of influenza virus, refers to a strain or subtype of influenza virus that greater than 50% of the human population has presumably not been exposed to. In specific embodiments, the phrase "majority of the population is naive to," refers to a strain or subtype of influenza virus that at least 60%, 70%, 75%, 80%, 85%, 90%, 95%, or 99% f the human population has presumably not been exposed to.

As used herein, the phrase "multiplicity of infection" or "MOI" is the average number of infectious virus particles per infected cell. The MOI is determined by dividing the number of infectious virus particles added (ml added×PFU/ml) by the number of cells added (ml added×cells/ml).

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

As used herein, the term "polypeptide" refers to a polymer of amino acids linked by amide bonds as is known to those of skill in the art. As used herein, the term polypeptide can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "prevent," "preventing" and "prevention" in the context of the administration of a therapy(ies) to a subject to prevent an influenza virus disease refer to one or more of the prophylactic/beneficial effects resulting from the administration of a therapy or a combination of therapies. In a specific embodiment, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition of the development or onset of an influenza virus disease or a symptom thereof; (ii) the inhibition of the recurrence of an influenza virus disease or a symptom associated therewith; and (iii) the reduction or inhibition in influenza virus infection and/or replication.

As used herein, the terms "purified" and "isolated" when used in the context of a polypeptide (including an antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide. In a specific embodiment, a chimeric influenza hemagglutinin (HA) polypeptide is chemically synthesized. In another specific embodiment, an influenza hemagglutinin stem domain polypeptide, an influenza hemagglutinin head domain polypeptide, and/or a chimeric influenza hemagglutinin polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the terms "stem domain polypeptide," "HA stem domain," "influenza virus hemagglutinin stem domain polypeptide" and "HA stalk domain" refer to polypeptide comprising or consisting of one or more polypeptide chains that make up a stem domain of an influenza hemagglutinin. A stem domain polypeptide might be a single polypeptide chain, two polypeptide chains or more polypeptide chains. Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). In specific embodiments, a stem domain polypeptide is derived from an influenza A H1 or H3 influenza virus hemagglutinin, or an influenza B influenza virus hemagglutinin.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide. For example, for influenza A virus, the globular head domain is generally understood to be present between two key cysteine residues in the HA1 portion of the HA molecule. These cysteine residues are identified as "Ap" and "Aq" in FIG. 1 for various influenza A viruses.

As used herein, the terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "premature human infant" refers to a human infant born at less than 37 weeks of gestational age.

As used herein, the term "human infant" refers to a newborn to 1 year old human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "seasonal influenza virus strain" refers to a strain of influenza virus to which a subject refers to a strain of influenza virus to which a subject population is exposed to on a seasonal basis. In specific embodiments, the term seasonal influenza virus strain refers to a strain of influenza A virus. In specific embodiments, the term seasonal influenza virus strain refers to a strain of influenza virus that belongs to the H1 or the H3 subtype, i.e., the two subtypes that presently persist in the human subject population. In other embodiments, the term seasonal influenza virus strain refers to a strain of influenza B virus.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to (i) a nucleic acid encoding a chimeric influenza hemagglutinin (HA) polypeptide, (ii) a chimeric influenza hemagglutinin (HA) polypeptide, or (iii) a vector or composition comprising a nucleic acid encoding a chimeric influenza hemagglutinin (HA) polypeptide or comprising a chimeric influenza hemagglutinin (HA) polypeptide. In some embodiments, the term "therapy" refers to an antibody that specifically binds to a chimeric influenza virus hemagglutinin polypeptide.

As used herein, the terms "treat," "treatment," and "treating" refer in the context of administration of a therapy(ies) to a subject to treat an influenza virus disease or infection to obtain a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of an influenza virus infection or a disease or a symptom associated therewith; (ii) the reduction in the duration of an influenza virus infection or a disease or a symptom associated therewith; (iii) the regression of an influenza virus infection or a disease or a symptom associated therewith; (iv) the reduction of the titer of an influenza virus; (v) the reduction in organ failure associated with an influenza virus infection or a disease associated therewith; (vi) the reduction in hospitalization of a subject; (vii) the reduction in hospitalization length; (viii) the increase in the survival of a subject; (ix) the elimination of an influenza virus infection or a disease or symptom associated therewith; (x) the inhibition of the progression of an influenza virus infection or a disease or a symptom associated therewith; (xi) the prevention of the spread of an influenza virus from a cell, tissue, organ or subject to another cell, tissue, organ or subject; (xii) the inhibition or reduction in the entry of an influenza virus into a host cell(s); (xiii) the inhibition or reduction in the replication of an influenza virus genome; (xiv) the inhibition or reduction in the synthesis of influenza virus proteins; (xv) the inhibition or reduction in the release of influenza virus particles from a host cell(s); and/or (xvi) the enhancement or improvement the therapeutic effect of another therapy.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIG. 1A, FIG. 1B, and FIG. 1C present a sequence alignment by CLUSTALW of representative sequences of 17 subtypes of influenza virus A hemagglutinin (SEQ ID NOS: 1-16 and 35, respectively). The residue designated $A_p$ is the cysteine residue in the HA1 N-terminal stem segment that forms or is capable of forming a disulfide bond with the residue designated $A_q$, a cysteine residue in an HA1 C-terminal stem segment. The residue designated $B_q$ represents the approximate N-terminal amino acid of the HA1 C-terminal short stem segments described herein. The residue designated $C_q$ represents the approximate N-terminal amino acid of the HA1 C-terminal long stem segments described herein. The residue designated $C_p$ represents the approximate C-terminal amino acid of the HA1 N-terminal long stem segments described herein.

FIG. 2 provides a schematic of chimeric HAs with a conserved H1 stalk domain and different globular head domains from distinct subtype HAs.

Figures 3A, 3B:
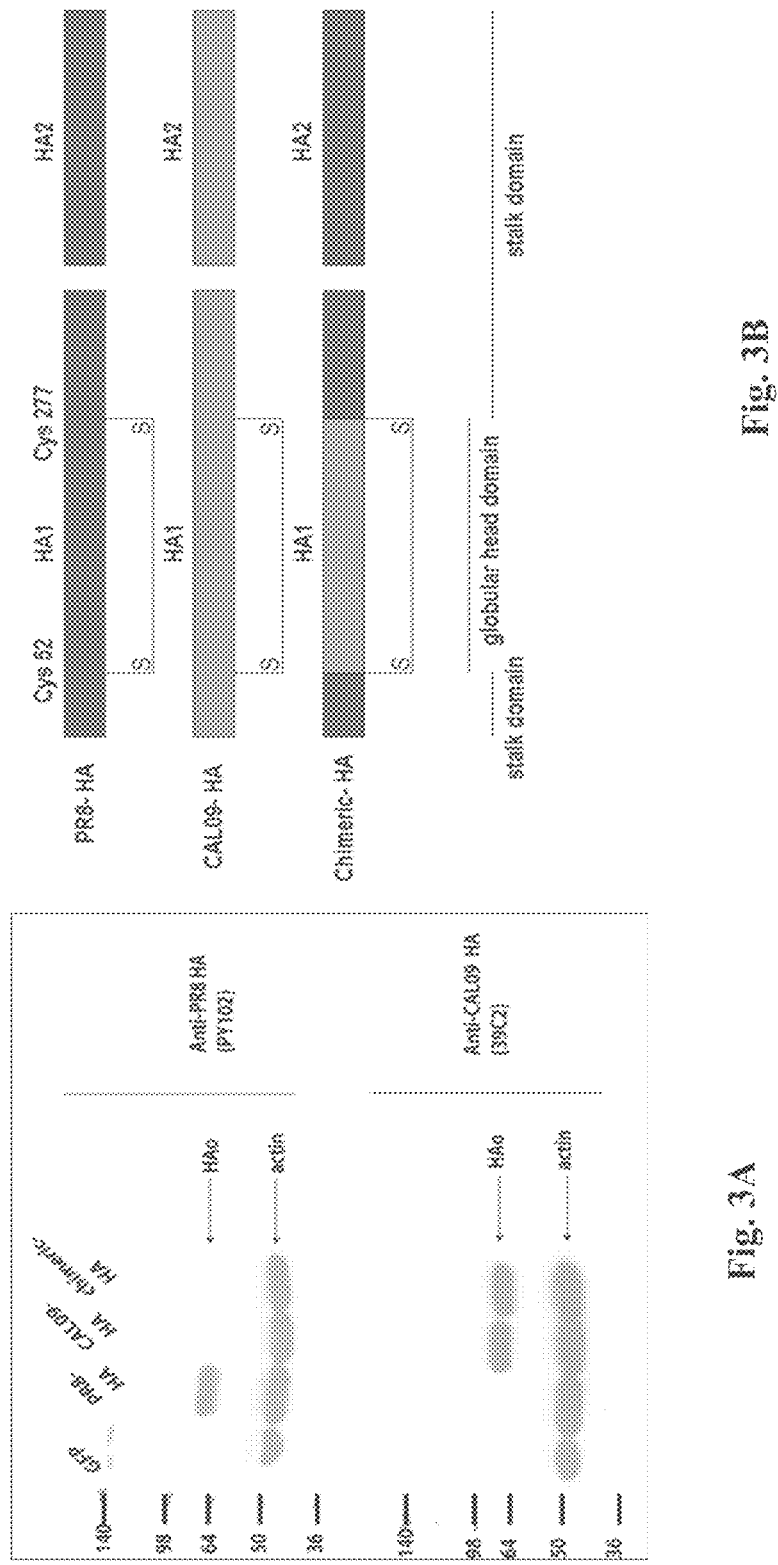

FIG. 3A and FIG. 3B provide a novel influenza vaccine and diagnostic tool platform to induce and analyze antibodies and reactive sera. FIG. 3A: Expression of chimeric HAs. Chimeric HAs consisting of the stalk domain of A/PR8/34 HA and the globular head domain of A/California/4/09 (chimeric HA) as well as wild type HAs (PR8-HA and CAL09-HA) and a GFP control were expressed in 293T cells. The upper Western blot was probed with a PR8-specific antibody (PY102) whereas the blot on the lower side was probed with an antibody specific for Cal09 (39C2). FIG. 3B: Schematic drawing of HA constructs expressed in A. The chimeric HA is composed of the A/PR/8/34 HA stalk domain and the 2009 A/California/04/09 globular head domain.

FIG. 4A and FIG. 4B provide a schematic of chimeric HAs. FIG. 4A: Basic structure of a chimeric HA. The globular head can be exchanged conveniently at disulfide bond Cys 52-Cys 277. FIG. 4B: Prime-boost regime with sequential administration of chimeric HAs consisting of a completely conserved stalk domain and a varying globular head domain.

Figure 5:
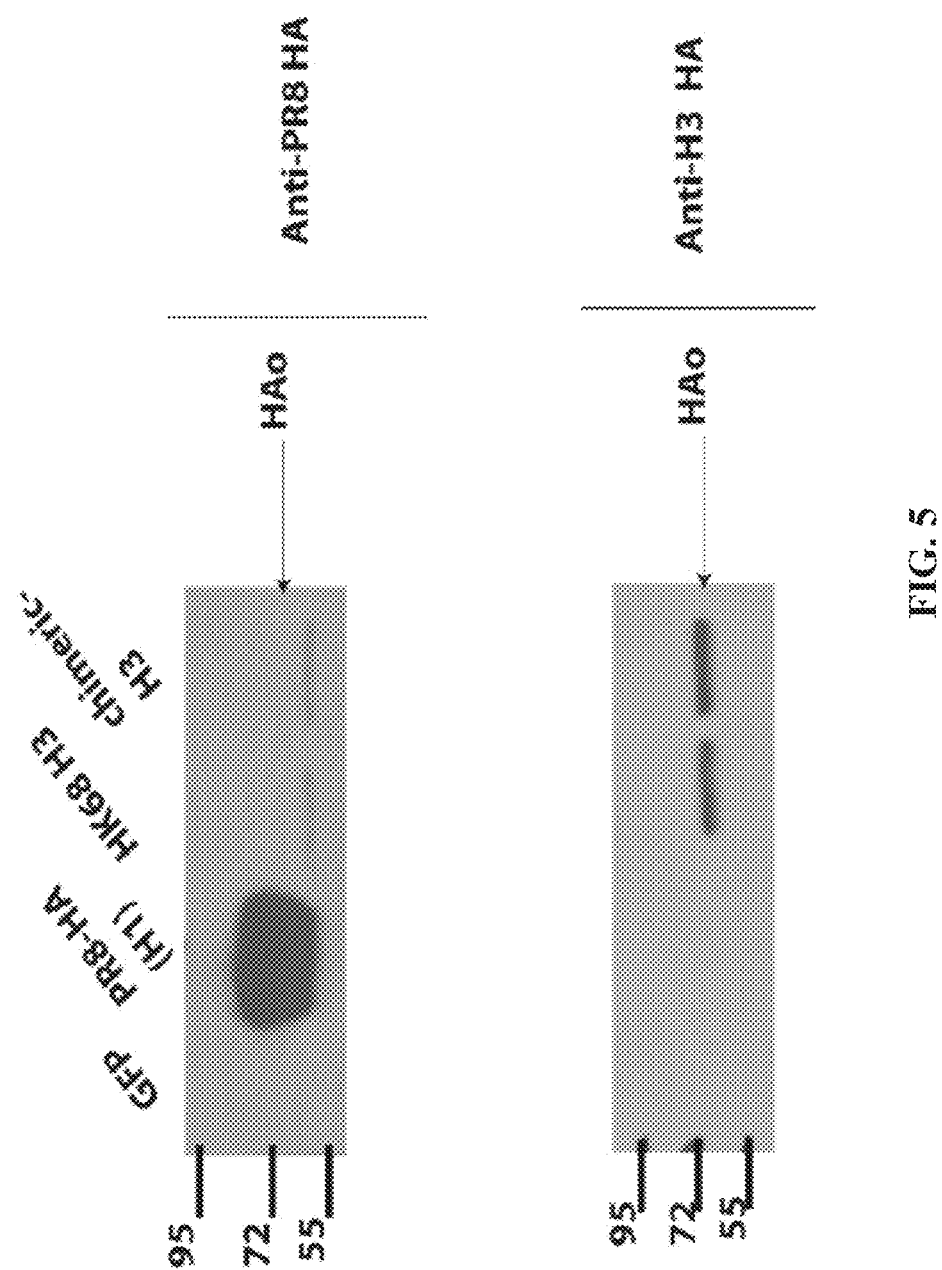

FIG. 5 describes generation of a chimeric HA with the stalk of an H1 HA and the globular head of an H3 HA. A chimeric HA consisting of the stalk domain of A/PR8/34 HA and the globular head domain of HK/68 (chimeric H3) as well as wild type HAs (PR8-HA and HK68 HA) were expressed in 293T cells. The upper Western blot was probed with a PR8-specific antibody whereas the blot on the lower side was probed with an antibody specific for H3.

Figure 6:
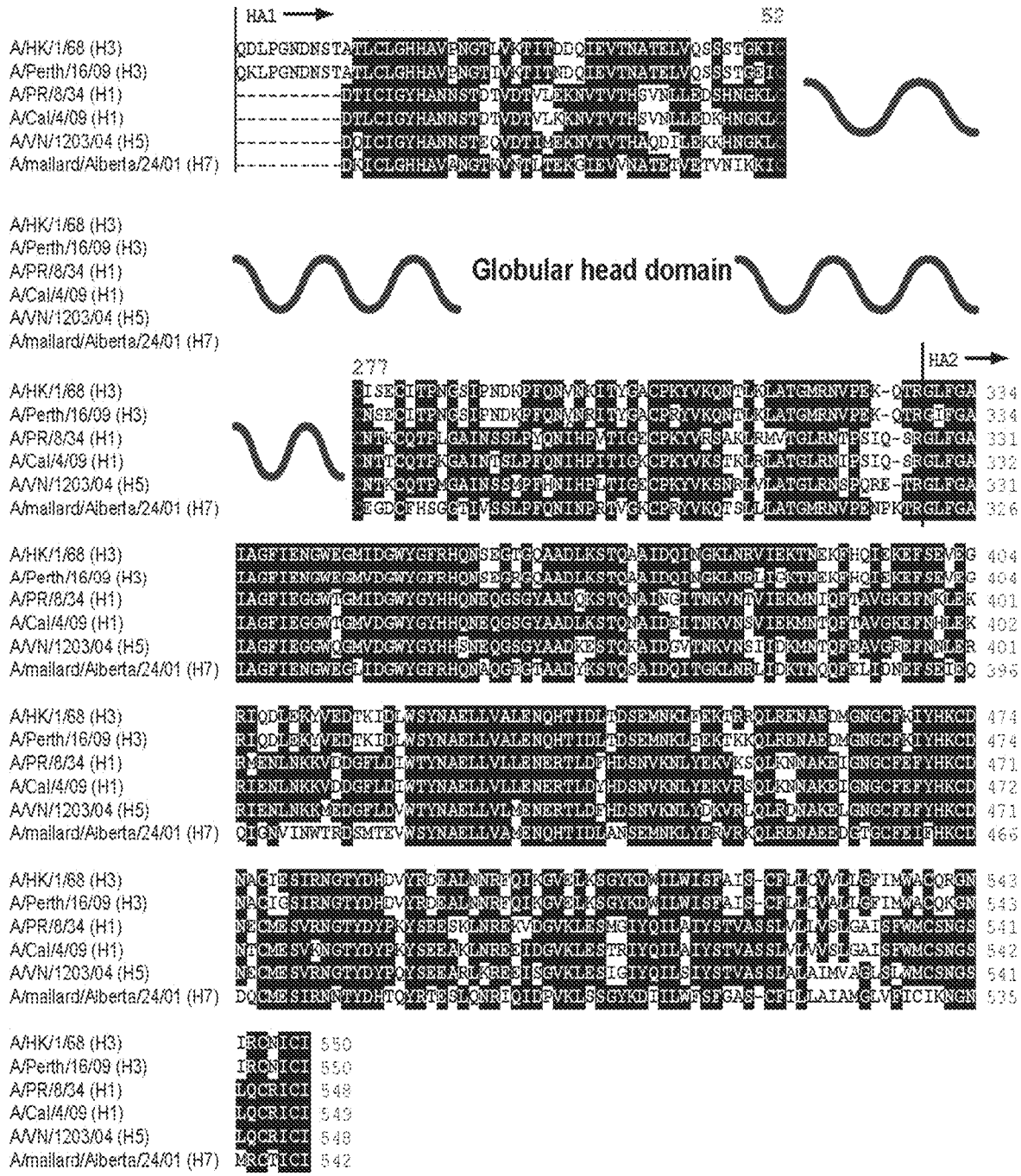

FIG. 6 depicts a sequence comparison of the hemagglutinin protein sequences of A/Hong Kong/1/1968 (H3), A/Perth/16/2009 (H3), A/PR/8/34 (H1), A/Cal/4/09 (H1), A/Viet Nam/1203/04 (H5), and A/mallard/Alberta/24/01 (H7). The Cys52 and Cys277 amino acid residues are specified (based on H3 numbering). The black shade indicates conserved amino acids. The black wavy line represents the globular head region of HAs. The starting points of HA1 and HA2 are indicated. Amino acid sequences from the N-terminus to Cys52 of the HA of each of A/Hong Kong/1/1968 (H3), A/Perth/16/2009 (H3), A/PR/8/34 (H1), A/Cal/4/09 (H1), A/Viet Nam/1203/04 (H5), and A/mallard/Alberta/24/01 (H7) are presented, and correspond to SEQ ID NOs. 23-28, respectively. Amino acid sequences from Cys277 of the HA of each of A/Hong Kong/1/1968 (H3), A/Perth/16/2009 (H3), A/PR/8/34 (H1), A/Cal/4/09 (H1), A/Viet Nam/1203/04 (H5), and A/mallard/Alberta/24/01 (H7) to the C-terminus are presented, and correspond to SEQ ID NOs. 29-37, respectively.

FIG. 7A and FIG. 7B depict a schematic of chimeric hemagglutinins. FIG. 7A: Construction diagram of the chimeric PR8-cH1 HA. The chimeric HA was constructed by swapping the globular head domain located between Cys52 and Cys277 of A/PR/8/34(H1) HA with that of the A/California/4/09(H1) HA. The resulting chimeric HA has the stalk region of A/PR8/34 (H1) HA with a globular head domain of the A/California/4/09 (H1) HA designated as PR8-cH1. FIG. 7B: Schematic of the folded structures of the different wild type and chimeric HAs, such as wild the type PR8 HA, the chimeric PR8-cH1 HA, the chimeric PR8-cH5 HA, the wild type Perth HA, and the chimeric Perth-cH7 HA (from left to right). The full-length HA structures were downloaded from the Protein Database (PDB): PR8 HA (PDB ID 1RU7) and Perth HA (represented by HK68 HA, PDB ID 1MQN). Final images were generated with PyMol (Delano Scientific).

FIG. 8A and FIG. 8B depict the surface expression and functional analysis of chimeric HA constructs. FIG. 8A: Surface expression of chimeric HA constructs was evaluated in transiently transfected cells. At 24 h post-transfection, 293T cells were trypsinized and cell surface expression of chimeric HA proteins were analyzed by flow cytometry. In the upper panels, mock-transfected cells (left shaded region) are compared to cells transfected with PR8 HA (right) or cells transfected with PR8-cH1 (right) or PR8-cH5 (right). In the bottom panels, mock-transfected cells (left shaded region) are compared to cells transfected with Perth and Perth-cH7 constructs (right). FIG. 8B: Luciferase-encoding pseudo-particles expressing chimeric HAs were used to infect MDCK cells. The relative light units (RLU) generated in the luciferase assay indicate that pseudo-particles expressing chimeric HAs were able to enter the cells.

FIG. 9A and FIG. 9B: describe the generation of recombinant viruses bearing chimeric hemagglutinins. FIG. 9A: Western blot analysis of the recombinant viruses. Extracts from MDCK cells mock infected or infected with the indicated viruses (16 hpi) at an MOI of 2 were prepared and probed with antibodies: anti-A/PR8/HA(H1) (PY102), anti-A/Cal/09/HA(H1) (29C1), anti-A/VN/HA(H5) (M08), anti-H3/HA (12D1), anti-H7 (NR-3125), anti-A/NP (HT103) and anti-GAPDH as an internal loading control. FIG. 9B: Immunofluorescence analysis of the MDCK cells infected with recombinant viruses using antibodies: anti-A/NP (HT103), anti-A/H1 HA (6F12), anti-A/PR8/HA (PY102), anti-A/Cal/09/HA (29C1), anti-A/VN/HA (M08), anti-H3/HA (12D1), and anti-A/H7 virus (NR-3152).

FIG. 10A and FIG. 10B: describe the growth kinetics and plaque phenotypes of recombinant viruses. FIG. 10A: 10-day old embryonated chicken eggs were infected with wild-type or recombinant virus with 100 pfu per egg and viral growth monitored for 72 hours post infection. FIG. 10B: The plaque phenotype of recombinant viruses was assessed by plaque assay. MDCK cells were infected with either a wild-type or recombinant virus and at 48 hours post infection immuno-stained to reveal plaque phenotype using the antibody against A/NP (HT103).

FIG. 11A, FIG. 11B, FIG. 11C, FIG. 11D, FIG. 11E, and FIG. 11F depict an immunofluorescence analysis of cells transfected with chimeric H6 hemagglutinin. 293T cells were transfected with 1 μg of pCAGGS plasmid expressing chimeric H6 hemagglutinin. Sera from animals that received DNA (FIG. 11A), Cal/09 infection (FIG. 11B), DNA and Cal/09 infection (FIG. 11C), or Cal/09 split vaccine (FIG. 11D) were added to transfected cells and visualized by fluorescence microscopy following incubation with an Alexa Fluor 594-conjugated anti-mouse IgG. As controls, the cross-reactive H1 stem antibody C179 (FIG. 11E) or the antibody PY102 (FIG. 11F) directed against the globular head of PR8 were added to transfected cells and visualized by fluorescence microscopy followed by incubation with an Alexa Fluor 594-conjugated anti-mouse IgG.

FIG. 12 demonstrates that DNA prime and chimeric virus boost confer protection to animals challenged with lethal influenza virus challenge. Animals were either treated with DNA alone, chimeric H9 virus alone, DNA prime and chimeric H9 virus boost, or with inactivated PR8 virus. Mice were then challenged with $5\times10^4$ PFU of PR8 virus, instilled intranasally, and the weight of the animals was monitored for 14 days.

FIG. 13 demonstrates reactivity of stalk specific antibodies to cH6 protein as determined by ELISA.

FIG. 14A and FIG. 14B depict a schematic representation of chimeric HA (cHA) proteins (FIG. 14A) and cHA expression in MDCK cells (FIG. 14B). Chimeric HA (cHA) proteins and recombinant chimeric virus. FIG. 14A: Schematic representation of cHAs. The globular head domain is defined as the intervening amino acid sequence between residues C52 and C277 (H3 numbering). Using this disulfide bond as the demarcation between head and stalk, exotic HA heads were introduced atop heterologous stalks. The stalk domain is defined as the remaining portions of HA1 and HA2 subunits. CT, cytoplasmic tail; SP, signal peptide; TM, transmembrane domain. The full-length HA structures were downloaded from the Protein Database (PDB): PR8 (H1) HA (PDB ID 1RU7) and A/guinea fowl/Hong Kong/WF10/99 HA [represented by A/swine/Hong Kong/9/98 (H9; PDB ID 1JSD)]. Final images were generated with PyMol (Delano Scientific). Because no structure of an H6 HA has been published, the image of the head-folding of the PR8 HA is used for the cH6/1 construct. FIG. 14B: Immunofluorescence to confirm expression of cHA. MDCK cells were infected with either WT PR8 or cH9/1 N3 virus, or they were mock-infected. Antibodies specific for the head and stalk of PR8 virus as well as an antibody with H9 reactivity were used to confirm cHA expression. (Magnification bar: 40×).

FIG. 15A, FIG. 15B, FIG. 15C, FIG. 15D and FIG. 15E show that adult patients infected with pandemic H1N1 virus have high titers of neutralizing antibodies that are reactive with the HA stalk. Reactivity of sera of pH1N1-infected adults (n=9), children not infected with pH1N1 (n=5), and adults not infected with pH1N1 virus (n=11) with cH6/1 protein (FIG. 15A), cH9/1 protein; (FIG. 15B), the LAH of the HA2 protein (anti-LAH antibody was used as a positive control; (FIG. 15C), H5 HA protein (mouse polyclonal serum raised against H5 HA was used as a positive control and a pan-H3 antibody, 12D1, was used as negative control; (FIG. 15D) (13), or H3 HA protein (12D1 was used as a positive control and mouse polyclonal serum raised against H5 HA was used as a negative control; (FIG. 15E). All were assessed by ELISA; data points represent average titers with SE or reactivity of pooled samples.

FIG. 16A, FIG. 16B, and FIG. 16C show that adult patients infected with pandemic H1N1 virus have high titers of neutralizing antibodies that are specific for the HA stalk (FIG. 16A and FIG. 16B). Sera from pH1N1-infected (n=14) and adults not infected with pH1N1 (n=5) were pooled separately, and total IgG from both pools was purified. Neutralizing capability of stalk antibodies was assessed by plaque reduction assay using cH9/1 N3 virus. Data points represent the mean and SE of two experiments. Plaques were immunostained with anti-H9 antibody G1-26. (FIG. 16B) shows plaque reduction of the four dilutions of sera shown along the top. (FIG. 16C) Pseudotype particle neutralization assay measures neutralizing antibody activity of the human-purified IgG preparations (sera from pH1N1-infected adults and adults not infected with pH1N1). Total IgG concentrations were 50, 10, and 2 µg/mL. As a positive control, the stalk-specific monoclonal antibody 6F12 was used.

FIG. 17A, FIG. 17B, and FIG. 17C show expression and function of cH6/1 and cH9/1 protein. FIG. 17A: Coomasie gel of 2 µg cH6/1 and cH9/1 protein. M, marker proteins. FIG. 17B: Western blot analysis of baculovirus expressed cHA proteins. Lane 1, cH6/1 protein; lane 2, cH9/1 protein; lane 3, WT PR8 HA; lane 4, WT H3 HA. Blots were probed with antibodies known to react with the stalk of PR8 virus (rabbit polyclonal anti-HA2) or H3 viruses (mouse mAb 12D1) and the globular head of H6 (goat polyclonal anti-H6) or H9 viruses (mouse mAb G1-26) to confirm the identity of baculovirus expressed cHAs. mAb 12D 1 reacts with both HA0 and HA2 (H3 protein preparation is cleaved, resulting in two distinct bands). FIG. 17C: Plaque assay of cH9/1 N3 reassortant virus. Reassortant cH9/1 N3 virus plaque phenotype is similar to plaques made by WT PR8 virus. Plaques were immunostained with PY102 and anti-H9 antibody G1-26.

Figure 18A:
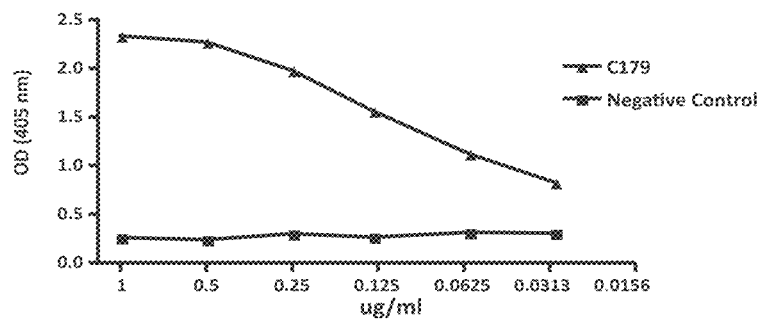
Figure 18B:
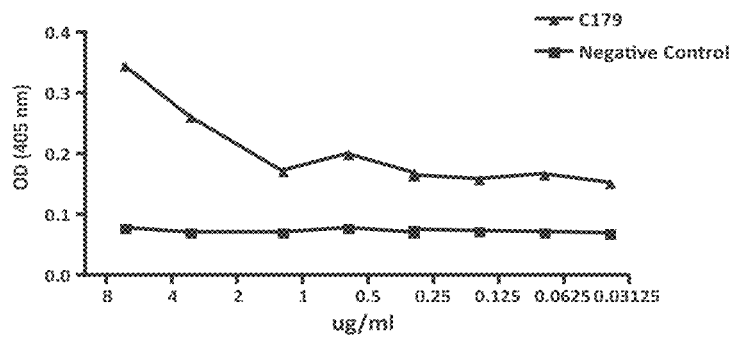
Figure 18C:
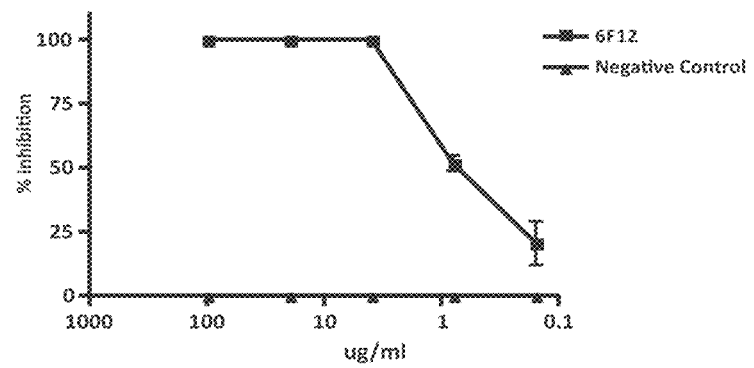
Figure 18D:
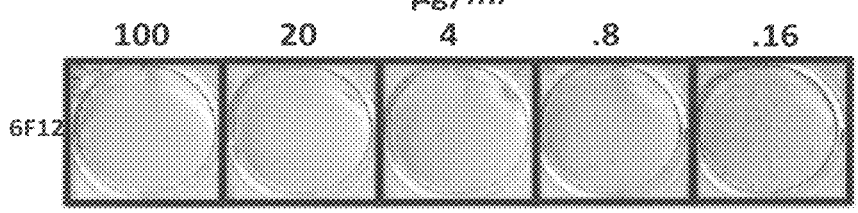

FIG. 18A, FIG. 18B, FIG. 18C, and FIG. 18D show that monoclonal antibodies directed against the stalk of influenza virus HA bind and neutralize cHAs. FIG. 18A: Stalk antibody C179 was used to test reactivity to cH6/1 baculovirus-expressed protein by ELISA. C179 reacted with cH9/1 in a dose-dependent manner. FIG. 18B: Stalk antibody C179 was used to test reactivity to cH9/1 baculovirus-expressed protein by ELISA. C179 reacted with cH9/1 in a dose-dependent manner (FIG. 18C and FIG. 18D). Antibody 6F12 neutralizes cH9/1 N3 virus replication. 6F12 was used to assess the ability of stalk-specific monoclonal antibodies to neutralize cH9/1 N3 virus by plaque reduction assay. FIG. 18D shows plaque reduction of cH9/1 N3 virus using five dilutions of mAb 6F12 (100, 20, 4, 0.8, and 0.16 µg/mL). Plaques were immunostained with anti-H9 antibody G1-26.

FIG. 19A and FIG. 19B depict schematics of chimeric hemagglutinins. FIG. 19A shows a diagram of wild-type and cH1/1 viruses. The chimeric HA was constructed by swapping the globular head domain located between Cys52 and Cys277 of PR8 (H1) HA with that of the A/California/4/09 (H1) HA. The resulting chimeric HA has the stalk region of A/PR8/34 (H1) HA with a globular head domain of the A/California/4/09 (H1) HA and is designated as cH1/1. FIG. 19B shows theoretical schematics of the folded structures of the different wild type and chimeric HAs. From left to right: wild type PR8 HA, the chimeric cH1/1 HA, the chimeric cH5/1 HA, the wild type Perth HA, the chimeric cH7/3 HA, and the chimeric cH5/3 HA.

FIG. 20 depicts a table comparing amino acid identity between H1, H3, H5 and H7 HAs used in this study. Percent amino acid identity was calculated using ClustalW (excluding the signal peptide). Percent amino acid identity is compared for full length HA, as well as the globular head and stalk domains. Grey bars indicate 100% identity.

Figure 21:
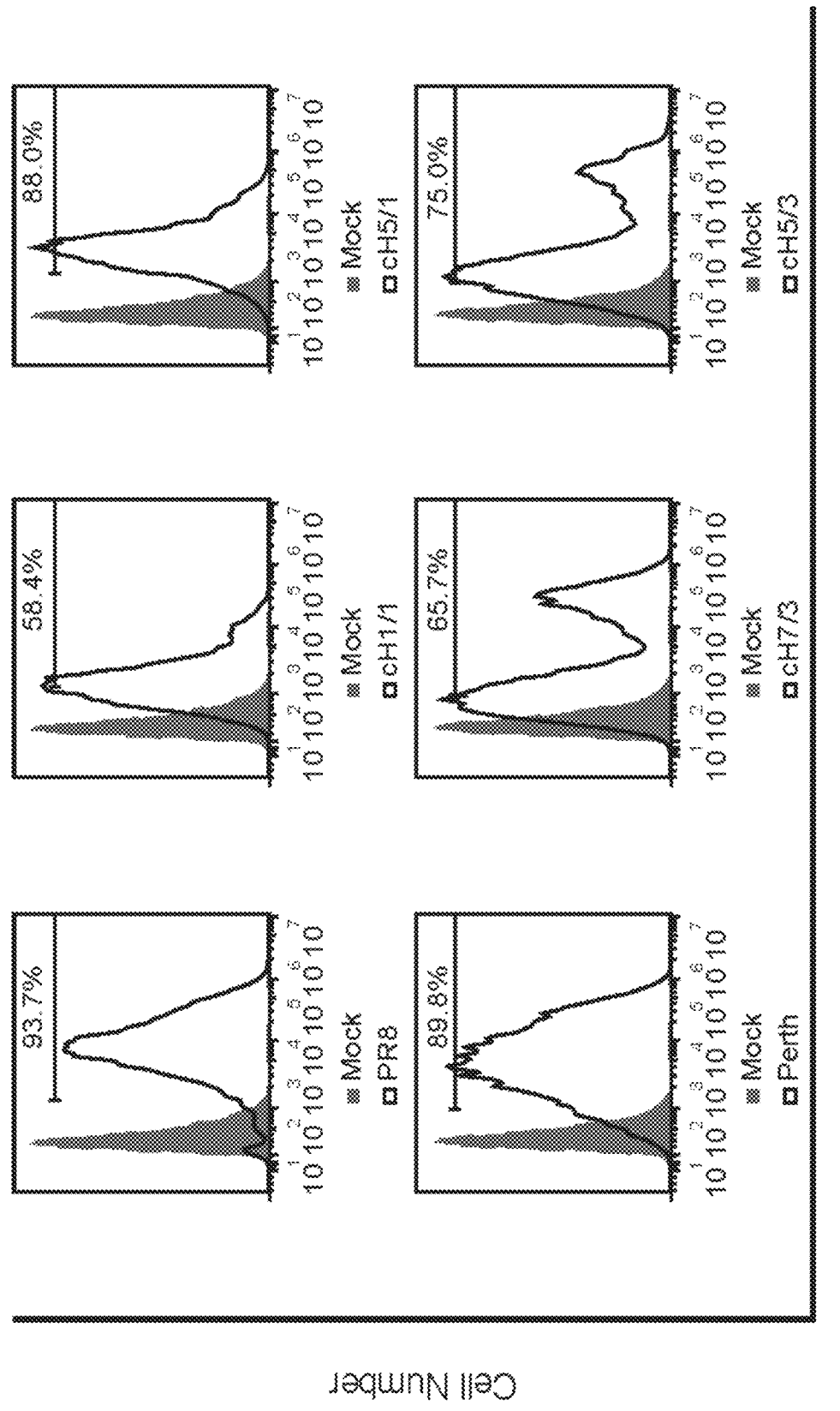

FIG. 21 shows the surface expression of chimeric HA constructs. Surface expression of chimeric HA constructs was evaluated in transiently transfected or infected cells. At 48 h post-transfection, 293T cells were trypsinized and cell surface expression of chimeric HA proteins were analyzed by flow cytometry. In the upper panels, mock-transfected cells (grey) are compared to cells transfected with PR8 HA (black line) or cells transfected with cH1/1 (black line) or cH5/1 (black line). In the center panels, mock-transfected cells (grey) are compared to cells transfected with Perth/09, cH7/3 (black line) and cH5/3 constructs (black line). In the bottom panels, MDCK cells were infected with Perth/09, cH7/3 and cH5/3 expressing recombinant viruses. At 12 h post-infection the cell surface expression of the different HAs were analyzed using flow cytometry.

Figure 22:
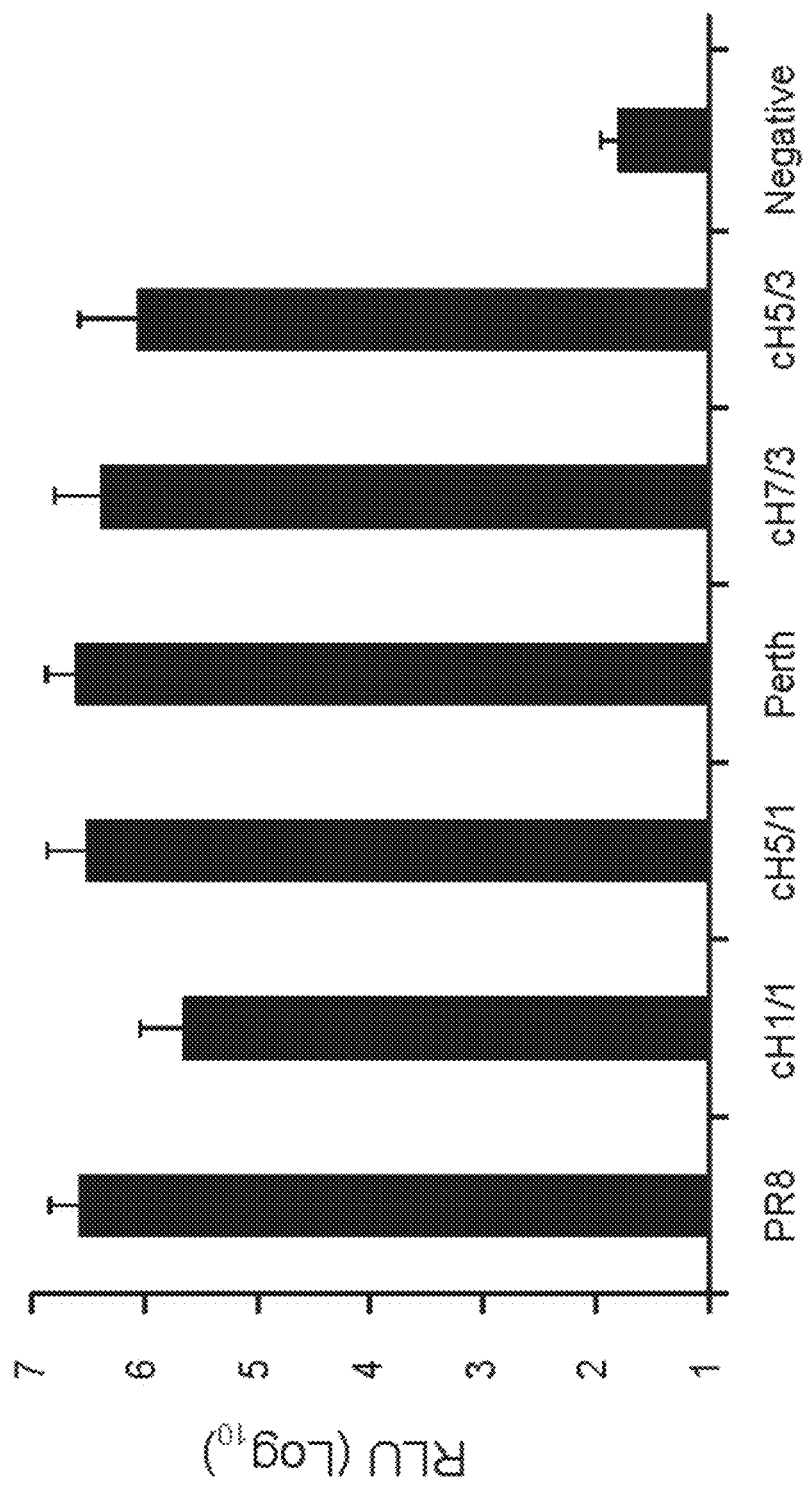

FIG. 22 demonstrates the ability of the chimeric HAs to enter MDCK cells. Luciferase-encoding pseudoparticles expressing chimeric HAs were used to transduce MDCK cells. The relative light units (RLU) generated in the luciferase assay indicates that pseudoparticles expressing chimeric HAs are able to enter cells.

Figure 23:
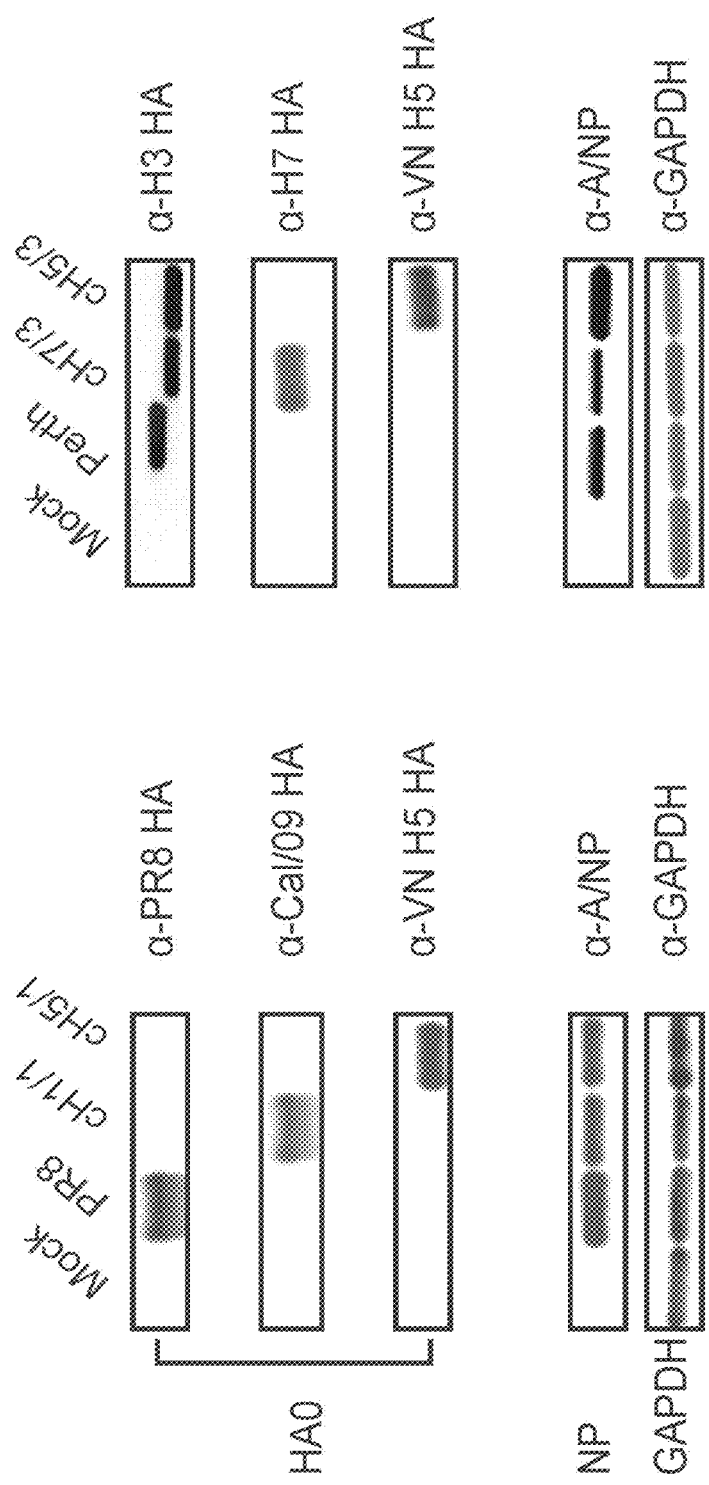

FIG. 23 shows a Western blot analysis of cells infected with the recombinant cHA-expressing viruses. Extracts from MDCK cells mock infected or infected with the indicated viruses at an MOI of 2 were prepared and probed with antibodies at 16 hpi: anti-A/PR8/HA (H1) (PY102), anti-A/Cal/09/HA (H1) (29E3), anti-A/VN/HA (H5) (mAb #8), anti-H3/HA (12D1), anti-H7 (NR-3152), anti-A/NP (HT103) and anti-GAPDH as an loading control.

Figure 24:
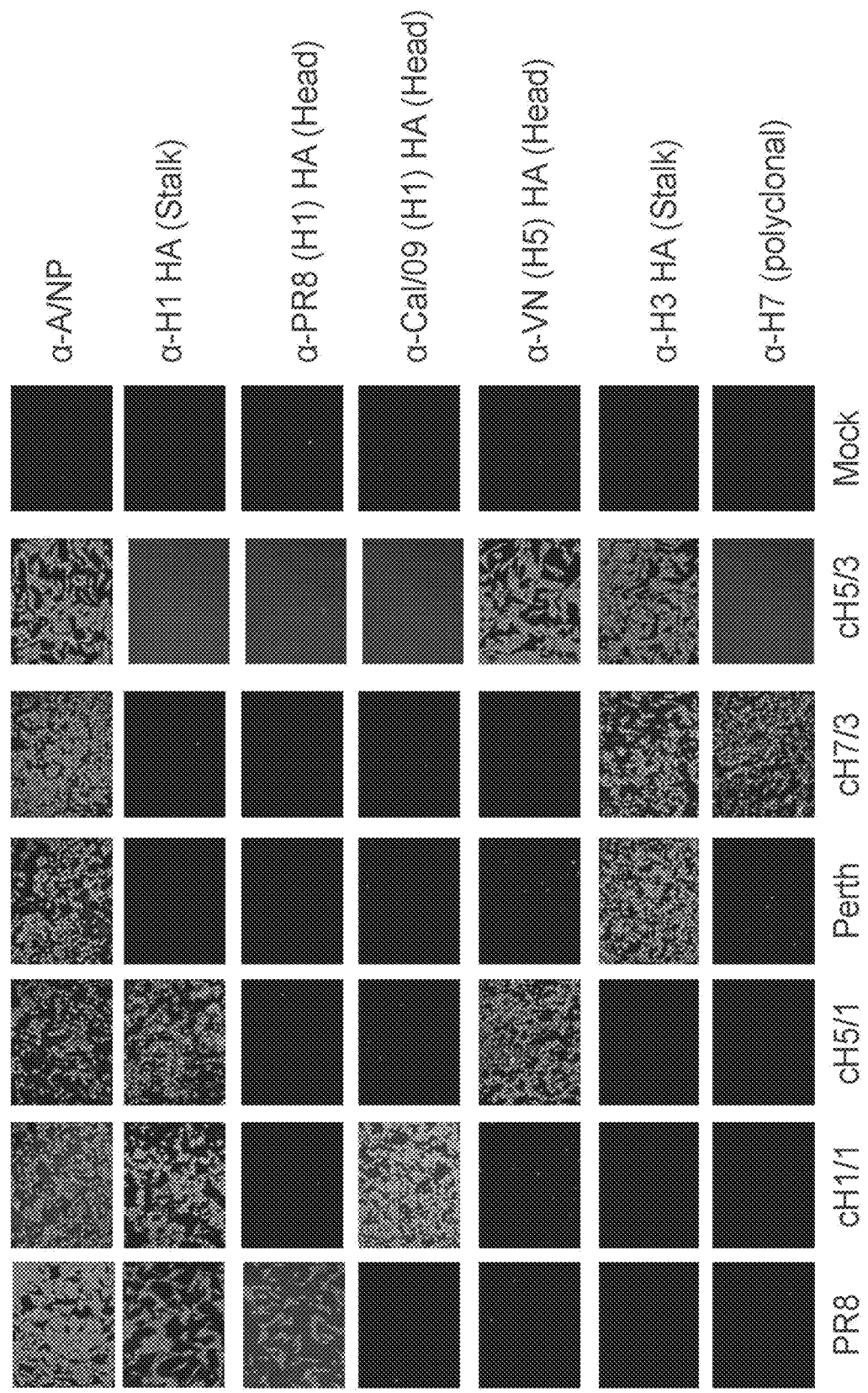

FIG. 24 depicts an immunofluorescence analysis of MDCK cells infected with recombinant viruses using antibodies: anti-A/NP (HT103), anti-A/H1 HA (6F12), anti-A/PR8/HA (PY102), anti-A/Cal/09/HA (29E3), anti-A/VN/HA (mAb #8), anti-H3/HA (12D1), and anti-A/H7 virus (NR-3152).

Figure 25A:
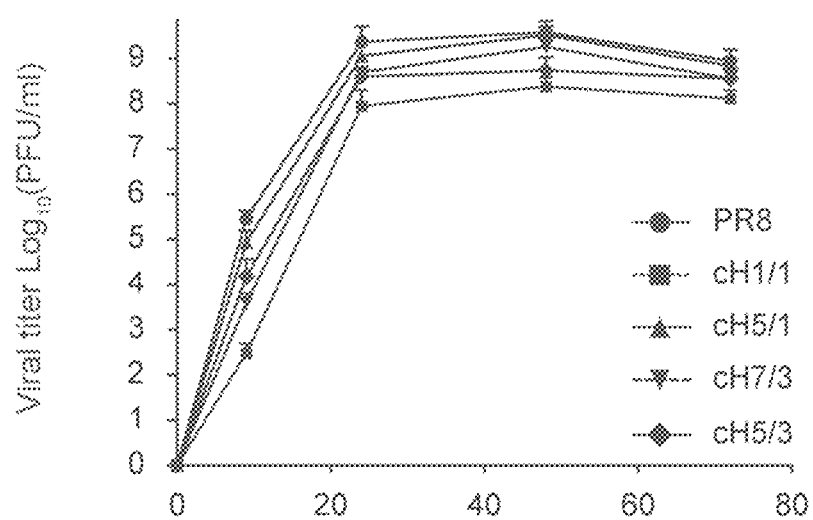
Figure 25B:
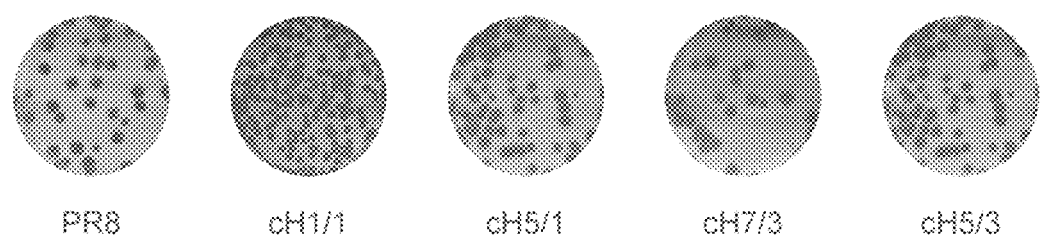

FIG. 25A and FIG. 25B depict the growth kinetics and plaque phenotypes of wild type and recombinant viruses. FIG. 25A: 10-day old embryonated chicken eggs were infected with 100 pfu per egg of wild-type or recombinant virus and viral growth was monitored for 72 hours post infection. Data points represent the average and standard deviation of experimental replicates. FIG. 25B: The plaque phenotypes of recombinant viruses were assessed by plaque assay. MDCK cells were infected with either a wild-type or recombinant virus. Cells were fixed 48 hours post infection and immunostained to reveal plaque phenotypes using the antibody against A/NP (HT103).

FIG. 26A and FIG. 26B depict that stalk-specific monoclonal antibody neutralizes cHA-expressing viruses and pseudotype particles. The ability of a mAb (KB2) to neutralize cHA-expressing viruses or pseudotype particles was assessed by plaque reduction assay (FIG. 26A) or pseudotype particle inhibition assay (FIG. 26B). MDCK cells were infected or transduce with cHA-expressing viruses or pseudotype particles in the presence of the indicated amount (ug/mL) of the mAb or without antibody. Plaque formation or luciferase activity was used as a readout to determine the degree of inhibition by the mAb. FIG. 26A: The mAb neutralizes cH1/1 (black boxes) and cH5/1 (black triangles) virus replication in a dose dependent manner, with 100% inhibition at concentrations above 100 ug/mL. Data points represent the average and standard deviation of experimental replicates. FIG. 26B: The mAb also inhibits entry of cH1/1 (black boxes) pseudotype particles in a dose dependent manner, with complete inhibition above 4 ug/mL. Data points represent the average and standard deviation of experimental replicates. The pseudotype inhibition assays were processed independently.

FIG. 27A, FIG. 27B, and FIG. 27C demonstrate that sequential vaccination with cHA constructs elicits HA stalk-specific antibodies and provides protection from lethal challenge. Mice were primed with 20 μg of cH9/1 protein, administered with adjuvant intranasally and intraperitoneally. Three weeks later, mice were boosted with 20 μg cH6/1 protein, administered with adjuvant intranasally and intraperitoneally. As controls, mice were primed and boosted in a similar fashion using BSA, or given inactivated FM1 virus intramuscularly. Animals were bled and challenged three weeks after the last vaccination with 5LD50 of A/Fort Monmouth/1/1947 (FM1) virus. FIG. 27A: ELISA plates were coated with cH5/1 N1 virus in order to assess the degree of stalk reactivity elicited through vaccination (BSA+BSA is the bottom line of the graph). FIG. 27B: Mice were weighed daily for 14 days to assess protection from challenge. FIG. 27C: Kaplan Meier curve depicting survival rate post challenge. cH9/1+cH6/1 vaccinated mice had a statistically higher survival rate compared to BSA controls (p=0.0003)

FIG. 28A, FIG. 28B, FIG. 28C, FIG. 28D, and FIG. 28E demonstrate that vaccination with cH6/1 elicits stalk-specific immunity that mediates protection from cH9/1 N1 viral challenge. Animals were inoculated with YAM-HA virus in order to simulate prior infection with or vaccination against influenza virus. Three weeks later, animals were vaccinated with cH6/1 or BSA with adjuvant, intranasally and intraperitoneally. Control animals were inoculated with wild-type B/Yamagata/16/1988 and vaccinated in a similar fashion with BSA, or given inactivated cH9/1 N1 virus intramuscularly. Animals were bled and challenged with 250$LD_{50}$ cH9/1 N1 virus three weeks after vaccination. FIG. 28A: Animals were weighed for 8 days in order to assess protection from challenge. On days 3-5, YAM-HA+cH6/1 animals demonstrated statistically less weight loss compared to the YAM-HA+BSA cohort ($p<0.05$). FIG. 28B: Kaplan Meier curve depicting survival. Statistically different survival rates were seen in the YAM-HA+cH6/1 group compared to the YAM-HA+BSA cohort (p=0.038), as well as naive and WT YAM+BSA animals ($p<0.0001$). Survival rate of YAM-HA+BSA cohort was not statistically different from that of the WT-YAM+BSA cohort (p=0.058). FIG. 28C: ELISA plates were coated with cH5/1 N1 virus in order to assess the degree of stalk reactivity elicited through vaccination. FIG. 28D: Results of a plaque reduction assay using the cH5/1 virus are depicted. FIG. 28E: Animals were vaccinated, bled and total IgG was harvested for H5-based pseudoparticle entry inhibition assay. Percent inhibition was assessed as a decrease in luciferase expression compared to controls.

FIG. 29A, FIG. 29B, and FIG. 29C demonstrate that vaccination with cH6/1 protects mice from lethal H5 influenza virus challenge. Animals were inoculated with YAM-HA virus in order to simulate prior infection with or vaccination against influenza virus. Three weeks later, animals were vaccinated with cH6/1 or BSA with adjuvant, intranasally and intraperitoneally. Control animals were inoculated with wild-type B/Yamagata/16/1988 and vaccinated in a similar fashion with BSA or given inactivated cH5/1 N1 virus intramuscularly. Animals were bled and challenged with 10$LD_{50}$ of the 2:6 H5 reassortant in the PR8 background (see, e.g., Steel et al., 2009, J Virol 83:1742-1753). FIG. 29A: Kaplan Meier curve depicting survival. Differences in survival rates approached statistical significance when comparing the YAM-HA+cH6/1 group to the YAM-HA+BSA cohort (p=0.06). FIG. 29B: Length of survival was on average longer in animals inoculated with YAM-HA and vaccinated with cH6/1 than animals vaccinated with BSA (p=0.037), as well as naive and WT YAM/BSA controls ($p<0.001$). FIG. 29C: ELISA plates were coated with cH5/1 N1 virus in order to assess the degree of stalk reactivity elicited through vaccination. 1:50 serum dilutions were plotted against % maximum weight loss. One value was determined to be an outlier and was omitted from analysis. For linear regression, $R^2=0.56$ and p=0.02.

FIG. 30A, FIG. 30B, FIG. 30C, FIG. 30D, FIG. 30E, FIG. 30F, FIG. 30G, FIG. 30H, FIG. 30I, and FIG. 30J demonstrate that vaccination with cHA elicits stalk-specific immunity that mediates protection from H1N1 virus challenge. (FIG. 30A-FIG. 30F) Animals were primed with DNA encoding cH9/1 and then were vaccinated with cH6/1 and boosted with cH5/1 soluble protein (n=10) or BSA (n=5), while positive control mice received inactivated virus intramuscularly (n=5). FIG. 30A: Animals were vaccinated and challenged with FM1 virus; mice were weighed daily, and weight loss over time is shown as change in percentage of initial weight. FIG. 30B: Graph depicting survival of challenged mice in (A). FIG. 30C: Animals were vaccinated and challenged with pH1N1 virus; mice were weighed daily, and weight loss over time is shown as change in percentage of initial weight. FIG. 30D: Graph depicting survival of challenged mice in FIG. 30C. FIG. 30E: Animals were vaccinated and challenged with PR8 virus; mice were weighed daily, and weight loss over time is shown as change in percentage of initial weight. FIG. 30F: Graph depicting survival of challenged mice in FIG. 30E. FIG. 30G: Reactivity to H1 HA of serum from animals vaccinated as described above in FIG. 30A-FIG. 30F and below in FIG. 30H-FIG. 30I and challenged with 5 $LD_{50}$ of A/FM/1/1947 (FIG. 30A, FIG. 30B), 10 $LD_{50}$ of A/Netherland/602/2009 (FIG. 30C, FIG. 30D), or 5 $LD_{50}$ of A/PR/8/1934 (FIG. 30E, FIG. 30F, FIG. 30H, FIG. 30I). FIG. 30H: Animals were vaccinated as described above in FIG. 30A-FIG. 30F (square, n=4) or were naive (triangle, n=3), while positive control mice received inactivated PR8 virus intramuscularly (X mark, n=5). CD8 T cells were depleted prior to challenge with PR8 virus. Mice were weighed daily, and weight loss over time is shown as change in percentage of initial weight. FIG. 30I: Graph depicting survival of challenged mice in FIG. 30H. FIG. 30J: Animals were vaccinated as described for FIG. 30A-FIG. 30F. Total IgG was purified for use in H2-based pseudoparticle entry inhibition assay. Percent inhibition was assessed as a decrease in luciferase expression compared to controls. Fab fragment CR6261 was used as a positive control.

FIG. 31A, FIG. 31B, and FIG. 31C. Schematic of wild type HA and expression constructs. FIG. 31A: Uncleaved full length influenza virus hemagglutinin. The signal peptide is the leftmost component, the HA ectodomain is the middle component and the transmembrane- and endodomain are the rightmost component. FIG. 31B: Expression construct with trimerization domain. The transmembrane- and endodomain was swapped with a thrombin cleavage site (third component from left), a T4 trimerization domain (fourth component from left) and a hexahistidine tag (6×his tag, fifth component from left) at position V503 (H3 numbering). FIG. 31C: Expression construct without trimerization domain. The transmembrane- and endodomain was swapped with a hexahistidine tag (6×his tag, rightmost component) at amino acid position 509 (H1, H2 and H5) or 508 (H3) respectively (H3 numbering).

Figure 32A:
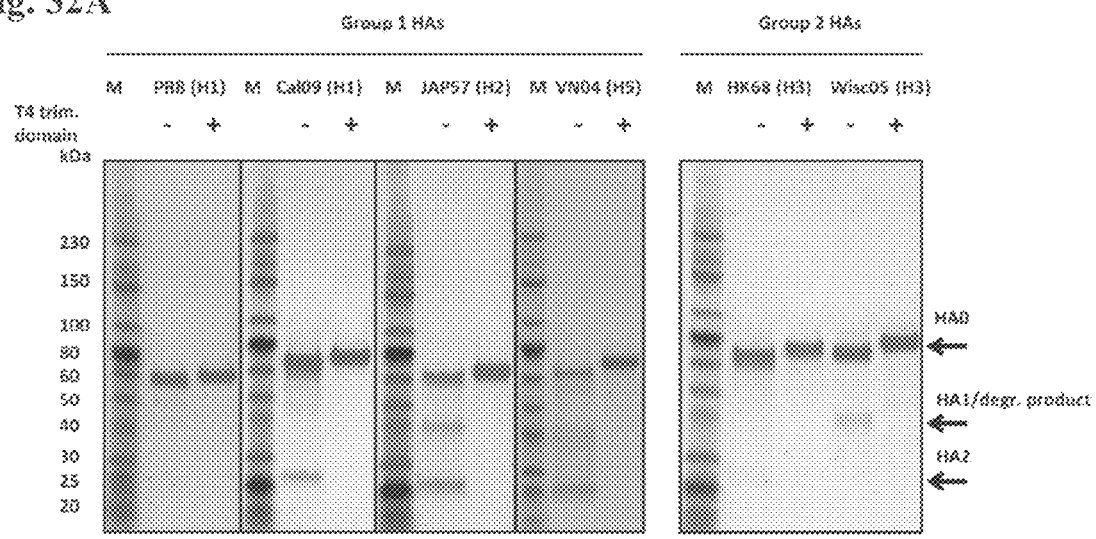
Figure 32B:
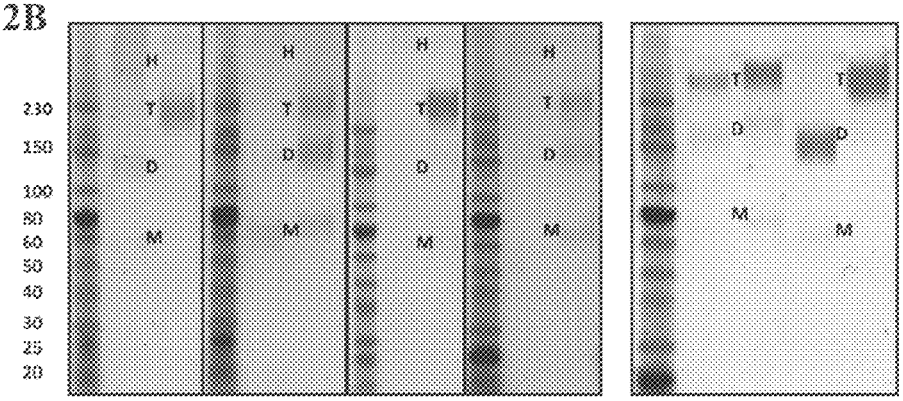
Figure 32C:
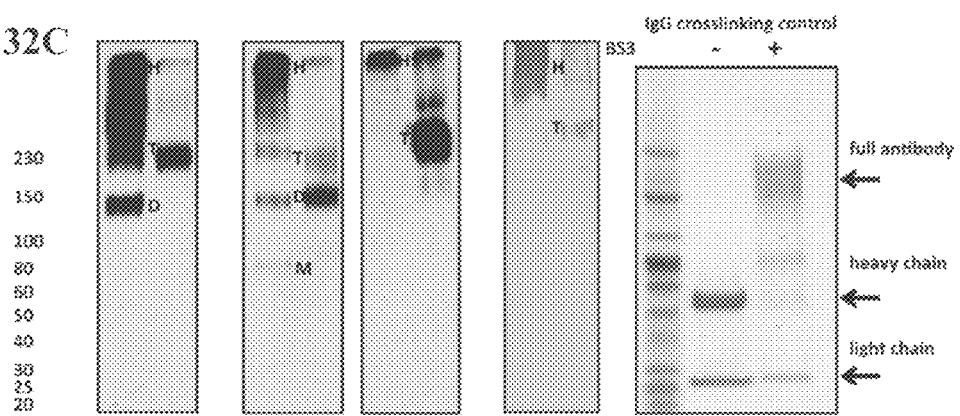

FIG. 32A, FIG. 32B, and FIG. 32C. Introduction of a trimerization domain influences stability and formation of oligomers in recombinant HAs. FIG. 32A: Analysis of recombinant HAs with and without trimerization domain by reducing, denaturing SDS-PAGE. Recombinant HAs that are expressed with trimerization domain (+) show higher stability than HAs expressed without (−). Uncleaved HA (HA0) and cleavage products (HA1/degr. product; HA2) are indicated by arrows. FIG. 32B: Reducing, denaturing SDS-PAGE analysis of crosslinked HAs. Different species of HA are indicated in the blot. High molecular multimers are indicated by H, trimers by T, dimers by D and monomers by M. FIG. 32C: Left panel (boxes 1-4): Western blot analysis of reduced, denatured and cross-linked group 1 HAs from B probed with a anti-hexahistidine-tag antibody. Right panel (rightmost box): Cross-linking control (IgG) with BS$^3$ analyzed on a SDS-PAGE. Different species (full antibody, heavy chain, light chain) are indicated by arrows. Molecular weights of the marker bands are indicated on the left of each panel.

Figure 33A:
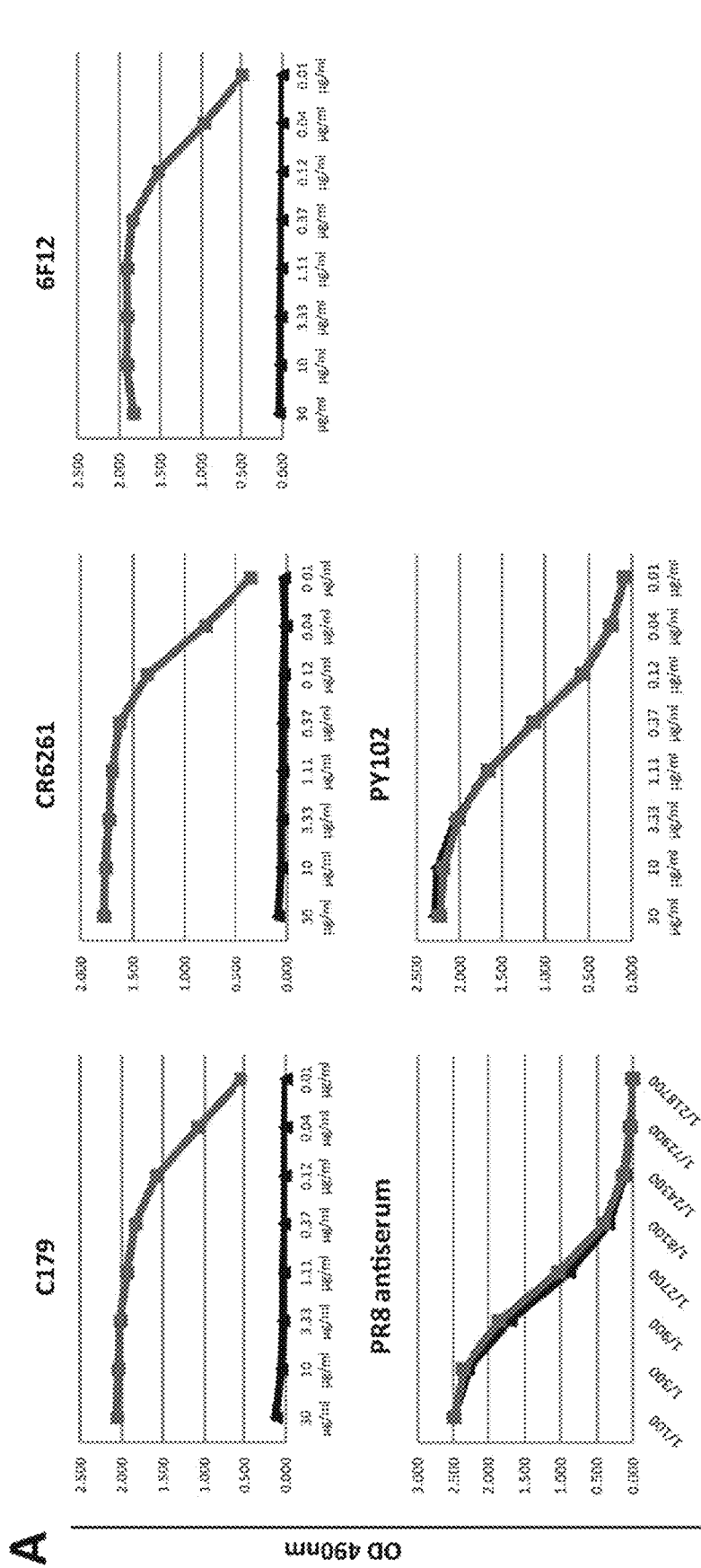
Figure 33B:
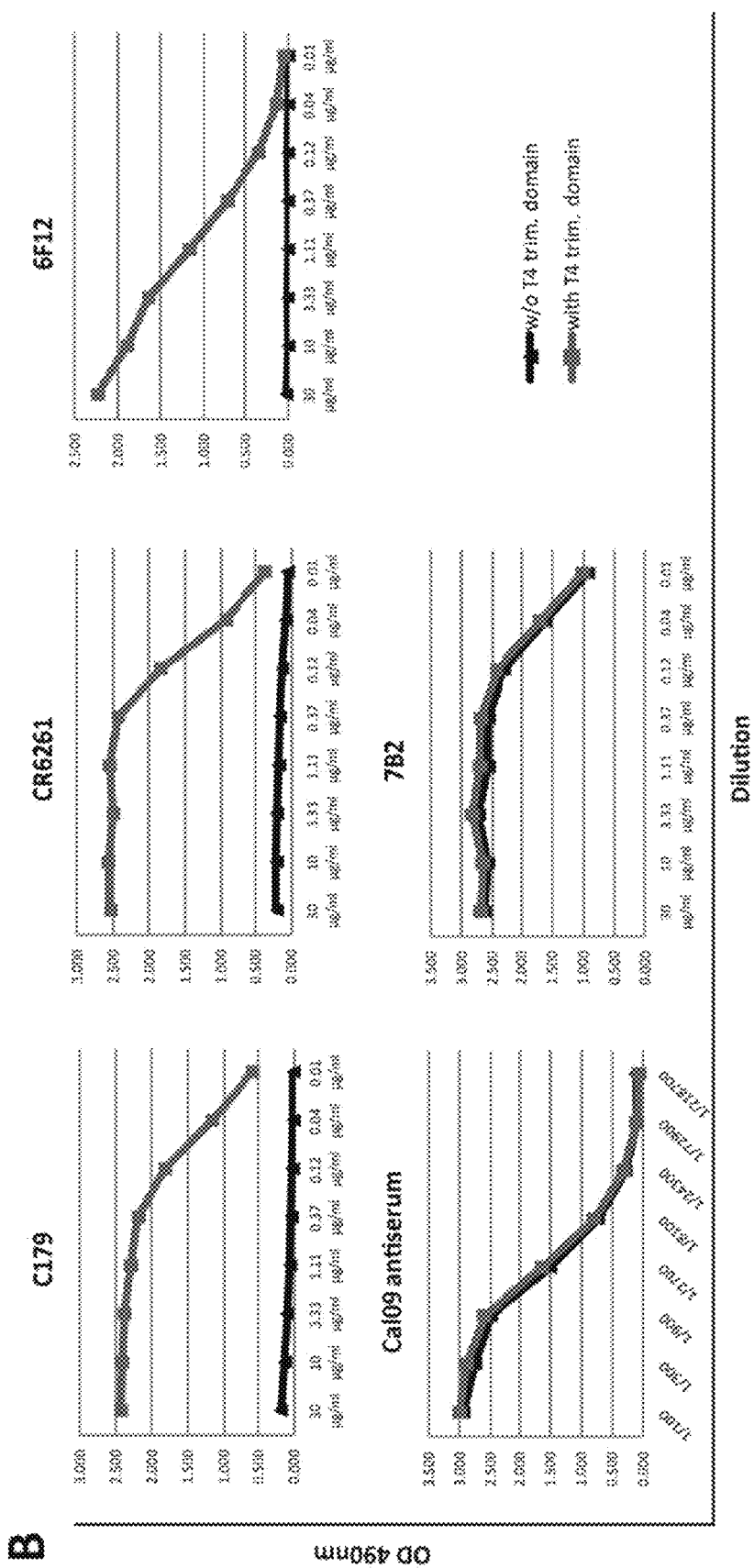

FIG. 33A and FIG. 33B. Binding of stalk-reactive antibodies to recombinant PR8 (H1) and Cal09 (H1) HAs. FIG. 33A: Binding of stalk-reactive antibodies C179, CR6261 and 6F12 and head-reactive antibody PY102 and PR8 antiserum to recombinant soluble PR8 HA without (w/o T4 trim. domain, triangle lines) or with (w/T4 trim. domain, boxed lines) trimerization domain. FIG. 33B: Binding of stalk-reactive antibodies C179, CR6261 and 6F12 and head-reactive antibody 7B2 and Cal09 antiserum to recombinant soluble Cal09 HA without (w/o T4 trim. domain, triangle lines) or with (w/T4 trim. domain, boxed lines) trimerization domain.

Figure 34A:
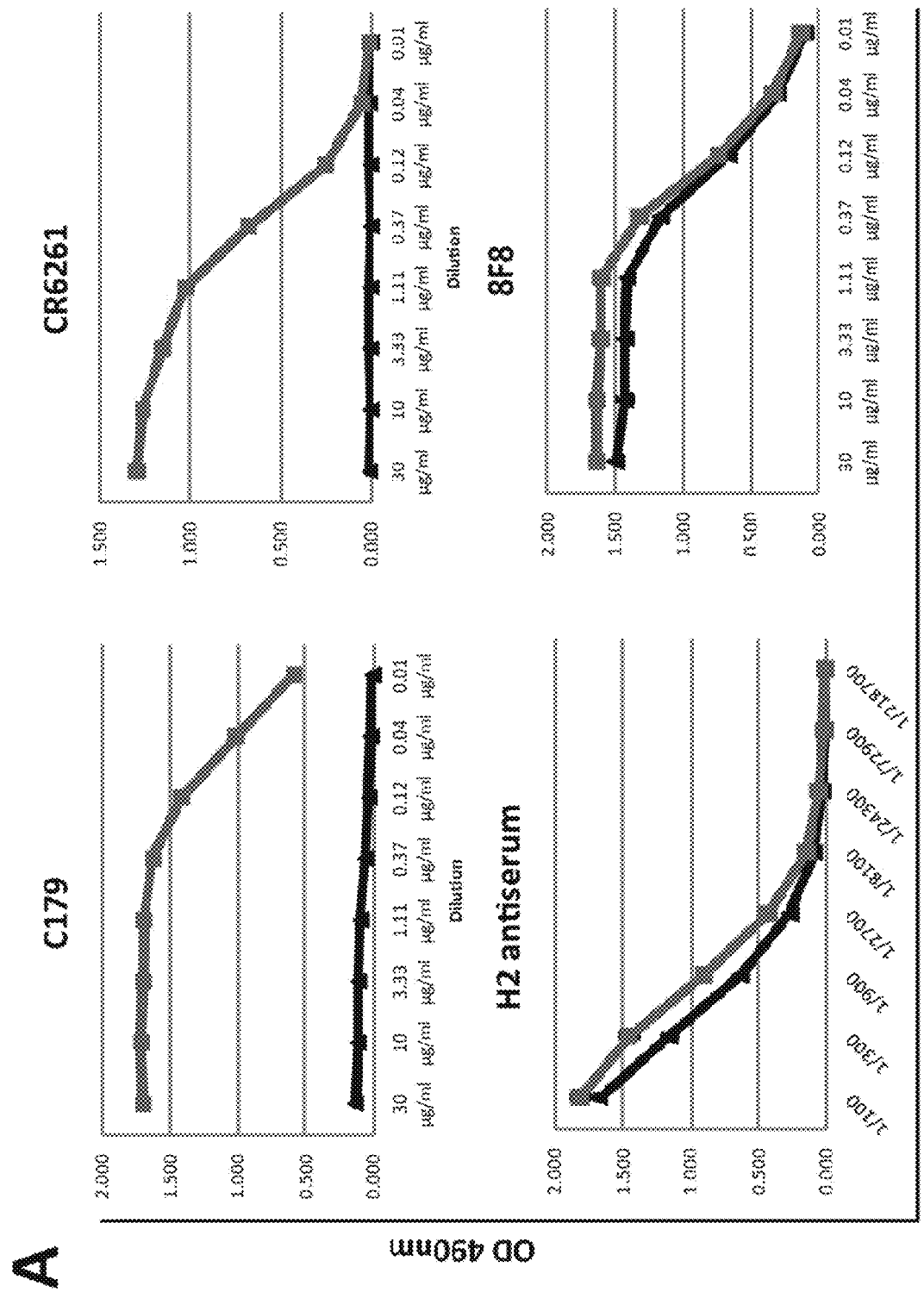
Figure 34B:
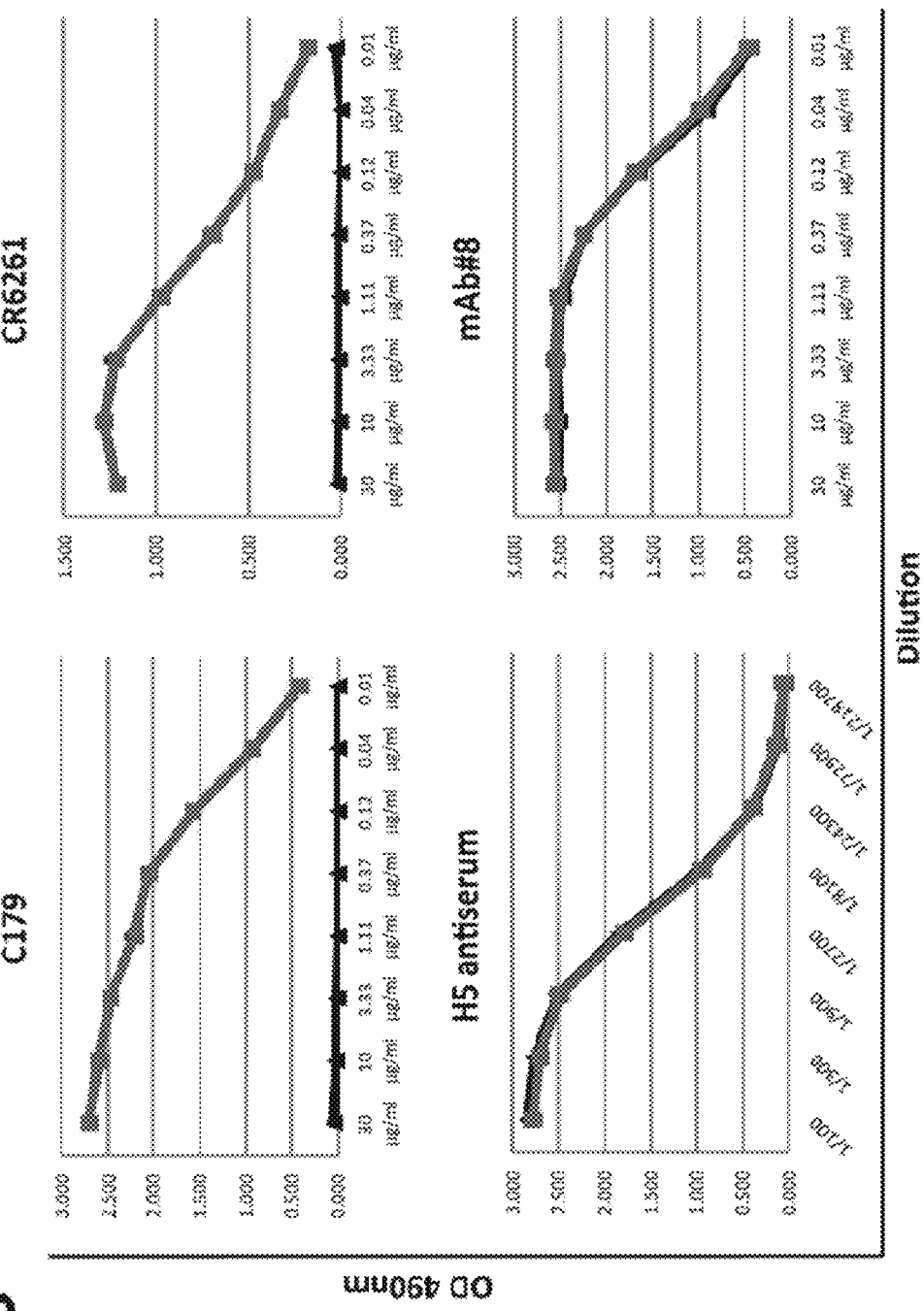

FIG. 34A and FIG. 34B. Binding of stalk-reactive antibodies to recombinant JAP57 (H2) and VN04 (H5) HAs. FIG. 34A: Binding of stalk-reactive antibodies C179 and CR6261 and head-reactive antibody 8F8 and H2 antiserum to recombinant soluble JAP57 HA without (w/o T4 trim. domain, triangle lines) or with (w/T4 trim. domain, boxed lines) trimerization domain. FIG. 34B: Binding of stalk-reactive antibodies C179 and CR6261 and head-reactive antibody mAb #8 and H5 antiserum to recombinant soluble VN04 HA without (w/o T4 trim. domain, triangle lines) or with (w/T4 trim. domain, boxed lines) trimerization domain.

Figure 35A:
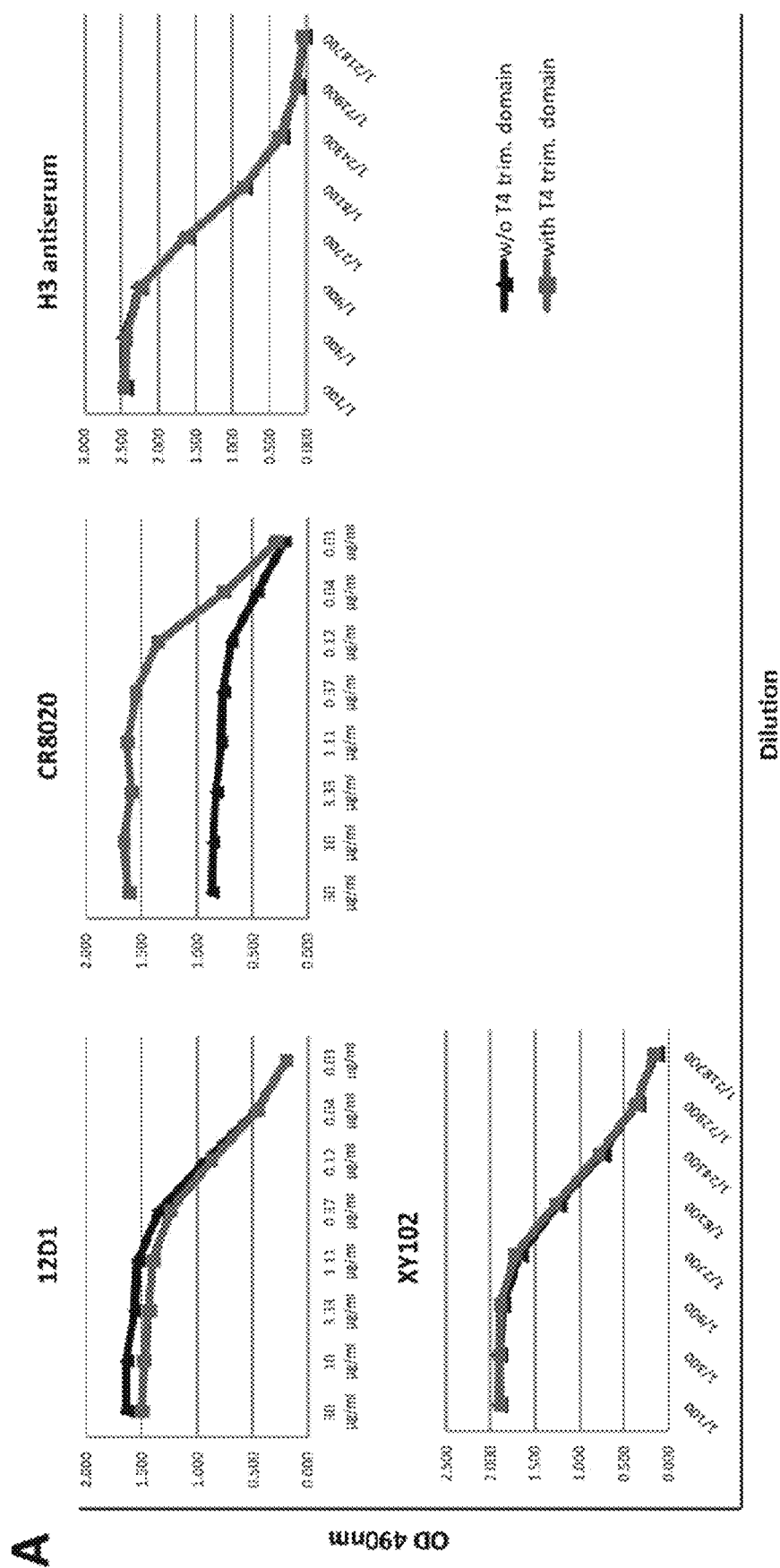
Figure 35B:
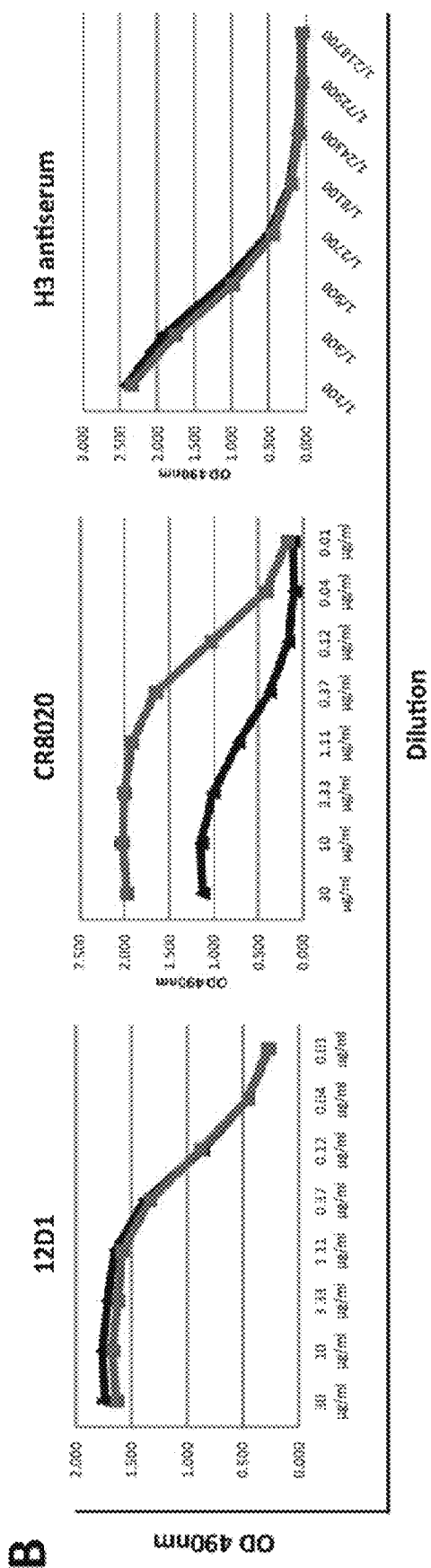

FIG. 35A and FIG. 35B. Binding of stalk-reactive antibodies to group 2 HAs. FIG. 35A: Binding of stalk-reactive antibodies 12D1 and CR8020 and head-reactive antibody XY102 and H3 antiserum to recombinant soluble HK68 HA without (w/o T4 trim. domain, triangle lines) or with (w/T4 trim. domain, boxed lines) trimerization domain. FIG. 35B: Binding of stalk-reactive antibodies 12D1 and CR8020 and H3 antiserum to recombinant soluble Wisc05 HA without (w/o T4 trim. domain, triangle lines) or with (w/T4 trim. domain, boxed lines) trimerization domain.

FIG. 36 depicts an exemplary chimeric influenza virus hemagglutinin polypeptide (SEQ ID NO: 21) comprising the stem domain of an influenza B virus (B/Florida/4/2006) and the globular head domain of an influenza A virus of the H5 subtype (A/Vietnam/1203/2004).

5. DETAILED DESCRIPTION

In one aspect, provided herein are chimeric influenza hemagglutinin (HA) polypeptides that induce a cross-protective immune response against the conserved HA stem domain of influenza viruses. The chimeric influenza HA polypeptides provided herein comprise a stable HA stem domain and a globular HA head domain that is heterologous to the stem domain (i.e. the head and stem domains are derived from different strains and/or subtypes of influenza virus).

In another aspect, provided herein are compositions comprising one or more of the chimeric influenza hemagglutinin polypeptides described herein (e.g., compositions comprising soluble chimeric influenza hemagglutinin polypeptides described herein, viruses comprising the chimeric influenza hemagglutinin polypeptides described herein, viruses comprising genomes engineered to encode the chimeric influenza hemagglutinin polypeptides described herein, expression vectors comprising the chimeric influenza hemagglutinin polypeptides described herein, expression vectors comprising genomes engineered to encode the chimeric influenza hemagglutinin polypeptides described herein, nucleic acids encoding the chimeric influenza hemagglutinin polypeptides described herein, etc.).

In another aspect, provided herein are vaccine formulations comprising one or more of the chimeric influenza hemagglutinin polypeptides described herein. In a specific embodiment, provided herein is a monovalent vaccine comprising one of the chimeric influenza hemagglutinin polypeptides described herein. In another specific embodiment, provided herein is a bivalent vaccine comprising two of the chimeric influenza hemagglutinin polypeptides described herein (i.e., two distinct chimeric influenza hemagglutinin polypeptides). In another specific embodiment, provided herein is a trivalent vaccine comprising three of the chimeric influenza hemagglutinin polypeptides described herein (i.e., three distinct chimeric influenza hemagglutinin polypeptides). The vaccine formulations provided herein may comprise, for example, subunit vaccines comprising one or more of the chimeric influenza hemagglutinin polypeptides described herein (e.g., compositions comprising chimeric influenza hemagglutinin polypeptides, e.g., soluble chimeric influenza hemagglutinin polypeptides); live influenza viruses (e.g., live attenuated influenza viruses) that express one or more of the chimeric influenza hemagglutinin polypeptides described herein; live influenza viruses (e.g., live attenuated influenza viruses) comprising a genome that encodes one or more of the chimeric influenza hemagglutinin polypeptides described herein; killed influenza viruses that express one or more of the chimeric influenza hemagglutinin polypeptides described herein; killed influenza viruses comprising a genome that encodes one or more of the chimeric influenza hemagglutinin polypeptides described herein; virus/viral-like particles ("VLPs") that contain one or more of the chimeric influenza hemagglutinin polypeptides described herein; split virus vaccines, wherein said virus expresses one or more of the chimeric influenza hemagglutinin polypeptides described herein and/or comprises a genome that encodes one or more of the chimeric influenza hemagglutinin polypeptides described herein; viral expression vectors (e.g., non-influenza virus expression vectors) that express one or more of the chimeric influenza hemagglutinin polypeptides described herein; and bacterial expression vectors that express one or more of the chimeric influenza hemagglutinin polypeptides described herein.

The vaccine formulations described herein can elicit highly potent and broadly neutralizing antibodies against the HA stem domain of the chimeric influenza hemagglutinin polypeptides. Such "universal" vaccines can be used to induce and/or boost cross-protective immune responses across influenza virus subtypes.

In another aspect, provided herein are methods of immunizing a subject against an influenza virus disease or infection comprising administering to the subject a composition comprising one or more of the chimeric influenza hemagglutinin (HA) polypeptides described herein or a vaccine formulation described herein.

In another aspect, provided herein are kits comprising one or more of the chimeric influenza hemagglutinin (HA) polypeptides described herein or a vaccine formulation described herein. The kits provided herein may further comprise one or more additional components, e.g., an antibody that specifically binds one or more of the chimeric influenza hemagglutinin (HA) polypeptides provided in the kit.

5.1 Chimeric Influenza Virus Hemagglutinin Polypeptides

Provided herein are chimeric influenza virus hemagglutinin polypeptides comprising or consisting of an influenza virus hemagglutinin globular head domain polypeptide and an influenza virus hemagglutinin stem domain polypeptide, wherein said influenza virus hemagglutinin head domain polypeptide is heterologous to said influenza virus hemagglutinin stem domain polypeptide (e.g., the influenza virus hemagglutinin globular head domain polypeptide and the influenza virus hemagglutinin stem domain polypeptide are derived from different influenza virus hemagglutinin subtypes).

A full-length influenza hemagglutinin typically comprises an HA1 domain and an HA2 domain. The stem domain is formed by two segments of the HA1 domain and most or all of the HA2 domain. The two segments of the HA1 domain are separated, in primary sequence, by the globular head domain (see, e.g., the amino acid residues between the residues designated $A_p$ and $A_q$ in FIG. 1). In certain embodiments, the chimeric influenza virus hemagglutinin polypeptides described herein maintain such a structure. That is, in certain embodiments, the chimeric influenza virus hemagglutinin polypeptides described herein comprise a stable stem structure composed of an HA1 domain and an HA2 domain, and a globular head domain separating the two segments of the HA1 domain (in primary sequence), wherein said globular head domain is heterologous to the stem domain formed by the other segments of the HA1 domain and the HA2 domain.

In certain embodiments, a chimeric influenza hemagglutinin (HA) polypeptide provided herein comprises (i) the stem domain of the hemagglutinin from an influenza virus of the H1 subtype and (ii) the globular head domain of the hemagglutinin from an influenza virus of the H5 subtype (sometimes referred to herein as a "cH5/1 chimeric influenza hemagglutinin polypeptide"). In a specific embodiment, the stem domain of a cH5/1 chimeric influenza hemagglutinin polypeptide is the stem domain of A/California/4/2009 (H1N1) HA (or the stem domain of an A/California/4/2009-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Vietnam/1203/2004 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Indonesia/5/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Anhui/1/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Bar headed goose/Quinghai/1A/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/turkey/Turkey/1/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Whooperswan/Mongolia/244/2005 (H5) HA.

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H5 subtype (sometimes referred to herein as a "cH5/3 chimeric influenza hemagglutinin polypeptide"). In a specific embodiment, the stem domain of a cH5/3 chimeric influenza hemagglutinin polypeptide is the stem domain of A/Victoria/361/2011 (H3N2) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Bar headed goose/Quinghai/1A/2005 (H5) HA. In another specific embodiment, the stem domain of a cH5/3 chimeric influenza hemagglutinin polypeptide is the stem domain of A/Victoria/361/2011 (H3N2)

HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Whooper-swan/Mongolia/244/2005 (H5) HA.

In another specific embodiment, the stem domain of a cH5/3 chimeric influenza hemagglutinin polypeptide is the stem domain of A/harbor seal/Massachusetts/1/2011 (H3N8) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Bar headed goose/Quinghai/1A/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Whooperswan/Mongolia/244/2005 (H5) HA.

In another specific embodiment, the stem domain of a cH5/3 chimeric influenza hemagglutinin polypeptide is the stem domain of A/Indiana/10/2011 (H3N2) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Bar headed goose/Quinghai/1A/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Whooper-swan/Mongolia/244/2005 (H5) HA.

In a specific embodiment, a cH5/3 chimeric influenza hemagglutinin polypeptide provided herein does not comprise the globular head domain of A/Vietnam/1203/2004 (H5) HA. In another specific embodiment, a cH5/3 chimeric influenza hemagglutinin polypeptide does not comprise the stem domain of A/Perth/16/2009 (H3) HA.

In another specific embodiment, the stem domain of a cH5/3 chimeric influenza hemagglutinin polypeptide is the stem domain of A/Perth/16/2009 (H3N2) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Bar headed goose/Quinghai/1A/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Whooperswan/Mongolia/244/2005 (H5) HA.

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H7 subtype (sometimes referred to herein as a "cH7/3 chimeric influenza hemagglutinin polypeptide"). In a specific embodiment, the stem domain of a cH7/3 chimeric influenza hemagglutinin polypeptide is the stem domain of A/Victoria/361/2011

(H3N2) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Rhea/NC/39482/93 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/mallard/Netherlands/12/2000 (H7) HA.

In another specific embodiment, the stem domain of a cH7/3 chimeric influenza hemagglutinin polypeptide is the stem domain of A/harbor seal/Massachusetts/1/2011 (H3N8) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Rhea/NC/39482/93 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/mallard/Netherlands/12/2000 (H7) HA.

In another specific embodiment, the stem domain of a cH7/3 chimeric influenza hemagglutinin polypeptide is the stem domain of A/Indiana/10/2011 (H3N2) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Rhea/NC/39482/93 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/mallard/Netherlands/12/2000 (H7) HA.

In another specific embodiment, the stem domain of a cH7/3 chimeric influenza hemagglutinin polypeptide is the stem domain of A/Perth/16/2009 (H3N2) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Canada/ 504/04 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/Perth/ 16/2009 (H3N2) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/mallard/ Alberta/24/2001 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Rhea/NC/39482/93 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/mallard/ Netherlands/12/2000 (H7) HA.

In a specific embodiment, a cH7/3 chimeric influenza hemagglutinin polypeptide provided herein does not comprise the globular head domain of A/mallard/Alberta/24/ 2001 (H7) HA. In another specific embodiment, a cH7/3 chimeric influenza hemagglutinin polypeptide does not comprise the stem domain of A/Perth/16/2009 (H3) HA.

In certain embodiments, a chimeric influenza hemagglutinin (HA) polypeptide provided herein comprises (i) the stem domain of the hemagglutinin from an influenza B virus and (ii) the globular head domain of the hemagglutinin from an influenza virus of the H5 subtype (sometimes referred to herein as a "cH5/B chimeric influenza hemagglutinin polypeptide"). In a specific embodiment, the stem domain of a cH5/B chimeric influenza hemagglutinin polypeptide is the stem domain of B/Malaysia/2506/2004 HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Indonesia/5/ 2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Bar headed goose/Quinghai/1A/ 2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Whooperswan/Mongolia/ 244/2005 (H5) HA.

In another specific embodiment, the stem domain of a cH5/B chimeric influenza hemagglutinin polypeptide is the stem domain of B/Florida/4/2006 HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Indonesia/5/ 2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Bar headed goose/Quinghai/1A/2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/turkey/Turkey/ 1/2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Whooperswan/Mongolia/244/2005 (H5) HA.

In another specific embodiment, the stem domain of a cH5/B chimeric influenza hemagglutinin polypeptide is the stem domain of B/Wisconsin/1/2010 HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Indonesia/5/ 2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Bar headed goose/Quinghai/1A/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Whooperswan/Mongolia/244/2005 (H5) HA.

In another specific embodiment, the stem domain of a cH5/B chimeric influenza hemagglutinin polypeptide is the stem domain of B/Brisbane/60/2008 HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Indonesia/5/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Bar headed goose/Quinghai/1A/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Whooperswan/Mongolia/244/2005 (H5) HA.

In certain embodiments, a chimeric influenza hemagglutinin (HA) polypeptide provided herein comprises (i) the stem domain of the hemagglutinin from an influenza B virus and (ii) the globular head domain of the hemagglutinin from an influenza virus of the H7 subtype (sometimes referred to herein as a "cH7/B chimeric influenza hemagglutinin polypeptide"). In a specific embodiment, the stem domain of a cH7/B chimeric influenza hemagglutinin polypeptide is the stem domain of B/Malaysia/2506/2004 HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Rhea/NC/39482/93 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/mallard/Massachusetts/12/2000 (H7) HA.

In another specific embodiment, the stem domain of a cH7/B chimeric influenza hemagglutinin polypeptide is the stem domain of B/Florida/4/2006 HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Rhea/NC/39482/93 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/mallard/Massachusetts/12/2000 (H7) HA.

In another specific embodiment, the stem domain of a cH7/B chimeric influenza hemagglutinin polypeptide is the stem domain of B/Wisconsin/1/2010 HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Rhea/NC/39482/93 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/mallard/Massachusetts/12/2000 (H7) HA.

In another specific embodiment, the stem domain of a cH7/B chimeric influenza hemagglutinin polypeptide is the stem domain of B/Brisbane/60/2008 HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Rhea/NC/39482/93 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/mallard/Massachusetts/12/2000 (H7) HA.

In certain embodiments, a chimeric influenza hemagglutinin (HA) polypeptide provided herein comprises (i) the stem domain of the hemagglutinin from an influenza B virus and (ii) the globular head domain of the hemagglutinin from a different influenza B virus strain (sometimes referred to herein as a "cB/B chimeric influenza hemagglutinin polypeptide"). In a specific embodiment, the stem domain of a cB/B chimeric influenza hemagglutinin polypeptide is the stem domain of B/Malaysia/2506/2004 HA. In another specific embodiment, the stem domain of a cB/B chimeric influenza hemagglutinin polypeptide is the stem domain of B/Malaysia/2506/2004 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Malaysia/2506/2004 HA and the globular head domain of the cB/B chimeric influenza hemagglutinin polypeptide is the globular head domain of B/seal/Netherlands/1/99 HA (or a B/seal/Netherlands/1/99-like influenza virus).

In another specific embodiment, the stem domain of a cB/B chimeric influenza hemagglutinin polypeptide is the stem domain of B/Florida/4/2006 HA. In another specific embodiment, the stem domain of a cB/B chimeric influenza hemagglutinin polypeptide is the stem domain of B/Florida/4/2006 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Florida/4/2006 HA and the globular head domain of the cB/B chimeric influenza hemagglutinin polypeptide is the globular head domain of B/seal/Netherlands/1/99 HA (or a B/seal/Netherlands/1/99-like influenza virus).

In another specific embodiment, the stem domain of a cB/B chimeric influenza hemagglutinin polypeptide is the stem domain of B/Wisconsin/1/2010 HA. In another specific embodiment, the stem domain of a cB/B chimeric influenza hemagglutinin polypeptide is the stem domain of B/Wisconsin/1/2010 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Wisconsin/1/2010 HA and the globular head domain of the cB/B chimeric influenza hemagglutinin polypeptide is the globular head domain of B/seal/Netherlands/1/99 HA (or a B/seal/Netherlands/1/99-like influenza virus).

In another specific embodiment, the stem domain of a cB/B chimeric influenza hemagglutinin polypeptide is the stem domain of B/Brisbane/60/2008 HA. In another specific embodiment, the stem domain of a cB/B chimeric influenza hemagglutinin polypeptide is the stem domain of B/Brisbane/60/2008 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Brisbane/60/2008 HA and the globular head domain of the cB/B chimeric influenza hemagglutinin polypeptide is the globular head domain of B/seal/Netherlands/1/99 HA (or a B/seal/Netherlands/1/99-like influenza virus).

In certain embodiments, a chimeric influenza virus hemagglutinin polypeptide provided herein is monomeric. In certain embodiments, a chimeric influenza virus hemagglutinin polypeptide provided herein is multimeric. In certain embodiments, a chimeric influenza virus hemagglutinin polypeptide provided herein is trimeric.

In certain embodiments, a chimeric influenza virus hemagglutinin polypeptide provided herein comprises a signal peptide. Typically, the signal peptide is cleaved during or after polypeptide expression and translation to yield a mature chimeric influenza virus hemagglutinin polypeptide. In certain embodiments, also provided herein are mature chimeric influenza virus hemagglutinin polypeptides that lack a signal peptide. In embodiments where a chimeric influenza virus hemagglutinin polypeptide provided herein comprises a signal peptide, the signal peptide might be based on any influenza virus signal peptide known to those of skill in the art. In certain embodiments, the signal peptides are based on influenza A signal peptides. In certain embodiments, the signal peptides are based on the signal peptide of an influenza A hemagglutinin selected from the group consisting of H1, H2, H3, H4, H5, H6, H7, H8, H9, H10, H11, H12, H13, H14, H15, H16, and H17. In certain embodiments, the signal peptide might be any signal peptide deemed useful to one of skill in the art.

In certain embodiments, a chimeric influenza virus hemagglutinin polypeptide provided herein comprises a luminal domain. In embodiments where a chimeric influenza virus hemagglutinin polypeptide provided herein comprises a luminal domain, the luminal domain might be based on any influenza luminal domain known to those of skill in the art. In certain embodiments, the luminal domains are based on influenza A luminal domains. In certain embodiments, the luminal domains are based on the luminal domain of an influenza A hemagglutinin selected from the group consisting of H1, H2, H3, H4, H5, H6, H7, H8, H9, H10, H11, H12, H13, H14, H15, H16, and H17. In certain embodiments, the luminal domain might be any luminal domain deemed useful to one of skill in the art. In certain embodiments, the luminal domains are from the same hemagglutinin as the stem domain. In certain embodiments, the luminal domains are from influenza virus strain or subtype as the stem domain HA2 subunit.

In certain embodiments, a chimeric influenza virus hemagglutinin polypeptide provided herein comprises a transmembrane domain. In embodiments where a chimeric influenza virus hemagglutinin polypeptide provided herein comprises a transmembrane domain, the transmembrane domain might be based on any influenza transmembrane domain known to those of skill in the art. In certain embodiments, the transmembrane domains are based on influenza A transmembrane domains. In certain embodiments, the transmembrane domains are based on a transmembrane domain of an influenza A hemagglutinin selected from the group consisting of H1, H2, H3, H4, H5, H6, H7, H8, H9, H10, H11, H12, H13, H14, H15, H16, and H17. In certain embodiments, the transmembrane domain might be any transmembrane domain deemed useful to one of skill in the art. In certain embodiments, the transmembrane domains are from the same hemagglutinin as the stem domain. In certain embodiments, the transmembrane domains are from influenza virus strain or subtype as the stem domain HA2 subunit.

In certain embodiments, a chimeric influenza virus hemagglutinin polypeptide provided herein comprises a cytoplasmic domain. In embodiments where a chimeric influenza virus hemagglutinin polypeptide provided herein comprises a cytoplasmic domain, the cytoplasmic domain might be based on any influenza cytoplasmic domain known to those of skill in the art. In certain embodiments, the cytoplasmic domains are based on influenza A cytoplasmic domains. In certain embodiments, the cytoplasmic domains are based on a cytoplasmic domain of an influenza A hemagglutinin selected from the group consisting of H1, H2, H3, H4, H5, H6, H7, H8, H9, H10, H11, H12, H13, H14, H15, H16, and H17. In certain embodiments, the cytoplasmic domain might be any cytoplasmic domain deemed useful to one of skill in the art. In certain embodiments, the cytoplasmic domains are from the same hemagglutinin as the stem domain. In certain embodiments, the cytoplasmic domains are from influenza virus strain or subtype as the stem domain HA2 subunit.

In certain embodiments, the chimeric influenza virus hemagglutinin polypeptides provided herein further comprise one or more polypeptide domains. Useful polypeptide domains include domains that facilitate purification, folding and cleavage of portions of a polypeptide. For example, a His tag (His-His-His-His-His-His, SEQ ID NO: 17), FLAG epitope or other purification tag can facilitate purification of a chimeric influenza virus hemagglutinin polypeptide provided herein. In some embodiments, the His tag has the sequence, $(His)_n$, wherein n is 2, 3, 4, 5, 6, 7, 8, 9, 10, 11, 12, 13, 14, 15, 16, 17, 18, 19, 20 or greater. A foldon, or trimerization, domain from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, *PLoSONE* 5(9): e12466. The foldon domain can have any foldon sequence known to those of skill in the art (see, e.g., Papanikolopoulou et al., 2004, *J. Biol. Chem.* 279(10):8991-8998, the contents of which are hereby incorporated by reference in their entirety). Examples include GSGYIPEAPRDGQAYVRKDGEWV-LLSTFL (SEQ ID NO:18). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO: 19). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:20)).

In certain embodiments, the chimeric influenza hemagglutinin polypeptides described herein are soluble polypeptides.

In certain embodiments, the influenza hemagglutinin stem domain polypeptides of the chimeric influenza virus hemagglutinin polypeptides described herein maintain the cysteine residues identified in influenza hemagglutinin polypeptides as Ap and Aq in FIG. 1, i.e., the cysteine residues identified in influenza hemagglutinin polypeptides as Ap and Aq in FIG. 1 are maintained in the chimeric influenza virus hemagglutinin polypeptides described herein. Thus, in certain embodiments, in the primary sequence of a chimeric influenza virus hemagglutinin polypeptide described herein: (i) the N-terminal segment of an influenza hemagglutinin stem domain polypeptide ends at the cysteine residue identified as Ap in FIG. 1, (ii) the C-terminal segment of an influenza hemagglutinin stem domain polypeptide begins at the cysteine residue identified as Aq in FIG. 1; and (iii) the influenza hemagglutinin head domain polypeptide (which is heterologous to the influenza hemagglutinin stem domain polypeptide) is between the N-terminal and C-terminal segments of the influenza hemagglutinin stem domain polypeptide.

In certain embodiments, the HA1 N-terminal stem segment of the chimeric influenza virus hemagglutinin polypeptides described herein does not end exactly at $A_p$ (e.g., Cys52 of an HA1 subunit from an H3 hemagglutinin), but at a residue in sequence and structural vicinity to $A_p$. For example, in certain embodiments, the HA1 N-terminal stem segment of the chimeric influenza virus hemagglutinin polypeptides described herein ends at $A_{p-1}$, $A_{p-2}$, $A_{p-3}$, $A_{p-4}$, $A_{p-5}$, $A_{p-6}$, $A_{p-7}$, $A_{p-8}$, $A_{p-9}$, $A_{p-10}$. In certain embodiments, the HA1 N-terminal stem segment of the chimeric influenza virus hemagglutinin polypeptides described herein ends in the range of $A_{p-1}$ to $A_{p-3}$, $A_{p-3}$ to $A_{p-5}$, $A_{p-5}$ to $A_{p-8}$, $A_{p-8}$ to $A_{p-10}$. For example, an HA1 N-terminal stem segment ending at $A_{p-10}$ would end at Leu42 of an H3 hemagglutinin. In certain embodiments, the HA1 N-terminal stem segment of the chimeric influenza virus hemagglutinin polypeptides described herein ends at $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, $A_{p+10}$. In certain embodiments, the HA1 N-terminal stem segment of the chimeric influenza virus hemagglutinin polypeptides described herein ends in the range of $A_{p+1}$ to $A_{p+5}$, $A_{p+5}$ to $A_{p+10}$. The end of an HA1 N-terminal stem segment should be selected in conjunction with the end of the HA1 C-terminal stem segment and the influenza hemagglutinin head domain polypeptide so that the resulting chimeric influenza virus hemagglutinin polypeptide is capable of forming a three-dimensional structure similar to a wild-type influenza hemagglutinin. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the HA1 C-terminal stem segment of the chimeric influenza virus hemagglutinin polypeptides described herein does not start exactly at $A_q$ (e.g., Cys277 of an HA1 subunit from an H3 hemagglutinin), but at a residue in sequence and structural vicinity to $A_q$. For example, in certain embodiments, the HA1 C-terminal stem segment of the chimeric influenza virus hemagglutinin polypeptides described herein starts at about $A_{q-1}$, $A_{q-2}$, $A_{q-3}$, $A_{q-4}$, $A_{q-5}$, $A_{q-6}$, $A_{q-7}$, $A_{q-8}$, $A_{q-9}$, $A_{q-10}$. In certain embodiments, the HA1 C-terminal stem segment of the chimeric influenza virus hemagglutinin polypeptides described herein starts in the range of $A_{q-1}$ to $A_{q-5}$, $A_{q-5}$ to $A_{q-10}$. For example, an HA1 C-terminal stem segment ending at $A_{q-10}$ would start at Isoleucine267 of an H3 hemagglutinin. In certain embodiments, the HA1 C-terminal stem segment of the chimeric influenza virus hemagglutinin polypeptides described herein starts at $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, $A_{q+10}$. In certain embodiments, the HA1 C-terminal stem segment of the chimeric influenza virus hemagglutinin polypeptides described herein starts in the range of $A_{q+1}$ to $A_{q+3}$, $A_{q+3}$ to $A_{q+5}$, $A_{q+5}$ to $A_{q+8}$, $A_{q+8}$ to $A_{q+10}$. The end of an HA1 N-terminal stem segment should be selected in conjunction with the start of the HA1 C-terminal stem segment and the influenza hemagglutinin head domain polypeptide so that the resulting chimeric influenza virus hemagglutinin polypeptide is capable of forming a three-dimensional structure similar to a wild-type influenza hemagglutinin. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In one example, an HA1 N-terminal stem segment of a chimeric influenza virus hemagglutinin polypeptide described herein may end at any one of hemagglutinin amino acid positions 45-48 (using H3 numbering) and an HA1 C-terminal stem segment of the chimeric influenza virus hemagglutinin polypeptide may start at any one of hemagglutinin amino acid positions 282-287 (using H3 numbering); and the heterologous head domain may begin at any one of amino acid positions 46-49 and end at any one of amino acid position 284-289 (using H3 numbering).

In certain embodiments, when the stem domain of the chimeric influenza virus hemagglutinin polypeptides described herein is derived from an influenza B virus, the HA1 N-terminal stem segment may end at, e.g., amino acid 35, 36, 37, 38, 39, 40, 41, 42, 43, 44, 45, 46, 47, 48, 49, or 50 of the HA (in primary amino acid sequence), and the HA1 C-terminal stem segment may begin at, e.g., amino acid 280, 281, 282, 283, 284, 285, 286, 287, 288, 289, 290, 291, 292, 293, 294, 295, 296, 297, 298, 299, or 300 of the HA (in primary amino acid sequence). The globular head domain of the chimeric influenza virus hemagglutinin polypeptide thus would be inserted between the HA1 N-terminal stem segment and the HA1 C-terminal stem segment of the influenza B virus stem domain. For example, in the HA of influenza virus B/Hong Kong/8/73(PDB:2RFT: GenBank:M10298.1), the HA1 N-terminal stem segment would begin with amino acids DRICT (SEQ ID NO:22), with "D" being position 1, and would end at amino acid position 42 (in primary sequence); and the HA1 C-terminal stem segment would begin at amino acid position 288 (in primary sequence) and continue to the end of the C-terminus of the HA.

In certain embodiments, a chimeric influenza hemagglutinin (HA) polypeptide described herein may be conjugated to heterologous proteins, e.g., a major histocompatibility complex (MHC) with or without heat shock proteins (e.g., Hsp10, Hsp20, Hsp30, Hsp40, Hsp60, Hsp70, Hsp90, or Hsp100). In certain embodiments, a chimeric influenza hemagglutinin (HA) polypeptide described herein may be conjugated to immunomodulatory molecules, such as proteins which would target the chimeric influenza hemagglutinin (HA) polypeptide to immune cells such as B cells (e.g., C3d) or T cells. In certain embodiments, chimeric influenza hemagglutinin (HA) polypeptide described herein may be conjugated to proteins which stimulate the innate immune system such as interferon type 1, alpha, beta, or gamma interferon, colony stimulating factors such as granulocyte-macrophage colony-stimulating factor (GM-CSF), interleukin (IL)-1, IL-2, IL-4, IL-5, L-6, L-7, L-12, IL-15, IL-18, IL-21, L-23, tumor necrosis factor (TNF)-β, TNFα, B7.1, B7.2, 4-1BB, CD40 ligand (CD40L), and drug-inducible CD40 (iCD40).

It will be understood by those of skill in the art that the chimeric influenza virus hemagglutinin polypeptides provided herein can be prepared according to any technique known by and deemed suitable to those of skill in the art, including the techniques described herein. In certain embodiments, the chimeric influenza virus hemagglutinin polypeptides are isolated.

5.2 Nucleic Acids Encoding Chimeric Influenza Virus Hemagglutinin (HA) Polypeptides Provided herein are nucleic acids that encode the chimeric influenza hemagglutinin (HA) polypeptides described herein (e.g., the chimeric influenza hemagglutinin (HA) polypeptides described in Section 5.1). Due to the degeneracy of the genetic code, any nucleic acid that encodes a chimeric influenza hemagglutinin (HA) polypeptide described herein is encompassed herein. In certain embodiments, nucleic acids corresponding to, or capable of hybridizing with, naturally occurring influenza virus nucleic acids encoding an HA1 N-terminal stem segment, an HA1 C-terminal stem segment, HA2 domain, luminal domain, transmembrane domain, and/or cytoplasmic domain are used to produce a chimeric influenza hemagglutinin (HA) polypeptide described herein.

Also provided herein are nucleic acids capable of hybridizing to a nucleic acid encoding a chimeric influenza hemagglutinin (HA) polypeptide described herein (e.g., the chimeric influenza hemagglutinin (HA) polypeptides described in Section 5.1). In certain embodiments, provided herein are nucleic acids capable of hybridizing to a fragment of a nucleic acid encoding a chimeric influenza hemagglutinin (HA) polypeptide described herein. In other embodiments, provided herein are nucleic acids capable of hybridizing to the full length nucleic acid encoding a chimeric influenza hemagglutinin (HA) polypeptide described herein. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid encoding a chimeric influenza hemagglutinin (HA) polypeptide described herein is isolated. In certain embodiments, an "isolated" nucleic acid refers to a nucleic acid molecule which is separated from other nucleic acid molecules which are present in the natural source of the nucleic acid. In other words, the isolated nucleic acid can comprise heterologous nucleic acids that are not associated with it in nature. In other embodiments, an "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In addition, provided herein are nucleic acids encoding the individual components of a chimeric influenza hemagglutinin (HA) polypeptide described herein, e.g., nucleic acids encoding the globular head domain, the HA1 N-terminal stem segment, the HA1 C-terminal stem segment and/or the HA2 domain a chimeric influenza hemagglutinin (HA) polypeptide described herein are provided herein. Nucleic acids encoding components of a chimeric influenza hemagglutinin (HA) polypeptide described herein may be assembled using standard molecular biology techniques known to the one of skill in the art so as to yield a chimeric influenza hemagglutinin (HA) polypeptide described herein.

5.3 Expression of Chimeric Influenza Virus Hemagglutinin (HA) Polypeptides

Provided herein are vectors, including expression vectors, containing a nucleic acid encoding a chimeric influenza hemagglutinin (HA) polypeptide described herein (e.g., the chimeric influenza hemagglutinin (HA) polypeptides described in Section 5.1). In a specific embodiment, the vector is an expression vector that is capable of directing the expression of a nucleic acid encoding a chimeric influenza hemagglutinin (HA) polypeptide described herein. Non-limiting examples of expression vectors include, but are not limited to, plasmids and viral vectors, such as replication defective retroviruses, adenoviruses, adeno-associated viruses and baculoviruses. Expression vectors also may include, without limitation, transgenic animals and non-mammalian cells/organisms, e.g., mammalian cells/organisms that have been engineered to perform mammalian N-linked glycosylation.

In some embodiments, provided herein are expression vectors encoding components of a chimeric influenza hemagglutinin (HA) polypeptide described herein. Such vectors may be used to express the components in one or more host cells and the components may be isolated and conjugated together with a linker using techniques known to one of skill in the art.

An expression vector comprises a nucleic acid encoding a chimeric influenza hemagglutinin (HA) polypeptide described herein in a form suitable for expression of the nucleic acid in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome.

Expression vectors can be designed for expression of a chimeric influenza hemagglutinin (HA) polypeptide described herein using prokaryotic (e.g., *E. coli*) or eukaryotic cells (e.g., insect cells (using baculovirus expression vectors, see, e.g., Treanor et al., 2007, JAMA, 297(14): 1577-1582 incorporated by reference herein in its entirety), yeast cells, plant cells, algae or mammalian cells). Examples of yeast host cells include, but are not limited to *S. pombe* and *S. cerevisiae* and examples, infra. Examples of mammalian host cells include, but are not limited to, Crucell Per.C6 cells, Vero cells, CHO cells, VERY cells, BHK cells, HeLa cells, COS cells, MDCK cells, 293 cells, 3T3 cells or WI38 cells. In certain embodiments, the hosts cells are myeloma cells, e.g., NSO cells, 45.6 TG1.7 cells, AF-2 clone 9B5 cells, AF-2 clone 9B5 cells, J558L cells, MOPC 315 cells, MPC-11 cells, NCI-H929 cells, NP cells, NSO/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include SJ9, SJ21, *Trichoplusia ni, Spodoptera fugiperda* and *Bombyx mori*. In a particular embodiment, a mammalian cell culture system (e.g. Chinese hamster ovary or baby hamster kidney cells) is used for expression of a chimeric influenza hemagglutinin (HA) polypeptide. In another embodiment, a plant cell culture system is used for expression of a chimeric influenza hemagglutinin (HA) polypeptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems. In specific embodiments, plant cell culture systems are not used for expression of a chimeric influenza hemagglutinin (HA) polypeptide described herein.

In certain embodiments, plants (e.g., plants of the genus *Nicotiana*) may be engineered to express a chimeric influenza hemagglutinin (HA) polypeptide described herein (e.g., a chimeric influenza hemagglutinin (HA) polypeptide described in Section 5.1). In specific embodiments, plants are engineered to express a chimeric influenza hemagglutinin (HA) polypeptide described herein via an agroinfiltration procedure using methods known in the art. For example, nucleic acids encoding a gene of interest, e.g., a gene encoding a chimeric influenza hemagglutinin (HA) polypeptide described herein, is introduced into a strain of *Agrobacterium*. Subsequently the strain is grown in a liquid culture and the resulting bacteria are washed and suspended into a buffer solution. The plants are then exposed (e.g., via injection or submersion) to the *Agrobacterium* that comprises the nucleic acids encoding a f1 chimeric influenza hemagglutinin (HA) polypeptide described herein such that the *Agrobacterium* transforms the gene of interest to a portion of the plant cells. The chimeric influenza hemagglutinin (HA) polypeptide is then transiently expressed by the plant and can isolated using methods known in the art and described herein. (For specific examples see Shoji et al., 2008, Vaccine, 26(23):2930-2934; and D'Aoust et al., 2008, J. Plant Biotechnology, 6(9):930-940). In a specific embodiment, the plant is a tobacco plant (e.g., *Nicotiana tabacum*). In another specific embodiment, the plant is a relative of the tobacco plant (e.g., *Nicotiana benthamiana*). In another specific embodiment, the chimeric influenza hemagglutinin (HA) polypeptides described herein are expressed in a species of soy. In another specific embodiment, the chimeric influenza hemagglutinin (HA) polypeptides described herein are expressed in a species of corn. In another specific embodiment, the chimeric influenza hemagglutinin (HA) polypeptides described herein are expressed in a species of rice In other embodiments, algae (e.g., *Chlamydomonas reinhardtii*) may be engineered to express a chimeric influenza hemagglutinin (HA) polypeptide described herein, e.g., a chimeric influenza hemagglutinin (HA) polypeptide described in Section 5.1 (see, e.g., Rasala et al., 2010, Plant Biotechnology Journal (Published online Mar. 7, 2010)).

In certain embodiments, the plants used to express the chimeric influenza hemagglutinin (HA) polypeptides described herein are engineered to express components of an N-glycosylation system (e.g., a bacterial or mammalian N-glycosylation system), i.e., the plants can perform N-glycosylation.

Plant cells that can be used to express the chimeric influenza hemagglutinin (HA) polypeptides described herein and methods for the production of proteins utilizing plant cell culture systems are described in, e.g., U.S. Pat. Nos. 5,929,304; 7,504,560; 6,770,799; 6,551,820; 6,136,320; 6,034,298; 5,914,935; 5,612,487; and 5,484,719, U.S. patent application publication Nos. 2009/0208477, 2009/0082548, 2009/0053762, 2008/0038232, 2007/0275014 and 2006/0204487, and Shoji et al., 2008, Vaccine, 26(23):2930-2934, and D'Aoust et al., 2008, J. Plant Biotechnology, 6(9):930-940 (which are incorporated herein by reference in their entirety).

The host cells comprising the nucleic acids that encode the chimeric influenza hemagglutinin (HA) polypeptide described herein can be isolated, e.g., the cells are outside of the body of a subject or are isolated (i.e., separated from) untransfected/untransformed host cells. In certain embodiments, the cells are engineered to express nucleic acids that encode the chimeric influenza hemagglutinin (HA) polypeptides described herein.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding chimeric influenza hemagglutinin (HA) polypeptide. In other embodiments, a host cell is stably transfected with an expression vector containing a nucleic acid encoding a chimeric influenza hemagglutinin (HA) polypeptide.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

As an alternative to recombinant expression of a chimeric influenza hemagglutinin (HA) polypeptide described herein using a host cell, an expression vector containing a nucleic acid encoding a chimeric influenza hemagglutinin (HA) polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a chimeric influenza hemagglutinin (HA) polypeptide described herein.

Once a chimeric influenza hemagglutinin (HA) polypeptide described herein has been produced, it may be isolated or purified by any method known in the art for isolation or purification of a protein, for example, by chromatography (e.g., ion exchange, affinity, particularly by affinity for the specific antigen or a "tag" associated with the antigen (e.g., a HIS tag, strep tag/strep II tag, a maltose binding protein, a glutatione S-transferase tag, myc tag, HA tag), by Protein A, and chromatography (e.g., sizing column chromatography, hydrophopic interaction chromatography (HIC), reversed phase chromatography, simulated moving bed chromatography, size eclusion chromatography, monolith chromatography, convective interaction media chromatography, lectin chromatography)), centrifugation, differential solubility, ultrafiltration, precipitation, or by any other standard technique for the isolation or purification of proteins. In specific embodiments, the isolated/purified chimeric influenza hemagglutinin (HA) polypeptides described herein are soluble, e.g., made soluble using any method known to those of skill in the art, e.g., the methods described herein (see, e.g., Section 6.6.1.2).

Provided herein are methods for producing a chimeric influenza hemagglutinin (HA) polypeptide described herein. In one embodiment, the method comprises culturing a host cell containing a nucleic acid encoding the polypeptide in a suitable medium such that the polypeptide is produced. In some embodiments, the method further comprises isolating the polypeptide from the medium or the host cell.

5.4 Influenza Virus Vectors

In one aspect, provided herein are influenza viruses containing a chimeric influenza hemagglutinin (HA) polypeptide described herein (e.g., a chimeric influenza hemagglutinin (HA) polypeptide described in Section 5.1). In a specific embodiment, the chimeric influenza hemagglutinin (HA) polypeptide described herein is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to a chimeric influenza hemagglutinin (HA) polypeptide described herein. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a chimeric influenza hemagglutinin (HA) polypeptide described herein may be produced by supplying in trans the chimeric influenza hemagglutinin (HA) polypeptide during production of virions using techniques known to one skilled in the art, such as reverse genetics and helper-free plasmid rescue. Alternatively, the replication of a parental influenza virus comprising a genome engineered to express a chimeric influenza hemagglutinin (HA) polypeptide described herein in cells susceptible to infection with the virus wherein hemagglutinin function is provided in trans will produce progeny influenza viruses containing the chimeric influenza hemagglutinin (HA) polypeptide.

In another aspect, provided herein are influenza viruses comprising a genome engineered to express a chimeric influenza hemagglutinin (HA) polypeptide described herein (e.g., a chimeric influenza hemagglutinin (HA) polypeptide described in Section 5.1). In a specific embodiment, the genome of a parental influenza virus is engineered to encode a chimeric influenza hemagglutinin (HA) polypeptide described herein, which is expressed by progeny influenza virus. In another specific embodiment, the genome of a parental influenza virus is engineered to encode a chimeric influenza hemagglutinin (HA) polypeptide described herein, which is expressed and incorporated into the virions of progeny influenza virus. Thus, the progeny influenza virus resulting from the replication of the parental influenza virus contain a chimeric influenza hemagglutinin (HA) polypeptide described herein. The virions of the parental influenza virus may have incorporated into them a chimeric influenza hemagglutinin (HA) polypeptide that contains a stem or head domain from the same or a different type, subtype or strain of influenza virus. Alternatively, the virions of the parental influenza virus may have incorporated into them a moiety that is capable of functionally replacing one or more of the activities of influenza virus hemagglutinin polypeptide (e.g., the receptor binding and/or fusogenic activities of influenza virus hemagglutinin). In certain embodiments, one or more of the activities of the influenza virus hemagglutinin polypeptide is provided by a fusion protein comprising (i) an ectodomain of a polypeptide heterologous to influenza virus fused to (ii) a transmembrane domain, or a transmembrane domain and a cytoplasmic domain of an influenza virus hemagglutinin polypeptide. In a specific embodiment, the virions of the parental influenza virus may have incorporated into them a fusion protein comprising (i) an ectodomain of a receptor binding/fusogenic polypeptide of an infectious agent other than influenza virus fused to (ii) a transmembrane domain, or a transmembrane domain and a cytoplasmic domain of an influenza virus hemagglutinin. For a description of fusion proteins that provide one or more activities of an influenza virus hemagglutinin polypeptide and methods for the production of influenza viruses engineered to express such fusion proteins, see, e.g., International patent application Publication No. WO 2007/064802, published Jun. 7, 2007 and U.S. patent application publication no. 2012/0122185; each of which is incorporated herein by reference in its entirety.

In certain embodiments, the influenza viruses engineered to express one or more of the chimeric influenza hemagglutinin (HA) polypeptides described herein comprise a neuraminidase (NA), or fragment thereof, that is from the same source (e.g., influenza virus strain or subtype) as that from which the globular head domain of the chimeric influenza hemagglutinin (HA) polypeptide is derived. In certain embodiments, the influenza viruses engineered to express one or more of the chimeric influenza hemagglutinin polypeptides described herein comprise a neuraminidase (NA), or fragment thereof, that is from the same source (e.g., influenza virus strain or subtype) as that from which the globular head domain of the chimeric influenza hemagglutinin polypeptide is derived, wherein the globular head domain is heterologous to the stem domain of the HA1 and/or HA2 subunits of the chimeric influenza hemagglutinin polypeptide. In certain embodiments, the influenza viruses engineered to express one or more of the chimeric influenza hemagglutinin polypeptides described herein comprise a neuraminidase (NA), or fragment thereof, that is from the same source (e.g., influenza virus strain or subtype) as that from which the HA stem domain of the chimeric influenza hemagglutinin polypeptide is derived.

In some embodiments, the virions of the parental influenza virus have incorporated into them a heterologous polypeptide. In certain embodiments, the genome of a parental influenza virus is engineered to encode a heterologous polypeptide and a chimeric influenza hemagglutinin (HA) polypeptide, which are expressed by progeny influenza virus. In specific embodiments, the chimeric influenza hemagglutinin (HA) polypeptide, the heterologous polypeptide, or both are incorporated into virions of the progeny influenza virus.

The heterologous polypeptide may be a polypeptide that targets the influenza virus to a particular cell type, such as an antibody that recognizes an antigen on a specific cell type or a ligand that binds a specific receptor on a specific cell type. In some embodiments, the targeting polypeptide replaces the target cell recognition function of the virus. In a specific embodiment, the heterologous polypeptide targets the influenza virus to the same cell types that influenza virus infects in nature. In other specific embodiments, the heterologous polypeptide targets the progeny influenza virus to immune cells, such as B cells, T cells, macrophages or dendritic cells. In some embodiments, the heterologous polypeptide recognizes and binds to cell-specific markers of antigen presenting cells, such as dendritic cells (e.g., such as CD44). In one embodiment, the heterologous polypeptide is DC-SIGN which targets the virus to dendritic cells. In another embodiment, the heterologous polypeptide is an antibody (e.g., a single-chain antibody) that targets the virus to an immune cell, which may be fused with a transmembrane domain from another polypeptide so that it is incorporated into the influenza virus virion. In some embodiments, the antibody is a CD20 antibody, a CD34 antibody, or an antibody against DEC-205. Techniques for engineering viruses to express polypeptides with targeting functions are known in the art. See, e.g., Yang et al., 2006, PNAS 103: 11479-11484 and United States patent application Publication No. 20080019998, published Jan. 24, 2008, and No. 20070020238, published Jan. 25, 2007, the contents of each of which are incorporated herein in their entirety.

In another embodiment, the heterologous polypeptide is a viral attachment protein. Non-limiting examples of viruses whose attachment protein(s) can be used in this aspect are viruses selected from the group of: Lassa fever virus, Hepatitis B virus, Rabies virus, Newcastle disease virus (NDV), a retrovirus such as human immunodeficiency virus, tick-borne encephalitis virus, vaccinia virus, herpesvirus, poliovirus, alphaviruses such as Semliki Forest virus, Ross River virus, and Aura virus (which comprise surface glycoproteins such as E1, E2, and E3), Borna disease virus, Hantaan virus, foamyvirus, and SARS-CoV virus.

In one embodiment, a flavivirus surface glycoprotein may be used, such as Dengue virus (DV) E protein. In some embodiments, a Sindbis virus glycoprotein from the alphavirus family is used (K. S. Wang, R. J. Kuhn, E. G. Strauss, S. Ou, J. H. Strauss, *J. Virol.* 66, 4992 (1992)). In certain embodiments, the heterologous polypeptide is derived from an NDV HN or F protein; a human immunodeficiency virus (HIV) gp160 (or a product thereof, such as gp41 or gp120); a hepatitis B virus surface antigen (HBsAg); a glycoprotein of herpesvirus (e.g., gD, gE); or VP 1 of poliovirus.

In another embodiment, the heterologous polypeptide is derived from any non-viral targeting system known in the art. In certain embodiments, a protein of a nonviral pathogen such as an intracellular bacteria or protozoa is used. In some embodiments, the bacterial polypeptide is provided by, e.g., *Chlamydia, Rikettsia, Coxelia, Listeria, Brucella*, or *Legionella*. In some embodiments, protozoan polypeptide is provided by, e.g., Plasmodia species, *Leishmania* spp., *Toxoplasma gondii*, or *Trypanosoma cruzi*. Other exemplary targeting systems are described in Waehler et al., 2007, "Engineering targeted viral vectors for gene therapy," Nature Reviews Genetics 8: 573-587, which is incorporated herein in its entirety.

In certain embodiments, the heterologous polypeptide expressed by an influenza virus has immunopotentiating (immune stimulating) activity. Non-limiting examples of immunopotentiating polypeptides include, but are not limited to, stimulation molecules, cytokines, chemokines, antibodies and other agents such as Flt-3 ligands. Specific examples of polypeptides with immunopotentiating activity include: interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40) (see, e.g., Hanks, B. A., et al. 2005. Nat Med 11:130-137, which is incorporated herein by reference in its entirety.)

Since the genome of influenza A and B viruses consist of eight (8) single-stranded, negative sense segments (influenza C viruses consist of seven (7) single-stranded, negative sense segments), the genome of a parental influenza virus may be engineered to express a chimeric influenza hemagglutinin (HA) polypeptide described herein (and any other polypeptide, such as a heterologous polypeptide) using a recombinant segment and techniques known to one skilled in the art, such a reverse genetics and helper-free plasmid rescue. In one embodiment, the recombinant segment comprises a nucleic acid encoding the chimeric influenza hemagglutinin (HA) polypeptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a specific embodiment, the recombinant segment uses the 3' and 5' noncoding and/or nontranslated sequences of segments of influenza viruses that are from a different or the same type, subtype or strain as the parental influenza virus. In some embodiments, the recombinant segment comprises the 3' noncoding region of an influenza virus hemagglutinin polypeptide, the untranslated regions of an influenza virus hemagglutinin polypeptide, and the 5' non-coding region of an influenza virus hemagglutinin polypeptide. In specific embodiments, the recombinant segment comprises the 3' and 5' noncoding and/or nontranslated sequences of the HA segment of an influenza virus that is the same type, subtype or strain as the influenza virus type, subtype or strain as the HA1 N-terminal stem segment, the HA1 C-terminal stem segment, the globular head domain, and/or the HA2 of a chimeric influenza hemagglutinin (HA) polypeptide. In certain embodiments, the recombinant segment encoding the chimeric influenza hemagglutinin (HA) polypeptide may replace the HA segment of a parental influenza virus. In some embodiments, the recombinant segment encoding the chimeric influenza hemagglutinin (HA) polypeptide may replace the NS 1 gene of the parental influenza virus. In some embodiments, the recombinant segment encoding the chimeric influenza hemagglutinin (HA) polypeptide may replace the NA gene of the parental influenza virus. Exemplary influenza virus strains that can be used to express the chimeric influenza hemagglutinin (HA) polypeptides described herein include Ann Arbor/i/50, A/Ann Arbor/6/60, A/Puerto Rico/8/34, A/South Dakota/6/2007, A/Uruguay/716/2007, A/California/07/2009, A/Perth/16/2009, A/Brisbane/59/2007, A/Brisbane/10/2007, A/Leningrad/134/47/57, B/Brisbane/60/2008, B/Yamagata/1/88, A/Panama/2007/99, A/Wyoming/3/03, and A/WSN/33.

In some embodiments, an influenza virus hemagglutinin gene segment encodes a chimeric influenza hemagglutinin (HA) polypeptide described herein. In specific embodiments, the influenza virus hemagglutinin gene segment and at least one other influenza virus gene segment comprise packaging signals that enable the influenza virus hemagglutinin gene segment and the at least one other gene segment to segregate together during replication of a recombinant influenza virus (see, Gao & Palese 2009, PNAS 106:15891-15896; International Application Publication No. WO11/014645; and U.S. Patent Application Publication No. 2012/0244183).

In some embodiments, the genome of a parental influenza virus may be engineered to express a chimeric influenza hemagglutinin (HA) polypeptide described herein using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. Nos. 6,887,699, 6,001,634, 5,854,037, 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238.). Thus, in certain embodiments, a parental influenza virus is engineered to contain a bicistronic RNA segment that expresses the chimeric influenza hemagglutinin (HA) polypeptide and another polypeptide, such as a gene expressed by the parental influenza virus. In some embodiments, the parental influenza virus gene is the HA gene. In some embodiments, the parental influenza virus gene is the NA gene. In some embodiments, the parental influenza virus gene is the NS 1 gene.

Techniques known to one skilled in the art may be used to produce an influenza virus containing a chimeric influenza hemagglutinin (HA) polypeptide described herein and an influenza virus comprising a genome engineered to express a chimeric influenza hemagglutinin (HA) polypeptide described herein. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing chimeric influenza hemagglutinin (HA) polypeptide described herein and an influenza virus comprising a genome engineered to express a chimeric influenza hemagglutinin (HA) polypeptide described herein. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; Neumann et al., 1999, Proc. Natl. Acad. Sci. USA 96:9345-9350; Enami and Enami, 2000, J. Virol. 74(12):5556-5561; and Pleschka et al., 1996, J. Virol. 70(6):4188-4192, which are incorporated herein by reference in their entireties.

The influenza viruses described herein may be propagated in any substrate that allows the virus to grow to titers that permit their use in accordance with the methods described herein. In one embodiment, the substrate allows the viruses to grow to titers comparable to those determined for the corresponding wild-type viruses. In certain embodiments, the substrate is one which is biologically relevant to the influenza virus or to the virus from which the HA function is derived. In a specific embodiment, an attenuated influenza virus by virtue of, e.g., a mutation in the NS 1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In certain embodiments, the virus is propagated in MDCK cells, Vero cells, 293T cells, or other cell lines known in the art. In certain embodiments, the virus is propagated in cells derived from embryonated eggs.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from two or more influenza A virus subtypes or strains.

In some embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from two or more influenza B virus subtypes or strains. In other embodiments, the influenza viruses, or influenza virus polypeptides, genes or genome segments for use as described herein are obtained or derived from a combination of influenza A and influenza B virus subtypes or strains.

In some embodiments, the influenza viruses, or influenza virus polypeptides, genes or genome segments for use as described herein are obtained or derived from an influenza C virus. In certain embodiments, the influenza viruses, or influenza virus polypeptides, genes or genome segments for use as described herein are obtained or derived from two or more influenza C virus subtypes or strains. In other embodiments, the influenza viruses, or influenza virus polypeptides, genes or genome segments for use as described herein are obtained or derived from a combination of influenza C virus and influenza A virus and/or influenza B virus subtypes or strains.

In certain embodiments, the influenza viruses provided herein have an attenuated phenotype. In specific embodiments, the attenuated influenza virus is based on influenza A virus. In other embodiments, the attenuated influenza virus is based on influenza B virus. In yet other embodiments, the attenuated influenza virus is based on influenza C virus. In other embodiments, the attenuated influenza virus may comprise genes or genome segments from one or more strains or subtypes of influenza A, influenza B, and/or influenza C virus. In some embodiments, the attenuated backbone virus comprises genes from an influenza A virus and an influenza B virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses). Alternatively, naturally occurring attenuated influenza viruses may be used as influenza virus backbones for the influenza virus vectors.

In one embodiment, an influenza virus may be attenuated, at least in part, by virtue of substituting the HA gene of the parental influenza virus with a chimeric influenza hemagglutinin (HA) polypeptide described herein. In some embodiments, an influenza virus may be attenuated, at least in part, by engineering the influenza virus to express a mutated NS1 gene that impairs the ability of the virus to antagonize the cellular interferon (IFN) response. Examples of the types of mutations that can be introduced into the influenza virus NS 1 gene include deletions, substitutions, insertions and combinations thereof. One or more mutations can be introduced anywhere throughout the NS 1 gene (e.g., the N-terminus, the C-terminus or somewhere in between) and/or the regulatory element of the NS 1 gene. In one embodiment, an attenuated influenza virus comprises a genome having a mutation in an influenza virus NS1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated influenza virus comprises a genome having a mutation in an influenza virus NS1 gene such that it encodes an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and influenza viruses comprising a mutated NS 1, see, e.g., U.S. Pat. Nos. 6,468,544 and 6,669,943; and Li et al., 1999, J. Infect. Dis. 179:1132-1138, each of which is incorporated by reference herein in its entirety.

In another embodiment, an influenza virus may be attenuated, at least in part, by mutating an NA or M gene of the virus as described in the literature.

5.5 Non-Influenza Virus Vectors

In one aspect, provided herein are non-influenza viruses containing a chimeric influenza hemagglutinin (HA) polypeptide described herein (e.g., a chimeric influenza hemagglutinin (HA) polypeptide described in Section 5.1). In a specific embodiment, the chimeric influenza hemagglutinin (HA) polypeptide described herein is incorporated into the virions of the non-influenza virus. In a specific embodiment, the chimeric influenza hemagglutinin (HA) polypeptide described herein is contained in/expressed by a purified (e.g., plaque purified) or isolated virus. The non-influenza viruses may be conjugated to moieties that target the viruses to particular cell types, such as immune cells. In some embodiments, the virions of the non-influenza virus have incorporated into them or express a heterologous polypeptide in addition to a chimeric influenza hemagglutinin (HA) polypeptide described herein. The heterologous polypeptide may be a polypeptide that has immunopotentiating activity, or that targets the non-influenza virus to a particular cell type, such as an antibody that recognizes an antigen on a specific cell type or a ligand that binds a specific receptor on a specific cell type. See Section 5.4 supra for examples of such heterologous polypeptides.

Non-influenza viruses containing/expressing a chimeric influenza hemagglutinin (HA) polypeptide described herein can be produced using techniques known to those skilled in the art. Non-influenza viruses containing a chimeric influenza hemagglutinin (HA) polypeptide described herein may be produced by supplying in trans the chimeric influenza hemagglutinin (HA) polypeptide during production of virions using techniques known to one skilled in the art. Alternatively, the replication of a parental non-influenza virus comprising a genome engineered to express a chimeric influenza hemagglutinin (HA) polypeptide described herein in cells susceptible to infection with the virus wherein hemagglutinin function is provided in trans will produce progeny viruses containing the chimeric influenza hemagglutinin (HA) polypeptide.

Any virus type, subtype or strain including, but not limited to, naturally occurring strains, variants or mutants, mutagenized viruses, reassortants and/or genetically modified viruses may be used as a non-influenza virus vector. In a specific embodiment, the parental non-influenza virus is not a naturally occurring virus. In another specific embodiment, the parental non-influenza virus is a genetically engineered virus. In certain embodiments, an enveloped virus is preferred for the expression of a membrane bound chimeric influenza hemagglutinin (HA) polypeptide described herein.

In an exemplary embodiment, the non-influenza virus vector is a Newcastle disease virus (NDV). In another embodiment, the non-influenza virus vector is a vaccinia virus. In another embodiment, the non-influenza virus vector is a baculovirus. In other exemplary, non-limiting, embodiments, the non-influenza virus vector is adenovirus, adeno-associated virus (AAV), hepatitis B virus, retrovirus (such as, e.g., a gammaretrovirus such as Mouse Stem Cell Virus (MSCV) genome or Murine Leukemia Virus (MLV), e.g., Moloney murine leukemia virus, oncoretrovirus, or lentivirus), an alphavirus (e.g., Venezuelan equine encephalitis virus), a rhabdovirus (such as vesicular stomatitis virus (VSV) or papillomaviruses), poxvirus (such as, e.g., vaccinia virus, a MVA-T7 vector, or fowlpox), metapneumovirus, measles virus, herpesvirus (such as herpes simplex virus), or foamyvirus. See, e.g., Lawrie and Tumin, 1993, Cur. Opin. Genet. Develop. 3, 102-109 (retroviral vectors); Bett et al., 1993, J. Virol. 67, 5911 (adenoviral vectors); Zhou et al., 1994, J. Exp. Med. 179, 1867 (adeno-associated virus vectors); Dubensky et al., 1996, J. Virol. 70, 508-519 (viral vectors from the pox family including vaccinia virus and the avian pox viruses and viral vectors from the alpha virus genus such as those derived from Sindbis and Semliki Forest Viruses); U.S. Pat. No. 5,643,576 (Venezuelan equine encephalitis virus); WO 96/34625 (VSV); Ohe et al., 1995, Human Gene Therapy 6, 325-333; Woo et al., WO 94/12629; Xiao & Brandsma, 1996, Nucleic Acids. Res. 24, 2630-2622 (papillomaviruses); and Bukreyev and Collins, 2008, Curr Opin Mol Ther. 10:46-55 (NDV), each of which is incorporated by reference herein in its entirety.

In a specific embodiment, the non-influenza virus vector is NDV. Any NDV type, subtype or strain may serve as the backbone that is engineered to express a chimeric influenza hemagglutinin (HA) polypeptide described herein, including, but not limited to, naturally-occurring strains, variants or mutants, mutagenized viruses, reassortants and/or genetically engineered viruses. In a specific embodiment, the NDV that serves as the backbone for genetic engineering is a naturally-occurring strain. In certain embodiments, the NDV that serves as the backbone for genetic engineering is a lytic strain. In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is a mesogenic strain. In other embodiments, the NDV that serves as the backbone for genetic engineering is a velogenic strain. Specific examples of NDV strains include, but are not limited to, the 73-T strain, Ulster strain, MTH-68 strain, Italien strain, Hickman strain, PV701 strain, Hitchner B 1 strain, La Sota strain, YG97 strain, MET95 strain, and F48E9 strain. In a specific embodiment, the NDV that serves as the backbone for genetic engineering is the Hitchner B 1 strain. In another specific embodiment, the NDV that serves as the backbone for genetic engineering is the La Sota strain.

In one embodiment, the NDV used as the backbone for a non-influenza virus vector is engineered to express a modified F protein in which the cleavage site of the F protein is replaced with one containing one or two extra arginine residues, allowing the mutant cleavage site to be activated by ubiquitously expressed proteases of the furin family. Specific examples of NDVs that express such a modified F protein include, but are not limited to, rNDV/F2aa and rNDV/F3aa. For a description of mutations introduced into a NDV F protein to produce a modified F protein with a mutated cleavage site, see, e.g., Park et al. (2006) "Engineered viral vaccine constructs with dual specificity: Avian influenza and Newcastle disease." PNAS USA 103: 8203-2808, which is incorporated herein by reference in its entirety.

In one embodiment, the non-influenza virus vector is a poxvirus. A poxvirus vector may be based on any member of the poxviridae, in particular, a vaccinia virus or an avipox virus (e.g., such as canarypox, fowlpox, etc.) that provides suitable sequences for vaccine vectors. In a specific embodiment, the poxviral vector is a vaccinia virus vector. Suitable vaccinia viruses include, but are not limited to, the Copenhagen (VC-2) strain (Goebel, et al., Virol 179: 247-266, 1990; Johnson, et al., Virol. 196: 381-401, 1993), modified Copenhagen strain (NYVAC) (U.S. Pat. No. 6,265,189), the WYETH strain and the modified Ankara (MVA) strain (Antoine, et al., Virol. 244: 365-396, 1998). Other suitable poxviruses include fowlpox strains such as ALVAC and TROVAC vectors that provide desirable properties and are highly attenuated (see, e.g., U.S. Pat. No. 6,265,189; Tartaglia et al., In AIDS Research Reviews, Koff, et al., eds., Vol. 3, Marcel Dekker, N.Y., 1993; and Tartaglia et al., 1990, Reviews in Immunology 10: 13-30, 1990).

Methods of engineering non-influenza viruses to express influenza polypeptides are well known in the art, as are methods for attenuating, propagating, and isolating and purifying such viruses. For such techniques with respect to NDV vectors, see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety. For such techniques with respect to poxviruses, see, e.g., Piccini, et al., Methods of Enzymology 153: 545-563, 1987; International Publication No. WO 96/11279; U.S. Pat. Nos. 4,769,330; 4,722,848; 4,769,330; 4,603,112; 5,110, 587; 5,174,993; EP 83 286; EP 206 920; Mayr et al., Infection 3: 6-14, 1975; and Sutter and Moss, Proc. Natl. Acad. Sci. USA 89: 10847-10851, 1992. In certain embodiments, the non-influenza virus is attenuated.

Exemplary considerations for the selection of a non-influenza virus vector, particularly for use in compositions for administration to a subject, are safety, low toxicity, stability, cell type specificity, and immunogenicity, particularly, antigenicity of the chimeric influenza hemagglutinin (HA) polypeptide described herein expressed by the non-influenza virus vector.

5.6 Virus-Like Particles and Virosomes

The chimeric influenza hemagglutinin (HA) polypeptides described herein (e.g., the chimeric influenza hemagglutinin (HA) polypeptides described in Section 5.1) can be incorporated into virus-like particle (VLP) vectors, e.g., purified/isolated VLPs. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLPs comprise a chimeric influenza hemagglutinin (HA) polypeptide described herein and a viral structural protein, such as HIV gag. In a specific embodiment, the VLPs comprise a chimeric influenza hemagglutinin (HA) polypeptide described herein and an HIV gag polypeptide.

Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992)89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein. In a specific embodiment, the VLPs comprising chimeric influenza hemagglutinin (HA) polypeptides described herein are generated using baculovirus. In other embodiments, the VLPs comprising chimeric influenza hemagglutinin (HA) polypeptide described herein are generated using 293T cells.

In specific embodiments, VLPs, e.g., VLPs comprising a chimeric influenza hemagglutinin (HA) polypeptide described herein, are expressed in cells (e.g., 293T cells). In certain embodiments, the VLPs are expressed in cells that express surface glycoproteins that comprise sialic acid. In accordance with such embodiments, the cells are cultured in the presence of neuraminidase (e.g., viral of bacterial neuraminidase). In certain embodiments, VLPs, e.g., VLPs comprising a chimeric influenza hemagglutinin (HA) polypeptide described herein, are expressed in cells that do not express surface glycoproteins that comprise sialic acid.

In a specific embodiment, a chimeric influenza hemagglutinin (HA) polypeptide described herein may be incorporated into a virosome. A virosome containing a chimeric influenza hemagglutinin (HA) polypeptide described herein may be produced using techniques known to those skilled in the art. For example, a virosome may be produced by disrupting a purified virus, extracting the genome, and reassembling particles with the viral proteins (e.g., a chimeric influenza hemagglutinin (HA) polypeptide described herein) and lipids to form lipid particles containing viral proteins.

5.7 Bacterial Vectors

In a specific embodiment, bacteria may be engineered to express a chimeric influenza hemagglutinin (HA) polypeptide described herein (e.g., a chimeric influenza hemagglutinin (HA) polypeptide described in Section 5.1). Suitable bacteria for expression of a chimeric influenza hemagglutinin (HA) polypeptide described herein include, but are not limited to, *Listeria, Salmonella, Shigella* sp., *Mycobacterium tuberculosis, E. coli, Neisseria meningitides, Brucella abortus, Brucella melitensis, Borrelia burgdorferi, Lactobacillus, Campylobacter, Lactococcus, Bifidobacterium*, and *Francisella tularensis*. In a specific embodiment, the bacteria engineered to express a chimeric influenza hemagglutinin (HA) polypeptide described herein are attenuated. Techniques for the production of bacteria engineered to express a heterologous polypeptide are known in the art and can be applied to the expression of a chimeric influenza hemagglutinin (HA) polypeptide described herein. See, e.g., United States Patent Application Publication No. 20080248066, published Oct. 9, 2008, and United States Patent Application Publication No. 20070207171, published Sep. 6, 2007, each of which are incorporated by reference herein in their entirety. In certain embodiments, the bacterial vectors used herein possess the ability to perform N-linked glycosylation, e.g., such bacteria naturally possess N-glycosylation machinery (e.g., *Campylobacter*) or have been genetically engineered to possess N-glycosylation machinery.

5.8 Generation of Antibodies Against Chimeric Influenza Hemagglutinin (HA) Polypeptides The chimeric influenza hemagglutinin (HA) polypeptides described herein (e.g., the chimeric influenza hemagglutinin (HA) polypeptides described in Section 5.1), nucleic acids encoding such polypeptides, or vectors comprising such nucleic acids or polypeptides described herein may be used to elicit neutralizing antibodies against influenza, for example, against the stalk region of an influenza virus hemagglutinin polypeptide. In a specific embodiment, the chimeric influenza hemagglutinin (HA) polypeptides, nucleic acids encoding such polypeptides, or vectors comprising such nucleic acids or polypeptides described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

In certain embodiments, human antibodies directed against the chimeric influenza hemagglutinin (HA) polypeptides described herein can be generated using non-human subjects (e.g., transgenic mice) that are capable of producing human antibodies. For example, human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. Companies such as Abgenix, Inc. (Freemont, Calif.), Genpharm (San Jose, Calif.), and Medarex, Inc. (Princeton, N.J.) can be engaged to provide human antibodies directed against a selected antigen. In addition, non-human subjects may be transplanted with human peripheral blood leukocytes, splenocytes, or bone marrow (e.g., Trioma Techniques XTL) so that human antibodies that bind to a chimeric influenza hemagglutinin (HA) polypeptide described herein are generated.

Alternatively, the chimeric influenza hemagglutinin (HA) polypeptides described herein may be used to screen for antibodies from antibody libraries. For example, an isolated chimeric influenza hemagglutinin (HA) polypeptide may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to the isolated chimeric influenza hemagglutinin (HA) polypeptide. Any screening assay, such as a panning assay, ELISA, surface plasmon resonance, or other antibody screening assay known in the art may be used to screen for antibodies that bind to the chimeric influenza hemagglutinin (HA) polypeptide. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies identified in the methods described herein may be tested for neutralizing activity and lack of autoreactivity using the biological assays known in the art or described herein. In one embodiment, an antibody isolated from a non-human animal or an antibody library neutralizes a hemagglutinin polypeptide from more than one influenza subtype. In some embodiments, an antibody elicited or identified using a chimeric influenza hemagglutinin (HA) polypeptide described herein, a nucleic acid encoding such a polypeptide, or a vector encoding such a nucleic acid or polypeptide neutralizes an influenza H3 virus. In some embodiments, an antibody elicited or identified using a chimeric influenza hemagglutinin (HA) polypeptide described herein, a nucleic acid encoding such a polypeptide, or a vector comprising such a nucleic acid or polypeptide neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more influenza A viruses and one or more influenza B viruses. In particular embodiments, the neutralizing antibody is not, or does not bind the same epitope as CR6261, CR6325, CR6329, CR6307, CR6323, 2A, D7, D8, F10, G17, H40, A66, D80, E88, E90, H98, C179 (produced by hybridoma FERM BP-4517; clones sold by Takara Bio, Inc. (Otsu, Shiga, Japan)), and/or AI3C (FERM BP-4516); or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. *Proc Natl Acad Sci USA* 105: 5986-5991; Sui et al. (2009) Structural and functional bases for broad-spectrum neutralization of avian and human influenza A viruses. *Nat Struct Mol Biol* 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/

US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9. In particular embodiments, the neutralizing antibody does not use the Ig VH1-69 segment. In some embodiments, the interaction of the neutralizing antibody with the antigen is not mediated exclusively by the heavy chain.

Antibodies identified or elicited using a chimeric influenza hemagglutinin (HA) polypeptide described herein, a nucleic acid encoding such a polypeptide, or a vector comprising such a nucleic acid or polypeptide include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a chimeric influenza hemagglutinin (HA) polypeptide described herein, nucleic acids encoding such a polypeptide or a vector comprising such a nucleic acid or polypeptide may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize hemagglutinin polypeptides and the specificity of the antibodies for the polypeptides may be tested prior to using the antibodies in passive immunotherapy.

Antibodies elicited or identified using a chimeric influenza hemagglutinin (HA) polypeptide described herein, a nucleic acid encoding such a polypeptide, or a vector comprising such a nucleic acid or polypeptide may be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

Antibodies elicited or identified using a chimeric influenza hemagglutinin (HA) polypeptide described herein, a nucleic acid encoding such a polypeptide, or a vector comprising such a nucleic acid or polypeptide may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann. Immunol. (Paris) 125c:373; Jerne et al., 1982, EMBO J. 1:234, incorporated herein by reference in its entirety).

5.9 Stimulation of Cells Chimeric Influenza Hemagglutinin (HA) Polypeptides

In another aspect, provided herein are methods for stimulating cells ex vivo with a chimeric influenza hemagglutinin (HA) polypeptide described herein (e.g., a chimeric influenza hemagglutinin (HA) polypeptide described in Section 5.1). Such cells, e.g., dendritic cells, may be used in vitro to generate antibodies against the chimeric influenza hemagglutinin (HA) polypeptide or may themselves be administered to a subject by, e.g., an adoptive transfer technique known in the art. See, e.g., United States patent application Publication No. 20080019998, published Jan. 24, 2008, which is incorporated herein by reference in its entirety, for a description of adoptive transfer techniques. In certain embodiments, when cells that have been stimulated ex vivo with a chimeric influenza hemagglutinin (HA) polypeptide described herein are administered to a subject, the cells are not mammalian cells (e.g., CB-1 cells).

In one non-limiting example, a vector, e.g., an influenza virus vector, engineered to express a chimeric influenza hemagglutinin (HA) polypeptide described herein can be used to generate dendritic cells (DCs) that express the chimeric influenza hemagglutinin (HA) polypeptide and display immunostimulatory properties directed against an influenza virus hemagglutinin polypeptide. Such DCs may be used to expand memory T cells and are potent stimulators of T cells, including chimeric influenza hemagglutinin (HA) polypeptide-specific cytotoxic T lymphocyte clones. See Strobel et al., 2000, Human Gene Therapy 11:2207-2218, which is incorporated herein by reference in its entirety.

A chimeric influenza hemagglutinin (HA) polypeptide described herein may be delivered to a target cell in any way that allows the polypeptide to contact the target cell, e.g., a DC, and deliver the polypeptide to the target cell. In certain embodiments, the chimeric influenza hemagglutinin (HA) polypeptide described herein is delivered to a subject, as described herein. In some such embodiments, cells contacted with the polypeptide may be isolated and propagated.

In certain embodiments, a chimeric influenza hemagglutinin (HA) polypeptide described herein is delivered to a target cell in vitro. Techniques known to one of skill in the art may be used to deliver the polypeptide to target cells. For example, target cells may be contacted with the polypeptide in a tissue culture plate, tube or other container. The polypeptide may be suspended in media and added to the wells of a culture plate, tube or other container. The media containing the polypeptide may be added prior to plating of the cells or after the cells have been plated. The target cells are preferably incubated with the polypeptide for a sufficient amount of time to allow the polypeptide to contact the cells. In certain embodiments, the cells are incubated with the polypeptide for about 1 hour or more, about 5 hours or more, about 10 hours or more, about 12 hours or more, about 16 hours or more, about 24, hours or more, about 48 hours or more, about 1 hour to about 12 hours, about 3 hours to about 6 hours, about 6 hours to about 12 hours, about 12 hours to about 24 hours, or about 24 hours to about 48 hours. In certain embodiments, wherein the chimeric influenza hemagglutinin (HA) polypeptide is in a virus, the contacting of the target cells comprises infecting the cells with the virus.

The target cells may be from any species, including, e.g., humans, mice, rats, rabbits and guinea pigs. In some embodiments, target cells are DCs obtained from a healthy subject or a subject in need of treatment. In certain embodiments, target cells are DCs obtained from a subject in whom it is desired to stimulate an immune response to the polypeptide. Methods of obtaining cells from a subject are well known in the art.

5.10 Compositions

The nucleic acids, vectors, polypeptides, bacteria, antibodies, and/or cells described herein (sometimes referred to herein as "active compounds") may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing or treating an influenza virus disease.

In one embodiment, a pharmaceutical composition comprises a chimeric influenza hemagglutinin (HA) polypeptide described herein (e.g., a chimeric influenza hemagglutinin (HA) polypeptide described in Section 5.1), in an admixture with a pharmaceutically acceptable carrier. In another embodiment, a pharmaceutical composition comprises a nucleic acid encoding a chimeric influenza hemagglutinin (HA) polypeptide described herein (e.g., a chimeric influenza hemagglutinin (HA) polypeptide described in Section 5.1), in an admixture with a pharmaceutically acceptable carrier. In another embodiment, a pharmaceutical composition comprises an expression vector comprising a nucleic acid encoding a chimeric influenza hemagglutinin (HA) polypeptide described herein (e.g., a chimeric influenza hemagglutinin (HA) polypeptide described in Section 5.1), in an admixture with a pharmaceutically acceptable carrier. In another embodiment, a pharmaceutical composition comprises an influenza virus or non-influenza virus containing a chimeric influenza hemagglutinin (HA) polypeptide described herein (e.g., a chimeric influenza hemagglutinin (HA) polypeptide described in Section 5.1), in an admixture with a pharmaceutically acceptable carrier. In another embodiment, a pharmaceutical composition comprises an influenza virus or non-influenza virus having a genome engineered to express a chimeric influenza hemagglutinin (HA) polypeptide described herein (e.g., a chimeric influenza hemagglutinin (HA) polypeptide described in Section 5.1), in admixture with a pharmaceutically acceptable carrier. In another embodiment, a pharmaceutical composition comprises a virus-like particle or virosome containing a chimeric influenza hemagglutinin (HA) polypeptide described herein (e.g., a chimeric influenza hemagglutinin (HA) polypeptide described in Section 5.1), in an admixture with a pharmaceutically acceptable carrier. In another embodiment, a pharmaceutical composition comprises a bacteria expressing or engineered to express a chimeric influenza hemagglutinin (HA) polypeptide described herein (e.g., a chimeric influenza hemagglutinin (HA) polypeptide described in Section 5.1), in an admixture with a pharmaceutically acceptable carrier. In another embodiment, a pharmaceutical composition comprises cells stimulated with a chimeric influenza hemagglutinin (HA) polypeptide described herein (e.g., a chimeric influenza hemagglutinin (HA) polypeptide described in Section 5.1), in an admixture with a pharmaceutically acceptable carrier.

In some embodiments, a pharmaceutical composition may comprise one or more other therapies in addition to a therapy that utilizes a chimeric influenza hemagglutinin (HA) polypeptide described herein.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. In some embodiments, the active compounds are prepared with carriers that increase the protection of the compound against rapid elimination from the body, such as a controlled release formulation, including implants and microencapsulated delivery systems. Methods for preparation of such formulations will be apparent to those skilled in the art. Liposomes or micelles can also be used as pharmaceutically acceptable carriers. These can be prepared according to methods known to those skilled in the art, for example, as described in U.S. Pat. No. 4,522,811. In certain embodiments, the pharmaceutical compositions comprise one or more adjuvants.

In specific embodiments, the immunogenic compositions described herein are monovalent formulations, e.g., monovalent formulations comprising a cH5/1 chimeric influenza hemagglutinin polypeptide described herein, a cH5/3 chimeric influenza hemagglutinin polypeptide described herein, a cH7/3 chimeric influenza hemagglutinin polypeptide described herein, a cH5/B chimeric influenza hemagglutinin polypeptide described herein, a cH7/B chimeric influenza hemagglutinin polypeptide described herein, or a cHB/B chimeric influenza hemagglutinin polypeptide described herein.

In other specific embodiments, the immunogenic compositions described herein are multivalent formulations, e.g., bivalent and trivalent formulations. In one example, a multivalent formulation comprises more than one vector expressing a chimeric influenza hemagglutinin (HA) polypeptide described herein. In certain embodiments, a multivalent formulation may comprise one or more different chimeric influenza hemagglutinin (HA) polypeptides described herein expressed using a single vector. In specific embodiments, a bivalent vaccine formulation provided herein may comprise a combination of a cH5/1 chimeric influenza hemagglutinin polypeptide described herein and a cH5/3 chimeric influenza hemagglutinin polypeptide described herein; or a combination of a cH5/1 chimeric influenza hemagglutinin polypeptide described herein and a cH7/3 chimeric influenza hemagglutinin polypeptide described herein. In specific embodiments, a trivalent vaccine formulation provided herein may comprise (i) a combination of a cH5/1 chimeric influenza hemagglutinin polypeptide described herein and a cH5/3 chimeric influenza hemagglutinin polypeptide described herein and either of a cH5/B, a cH7/B, or a cB/B chimeric influenza hemagglutinin polypeptide described herein; or (ii) a combination of a cH5/1 chimeric influenza hemagglutinin polypeptide described herein and a cH7/3 chimeric influenza hemagglutinin polypeptide described herein and either of a cH5/B, a cH7/B, or a cB/B chimeric influenza hemagglutinin polypeptide described herein.

In certain embodiments, the pharmaceutical compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative. In a specific embodiment, thimerosal is used during the manufacture of a pharmaceutical composition described herein and the thimerosal is removed via purification steps following production of the pharmaceutical composition, i.e., the pharmaceutical composition contains trace amounts of thimerosal (<0.3 μg of mercury per dose after purification; such pharmaceutical compositions are considered thimerosal-free products).

In certain embodiments, the pharmaceutical compositions described herein additionally comprise egg protein (e.g., ovalbumin or other egg proteins). The amount of egg protein in the pharmaceutical compositions described herein may range from about 0.0005 to about 1.2. g of egg protein to 1 ml of pharmaceutical composition. In other embodiments, the pharmaceutical compositions described herein do not comprise egg protein.

In certain embodiments, the pharmaceutical compositions described herein additionally comprise one or more antimicrobial agents (e.g., antibiotics) including, but not limited to gentamicin, neomycin, polymyxin (e.g., polymyxin B), and kanamycin, streptomycin. In other embodiments, the pharmaceutical compositions described herein do not comprise any antibiotics.

In certain embodiments, the pharmaceutical compositions described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions described herein additionally comprise gelatin. In other embodiments, the pharmaceutical compositions described herein do not comprise gelatin.

In certain embodiments, the pharmaceutical compositions described herein additionally comprise one or more buffers, e.g., phosphate buffer and sucrose phosphate glutamate buffer. In other embodiments, the pharmaceutical compositions described herein do not comprise buffers.

In certain embodiments, the pharmaceutical compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the pharmaceutical compositions described herein do not comprise salts.

In specific embodiments, the pharmaceutical compositions described herein are low-additive influenza virus vaccines, i.e., the pharmaceutical compositions do not comprise one or more additives commonly found in influenza virus vaccines. Low-additive influenza vaccines have been described (see, e.g., International Application No. PCT/IB2008/002238 published as International Publication No. WO 09/001217 which is herein incorporated by reference in its entirety).

The pharmaceutical compositions described herein can be included in a container, pack, or dispenser together with instructions for administration.

The pharmaceutical compositions described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110776, which is herein incorporated by reference in its entirety, for methods of storing compositions comprising influenza vaccines without refrigeration).

In certain embodiments, when the active compound in a pharmaceutical composition described herein is a cell engineered to express a chimeric influenza hemagglutinin (HA) polypeptide described herein, the cells in the pharmaceutical composition are not mammalian cells (e.g., CB-1 cells).

5.10.1 Subunit Vaccines

In a specific embodiment, provided herein are subunit vaccines comprising a chimeric influenza hemagglutinin (HA) polypeptide described herein. In some embodiments, a subunit vaccine comprises a chimeric influenza hemagglutinin (HA) polypeptide described herein and one or more surface glycoproteins (e.g., influenza virus neuraminidase), other targeting moieties, or adjuvants. In specific embodiments, a subunit vaccine comprises a single chimeric influenza hemagglutinin (HA) polypeptide described herein. In other embodiments, a subunit vaccine comprises two, three, four or more chimeric influenza hemagglutinin (HA) polypeptides described herein. In specific embodiments, the chimeric influenza hemagglutinin (HA) polypeptides used in a subunit vaccine are not membrane-bound, i.e., are soluble.

The subunit vaccines provided herein comprise an effective amount of chimeric influenza hemagglutinin (HA) polypeptide. In certain embodiments, the subunit vaccines provided herein comprise about 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, or 150 μg of one or more chimeric influenza hemagglutinin (HA) polypeptides described herein. In certain embodiments, the subunit vaccines provided herein comprise about 5-10, 10-20, 20-30, 30-40, 40-50, 50-60, 60-70, 70-80, 80-90, 90-100, 100-110, 110-120, 120-130, 130-140, or 140-150 μg of one or more chimeric influenza hemagglutinin (HA) polypeptides described herein.

In a specific embodiment, a monovalent subunit vaccine provided herein comprises between 7.5 μg to 90 μg of a chimeric influenza hemagglutinin (HA) polypeptide described herein. In another specific embodiment, a bivalent subunit vaccine provided herein comprises between 7.5 μg to 90 μg of a first chimeric influenza hemagglutinin (HA) polypeptide described herein and between 7.5 μg to 90 μg of a second chimeric influenza hemagglutinin (HA) polypeptide described herein. In another specific embodiment, a trivalent subunit vaccine provided herein comprises between 7.5 μg to 90 μg of a first chimeric influenza hemagglutinin (HA) polypeptide described herein, between 7.5 μg to 90 μg of a second chimeric influenza hemagglutinin (HA) polypeptide described herein, and between 7.5 μg to 90 μg of a third chimeric influenza hemagglutinin (HA) polypeptide described herein.

In certain embodiments, provided herein are subunit vaccines comprising about 10 μg to about 60 μg of one or more chimeric influenza hemagglutinin (HA) polypeptides described herein, about 0.001% to 0.01% thimerosal, about 0.1 μg to about 1.0 μg chicken egg protein, about 1.0 μg to about 5.0 μg polymyxin, about 1.0 μg to about 5.0 μg neomycin, about 0.1 μg to about 0.5 μg betapropiolactone, and about 0.001 to about 0.05% w/v of nonylphenol ethoxylate per dose.

In a specific embodiment, a subunit vaccine provided herein comprises or consists of a 0.5 ml dose that comprises 45 μg of a chimeric influenza hemagglutinin (HA) polypeptide described herein, ≤1.0 μg of mercury (from thimerosal), ≤1.0 μg chicken egg protein (i.e., ovalbumin), ≤3.75 μg polymyxin, and ≤2.5 μg neomycin. In some embodiments, a subunit vaccine provided herein additionally comprises or consists of not more than 0.5 μg betapropiolactone, and not more than 0.015% w/v of nonylphenol ethoxylate per dose. In some embodiments, the 0.5 ml dose subunit vaccine is packaged in a pre-filled syringe.

In a specific embodiment, a subunit vaccine provided herein consists of a 5.0 ml multidose vial (0.5 ml per dose) that comprises 45 μg of a chimeric influenza hemagglutinin (HA) polypeptide described herein, 25.0 μg of mercury (from thimerosal), ≤1.0 μg chicken egg protein (i.e., ovalbumin), ≤3.75 μg polymyxin, and ≤2.5 μg neomycin. In some embodiments, a subunit vaccine provided herein additionally comprises or consists of not more than 0.5 μg betapropiolactone, and not more than 0.015% w/v of nonylphenol ethoxylate per dose.

In a specific embodiment, the subunit vaccine is prepared using influenza virus that was propagated in embryonated chicken eggs (i.e., the components of the subunit vaccine (e.g., a chimeric influenza hemagglutinin (HA) polypeptide described herein) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a chimeric influenza hemagglutinin (HA) polypeptide described herein) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) (i.e., the components of the subunit vaccine (e.g., a chimeric influenza hemagglutinin (HA) polypeptide) are isolated from virus that was propagated in mammalian cells). In another specific embodiment, the chimeric influenza hemagglutinin (HA) polypeptides in the subunit vaccines provided herein are prepared using an expression vector, e.g., a viral vector, plant vector or a bacterial vector (i.e., the chimeric influenza hemagglutinin (HA) polypeptide in the subunit vaccine are obtained/isolated from an expression vector).

In a specific embodiment, provided herein is a monovalent subunit vaccine comprising a chimeric influenza hemagglutinin (HA) polypeptide described herein. In a specific embodiment, provided herein is a monovalent subunit vaccine comprising a cH5/1 chimeric influenza hemagglutinin polypeptide (e.g., a cH5/1 chimeric influenza hemagglutinin polypeptide described in Section 5.1). In another specific embodiment, provided herein is a monovalent subunit vaccine comprising a cH5/3 chimeric influenza hemagglutinin polypeptide (e.g., a cH5/3 chimeric influenza hemagglutinin polypeptide described in Section 5.1). In another specific embodiment, provided herein is a monovalent subunit vaccine comprising a cH7/3 chimeric influenza hemagglutinin polypeptide (e.g., a cH7/3 chimeric influenza hemagglutinin polypeptide described in Section 5.1). In another specific embodiment, provided herein is a monovalent subunit vaccine comprising a cH5/B chimeric influenza hemagglutinin polypeptide (e.g., a cH5/B chimeric influenza hemagglutinin polypeptide described in Section 5.1). In another specific embodiment, provided herein is a monovalent subunit vaccine comprising a cH7/B chimeric influenza hemagglutinin polypeptide (e.g., a cH7/1 chimeric influenza hemagglutinin polypeptide described in Section 5.1). In another specific embodiment, provided herein is a monovalent subunit vaccine comprising a cB/B chimeric influenza hemagglutinin polypeptide (e.g., a B/B chimeric influenza hemagglutinin polypeptide described in Section 5.1).

In specific embodiments, provided herein are bivalent subunit vaccines comprising a chimeric influenza hemagglutinin (HA) polypeptide described herein. In a specific embodiment, provided herein is a bivalent subunit vaccine comprising a cH5/1 chimeric influenza hemagglutinin polypeptide and a cH5/3 chimeric influenza hemagglutinin polypeptide. In another specific embodiment, provided herein is a bivalent subunit vaccine comprising a cH5/1 chimeric influenza hemagglutinin polypeptide and a cH7/3 chimeric influenza hemagglutinin polypeptide. In another specific embodiment, provided herein is a bivalent subunit vaccine comprising a cH5/1 chimeric influenza hemagglutinin polypeptide and a cH5/B chimeric influenza hemagglutinin polypeptide. In another specific embodiment, provided herein is a bivalent subunit vaccine comprising a cH5/1 chimeric influenza hemagglutinin polypeptide and a cH7/B chimeric influenza hemagglutinin polypeptide. In another specific embodiment, provided herein is a bivalent subunit vaccine comprising a cH5/1 chimeric influenza hemagglutinin polypeptide and a cB/B chimeric influenza hemagglutinin polypeptide.

In another specific embodiment, provided herein is a bivalent subunit vaccine comprising a cH5/3 chimeric influenza hemagglutinin polypeptide and a cH7/3 chimeric influenza hemagglutinin polypeptide. In another specific embodiment, provided herein is a bivalent subunit vaccine comprising a cH5/3 chimeric influenza hemagglutinin polypeptide and a cH5/B chimeric influenza hemagglutinin polypeptide. In another specific embodiment, provided herein is a bivalent subunit vaccine comprising a cH5/3 chimeric influenza hemagglutinin polypeptide and a cH7/B chimeric influenza hemagglutinin polypeptide. In another specific embodiment, provided herein is a bivalent subunit vaccine comprising a cH5/3 chimeric influenza hemagglutinin polypeptide and a cB/B chimeric influenza hemagglutinin polypeptide.

In another specific embodiment, provided herein is a bivalent subunit vaccine comprising a cH7/3 chimeric influenza hemagglutinin polypeptide and a cH5/B chimeric influenza hemagglutinin polypeptide. In another specific embodiment, provided herein is a bivalent subunit vaccine comprising a cH7/3 chimeric influenza hemagglutinin polypeptide and a cH7/B chimeric influenza hemagglutinin polypeptide. In another specific embodiment, provided herein is a bivalent subunit vaccine comprising a cH7/3 chimeric influenza hemagglutinin polypeptide and a cB/B chimeric influenza hemagglutinin polypeptide.

In another specific embodiment, provided herein is a bivalent subunit vaccine comprising a cH5/B chimeric influenza hemagglutinin polypeptide and a cH7/B chimeric influenza hemagglutinin polypeptide. In another specific embodiment, provided herein is a bivalent subunit vaccine comprising a cH5/B chimeric influenza hemagglutinin polypeptide and a cB/B chimeric influenza hemagglutinin polypeptide.

In another specific embodiment, provided herein is a bivalent subunit vaccine comprising a cH7/B chimeric influenza hemagglutinin polypeptide and a cB/B chimeric influenza hemagglutinin polypeptide.

In specific embodiments, provided herein are trivalent subunit vaccines comprising viruses that contain and/or comprise a genome that encodes a chimeric influenza hemagglutinin (HA) polypeptide described herein. In a specific embodiment, provided herein is a trivalent subunit vaccine comprising a cH5/1 chimeric influenza hemagglutinin polypeptide, a cH5/3 chimeric influenza hemagglutinin polypeptide, and a cH5/B chimeric influenza hemagglutinin polypeptide. In another specific embodiment, provided herein is a trivalent subunit vaccine comprising a cH5/1 chimeric influenza hemagglutinin polypeptide, a cH5/3 chimeric influenza hemagglutinin polypeptide, and a cH7/B chimeric influenza hemagglutinin polypeptide. In another specific embodiment, provided herein is a trivalent subunit vaccine comprising a cH5/1 chimeric influenza hemagglutinin polypeptide, a cH5/3 chimeric influenza hemagglutinin polypeptide, and a cB/B chimeric influenza hemagglutinin polypeptide.

In another specific embodiment, provided herein is a trivalent subunit vaccine comprising a cH5/1 chimeric influenza hemagglutinin polypeptide, a cH7/3 chimeric influenza hemagglutinin polypeptide, and a cH5/B chimeric influenza hemagglutinin polypeptide. In another specific embodiment, provided herein is a trivalent subunit vaccine comprising a cH5/1 chimeric influenza hemagglutinin polypeptide, a cH7/3 chimeric influenza hemagglutinin polypeptide, and a cH7/B chimeric influenza hemagglutinin polypeptide. In another specific embodiment, provided herein is a trivalent subunit vaccine comprising a cH5/1 chimeric influenza hemagglutinin polypeptide, a cH7/3 chimeric influenza hemagglutinin polypeptide, and a cB/B chimeric influenza hemagglutinin polypeptide.

In a specific embodiment, a subunit vaccine provided herein does not comprise a cH5/3 chimeric influenza hemagglutinin polypeptide comprising the globular head domain of A/Vietnam/1203/2004 (H5). In another specific embodiment, a subunit vaccine provided herein does not comprise cH5/3 chimeric influenza hemagglutinin polypeptide comprising the stem domain of A/Perth/16/2009 (H3).

In a specific embodiment, a subunit vaccine provided herein does not comprise a cH7/3 chimeric influenza hemagglutinin polypeptide comprising the globular head domain of A/mallard/Alberta/24/2001 (H7). In another specific embodiment, a subunit vaccine provided herein does not comprise a cH7/3 chimeric influenza hemagglutinin polypeptide comprising the stem domain of A/Perth/16/2009 (H3).

5.10.2 Live Virus Vaccines

In one embodiment, provided herein are immunogenic compositions (e.g., vaccines) comprising live virus containing a chimeric influenza hemagglutinin (HA) polypeptide described herein. In another embodiment, provided herein are immunogenic compositions (e.g., vaccines) comprising live virus that is engineered to encode a chimeric influenza hemagglutinin (HA) polypeptide described herein, which is expressed by progeny virus produced in the subjects administered the compositions. In specific embodiments, the chimeric influenza hemagglutinin (HA) polypeptide is membrane-bound. In other specific embodiments, the chimeric influenza hemagglutinin (HA) polypeptide is not membrane-bound, i.e., it is soluble. In particular embodiments, the live virus is an influenza virus, such as described in Section 5.4, supra. In other embodiments, the live virus is a non-influenza virus, such as described in Section 5.5, supra. In some embodiments, the live virus is attenuated. In some embodiments, an immunogenic composition comprises two, three, four or more live viruses containing or engineered to express two, three, four or more different chimeric influenza hemagglutinin (HA) polypeptide described herein.

In certain embodiments, provided herein are immunogenic compositions (e.g., vaccines) comprising about $10^5$ to about $10^{10}$ fluorescent focus units (FFU) of live attenuated influenza virus containing one or more chimeric influenza hemagglutinin (HA) polypeptide described herein, about 0.1 to about 0.5 mg monosodium glutamate, about 1.0 to about 5.0 mg hydrolyzed procine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 µg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated influenza virus containing one or more chimeric influenza hemagglutinin (HA) polypeptide described herein, 0.188 mg monosodium glutamate, 2.0 mg hydrolyzed procine gelatin, 2.42 mg arginine, 13.68 mg sucrose, 2.26 mg dibasic potassium phosphate, 0.96 mg monobasic potassium phosphate, and <0.015 µg/ml gentamicin sulfate per dose. In some embodiments, the immunogenic compositions (e.g., vaccines) are packaged as pre-filled sprayers containing single 0.2 ml doses.

In a specific embodiment, the live virus that contains a chimeric influenza hemagglutinin (HA) polypeptide described herein is propagated in embryonated chicken eggs before its use in an immunogenic composition described herein. In another specific embodiment, the live virus that contains a chimeric influenza hemagglutinin (HA) polypeptide described herein is not propagated in embryonated chicken eggs before its use in an immunogenic composition described herein. In another specific embodiment, the live virus that contains a chimeric influenza hemagglutinin (HA) polypeptide described herein is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

In a specific embodiment, provided herein is a monovalent live virus vaccine comprising a chimeric influenza hemagglutinin (HA) polypeptide described herein. In a specific embodiment, provided herein is a monovalent live virus vaccine comprising a virus that contains and/or comprises a genome that encodes a cH5/1 chimeric influenza hemagglutinin polypeptide (e.g., a cH5/1 chimeric influenza hemagglutinin polypeptide described in Section 5.1). In another specific embodiment, provided herein is a monovalent live virus vaccine comprising a virus that contains and/or comprises a genome that encodes a cH5/3 chimeric influenza hemagglutinin polypeptide (e.g., a cH5/3 chimeric influenza hemagglutinin polypeptide described in Section 5.1). In another specific embodiment, provided herein is a live virus vaccine comprising a virus that contains and/or comprises a genome that encodes a cH7/3 chimeric influenza hemagglutinin polypeptide (e.g., a cH7/3 chimeric influenza hemagglutinin polypeptide described in Section 5.1). In another specific embodiment, provided herein is a monovalent live virus vaccine comprising a virus that contains and/or comprises a genome that encodes a cH5/B chimeric influenza hemagglutinin polypeptide (e.g., a cH5/B chimeric influenza hemagglutinin polypeptide described in Section 5.1). In another specific embodiment, provided herein is a monovalent live virus vaccine comprising a virus that contains and/or comprises a genome that encodes a cH7/B chimeric influenza hemagglutinin polypeptide (e.g., a cH7/1 chimeric influenza hemagglutinin polypeptide described in Section 5.1). In another specific embodiment, provided herein is a monovalent live virus vaccine comprising a virus that contains and/or comprises a genome that encodes a cB/B chimeric influenza hemagglutinin polypeptide (e.g., a B/B chimeric influenza hemagglutinin polypeptide described in Section 5.1).

In specific embodiments, provided herein are bivalent live virus vaccines comprising viruses that contain and/or comprise a genome that encodes a chimeric influenza hemagglutinin (HA) polypeptide described herein. In a specific embodiment, provided herein is a bivalent live virus vaccine comprising a virus that contains and/or comprises a genome that encodes a cH5/1 chimeric influenza hemagglutinin polypeptide and a virus that contains and/or comprises a genome that encodes a cH5/3 chimeric influenza hemagglutinin polypeptide. In another specific embodiment, provided herein is a bivalent live virus vaccine comprising a virus that contains and/or comprises a genome that encodes a cH5/1 chimeric influenza hemagglutinin polypeptide and a virus that contains and/or comprises a genome that encodes a cH7/3 chimeric influenza hemagglutinin polypeptide. In another specific embodiment, provided herein is a bivalent live virus vaccine comprising a virus that contains and/or comprises a genome that encodes a cH5/1 chimeric influenza hemagglutinin polypeptide and a virus that contains and/or comprises a genome that encodes a cH5/B chimeric influenza hemagglutinin polypeptide. In another specific embodiment, provided herein is a bivalent live virus vaccine comprising a virus that contains and/or comprises a genome that encodes a virus that contains and/or comprises a genome that encodes a cH5/1 chimeric influenza hemagglutinin polypeptide and a virus that contains and/or comprises a genome that encodes a cH7/B chimeric influenza hemagglutinin polypeptide. In another specific embodiment, provided herein is a bivalent live virus vaccine comprising a virus that contains and/or comprises a genome that encodes a cH5/1 chimeric influenza hemagglutinin polypeptide and a virus that contains and/or comprises a genome that encodes a cB/B chimeric influenza hemagglutinin polypeptide.

In another specific embodiment, provided herein is a bivalent live virus vaccine comprising a virus that contains and/or comprises a genome that encodes a cH5/3 chimeric influenza hemagglutinin polypeptide and a virus that contains and/or comprises a genome that encodes a cH7/3 chimeric influenza hemagglutinin polypeptide. In another specific embodiment, provided herein is a bivalent live virus vaccine comprising a virus that contains and/or comprises a genome that encodes a cH5/3 chimeric influenza hemagglutinin polypeptide and a virus that contains and/or comprises a genome that encodes a cH5/B chimeric influenza hemagglutinin polypeptide. In another specific embodiment, provided herein is a bivalent live virus vaccine comprising a virus that contains and/or comprises a genome that encodes a cH5/3 chimeric influenza hemagglutinin polypeptide and a virus that contains and/or comprises a genome that encodes a cH7/B chimeric influenza hemagglutinin polypeptide. In another specific embodiment, provided herein is a bivalent live virus vaccine comprising a virus that contains and/or comprises a genome that encodes a cH5/3 chimeric influenza hemagglutinin polypeptide and a virus that contains and/or comprises a genome that encodes a cB/B chimeric influenza hemagglutinin polypeptide.

In another specific embodiment, provided herein is a bivalent live virus vaccine comprising a virus that contains and/or comprises a genome that encodes a cH7/3 chimeric influenza hemagglutinin polypeptide and a virus that contains and/or comprises a genome that encodes a cH5/B chimeric influenza hemagglutinin polypeptide. In another specific embodiment, provided herein is a bivalent live virus vaccine comprising a virus that contains and/or comprises a genome that encodes a cH7/3 chimeric influenza hemagglutinin polypeptide and a virus that contains and/or comprises a genome that encodes a cH7/B chimeric influenza hemagglutinin polypeptide. In another specific embodiment, provided herein is a bivalent live virus vaccine comprising a virus that contains and/or comprises a genome that encodes a cH7/3 chimeric influenza hemagglutinin polypeptide and a virus that contains and/or comprises a genome that encodes a cB/B chimeric influenza hemagglutinin polypeptide.

In another specific embodiment, provided herein is a bivalent live virus vaccine comprising a virus that contains and/or comprises a genome that encodes a cH5/B chimeric influenza hemagglutinin polypeptide and a virus that contains and/or comprises a genome that encodes a cH7/B chimeric influenza hemagglutinin polypeptide. In another specific embodiment, provided herein is a bivalent live virus vaccine comprising a virus that contains and/or comprises a genome that encodes a cH5/B chimeric influenza hemagglutinin polypeptide and a virus that contains and/or comprises a genome that encodes a cB/B chimeric influenza hemagglutinin polypeptide.

In another specific embodiment, provided herein is a bivalent live virus vaccine comprising a virus that contains and/or comprises a genome that encodes a cH7/B chimeric influenza hemagglutinin polypeptide and a virus that contains and/or comprises a genome that encodes a cB/B chimeric influenza hemagglutinin polypeptide.

In specific embodiments, provided herein are trivalent live virus vaccines comprising viruses that contain and/or comprise a genome that encodes a chimeric influenza hemagglutinin (HA) polypeptide described herein. In a specific embodiment, provided herein is a trivalent live virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cH5/B chimeric influenza hemagglutinin polypeptide. In another specific embodiment, provided herein is a trivalent live virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cH7/B chimeric influenza hemagglutinin polypeptide. In another specific embodiment, provided herein is a trivalent live virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cB/B chimeric influenza hemagglutinin polypeptide.

In another specific embodiment, provided herein is a trivalent live virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cH5/B chimeric influenza hemagglutinin polypeptide. In another specific embodiment, provided herein is a trivalent live virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cH7/B chimeric influenza hemagglutinin polypeptide. In another specific embodiment, provided herein is a trivalent live virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cB/B chimeric influenza hemagglutinin polypeptide.

In a specific embodiment, a live virus vaccine provided herein does not comprise a virus that contains and/or comprises a genome that encodes a cH5/3 chimeric influenza hemagglutinin polypeptide comprising the globular head domain of A/Vietnam/1203/2004 (H5). In another specific embodiment, a live virus vaccine provided herein does not comprise a virus that contains and/or comprises a genome that encodes a cH5/3 chimeric influenza hemagglutinin polypeptide comprising the stem domain of A/Perth/16/2009 (H3).

In a specific embodiment, a live virus vaccine provided herein does not comprise a virus that contains and/or comprises a genome that encodes a cH7/3 chimeric influenza hemagglutinin polypeptide comprising the globular head domain of A/mallard/Alberta/24/2001 (H7). In another specific embodiment, a live virus vaccine provided herein does not comprise a virus that contains and/or comprises a genome that encodes a cH7/3 chimeric influenza hemagglutinin polypeptide comprising the stem domain of A/Perth/16/2009 (H3).

5.10.3 Inactivated Virus Vaccines

In one embodiment, provided herein are immunogenic compositions (e.g., vaccines) comprising an inactivated virus containing a chimeric influenza hemagglutinin (HA) polypeptide described herein. In specific embodiments, the chimeric influenza hemagglutinin (HA) polypeptide is membrane-bound. In particular embodiments, the inactivated virus is an influenza virus, such as described in Section 5.4, supra. In other embodiments, the inactivated virus is a non-influenza virus, such as described in Section 5.5, supra. In some embodiments, an immunogenic composition comprises two, three, four or more inactivated viruses containing two, three, four or more different chimeric influenza hemagglutinin (HA) polypeptides described herein. In certain embodiments, the inactivated virus immunogenic compositions comprise one or more adjuvants.

Techniques known to one of skill in the art may be used to inactivate viruses containing a chimeric influenza hemagglutinin (HA) polypeptide described herein. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In certain embodiments, provided herein are immunogenic compositions (e.g., vaccines) comprising inactivated influenza virus such that each dose of the immunogenic composition comprises about 7.5 µg to about 90 µg, or about 15 to about 60 µg, of a chimeric influenza hemagglutinin (HA) polypeptide described herein, about 1.0 to about 5.0 mg sodium chloride, about 20 to about 100 µg monobasic sodium phosphate, about 100 to about 500 µg dibasic sodium phosphate, about 5 to about 30 µg monobasic potassium phosphate, about 5 to about 30 µg potassium chloride, and about 0.5 to about 3.0 µg calcium chloride. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In certain embodiments, provided herein are immunogenic compositions (e.g., vaccines) comprising inactivated influenza virus such that each dose of the immunogenic composition comprises about 7.5 µg to about 90 µg, or about 15 to about 60 µg, of a chimeric influenza hemagglutinin (HA) polypeptide described herein, about 0.001% to 0.01% thimerosal, about 1.0 to about 5.0 mg sodium chloride, about 20 to about 100 µg monobasic sodium phosphate, about 100 to about 500 µg dibasic sodium phosphate, about 5 to about 30 µg monobasic potassium phosphate, about 5 to about 30 µg potassium chloride, and about 0.5 to about 3.0 µg calcium chloride per dose. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In a specific embodiment, immunogenic compositions (e.g., vaccines) provided herein are packaged as single 0.25 ml doses and comprise 22.5 µg of a chimeric influenza hemagglutinin (HA) polypeptide described herein, 2.05 mg sodium chloride, 40 µg monobasic sodium phosphate, 150

µg dibasic sodium phosphate, 10 µg monobasic potassium phosphate, 10 µg potassium chloride, and 0.75 µg calcium chloride per dose.

In a specific embodiment, immunogenic compositions (e.g., vaccines) provided herein are packaged as single 0.5 ml doses and comprise 45 gig of a chimeric influenza hemagglutinin (HA) polypeptide described herein, 4.1 mg sodium chloride, 80 µg monobasic sodium phosphate, 300 µg dibasic sodium phosphate, 20 µg monobasic potassium phosphate, 20 µg potassium chloride, and 1.5 µg calcium chloride per dose.

In a specific embodiment, immunogenic compositions (e.g., vaccines) are packaged as multi-dose formulations comprising or consisting of 5.0 ml of vaccine (0.5 ml per dose) and comprise 24.5 µg of mercury (from thimerosal), 45 µg of a chimeric influenza hemagglutinin (HA) polypeptide described herein, 4.1 mg sodium chloride, 80 µg monobasic sodium phosphate, 300 µg dibasic sodium phosphate, 20 µg monobasic potassium phosphate, 20 µg potassium chloride, and 1.5 gig calcium chloride per dose.

In a specific embodiment, the inactivated virus that contains a chimeric influenza hemagglutinin (HA) polypeptide described herein is propagated in embryonated chicken eggs before its inactivation and subsequent use in an immunogenic composition described herein. In another specific embodiment, the inactivated virus that contains a chimeric influenza hemagglutinin (HA) polypeptide described herein is not propagated in embryonated chicken eggs before its inactivation and subsequent use in an immunogenic composition described herein. In another specific embodiment, the inactivated virus that contains a chimeric influenza hemagglutinin (HA) polypeptide described herein is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its inactivation and subsequent use in an immunogenic composition described herein.

In a specific embodiment, provided herein is a monovalent inactivated virus vaccine comprising a chimeric influenza hemagglutinin (HA) polypeptide described herein. In a specific embodiment, provided herein is a monovalent inactivated virus vaccine comprising a virus that contains and/or comprises a genome that encodes a cH5/1 chimeric influenza hemagglutinin polypeptide (e.g., a cH5/1 chimeric influenza hemagglutinin polypeptide described in Section 5.1). In another specific embodiment, provided herein is a monovalent inactivated virus vaccine comprising a virus that contains and/or comprises a genome that encodes a cH5/3 chimeric influenza hemagglutinin polypeptide (e.g., a cH5/3 chimeric influenza hemagglutinin polypeptide described in Section 5.1). In another specific embodiment, provided herein is a monovalent inactivated virus vaccine comprising a virus that contains and/or comprises a genome that encodes a cH7/3 chimeric influenza hemagglutinin polypeptide (e.g., a cH7/3 chimeric influenza hemagglutinin polypeptide described in Section 5.1). In another specific embodiment, provided herein is a monovalent inactivated virus vaccine comprising a virus that contains and/or comprises a genome that encodes a cH5/B chimeric influenza hemagglutinin polypeptide (e.g., a cH5/B chimeric influenza hemagglutinin polypeptide described in Section 5.1). In another specific embodiment, provided herein is a monovalent inactivated virus vaccine comprising a virus that contains and/or comprises a genome that encodes a cH7/B chimeric influenza hemagglutinin polypeptide (e.g., a cH7/1 chimeric influenza hemagglutinin polypeptide described in Section 5.1). In another specific embodiment, provided herein is a monovalent inactivated virus vaccine comprising a virus that contains and/or comprises a genome that encodes a cB/B chimeric influenza hemagglutinin polypeptide (e.g., a B/B chimeric influenza hemagglutinin polypeptide described in Section 5.1).

In specific embodiments, provided herein are bivalent inactivated virus vaccines comprising viruses that contain and/or comprise a genome that encodes a chimeric influenza hemagglutinin (HA) polypeptide described herein. In a specific embodiment, provided herein is a bivalent inactivated virus vaccine comprising a virus that contains and/or comprises a genome that encodes a cH5/1 chimeric influenza hemagglutinin polypeptide and a virus that contains and/or comprises a genome that encodes a cH5/3 chimeric influenza hemagglutinin polypeptide. In another specific embodiment, provided herein is a bivalent inactivated virus vaccine comprising a virus that contains and/or comprises a genome that encodes a cH5/1 chimeric influenza hemagglutinin polypeptide and a virus that contains and/or comprises a genome that encodes a cH7/3 chimeric influenza hemagglutinin polypeptide. In another specific embodiment, provided herein is a bivalent inactivated virus vaccine comprising a virus that contains and/or comprises a genome that encodes a cH5/1 chimeric influenza hemagglutinin polypeptide and a virus that contains and/or comprises a genome that encodes a cH5/B chimeric influenza hemagglutinin polypeptide. In another specific embodiment, provided herein is a bivalent inactivated virus vaccine comprising a virus that contains and/or comprises a genome that encodes a virus that contains and/or comprises a genome that encodes a cH5/1 chimeric influenza hemagglutinin polypeptide and a virus that contains and/or comprises a genome that encodes a cH7/B chimeric influenza hemagglutinin polypeptide. In another specific embodiment, provided herein is a bivalent inactivated virus vaccine comprising a virus that contains and/or comprises a genome that encodes a cH5/1 chimeric influenza hemagglutinin polypeptide and a virus that contains and/or comprises a genome that encodes a cB/B chimeric influenza hemagglutinin polypeptide.

In another specific embodiment, provided herein is a bivalent inactivated virus vaccine comprising a virus that contains and/or comprises a genome that encodes a cH5/3 chimeric influenza hemagglutinin polypeptide and a virus that contains and/or comprises a genome that encodes a cH7/3 chimeric influenza hemagglutinin polypeptide. In another specific embodiment, provided herein is a bivalent inactivated virus vaccine comprising a virus that contains and/or comprises a genome that encodes a cH5/3 chimeric influenza hemagglutinin polypeptide and a virus that contains and/or comprises a genome that encodes a cH5/B chimeric influenza hemagglutinin polypeptide. In another specific embodiment, provided herein is a bivalent inactivated virus vaccine comprising a virus that contains and/or comprises a genome that encodes a cH5/3 chimeric influenza hemagglutinin polypeptide and a virus that contains and/or comprises a genome that encodes a cH7/B chimeric influenza hemagglutinin polypeptide. In another specific embodiment, provided herein is a bivalent inactivated virus vaccine comprising a virus that contains and/or comprises a genome that encodes a cH5/3 chimeric influenza hemagglutinin polypeptide and a virus that contains and/or comprises a genome that encodes a cB/B chimeric influenza hemagglutinin polypeptide.

In another specific embodiment, provided herein is a bivalent inactivated virus vaccine comprising a virus that contains and/or comprises a genome that encodes a cH7/3 chimeric influenza hemagglutinin polypeptide and a virus that contains and/or comprises a genome that encodes a cH5/B chimeric influenza hemagglutinin polypeptide. In another specific embodiment, provided herein is a bivalent inactivated virus vaccine comprising a virus that contains and/or comprises a genome that encodes a cH7/3 chimeric influenza hemagglutinin polypeptide and a virus that contains and/or comprises a genome that encodes a cH7/B chimeric influenza hemagglutinin polypeptide. In another specific embodiment, provided herein is a bivalent inactivated virus vaccine comprising a virus that contains and/or comprises a genome that encodes a cH7/3 chimeric influenza hemagglutinin polypeptide and a virus that contains and/or comprises a genome that encodes a cB/B chimeric influenza hemagglutinin polypeptide.

In another specific embodiment, provided herein is a bivalent inactivated virus vaccine comprising a virus that contains and/or comprises a genome that encodes a cH5/B chimeric influenza hemagglutinin polypeptide and a virus that contains and/or comprises a genome that encodes a cH7/B chimeric influenza hemagglutinin polypeptide. In another specific embodiment, provided herein is a bivalent inactivated virus vaccine comprising a virus that contains and/or comprises a genome that encodes a cH5/B chimeric influenza hemagglutinin polypeptide and a virus that contains and/or comprises a genome that encodes a cB/B chimeric influenza hemagglutinin polypeptide.

In another specific embodiment, provided herein is a bivalent inactivated virus vaccine comprising a virus that contains and/or comprises a genome that encodes a cH7/B chimeric influenza hemagglutinin polypeptide and a virus that contains and/or comprises a genome that encodes a cB/B chimeric influenza hemagglutinin polypeptide.

In specific embodiments, provided herein are trivalent inactivated virus vaccines comprising viruses that contain and/or comprise a genome that encodes a chimeric influenza hemagglutinin (HA) polypeptide described herein. In a specific embodiment, provided herein is a trivalent inactivated virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cH5/B chimeric influenza hemagglutinin polypeptide. In another specific embodiment, provided herein is a trivalent inactivated virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cH7/B chimeric influenza hemagglutinin polypeptide. In another specific embodiment, provided herein is a trivalent inactivated virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cB/B chimeric influenza hemagglutinin polypeptide.

In another specific embodiment, provided herein is a trivalent inactivated virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cH5/B chimeric influenza hemagglutinin polypeptide. In another specific embodiment, provided herein is a trivalent inactivated virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cH7/B chimeric influenza hemagglutinin polypeptide. In another specific embodiment, provided herein is a trivalent inactivated virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cB/B chimeric influenza hemagglutinin polypeptide.

In a specific embodiment, an inactivated virus vaccine provided herein does not comprise a virus that contains and/or comprises a genome that encodes a cH5/3 chimeric influenza hemagglutinin polypeptide comprising the globular head domain of A/Vietnam/1203/2004 (H5). In another specific embodiment, an inactivated virus vaccine provided herein does not comprise a virus that contains and/or comprises a genome that encodes a cH5/3 chimeric influenza hemagglutinin polypeptide comprising the stem domain of A/Perth/16/2009 (H3).

In a specific embodiment, an inactivated virus vaccine provided herein does not comprise a virus that contains and/or comprises a genome that encodes a cH7/3 chimeric influenza hemagglutinin polypeptide comprising the globular head domain of A/mallard/Alberta/24/2001 (H7). In another specific embodiment, an inactivated virus vaccine provided herein does not comprise a virus that contains and/or comprises a genome that encodes a cH7/3 chimeric influenza hemagglutinin polypeptide comprising the stem domain of A/Perth/16/2009 (H3).

5.10.4 Split Virus Vaccines

In one embodiment, an immunogenic composition comprising a chimeric influenza hemagglutinin (HA) polypeptide described herein is a split virus vaccine. In some embodiments, split virus vaccine contains two, three, four or more different chimeric influenza hemagglutinin (HA) polypeptides described herein. In certain embodiments, the chimeric influenza hemagglutinin (HA) polypeptide is/was membrane-bound. In certain embodiments, the split virus vaccines comprise one or more adjuvants.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100—A registered trademark of Union Carbide, Co.) producing a "split virus." The split virus is then further purified by chemical means and suspended in sodium phosphate-buffered isotonic sodium chloride solution.

In certain embodiments, provided herein are split virus vaccines comprising about about 7.5 µg to about 90 µg, or 10 µg to about 60 µg, of one or more chimeric influenza hemagglutinin (HA) polypeptide described herein, about 0.01 to about 1.0 mg octoxynol-10 (TRITON X-100®, about 0.5 to 0.5 mg α-tocopheryl hydrogen succinate, about 0.1 to 1.0 mg polysorbate 80 (Tween 80), about 0.001 to about 0.003 µg hydrocortisone, about 0.05 to about 0.3 µg gentamcin sulfate, about 0.5 to about 2.0 µg chicken egg protein (ovalbumin), about 25 to 75 µg formaldehyde, and about 25 to 75 µg sodium deoxycholate.

In a specific embodiment, a split virus vaccine provided herein comprises or consists of a 0.5 ml dose that comprises 45 µg of a chimeric influenza hemagglutinin (HA) polypeptide described herein, ≤0.085 mg octoxynol-10 (TRITON X-100®, ≤0.1 mg α-tocopheryl hydrogen succinate, ≤0.415 mg polysorbate 80 (Tween 80), ≤0.0016 µg hydrocortisone, ≤0.15 µg gentamcin sulfate, ≤1.0 chicken egg protein (ovalbumin), ≤50 µg formaldehyde, and ≤50 µg sodium deoxycholate. In some embodiments, the 0.5 ml dose subunit vaccine is packaged in a pre-filled syringe.

In a specific embodiment, the split virus vaccine is prepared using influenza virus that was propagated in embryonated chicken eggs. In another specific embodiment, the split virus vaccine is prepared using influenza virus that was not propagated in embryonated chicken eggs. In another specific embodiment, the split virus vaccine is prepared using influenza virus that was propagated in mammalian cells, e.g., immortalized human cells (see, e.g., PCT/EP2006/067566 published as WO 07/045674 which is herein incorporated by reference in its entirety) or canine kidney cells such as MDCK cells (see, e.g., PCT/IB2007/003536 published as WO 08/032219 which is herein incorporated by reference in its entirety).

In a specific embodiment, provided herein is a monovalent split virus vaccine comprising a chimeric influenza hemagglutinin (HA) polypeptide described herein. In a specific embodiment, provided herein is a monovalent split virus vaccine comprising a virus that contains and/or comprises a genome that encodes a cH5/1 chimeric influenza hemagglutinin polypeptide (e.g., a cH5/1 chimeric influenza hemagglutinin polypeptide described in Section 5.1). In another specific embodiment, provided herein is a monovalent split virus vaccine comprising a virus that contains and/or comprises a genome that encodes a cH5/3 chimeric influenza hemagglutinin polypeptide (e.g., a cH5/3 chimeric influenza hemagglutinin polypeptide described in Section 5.1). In another specific embodiment, provided herein is a monovalent split virus vaccine comprising a virus that contains and/or comprises a genome that encodes a cH7/3 chimeric influenza hemagglutinin polypeptide (e.g., a cH7/3 chimeric influenza hemagglutinin polypeptide described in Section 5.1). In another specific embodiment, provided herein is a monovalent split virus vaccine comprising a virus that contains and/or comprises a genome that encodes a cH5/B chimeric influenza hemagglutinin polypeptide (e.g., a cH5/B chimeric influenza hemagglutinin polypeptide described in Section 5.1). In another specific embodiment, provided herein is a monovalent split virus vaccine comprising a virus that contains and/or comprises a genome that encodes a cH7/B chimeric influenza hemagglutinin polypeptide (e.g., a cH7/1 chimeric influenza hemagglutinin polypeptide described in Section 5.1). In another specific embodiment, provided herein is a monovalent split virus vaccine comprising a virus that contains and/or comprises a genome that encodes a cB/B chimeric influenza hemagglutinin polypeptide (e.g., a B/B chimeric influenza hemagglutinin polypeptide described in Section 5.1).

In specific embodiments, provided herein are bivalent split virus vaccines comprising viruses that contain and/or comprise a genome that encodes a chimeric influenza hemagglutinin (HA) polypeptide described herein. In a specific embodiment, provided herein is a bivalent split virus vaccine comprising a virus that contains and/or comprises a genome that encodes a cH5/1 chimeric influenza hemagglutinin polypeptide and a virus that contains and/or comprises a genome that encodes a cH5/3 chimeric influenza hemagglutinin polypeptide. In another specific embodiment, provided herein is a bivalent split virus vaccine comprising a virus that contains and/or comprises a genome that encodes a cH5/1 chimeric influenza hemagglutinin polypeptide and a virus that contains and/or comprises a genome that encodes a cH7/3 chimeric influenza hemagglutinin polypeptide. In another specific embodiment, provided herein is a bivalent split virus vaccine comprising a virus that contains and/or comprises a genome that encodes a cH5/1 chimeric influenza hemagglutinin polypeptide and a virus that contains and/or comprises a genome that encodes a cH5/B chimeric influenza hemagglutinin polypeptide. In another specific embodiment, provided herein is a bivalent split virus vaccine comprising a virus that contains and/or comprises a genome that encodes a virus that contains and/or comprises a genome that encodes a cH5/1 chimeric influenza hemagglutinin polypeptide and a virus that contains and/or comprises a genome that encodes a cH7/B chimeric influenza hemagglutinin polypeptide. In another specific embodiment, provided herein is a bivalent split virus vaccine comprising a virus that contains and/or comprises a genome that encodes a cH5/1 chimeric influenza hemagglutinin polypeptide and a virus that contains and/or comprises a genome that encodes a cB/B chimeric influenza hemagglutinin polypeptide.

In another specific embodiment, provided herein is a bivalent split virus vaccine comprising a virus that contains and/or comprises a genome that encodes a cH5/3 chimeric influenza hemagglutinin polypeptide and a virus that contains and/or comprises a genome that encodes a cH7/3 chimeric influenza hemagglutinin polypeptide. In another specific embodiment, provided herein is a bivalent split virus vaccine comprising a virus that contains and/or comprises a genome that encodes a cH5/3 chimeric influenza hemagglutinin polypeptide and a virus that contains and/or comprises a genome that encodes a cH5/B chimeric influenza hemagglutinin polypeptide. In another specific embodiment, provided herein is a bivalent split virus vaccine comprising a virus that contains and/or comprises a genome that encodes a cH5/3 chimeric influenza hemagglutinin polypeptide and a virus that contains and/or comprises a genome that encodes a cH7/B chimeric influenza hemagglutinin polypeptide. In another specific embodiment, provided herein is a bivalent split virus vaccine comprising a virus that contains and/or comprises a genome that encodes a cH5/3 chimeric influenza hemagglutinin polypeptide and a virus that contains and/or comprises a genome that encodes a cB/B chimeric influenza hemagglutinin polypeptide.

In another specific embodiment, provided herein is a bivalent split virus vaccine comprising a virus that contains and/or comprises a genome that encodes a cH7/3 chimeric influenza hemagglutinin polypeptide and a virus that contains and/or comprises a genome that encodes a cH5/B chimeric influenza hemagglutinin polypeptide. In another specific embodiment, provided herein is a bivalent split virus vaccine comprising a virus that contains and/or comprises a genome that encodes a cH7/3 chimeric influenza hemagglutinin polypeptide and a virus that contains and/or comprises a genome that encodes a cH7/B chimeric influenza hemagglutinin polypeptide. In another specific embodiment, provided herein is a bivalent split virus vaccine comprising a virus that contains and/or comprises a genome that encodes a cH7/3 chimeric influenza hemagglutinin polypeptide and a virus that contains and/or comprises a genome that encodes a cB/B chimeric influenza hemagglutinin polypeptide.

In another specific embodiment, provided herein is a bivalent split virus vaccine comprising a virus that contains and/or comprises a genome that encodes a cH5/B chimeric influenza hemagglutinin polypeptide and a virus that contains and/or comprises a genome that encodes a cH7/B chimeric influenza hemagglutinin polypeptide. In another specific embodiment, provided herein is a bivalent split virus vaccine comprising a virus that contains and/or comprises a genome that encodes a cH5/B chimeric influenza hemagglutinin polypeptide and a virus that contains and/or comprises a genome that encodes a cB/B chimeric influenza hemagglutinin polypeptide.

In another specific embodiment, provided herein is a bivalent split virus vaccine comprising a virus that contains and/or comprises a genome that encodes a cH7/B chimeric influenza hemagglutinin polypeptide and a virus that contains and/or comprises a genome that encodes a cB/B chimeric influenza hemagglutinin polypeptide.

In specific embodiments, provided herein are trivalent split virus vaccines comprising viruses that contain and/or comprise a genome that encodes a chimeric influenza hemagglutinin (HA) polypeptide described herein. In a specific embodiment, provided herein is a trivalent split virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cH5/B chimeric influenza hemagglutinin polypeptide. In another specific embodiment, provided herein is a trivalent split virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cH7/B chimeric influenza hemagglutinin polypeptide. In another specific embodiment, provided herein is a trivalent split virus vaccine comprising a virus that contains and/or comprises a genome that encodes a cH5/1 chimeric influenza hemagglutinin polypeptide, a virus that contains and/or comprises a genome that encodes a cH5/3 chimeric influenza hemagglutinin polypeptide, and a virus that contains and/or comprises a genome that encodes a cB/B chimeric influenza hemagglutinin polypeptide.

In another specific embodiment, provided herein is a trivalent split virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cH5/B chimeric influenza hemagglutinin polypeptide. In another specific embodiment, provided herein is a trivalent split virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cH7/B chimeric influenza hemagglutinin polypeptide. In another specific embodiment, provided herein is a trivalent split virus vaccine comprising a virus that contains and/or comprises a genome that encodes a cH5/1 chimeric influenza hemagglutinin polypeptide, a virus that contains and/or comprises a genome that encodes a cH7/3 chimeric influenza hemagglutinin polypeptide, and a virus that contains and/or comprises a genome that encodes a cB/B chimeric influenza hemagglutinin polypeptide.

In a specific embodiment, a split virus vaccine provided herein does not comprise a virus that contains and/or comprises a genome that encodes a cH5/3 chimeric influenza hemagglutinin polypeptide comprising the globular head domain of A/Vietnam/1203/2004 (H5). In another specific embodiment, a split virus vaccine provided herein does not comprise a virus that contains and/or comprises a genome that encodes a cH5/3 chimeric influenza hemagglutinin polypeptide comprising the stem domain of A/Perth/16/2009 (H3).

In a specific embodiment, a split virus vaccine provided herein does not comprise a virus that contains and/or comprises a genome that encodes a cH7/3 chimeric influenza hemagglutinin polypeptide comprising the globular head domain of A/mallard/Alberta/24/2001 (H7). In another specific embodiment, a split virus vaccine provided herein does not comprise a virus that contains and/or comprises a genome that encodes a cH7/3 chimeric influenza hemagglutinin polypeptide comprising the stem domain of A/Perth/16/2009 (H3).

5.10.5 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a chimeric influenza hemagglutinin (HA) polypeptide described herein, but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to chimeric influenza hemagglutinin (HA) polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents described in Section 5.4, supra. It should be understood that different formulations of chimeric influenza hemagglutinin (HA) polypeptides described herein may comprise different adjuvants or may comprise the same adjuvant.

5.11 Prophylactic and Therapeutic Uses

In one aspect, provided herein are methods for inducing an immune response in a subject utilizing an active compound (e.g., a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein. In a specific embodiment, a method for inducing an immune response to an influenza virus hemagglutinin (HA) polypeptide in a subject comprises administering to a subject in need thereof an effective amount of a chimeric influenza hemagglutinin (HA) polypeptide described herein or an immunogenic composition thereof (e.g., a vaccine formulation thereof). In another embodiment, a method for inducing an immune response to an influenza virus hemagglutinin polypeptide in a subject comprises administering to a subject in need thereof an effective amount of a nucleic acid encoding a chimeric influenza hemagglutinin (HA) polypeptide described herein or an immunogenic composition thereof. In another embodiment, a method for inducing an immune response to an influenza virus hemagglutinin polypeptide in a subject comprises administering to a subject in need thereof an effective amount of a viral vector containing or expressing a chimeric influenza hemagglutinin (HA) polypeptide described herein or an immunogenic composition thereof. In yet another embodiment, a method for inducing an immune response to an influenza virus hemagglutinin polypeptide in a subject comprises administering to a subject in need thereof an effective amount of cells stimulated with a chimeric influenza hemagglutinin (HA) polypeptide described herein or a pharmaceutical composition thereof. In certain embodiments, a chimeric influenza hemagglutinin (HA) polypeptide described herein used in the method is a purified chimeric influenza hemagglutinin (HA) polypeptide described herein derived from a mammalian cell, a plant cell, or an insect cell.

In a specific embodiment, a method for inducing an immune response to an influenza virus hemagglutinin polypeptide in a subject comprises administering to a subject in need thereof a subunit vaccine described herein (see Section 5.10.1). In another embodiment, a method for inducing an immune response to an influenza virus hemagglutinin polypeptide in a subject comprises administering to a subject in need thereof a live virus vaccine described herein (see Section 5.10.2). In particular embodiments, the live virus vaccine comprises an attenuated virus. In another embodiment, a method for inducing an immune response to an influenza virus hemagglutinin polypeptide in a subject comprises administering to a subject in need thereof an inactivated virus vaccine described herein (see Section 5.10.3). In another embodiment, a method for inducing an immune response to an influenza virus hemagglutinin polypeptide in a subject comprises administering to a subject in need thereof a split virus vaccine described herein (see Section 5.10.4). In another embodiment, a method for inducing an immune response to an influenza virus hemagglutinin polypeptide in a subject comprises administering to a subject in need thereof a virus-like particle vaccine described herein (see Section 5.6). In another embodiment, a method for inducing an immune response to an influenza hemagglutinin polypeptide comprises administering to a subject in need thereof a virosome described herein (see Section 5.6). In another embodiment, a method for inducing an immune response to an influenza hemagglutinin polypeptide comprises administering to a subject in need thereof a bacteria expressing or engineered to express a chimeric influenza hemagglutinin (HA) polypeptide described herein or a composition thereof (see Section 5.7). In certain embodiments, a chimeric influenza hemagglutinin (HA) polypeptide described herein used in the method is a purified chimeric influenza hemagglutinin (HA) polypeptide described herein derived from a mammalian cell, a plant cell, or an insect cell.

In some embodiments, the immune response induced by an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein is effective to prevent and/or treat an influenza virus infection caused by any subtype or strain of influenza virus. In some embodiments, the immune response induced by an active compound or a composition (e.g., vaccine formulation) described herein is effective to prevent and/or treat an influenza virus infection caused by one or more strains within the same subtype of influenza virus. In some embodiments, the immune response induced by an active compound or a composition (e.g., vaccine formulation) described herein is effective to prevent and/or treat an influenza virus infection caused by multiple strains of the same subtype of influenza virus.

In some embodiments, the immune response induced by an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein is effective to prevent and/or treat an influenza virus infection caused by (i) H1N1 and H1N2 subtypes; (ii) H1N1 and H3N1 subtypes; (iii) H1N2 and H3N2 subtypes; and/or (iv) any of the combinations of (i)-(iii) and influenza B.

In certain embodiments, the immune response induced by an active compound or a composition (e.g., vaccine formulation) described herein is effective to prevent and/or treat an influenza virus infection caused by a subtype of influenza virus that belongs to one HA group (e.g., Group 1, which comprises H1, H2, H5, H6, H8, H9, H11, H12, H13, and H16) and not the other HA group (e.g., Group 2, which comprises H3, H4, H7, H10, H14, and H15). For example, the immune response induced may be effective to prevent and/or treat an influenza virus infection caused by an influenza virus that belongs to the HA group consisting of H11, H13, H16, H9, H8, H12, H6, H1, H5 and/or H2. Alternatively, the immune response induced may be effective to prevent and/or treat an influenza virus infection caused by an influenza virus that belongs to the HA group consisting of H3, H4, H14, H10, H15 and/or H7. In some embodiments, the immune response induced by an active compound or a composition (e.g., vaccine formulation) described herein is effective to prevent and/or treat an influenza virus infection caused by one, two, three, four or five subtypes of influenza virus. In certain embodiments, the immune response induced by an active compound or a composition (e.g., vaccine formulation) described herein is effective to prevent and/or treat an influenza virus infection caused by six, seven, eight, nine, ten, eleven, twelve, thirteen, fourteen or fifteen subtypes of influenza virus. In a specific embodiment, the immune response induced by an active compound or a composition (e.g., vaccine formulation) described herein is effective to prevent and/or treat an influenza virus infection caused by one, two, or more strains of an influenza virus that belongs to the H1 HA group and/or one, two, or more strains of an influenza virus that belongs to the H2 HA group. In another specific embodiment, the immune response induced by an active compound or a composition (e.g., vaccine formulation) described herein is effective to prevent and/or treat an influenza virus infection caused by one, two, or more strains of an influenza virus that belongs to the H1 HA group; one, two, or more strains of an influenza virus that belongs to the H3 HA group; and/or one, two, or more influenza B virus strains.

In some embodiments, the immune response induced by an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein is effective to prevent and/or treat an influenza virus infection caused by both H1N1 and H2N2 subtypes. In other embodiments, the immune response induced by an active compound or a composition (e.g., vaccine formulation) described herein is not effective to prevent and/or treat an influenza virus infection caused by both H1N1 and H2N2 subtypes. In some embodiments, the immune response induced by an active compound or a composition (e.g., vaccine formulation) described herein is effective to prevent and/or treat an influenza virus infection caused by H1N1, H2N2, and H3N2 subtypes. In some embodiments, the immune response induced by an active compound or a composition (e.g., vaccine formulation) described herein is effective to prevent and/or treat an influenza virus infection caused by H3N2 subtypes. In other embodiments, the immune response induced by an active compound or a composition (e.g., vaccine formulation) described herein is not effective to prevent and/or treat an influenza virus infection caused by H3N2 subtypes.

In certain embodiments, the immune response induced by an active compound or a composition (e.g., vaccine formulation) described herein is effective to prevent and/or treat an influenza virus disease caused by a subtype of influenza virus that belongs to one HA group and not the other HA group. For example, the immune response induced may be effective to prevent and/or treat an influenza virus disease caused by an influenza virus that belongs to the HA group consisting of H11, H13, H16, H9, H8, H12, H6, H1, H5 and/or H2. Alternatively, the immune response induced may be effective to prevent and/or treat an influenza virus disease caused by an influenza virus that belongs to the HA group consisting of H3, H4, H14, H10, H15 and/or H7. In some embodiments, the immune response induced by an active compound or a composition (e.g., vaccine formulation) described herein is effective to prevent and/or treat an influenza virus disease caused by any of one, two, three, four or five subtypes of influenza virus. In certain embodiments, the immune response induced by an active compound or a composition (e.g., vaccine formulation) described herein is effective to prevent and/or treat an influenza virus disease caused by any of six, seven, eight, nine, ten, eleven, twelve, thirteen, fourteen or fifteen subtypes of influenza virus. In some embodiments, the immune response induced by an active compound or a composition (e.g., vaccine formulation) described herein is effective to prevent and/or treat an influenza virus disease caused by one or more strains within the same subtype of influenza virus.

In some embodiments, the immune response induced by an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein is effective to reduce symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein is effective to reduce the hospitalization of a subject suffering from an influenza virus disease/infection. In some embodiments, the immune response induced by an active compound or a composition (e.g., vaccine formulation) described herein is effective to reduce the duration of hospitalization of a subject suffering from an influenza virus disease/infection.

In another aspect, provided herein are methods for preventing and/or treating an influenza virus infection in a subject utilizing an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition (e.g., vaccine formulation) described herein. In one embodiment, a method for preventing or treating an influenza virus infection in a subject comprises administering to a subject in need thereof a chimeric influenza hemagglutinin (HA) polypeptide described herein, a nucleic acid encoding such a polypeptide, a vector containing or expressing such a polypeptide, or a composition of any one of the foregoing. In a specific embodiment, a method for preventing or treating an influenza virus infection in a subject comprises administering to a subject in need thereof a subunit vaccine, a live virus vaccine, an inactivated virus vaccine, a split virus vaccine or a virus-like particle vaccine described herein.

In another aspect, provided herein are methods for preventing and/or treating an influenza virus disease in a subject utilizing a chimeric influenza hemagglutinin (HA) polypeptide described herein, a nucleic acid encoding such a polypeptide, a vector containing or expressing such a polypeptide, or cells stimulated with such a polypeptide, or a composition (e.g., vaccine formulation) described herein. In a specific embodiment, a method for preventing or treating an influenza virus disease in a subject comprises administering to a subject in need thereof an effective amount of a chimeric influenza hemagglutinin (HA) polypeptide described herein or an immunogenic composition thereof. In another embodiment, a method for preventing or treating an influenza virus disease in a subject comprises administering to a subject in need thereof an effective amount of a nucleic acid encoding a chimeric influenza hemagglutinin (HA) polypeptide described herein or an immunogenic composition thereof. In another embodiment, a method for preventing or treating an influenza virus disease in a subject comprises administering to a subject in need thereof an effective amount of a viral vector containing or expressing a chimeric influenza hemagglutinin (HA) polypeptide described herein or an immunogenic composition thereof. In yet another embodiment, a method for preventing or treating an influenza virus disease in a subject comprises administering to a subject in need thereof an effective amount of cells stimulated with a chimeric influenza hemagglutinin (HA) polypeptide described herein or a pharmaceutical composition thereof.

In a specific embodiment, a method for preventing or treating an influenza virus disease in a subject comprises administering to a subject in need thereof a subunit vaccine described herein. In another embodiment, a method for preventing or treating an influenza virus disease in a subject comprises administering to a subject in need thereof a live virus vaccine described herein. In particular embodiments, the live virus vaccine comprises an attenuated virus. In another embodiment, a method for preventing or treating an influenza virus disease in a subject comprises administering to a subject in need thereof an inactivated virus vaccine described herein. In another embodiment, a method for preventing or treating an influenza virus disease in a subject comprises administering to a subject in need thereof a split virus vaccine described herein. In another embodiment, a method for preventing or treating an influenza virus disease comprises administering to a subject in need thereof a virus-like particle vaccine described herein. In another embodiment, a method for preventing or treating an influenza virus disease in a subject, comprising administering to a subject in need thereof a virosome described herein. In another embodiment, a method for preventing or treating an influenza virus disease in a subject comprising administering to a subject in need thereof a bacteria expressing or engineered to express a chimeric influenza hemagglutinin (HA) polypeptide described herein or a composition thereof.

In another aspect, provided herein are methods of preventing and/or treating an influenza virus disease in a subject by administering neutralizing antibodies described herein (see Section 5.9). In a specific embodiment, a method for preventing or treating an influenza virus disease in a subject comprises administering to a subject in need thereof an effective amount of a neutralizing antibody described herein, or a pharmaceutical composition thereof. In particular embodiments, the neutralizing antibody is a monoclonal antibody. In certain embodiments, the neutralizing antibody is not CR6261, CR6325, CR6329, CR6307, CR6323, 2A, D7, D8, F10, G17, H40, A66, D80, E88, E90, H98, C179 (FERM BP-4517), AI3C (FERM BP-4516) or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9.

In certain embodiments, the methods for preventing or treating an influenza virus disease or infection in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

5.11.1 Combination Therapies

In various embodiments, a chimeric influenza hemagglutinin (HA) polypeptide described herein, a nucleic acid encoding such a polypeptide, a vector (e.g., a viral vector or a bacteria) containing or expressing such a polypeptide, cells stimulated with such a polypeptide, or a neutralizing antibody may be administered to a subject in combination with one or more other therapies (e.g., antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the treatment or prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may used in combination with an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In specific embodiments, the anti-viral agent is an immunomodulatory agent that is specific for a viral antigen. In particular embodiments, the viral antigen is an influenza virus polypeptide other than a hemagglutinin polypeptide. In other embodiments, the viral antigen is an influenza virus hemagglutinin polypeptide.

Any anti-bacterial agents known to one of skill in the art may used in combination with an active compound (e.g., a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or pharmaceutical composition described herein. Non-limiting examples of anti-bacterial agents include Amikacin, Amoxicillin, Amoxicillin-clavulanic acid, Amphotericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In some embodiments, a combination therapy comprises active immunization with a chimeric influenza hemagglutinin (HA) polypeptide described herein, or one or more expression vectors described herein and passive immunization with one or more neutralizing antibodies generated and/or identified using a chimeric influenza hemagglutinin (HA) polypeptide described herein. In some embodiments, a combination therapy comprises immunization with one or more expression vectors described herein and administration of cells (e.g., by adoptive transfer) stimulated with a chimeric influenza hemagglutinin (HA) polypeptide described herein.

In some embodiments, a combination therapy comprises administration of two or more different expression vectors described herein.

In some embodiments, a combination therapy comprises active immunization with an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) that induces an immune response to one, two, three, or more HA subtypes in one HA group (e.g., Group 1) in combination with an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) that induces an immune response to one, two, three, or more HA subtypes in the other HA group (e.g., Group 2).

In some embodiments, a combination therapy comprises active immunization with two or more chimeric influenza hemagglutinin (HA) polypeptides described herein.

5.11.2 Patient Populations

In certain embodiments, an active compound (e.g., a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In one embodiment, an active compound or composition described herein is administered to a subject that does not have a disease caused by the specific influenza virus, or has not been and is not infected with the specific influenza virus to which the chimeric influenza hemagglutinin (HA) polypeptide described herein induces an immune response. An active compound or composition described herein may also be administered to a subject that is and/or has been infected with the influenza virus or another type, subtype or strain of the influenza virus to which the chimeric influenza hemagglutinin (HA) polypeptide induces an immune response.

In certain embodiments, an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization). In some embodiments, an active compound or composition described herein is administered to a patient that is infected with or has been diagnosed with a different type of influenza virus than that of the influenza virus from which the head domain of the chimeric influenza hemagglutinin (HA) polypeptide of the active compound or composition was derived.

In certain embodiments, an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is administered to a patient that may be or is infected with an influenza virus that belongs to the same HA group as that of the head domain of the chimeric influenza hemagglutinin (HA) polypeptide. In certain embodiments, an active compound or composition described herein is administered to a patient that may be or is infected with an influenza virus of the same subtype as that of the head domain of the chimeric influenza hemagglutinin (HA) polypeptide.

In some embodiments, a subject to be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In certain embodiments, a subject to be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is a human adult. In certain embodiments, a subject to be administered an active compound or composition described herein is a human adult more than 50 years old. In certain embodiments, a subject to be administered an active compound or composition described herein is an elderly human subject.

In certain embodiments, a subject to be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is a human child. In certain embodiments, a subject to be administered an active compound or composition described herein is a human infant. In certain embodiments, a subject to whom an active compound or composition described herein is administered is not an infant of less than 6 months old. In a specific embodiment, a subject to be administered an active compound or composition described herein is a human 2 years old or younger. In another specific embodiment, a subject to be administered an active compound or composition described herein is a human 5 years old or younger. In another specific embodiment, a subject to be administered an active compound or composition described herein is a human 1-5 years old.

In specific embodiments, a subject to be administered an active compound (i.e., a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is any infant or child more than 6 months of age and any adult over 50 years of age. In other embodiments, the subject is an individual who is pregnant. In another embodiment, the subject is an individual who may or will be pregnant during the influenza season (e.g., generally, November to April in the Northern hemisphere). In specific embodiments, a subject to be administered an active compound or composition described herein is a woman who has given birth 1, 2, 3, 4, 5, 6, 7, or 8 weeks earlier.

In some embodiments, the human subject to be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is any individual at increased risk of influenza virus infection or disease resulting from influenza virus infection (e.g., an immunocompromised or immunodeficient individual). In some embodiments, the human subject to be administered an active compound or composition described herein is any individual in close contact with an individual with increased risk of influenza virus infection or disease resulting from influenza virus infection (e.g., immunocompromised or immunosuppressed individuals).

In some embodiments, the human subject to be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is an individual affected by any condition that increases susceptibility to influenza virus infection or complications or disease resulting from influenza virus infection. In other embodiments, an active compound or composition described herein is administered to a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, chronic obstructive pulmonary disease (COPD), emphysema, asthma, or bacterial infections (e.g., infections caused by *Haemophilus influenzae, Streptococcus pneumoniae, Legionella pneumophila*, and *Chlamydia trachomatus*); cardiovascular disease (e.g., congenital heart disease, congestive heart failure, and coronary artery disease); endocrine disorders (e.g., diabetes), neurological and neuron-developmental conditions (e.g., disorders of the brain, the spinal cord, the peripheral nerve, and muscle (such as cerebral palsy, epilepsy (seizure disorders), stroke, intellectual disability (e,g, mental retardation), muscular dystrophy, and spinal cord injury)).

In some embodiments, the human subject to be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is an individual that resides in a group home, such as a nursing home. In some embodiments, the human subject to be administered an active compound or composition described herein works in, or spends a significant amount of time in, a group home, e.g., a nursing home. In some embodiments, the human subject to be administered an active compound or composition described herein is a health care worker (e.g., a doctor or nurse). In some embodiments, the human subject to be administered an active compound or composition described herein is a smoker. In a specific embodiment, the human subject to be administered an active compound or composition described herein is immunocompromised or immunosuppressed.

In addition, subjects at increased risk of developing complications from influenza who may be administered an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein include: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, subjects for administration of an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein include healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza.

In some embodiments, a subject for whom administration of an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is contraindicated include any individual for whom influenza vaccination is contraindicated, such as: infants younger than six months of age; and individuals who have had an anaphylactic reaction (allergic reactions that cause difficulty breathing, which is often followed by shock) to eggs, egg products, or other components used in the production of the immunogenic formulation. In certain embodiments, when administration of an active compound or composition described herein is contraindicated due to one or more components used in the production of the immunogenic formulation (e.g., due to the presence of egg or egg products), the active compound or composition may be produced in a manner that does not include the component that causes the administration of an active compound or composition to be contraindicated (e.g., the active compound or composition may be produced without the use of eggs or egg products).

In some embodiments, it may be advisable not to administer a live virus vaccine to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; children and adolescents (2-17 years of age) receiving aspirin or aspirin-containing medications, because of the complications associated with aspirin and wild-type influenza virus infections in this age group; individuals with a history of asthma or other reactive airway diseases; individuals with chronic underlying medical conditions that may predispose them to severe influenza infections; individuals with a history of Guillain-Barre syndrome; individuals with acute serious illness with fever; or individuals who are moderately or severely ill. For such individuals, administration of inactivated virus vaccines, split virus vaccines, subunit vaccines, virosomes, virus-like particles or the non-viral vectors described herein may be preferred. In certain embodiments, subjects preferably administered a live virus vaccine may include healthy children and adolescents, ages 2-17 years, and healthy adults, ages 18-49.

In certain embodiments, an immunogenic formulation comprising a live virus vector is not given concurrently with other live-virus vaccines.

5.12 Modes of Administration

5.12.1 Routes of Delivery

An active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In cases where the antigen is a viral vector, a virus-like particle vector, or a bacterial vector, for example, it may be preferable to introduce an immunogenic composition via the natural route of infection of the backbone virus or bacteria from which the vector was derived. Alternatively, it may be preferable to introduce a chimeric influenza hemagglutinin (HA) polypeptide described herein via the natural route of infection of the influenza virus from which polypeptide is derived. The ability of an antigen, particularly a viral vector, to induce a vigorous secretory and cellular immune response can be used advantageously. For example, infection of the respiratory tract by a viral vector may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In a specific embodiment, a subunit vaccine is administered intramuscularly. In another embodiment, a live influenza virus vaccine is administered intranasally. In another embodiment, an inactivated influenza virus vaccine, or a split influenza virus vaccine is administered intramuscularly. In another embodiment, a virus-like particle or composition thereof is administered intramuscularly.

In some embodiments, cells stimulated with a f1 chimeric influenza hemagglutinin (HA) polypeptide described herein in vitro may be introduced (or re-introduced) into a subject using techniques known to one of skill in the art. In some embodiments, the cells can be introduced into the dermis, under the dermis, or into the peripheral blood stream. In some embodiments, the cells introduced into a subject are preferably cells derived from that subject, to avoid an adverse immune response. In other embodiments, cells also can be used that are derived from a donor host having a similar immune background. Other cells also can be used, including those designed to avoid an adverse immunogenic response.

5.12.2 Dosage and Frequency of Administration

The amount of an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition which will be effective in the treatment and/or prevention of an influenza virus infection or an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for nucleic acids encoding a chimeric influenza hemagglutinin (HA) polypeptide described herein range from about 10 ng to 1 g, 100 ng to 100 mg, 1 μg to 10 mg, or 30-300 μg nucleic acid, e.g., DNA, per patient.

In certain embodiments, exemplary doses for a chimeric influenza hemagglutinin (HA) polypeptide described herein (e.g., as provided in split virus vaccines and subunit vaccines) range from about 0.5 μg to 1.0 μg, 1.0 μg to 2.0 μg, 2.0 μg to 5.0 μg, 5.0 μg to 10 μg, 15 μg to 25 μg, 25 μg to 50 μg, 50 μg to 100 μg, 100 μg to 500 μg, or 500 μg to 1.0 mg, of chimeric influenza hemagglutinin (HA) polypeptide per kilogram of the patient. In other embodiments, exemplary doses for a chimeric influenza hemagglutinin (HA) polypeptide described herein range from about 0.5 μg to 1.0 μg, 1.0 μg to 2.0 μg, 2.0 μg to 5.0 μg, 5.0 μg to 10 μg, 15 μg to 25 jag, 25 μg to 50 μg, 50 μg to 100 μg, 100 μg to 500 μg, 250 μg to 500 μg, 500 μg to 1.0 mg, or 750 μg to 1 mg of chimeric influenza hemagglutinin (HA) polypeptide per dose, and can be administered to a subject once, twice, three times or more than three times with intervals as often as needed.

Doses for infectious viral vectors may vary from 10-100, or more, virions per dose. In some embodiments, suitable dosages of a virus vector are $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu, and can be administered to a subject once, twice, three or more times with intervals as often as needed.

In certain embodiments, exemplary doses for VLPs range from about 0.01 μg to about 100 mg, about 0.1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 μg, about 15 μg to about 75 μg, about 5 μg to about 50 g, about 10 μg to about 50 μg, about 15 μg to about 45 μg, about 20 μg to about 40 μg, or about 25 to about 35 μg per kilogram of the patient.

In one embodiment, an inactivated vaccine is formulated such that it contains about 5 g to about 50 μg, about 10 μg to about 50 μg, about 15 μg to about 100 μg, about 15 μg to about 75 μg, about 15 μg to about 50 μg, about 15 μg to about 30 μg, about 20 μg to about 50 μg, about 25 μg to about 40 μg, about 25 μg to about 35 μg of a chimeric influenza hemagglutinin (HA) polypeptide.

In certain embodiments, an active compound i.e., a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide, or composition is administered to a subject once as a single dose. For example, subjects (e.g., older subjects) that have previously been exposed to influenza may not require multiple administrations of an active compound described herein or composition thereof, but, rather may be sufficiently vaccinated by a single immunization with an active compound described herein or composition thereof. Alternatively, subjects (e.g., older subjects) that have previously been exposed to influenza may require multiple administrations of an active compound described herein or composition thereof, but may require less of such administrations than required by naive subjects (i.e., subjects not previously exposed to influenza) to become sufficiently vaccinated. Accordingly, in certain embodiments, naive subjects may require a first immunization (e.g., priming) with an active compound described herein or composition thereof followed by one, two, or more additional immunizations (e.g., boostings) with an active compound described herein or composition thereof.

In a specific embodiment, where a subject is administered more than one active compounds described herein or compositions thereof in succession (e.g., as part of an immunization regimen), the chimeric influenza hemagglutinin (HA) polypeptides of the active compounds or compositions thereof used in the successive administrations (i.e., the administrations that take place after the first administration) differ from the chimeric influenza hemagglutinin (HA) polypeptide of the active compound or composition thereof used in the first administration. In specific embodiments, the chimeric influenza hemagglutinin (HA) polypeptides of the active compounds or compositions thereof used in the successive administrations comprise a different globular head domain than the chimeric influenza hemagglutinin (HA) polypeptide of the active compound or composition thereof used in the first administration but comprise the same HA stem domain as the chimeric influenza hemagglutinin (HA) polypeptide of the active compound or composition thereof used in the first administration but comprise the same HA stem domain. In specific embodiments, the chimeric influenza hemagglutinin (HA) polypeptides of the active compounds or compositions thereof used in the successive administrations comprise a different globular head domain and a different HA stem domain than the chimeric influenza hemagglutinin (HA) polypeptide of the active compound or composition thereof used in the first administration.

In certain embodiments, an active compound or composition (e.g., composition comprising an active compound) is administered to a subject as a single dose followed by a second dose 3 to 6 weeks later. In certain embodiments, an active compound or composition is administered to a subject as a single dose followed by a second dose 3 to 6 weeks later, which is followed by administration of a third dose 3 to 6 weeks later. In certain embodiments, the second and/or third administrations may utilize a different active compound or composition. In specific embodiments, the globular head domain of each chimeric influenza hemagglutinin (HA) polypeptide in the active compounds or compositions administered are different from one another, e.g., the first and second, or the first, second, and third administrations each use a different active compound or composition, wherein at least the globular head domain of the chimeric influenza hemagglutinin (HA) polypeptide in each active compound or composition administered differs. In accordance with these embodiments, booster inoculations may be administered to the subject at, e.g., 3 to 6 month, 6 to 9 month, or 6 to 12 month intervals following the second inoculation. In certain embodiments, the booster inoculations may utilize a different active compound or composition. In certain embodiments, the first (priming) administration comprises a full-length hemagglutinin or fragment thereof (or a nucleic acid encoding the same) and the second (booster) administration comprises administration of a chimeric influenza hemagglutinin (HA) polypeptide described herein (or a nucleic acid encoding the same, a VLP comprising the same, or a virus or bacteria expressing the same). In some embodiments, the administration of the same active compound or composition may be repeated and the administrations may be separated by at least 1 day, 2 days, 3 days, 5 days, 10 days, 15 days, 30 days, 45 days, 2 months, 75 days, 3 months, or at least 6 months. In certain embodiments, an active compound or composition is administered to a subject as a single dose once per year.

In specific embodiments for administration to children, two doses of an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition, given at least one month apart, are administered to a child. In specific embodiments for administration to adults, a single dose is given. In another embodiment, two doses of an active compound or composition, given at least one month apart, are administered to an adult. In another embodiment, a young child (six months to nine years old) may be administered an active compound or composition for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an influenza vaccine, e.g., an immunogenic formulation described herein, for the first time. In certain embodiments, for children 6-35 months of age, a half dose (0.25 ml) may be preferred, in contrast to 0.5 ml which may be preferred for subjects over three years of age.

In a specific embodiment, for administration to human infants, two doses of a chimeric influenza hemagglutinin (HA) polypeptide described herein or a composition thereof and/or one or more of the nucleic acids, vectors, VLPs, or virosomes described herein, are administered to an infant, wherein the influenza virus hemagglutinin head domain of the chimeric influenza hemagglutinin (HA) polypeptide used in the first dose is from a different strain or subtype than the influenza virus hemagglutinin head domain of the chimeric influenza hemagglutinin (HA) polypeptide used in the second dose. The first and second administrations may be separated by at least 1 day, 2 days, 3 days, 5 days, 10 days, 15 days, 30 days, 45 days, 2 months, 75 days, 3 months, or at least 6 months.

In a specific embodiment, for administration to human infants, three doses of a chimeric influenza hemagglutinin (HA) polypeptide described herein described herein or a composition thereof and/or one or more of the nucleic acids, vectors, VLPs, or virosomes described herein, are administered to an infant, wherein the influenza virus hemagglutinin head domains of the chimeric influenza hemagglutinin (HA) polypeptides used in the first, second, and third doses are from different strains or subtypes of influenza virus. The first, second, and third administrations may be separated by at least 1 day, 2 days, 3 days, 5 days, 10 days, 15 days, 30 days, 45 days, 2 months, 75 days, 3 months, or at least 6 months.

In particular embodiments, an active compound (e.g, a chimeric influenza hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition is administered to a subject in the fall or winter, i.e., prior to or during the influenza season in each hemisphere. In one embodiment, children are administered their first dose early in the season, e.g., late September or early October in the Northern hemisphere, so that the second dose can be given prior to the peak of the influenza season.

For passive immunization with an antibody (e.g., an antibody generated and/or identified using a chimeric influenza hemagglutinin (HA) polypeptide described herein), the dosage ranges from about 0.0001 to 100 mg/kg, and more usually 0.01 to 5 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the chimeric influenza hemagglutinin (HA) polypeptide in the patient.

5.13 Biological Assays 5.13.1 Assays for Testing Activity of Chimeric Influenza Virus Hemagglutinin Polypeptides Assays for testing the expression of a chimeric influenza hemagglutinin (HA) polypeptide in a vector disclosed herein may be conducted using any assay known in the art. For example, an assay for incorporation into a viral vector comprises growing the virus, purifying the viral particles by centrifugation through a sucrose cushion, and subsequent analysis for chimeric influenza hemagglutinin (HA) polypeptide expression by an immunoassay, such as Western blotting, using methods well known in the art. Methods for determining whether a hemagglutinin polypeptide is chimeric are known to those of skill in the art and described herein.

In one embodiment, a chimeric influenza hemagglutinin (HA) polypeptide disclosed herein is assayed for proper folding and functionality by testing its ability to bind specifically to a neutralizing antibody directed to an influenza virus hemagglutinin polypeptide, such as the stalk region of the polypeptide, using any assay for antibody-antigen interaction known in the art. Neutralizing antibodies for use in such assays include, for example, the neutralizing antibodies described in Ekiert et al., 2009, Science Express, 26 Feb. 2009; Kashyap et al., 2008, Proc Natl Acad Sci USA 105: 5986-5991; Sui et al. 2009, Nature Structural and Molecular Biology, 16:265-273; Wang et al., 2010, PLOS Pathogens 6(2):1-9; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. These antibodies include CR6261, CR6325, CR6329, CR6307, CR6323, 2A, D7, D8, F10, G17, H40, A66, D80, E88, E90, H98, C179 (FERM BP-4517), AI3C (FERM BP-4516), among others.

In another embodiment, a chimeric influenza hemagglutinin (HA) polypeptide disclosed herein is assayed for proper folding by determination of the structure or conformation of the chimeric influenza hemagglutinin (HA) polypeptide using any method known in the art such as, e.g., NMR, X-ray crystallographic methods, or secondary structure prediction methods, e.g., circular dichroism.

5.13.2 Assays for Testing Activity of Antibodies Generated Using Chimeric Influenza Virus Hemagglutinin Polypeptides Antibodies described herein may be characterized in a variety of ways known to one of skill in the art (e.g. ELISA, Surface Plasmon resonance display (BIAcore), Western blot, immunofluorescence, immunostaining and/or microneutralization assays). In some embodiments, antibodies are assayed for the ability to specifically bind to a chimeric influenza hemagglutinin (HA) polypeptide, or a vector comprising said polypeptide. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403, 484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to the chimeric influenza hemagglutinin (HA) polypeptide and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to a chimeric influenza hemagglutinin (HA) polypeptide and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for a chimeric influenza hemagglutinin (HA) polypeptide and the binding off-rates can be determined from the data by Scatchard plot analysis. Competition with a second antibody can also be determined using radioimmunoassays. In this case, a chimeric influenza hemagglutinin (HA) polypeptide is incubated with the test antibody conjugated to a labeled compound (e.g., $^3$H or $^{125}$I) in the presence of increasing amounts of an unlabeled second antibody.

In certain embodiments, antibody binding affinity and rate constants are measured using the KinExA 3000 System (Sapidyne Instruments, Boise, Id.). In some embodiments, surface plasmon resonance (e.g., BIAcore kinetic) analysis is used to determine the binding on and off rates of the antibodies to an influenza virus hemagglutinin polypeptide. BIAcore kinetic analysis comprises analyzing the binding and dissociation of a chimeric influenza hemagglutinin (HA) polypeptide from chips with immobilized antibodies to chimeric influenza hemagglutinin (HA) polypeptide on their surface. A typical BIAcore kinetic study involves the injection of 250 L of an antibody reagent (mAb, Fab) at varying concentration in HBS buffer containing 0.005% Tween-20 over a sensor chip surface, onto which has been immobilized the chimeric influenza hemagglutinin (HA) polypeptide. The flow rate is maintained constant at 75 µL/min. Dissociation data is collected for 15 min or longer as necessary. Following each injection/dissociation cycle, the bound antibody is removed from the influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-NH$_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The neutralizing activity of an antibody can be determined utilizing any assay known to one skilled in the art. Antibodies described herein can be assayed for their ability to inhibit the binding of an influenza virus, or any other composition comprising a chimeric influenza hemagglutinin (HA) polypeptide (e.g., a VLP, liposome, or detergent extract), to its host cell receptor (i.e., sialic acid) using techniques known to those of skill in the art. For example, cells expressing influenza virus receptors can be contacted with a composition comprising a chimeric influenza hemagglutinin (HA) polypeptide described herein in the presence or absence of the antibody and the ability of the antibody to inhibit the antigen's binding can measured by, for example, flow cytometry or a scintillation assay. The composition comprising a chimeric influenza hemagglutinin (HA) polypeptide described herein or the antibody can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between the composition comprising a chimeric influenza hemagglutinin (HA) polypeptide described herein and a cell receptor. Alternatively, the ability of antibodies to inhibit a chimeric influenza hemagglutinin (HA) polypeptide described herein from binding to its receptor can be determined in cell-free assays. For example, a composition comprising a chimeric influenza hemagglutinin (HA) polypeptide described herein can be contacted with an antibody and the ability of the antibody to inhibit the composition comprising the chimeric influenza hemagglutinin (HA) polypeptide from binding to a cell receptor can be determined. In a specific embodiment, the antibody is immobilized on a solid support and the composition comprising an influenza virus hemagglutinin polypeptide is labeled with a detectable compound. Alternatively, a composition comprising a chimeric influenza hemagglutinin (HA) polypeptide described herein is immobilized on a solid support and the antibody is labeled with a detectable compound. In certain embodiments, the ability of an antibody to inhibit a chimeric influenza hemagglutinin (HA) polypeptide described herein from binding to a cell receptor is determined by assessing the percentage of binding inhibition of the antibody relative to a control (e.g., an antibody known to inhibit the chimeric influenza hemagglutinin (HA) polypeptide from binding to the cell receptor).

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

In one embodiment, virus-host membrane fusion is detected using a model system of cell fusion. In an exemplary cell fusion assay, cells (e.g., HeLa cells) are transfected with a plasmid encoding a chimeric influenza hemagglutinin (HA) polypeptide described herein and contacted and exposed to a buffer that allows the chimeric influenza hemagglutinin (HA) polypeptide fusion function (e.g., pH 5.0 buffer) in the presence of an antibody. An antibody is neutralizing if it reduces or inhibits syncytia formation compared to a negative control (e.g., syncytia formation in the presence of a control antibody or in the absence of antibody).

In other embodiments, virus-host membrane fusion is assayed using an in vitro liposome-based assay. In an exemplary assay, the host cell receptor is reconstituted into liposomes containing one half of a reporter. A chimeric influenza hemagglutinin (HA) polypeptide described herein is reconstituted into another set of liposomes containing another half of a reporter. When the two liposome populations are mixed together, fusion is detected by reconstitution of the reporter, for example, an enzymatic reaction that can be detected colorimetrically. The antibody inhibits fusion if reporter activity is reduced or inhibited compared to reporter activity in an assay conducted in the absence of antibody or in the presence of a control antibody. In certain embodiments, the ability of an antibody to inhibit fusion is determined by assessing the percentage of fusion in the presence of the antibody relative to the percentage of fusion in the presence a control.

5.13.3 Assays for Testing Activity of Stimulated Cells

Cells stimulated in accordance with the methods described herein may be analyzed, for example, for integration, transcription and/or expression of the polynucleotide or gene(s) of interest, the number of copies of the gene integrated, and the location of the integration. Such analysis may be carried out at any time and may be carried out by any methods known in the art. In other embodiments, successful stimulation of the target cell with a chimeric influenza hemagglutinin (HA) polypeptide described herein is determined by detecting production of neutralizing antibodies against the chimeric influenza hemagglutinin (HA) polypeptide using methods known in the art or described herein.

In certain embodiments, subjects in which the stimulated cells, e.g., DCs, are administered can be analyzed for location of the cells, expression of a vector-delivered polynucleotide or gene encoding the chimeric influenza hemagglutinin (HA) polypeptide, stimulation of an immune response (e.g., production of neutralizing antibodies against the chimeric influenza hemagglutinin (HA) polypeptide), and/or monitored for symptoms associated with influenza virus infection or a disease associated therewith by any methods known in the art or described herein.

Reporter assays can be used to determine the specificity of the targeting of the chimeric influenza hemagglutinin (HA) polypeptide described herein. For example, a mixed population of bone marrow cells can be obtained from a subject and cultured in vitro. The chimeric influenza hemagglutinin (HA) polypeptide can be administered to the mixed population of bone marrow cells, and expression of a reporter gene associated with the f1 chimeric influenza hemagglutinin (HA) polypeptide can be assayed in the cultured cells. In some embodiments, at least about 50%, more preferably at least about 60%, 70%, 80% or 90%, still more preferably at least about 95% of stimulated cells in the mixed cell population are dendritic cells.

5.13.4 Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, MDCK cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of antibodies (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

5.13.5 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Active compounds (e.g., chimeric influenza hemagglutinin (HA) polypeptides described herein) or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an active compound (e.g., chimeric influenza hemagglutinin (HA) polypeptides described herein) can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An active compound that exhibits large therapeutic indices is preferred. While an active compound that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an active compound for use in humans. The dosage of such agents lies preferably within a range of circulating concentrations that include the $ED_{50}$ with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of the active compounds and compositions described herein, for example, by measuring viral infection or a condition or symptoms associated therewith.

5.13.6 In Vivo Antiviral Activity

Active compounds (e.g., chimeric influenza hemagglutinin (HA) polypeptides described herein) and compositions thereof can be assayed in vivo for the desired therapeutic or prophylactic activity prior to use in humans. For example, in vivo assays can be used to determine whether it is preferable to administer an active compound or composition thereof and/or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. To assess the use of an active compound or composition thereof to treat an influenza virus infection or disease associated therewith, the compound or composition may be administered after infecting the animal with influenza virus. In a specific embodiment, an active compound or composition thereof is administered to the animal more than one time.

Active compounds (e.g., chimeric influenza hemagglutinin (HA) polypeptides described herein) and compositions thereof can be tested for antiviral activity in animal model systems including, but are not limited to, rats, mice, chicken, cows, monkeys, pigs, ferrets, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this section.

In general, animals are infected with influenza virus and concurrently or subsequently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound (e.g., chimeric influenza hemagglutinin (HA) polypeptides described herein) or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS, 2006, 103: 9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.13.6.1.1 Assays in Humans

In one embodiment, an active compound (e.g., chimeric influenza hemagglutinin (HA) polypeptides described herein) or composition thereof that modulates replication of an influenza virus are assessed in infected human subjects. In accordance with this embodiment, an active compound or composition thereof is administered to the human subject, and the effect of the active compound or composition on viral replication is determined by, e.g., analyzing the level of the virus or viral nucleic acids in a biological sample (e.g., serum or plasma). An active compound or composition thereof that alters virus replication can be identified by comparing the level of virus replication in a subject or group of subjects treated with a control to that in a subject or group of subjects treated with an active compound or composition thereof. Alternatively, alterations in viral replication can be identified by comparing the level of the virus replication in a subject or group of subjects before and after the administration of an active compound or composition thereof. Techniques known to those of skill in the art can be used to obtain the biological sample and analyze the mRNA or protein expression.

In another embodiment, the effect of an active compound (e.g., chimeric influenza hemagglutinin (HA) polypeptides described herein) or composition thereof on the severity of one or more symptoms associated with an influenza virus infection/disease are assessed in an infected subject. In accordance with this embodiment, an active compound or composition thereof or a control is administered to a human subject suffering from influenza virus infection and the effect of the active compound or composition on one or more symptoms of the virus infection is determined. An active compound or composition thereof that reduces one or more symptoms can be identified by comparing the subjects treated with a control to the subjects treated with the active compound or composition. In a specific embodiment, administration of an active compound (e.g., chimeric influenza hemagglutinin (HA) polypeptides described herein) or composition thereof results in a decrease in hospitalization of a human or population of humans caused by influenza virus disease or infection. In another specific embodiment, administration of an active compound or composition thereof results in a reduced need for respiratory/breathing assistance in a human or population of humans with an influenza virus disease or infection. In another specific embodiment, administration of an active compound or composition thereof results in a reduced length of illness of a human or population of humans with an influenza virus disease or infection. In another specific embodiment, administration of an active compound or composition thereof results in improvement (e.g., an increase) in lung volume as assessed by, e.g., whole body or lung plethysmography. In another embodiment, an active compound or composition thereof is administered to a healthy human subject and monitored for efficacy as a vaccine (e.g., the subject is monitored for the onset of symptoms of influenza virus infection; the ability of influenza virus to infect the subject; and/or a reduction in/absence of one or more symptoms associated with influenza virus infection). Techniques known to physicians familiar with infectious diseases can be used to determine whether an active compound or composition thereof reduces one or more symptoms associated with the influenza virus disease.

5.14 Assessment of Antibodies in a Subject

In another aspect, a chimeric influenza hemagglutinin (HA) polypeptide described herein, or virus expressing a chimeric influenza hemagglutinin (HA) polypeptide described herein, can be used to assess the antibody response of a subject (e.g., a naive subject or an immunized/vaccinated subject) or a population of subjects to an influenza virus hemagglutinin polypeptide (e.g., a chimeric influenza hemagglutinin (HA) polypeptide described herein). In specific embodiments, a chimeric influenza virus hemagglutinin polypeptide or a virus expressing a chimeric influenza virus hemagglutinin polypeptide can be used to assess the presence of stem-specific antibodies in the subject or population of subjects.

In a specific embodiment, the antibody response of a subject or a population of subjects that has been an immunized/vaccinated with an influenza virus hemagglutinin polypeptide (e.g., a chimeric influenza hemagglutinin (HA) polypeptide described herein, or a virus expressing a chimeric influenza hemagglutinin (HA) polypeptide described herein), is assessed to identify the types of stalk-specific antibodies in the subject or population of subjects. Such an assessment may allow for the identification surrogate markers/endpoints important in determining the clinical response to administration of an influenza virus HA polypeptide polypeptide(s) (e.g., a chimeric influenza hemagglutinin (HA) polypeptide described herein, or a virus expressing a chimeric influenza hemagglutinin (HA) polypeptide described herein) described herein. In such an approach, a biological sample, e.g., blood, from the subject or population of subjects may be isolated and tested directly for the presence of antibodies, or may be processed (e.g., to obtain sera) and subsequently tested for the presence of antibodies. Such antibody testing can utilize assays known in the art, e.g., ELISA.

In another specific embodiment, the antibody profile of a naive subject (i.e., a subject that has not been immunized/vaccinated with an influenza virus HA polypeptide(s) (e.g., a chimeric influenza hemagglutinin (HA) polypeptide described herein), or a virus expressing an influenza virus HA polypeptide(s) (e.g., a chimeric influenza hemagglutinin (HA) polypeptide described herein)) or a population of naive subjects is assessed to determine whether said subject or population of subjects possesses globular head-specific and/or stem specific antibodies against various influenza virus strains or subtypes. Such an assessment may allow for the generation of a chimeric influenza hemagglutinin (HA) polypeptide, or viruses expressing chimeric influenza hemagglutinin (HA) polypeptides, that are suitable for administration to said subject or population of subjects. Such an assessment may determine an immunization strategy for the patient.

In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a chimeric influenza virus hemagglutinin polypeptide described herein, wherein said chimeric influenza virus hemagglutinin polypeptide comprises a stem domain from the strain or subtype of interest. In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a virus expressing/containing a chimeric influenza virus hemagglutinin polypeptide described herein, wherein said chimeric influenza virus hemagglutinin polypeptide comprises a stem domain from the strain or subtype of interest.

5.15 Kits

Provided herein is a pharmaceutical pack or kit comprising one or more containers filled with one or more of the ingredients of the pharmaceutical/immunogenic compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein. In one embodiment, a kit comprises an active compound described herein, preferably one or more chimeric influenza hemagglutinin (HA) polypeptide described herein, in one or more containers. In certain embodiments, a kit comprises a vaccine described herein, e.g., a split virus vaccine, a subunit vaccine, an inactivated influenza virus vaccine, or a live influenza virus vaccine, wherein said vaccine comprises one or more chimeric influenza hemagglutinin (HA) polypeptides described herein. In a specific embodiment, provided herein are kits comprising a chimeric influenza virus hemagglutinin polypeptide described herein and instructions for using the chimeric influenza virus hemagglutinin polypeptide to assess the antibodies present in a subject. In another specific embodiment, provided herein are kits comprising a chimeric influenza virus hemagglutinin polypeptide described herein for use in methods of assaying for the presence of HA stem domain specific antibodies in a sample.

In a specific embodiment, a kit provided herein comprises a cH5/1 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide), a cH5/3 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide), a cH7/3 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide), a cH5/B chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide), a cH7/B chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide), or a cHB/B chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide).

In another specific embodiment, a kit provided herein comprises a combination of a cH5/1 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide) and a cH5/3 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide); or a combination of a cH5/1 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide) and a cH7/3 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide).

In another specific embodiment, a kit provided herein comprises a combination of a cH5/1 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide) and a cH5/3 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide) and either of a cH5/B, a cH7/B, or a cB/B chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide).

In another specific embodiment, a kit provided herein comprises a combination of a cH5/1 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide) and a cH7/3 chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide) and either of a cH5/B, a cH7/B, or a cB/B chimeric influenza hemagglutinin polypeptide described herein (or a nucleic acid encoding such a polypeptide, a vector (e.g., a viral vector, or a bacteria) containing or expressing such a polypeptide, or cells stimulated with such a polypeptide).

6. EXAMPLES

6.1 Example 1: Chimeric Influenza Virus Hemagglutinin Polypeptides

This example describes chimeric influenza virus hemagglutinin polypeptides and methods for inducing high levels of cross-neutralizing HA stalk antibodies in a subject comprising administration of said chimeric influenza virus hemagglutinin polypeptides. As described in this example, chimeric influenza virus hemagglutinin were generated that were successfully expressed by influenza virus and by cells engineered to express the chimeric influenza virus hemagglutinin. The chimeric influenza virus hemagglutinin were successfully recovered in their proper conformation, as evidenced by antibody recognition of both the stem and head domains of the chimeric influenza virus hemagglutinin.

FIG. 2 depicts chimeric influenza virus hemagglutinins (HAs), comprising the stem/stalk domain of an H1 subtype of influenza virus and the heterologous globular head domains of other influenza virus subtypes (H2, H3, and H5). Following the strategy outline in FIG. 2, an influenza virus was generated that comprises a chimeric HA composed of a stem domain derived from an H1N1 (PR8-H1N1) influenza virus and the globular head domain of the 2009 pandemic H1 HA (Cal/09). The globular head domains of the HAs of the two viruses are very distinct (~70% amino acid identity) whereas the stem domains are highly conserved but still divergent (~89% amino acid identity). As demonstrated in FIG. 3, the chimeric HAs with the same stem domain but very different HA heads within the same subtype were expressed.

In addition, a chimeric HA consisting of the stalk domain of A/PR8/34 HA and the globular head domain of HK/68 (chimeric H3) as well as wild type HAs (PR8-HA and HK68 HA) were expressed in 293T cells. FIG. 5 demonstrates that it is also possible to express stable chimeric HAs with the same stem domain (derived from the H1 subtype HA) and with a globular head from a different subtype (H3).

Thus, HA immunogens that completely share the HA stem domain but are highly divergent in their globular heads were designed. Repeated immunizations with these constructs should result in high levels of cross-neutralizing antibodies against the common stem domain of the HA. An improved vaccine strategy thus uses chimeric HAs with a constant stem/stalk domain and a changing globular head to induce robust cross-neutralizing anti-stem domain antibodies. A constant stem domain of, e.g., the H1 HA from A/PR/8/34 can be used together with globular heads from different group 1 HAs (H1, H2, H5, H9) to make a panel of either recombinant inactivated viruses, recombinant attenuated viruses or recombinant HAs (FIG. 4). A similar panel for group 2 HAs based on the stem domain of, e.g., H3 HA of an X31 virus, in combination with H3, H4 and H7 globular heads can provide the basis for a group 2 HA universal vaccine. Recombinant viruses can be rescued on an influenza virus vaccine backbone, such as PR/8 or cold-adapted influenza viruses, grown by standard techniques and used as inactivated or attenuated vaccines. Recombinant HAs can be expressed in insect cells that are able to perform mammalian-like glycosylation (MIMIC Sf9) or by transient transfection of, e.g., 293 T or Vero cells, and then can be purified by Ni-chelat chromatography with the help of a C-terminal his tag. Other strategies can include the use of DNA vaccines expressing the chimeric HAs or other vectors, such as adenovirus vectors, expressing the chimeric HAs.

6.2 Example 2: Viruses Expressing Chimeric Influenza Virus Hemagglutinin Polypeptides This example describes several functional chimeric influenza virus hemagglutinins encompassing a variety of globular head and stalk combinations from different hemagglutinin subtypes as well as recombinant influenza viruses expressing these chimeric hemagglutinins, which had growth properties similar to those of wild-type influenza viruses.

6.2.1 Materials and Methods 6.2.1.1 Cells and Viruses 293T and MDCK cells were obtained from the American Type Culture Collection (ATCC, Manassas, Va.) and were maintained either in Dulbecco's minimal essential medium (DMEM) or in MEM (Gibco, Invitrogen) supplemented with 10% fetal calf serum (HyClone; Thermo Scientific) and penicillin-streptomycin (Gibco, Invitrogen).

All A/PR/8/34 recombinant viruses were grown in 10-day old embryonated chicken eggs at 37° C. for 2 days.

6.2.1.2 Construction of plasmids

Plasmids encoding the different chimeric hemagglutinins were constructed by a similar strategy adapted from constructing reverse genetics plasmids for generating recombinant viruses as previously described (see, e.g., Fodor et al., 1999, J Virol 73:9679-9682; and Hai et al., 2008, J Virol 82:10580-10590). Briefly, the different segments of chimeric HA were amplified by PCR with primers containing SapI sites, digested with SapI, and cloned into the SapI sites of the pDZ vector that contains the human RNA polymerase I promoter and the mouse RNA polymerase I terminator (see, e.g. Quinlivan et al., 2005, J Virol 79:8431-8439), through multi-segmental ligation.

6.2.1.3 Flow Cytometric Analysis

To assess levels of hemagglutinin proteins at the cell surface, 293T cells were transfected with 1 μg of the appropriate plasmid using Lipofectamine 2000 (Invitrogen) according to the manufacturer's instructions. At 24 h post-transfection, cells were trypsinized and resuspended in PBS containing 2% FBS prior to staining them with the monoclonal antibody (mAb) 6F12 against H1 HAs at a 1/1000 dilution or with the mAb 12D1 against H3 HAs (see Wang et al., 2010, PLoS Pathog 6:e1000796) at a 1/400 dilution. Stained cells were enumerated on a Beckman Coulter Cytomics FC 500 flow cytometer, and the results were analyzed using FlowJo software.

6.2.1.4 Pseudoparticle Generation and Entry Assay

The procedure for pseudo-particle production was adapted from previous studies (see, e.g., Evans et al., 2007, Nature 446:801-805; and Sui et al., 2011, Clin Infect Dis 52:1003-1009). Briefly, 293-T cells were co-transfected with four plasmids encoding (i) a pro-virus containing the desired reporter (V1-GLuc), (ii) HIV Gag-Pol, (iii) the different chimeric hemagglutinin protein and (iv) influenza A PR8 neuraminidase (NA). Supernatants were collected 72 h post-transfection and subsequently, filtered (0.45 m pore size). All transductions and infection assays using pseudo-particles were performed in the presence of 1 μg/ml polybrene (Sigma, St. Louis, Mo.) (see Sui et al., 2011, Clin Infect Dis 52:1003-1009).

The entry assay was performed through infecting MDCK cells with pseudo-particles with different chimeric hemagglutinin containing the G-Luc reporter. Twenty-four hours post-infection, cells were washed three times with fresh medium to remove G-Luc protein that was present in the pseudo-particle inoculum. Forty-eight hours post-infection luciferase assays were performed (see Evans et al., 2007, Nature 446:801-805).

6.2.1.5 Rescue of Recombinant Chimeric Influenza a Viruses

Rescue of influenza A viruses from plasmid DNA was performed as previously described (see, e.g., Fodor et al., 1999, J Virol 73:9679-9682; and Hai et al., 2008, J Virol 82:10580-10590). To generate the recombinant wild-type (rWT) PR8 virus, 293T cells were co-transfected with 1 μg of each of the 8 pDZ PR8 rescue plasmids using Lipofectamine 2000 (Invitrogen, Carlsbad, Calif.). The viruses expressing different chimeric HA were generated in the same way but substituting the HA plasmid by the corresponding chimeric one to recover the corresponding chimeric viruses. At 6 h post-transfection, the medium was replaced with DMEM containing 0.3% bovine serum albumin (BSA), 10 mM HEPES, and 1.5 μg/ml TPCK (L-1-tosylamide-2-phenylethyl chloromethyl ketone)-treated trypsin. After 24 hours post-transfection, virus-containing supernatant was inoculated into 8-day old embryonated chicken eggs. Allantoic fluid was harvested after 2 days of incubation at 37° C. and assayed for the presence of virus by hemagglutination of chicken red blood cells and by plaque formation in MDCK cells.

6.2.1.6 Virus Growth Kinetics Assay

To analyze the replication characteristics of recombinant viruses, 10-day old embryonated chicken eggs were inoculated with 100 pfu of each respective virus. Allantoic fluid was harvested and subsequently assayed for viral growth at 0, 9, 24, 48, and 72 h post-infection (hpi). The titers of virus present in allantoic fluid were determined by plaque assay on MDCK cells.

6.2.1.7 Immunostaining of Plaques

Plaques were visualized by immunostaining with the mAb (HT103) against the influenza A NP protein.

6.2.1.8 Western Blot and Indirect Immunofluorescence Analysis

One well of a 12-well dish of confluent MDCK cells was infected (multiplicity of infection [MOI] of 2) with indicated recombinant influenza viruses or mock infected with phosphate-buffered saline (PBS) for 1 h at 37° C. At 12 h post-infection (hpi), cells were lysed in 1× protein loading buffer as described previously (see, e.g., Hai et al., 2008, J Virol 82:10580-10590). The reduced cell lysates were analyzed by Western blot analysis by using mAbs against, A/NP (HT103), A/PR8/HA (PY102), A/Cal/09/HA (29C1), A/VN/HA (M08) (20), A/H3/HA (12D1). The detection of Perth-cH7 used a goat polyclonal sera, NR-3152, against A/FPV/Dutch/27 (H7) virus, which was obtained from the BEI Resources. The mAb anti-Glyceraldehyde 3-phosphate dehydrogenase (GAPDH) loading control antibody was from Abcam. All the proteins of interest were visualized using an enhanced chemiluminescence protein detection system (PerkinElmer Life Sciences, Boston, Mass.).

For immunofluorescence analysis, confluent monolayers of MDCK cells on 15-mm coverslips were infected with recombinant viruses at an MOI of 2. At 15 hpi, cells were fixed and permeabilized with methanol-acetone (ratio, 1:1) at −20° C. for 20 min. After being blocked with 1% bovine serum albumin in PBS containing 0.1% Tween 20, cells were incubated for 1 h with the antibody directed against A/NP (HT103), A/H1/HA (6F12), A/PR8/HA (PY102), A/Cal/09/HA (29C1), A/VN/HA (M08) (20), A/H3/HA (12D1), and A/H7 virus (NR-3152) as mentioned above. After three washes with PBS containing 0.1% Tween 20, cells were incubated for 1 h with Alexa Fluor 594-conjugated anti-mouse immunoglobulin G (IgG; Invitrogen, Carlsbad, Calif.) or Alexa Fluor 594-conjugated anti-goat immunoglobulin G (IgG, Invitrogen, Carlsbad, Calif.). Following the final three washes, infected cells were analyzed by fluorescence microscopy with an Olympus IX70 microscope.

6.2.2 Results 6.2.2.1 Generation of Chimeric Hemagglutinins

In order to gain information regarding the conservation of the cysteine residues forming the Cys52-Cys277 disulfide bond, an alignment of the influenza A virus HA sequences of the H1, H3, H5 and H7 subtypes was generated (see FIG. 6). The sequences of the HA1 subunits are less conserved than those of the HA2 subunits, mainly due to the presence of immuno-dominant antigenic sites on the globular head domain. The more conserved HA2 chains comprise the stalk regions anchoring the HA molecules to the viral envelope. The alignment demonstrates that Cys52 and Cys277 and the amino acids towards both ends are conserved across selected subtypes. Henceforth, the hemagglutinin sequences N-terminal to Cys52 and C-terminal to Cys277 are defined as the stalk domain (FIG. 6). The intervening sequence is considered in this example to be the head domain.

A chimeric hemagglutinin construct (PR8-cH1) containing the pandemic H1 Cal/09 HA globular head domain with the stalk region from the PR8 (H1) HA was first generated (FIG. 7A). A chimeric HA (PR8-cH5) containing the globular head from the VN1203 (H5) HA with the stalk from the PR8 (H1) HA also was generated (FIG. 7B). Since all 16 subtypes of influenza HA are grouped into two phylogenetic groups (groups 1 and 2) (see, e.g., Sui et al., 2009, Nat Struct Mol Biol 16:265-273) and H1 and H5 HAs both belong to group 1, a similar strategy to generate a chimeric HA bearing the A/Alberta/24/01 (H7) head domain with the stalk region from A/Perth/16/2009 (H3) HA (Perth-cH7) (FIG. 7B) was applied. Both H7 and H3 are members from the group 2 phylogenetic group (see, e.g., Sui et al., 2009, Nat Struct Mol Biol 16:265-273).

Figure 8A:
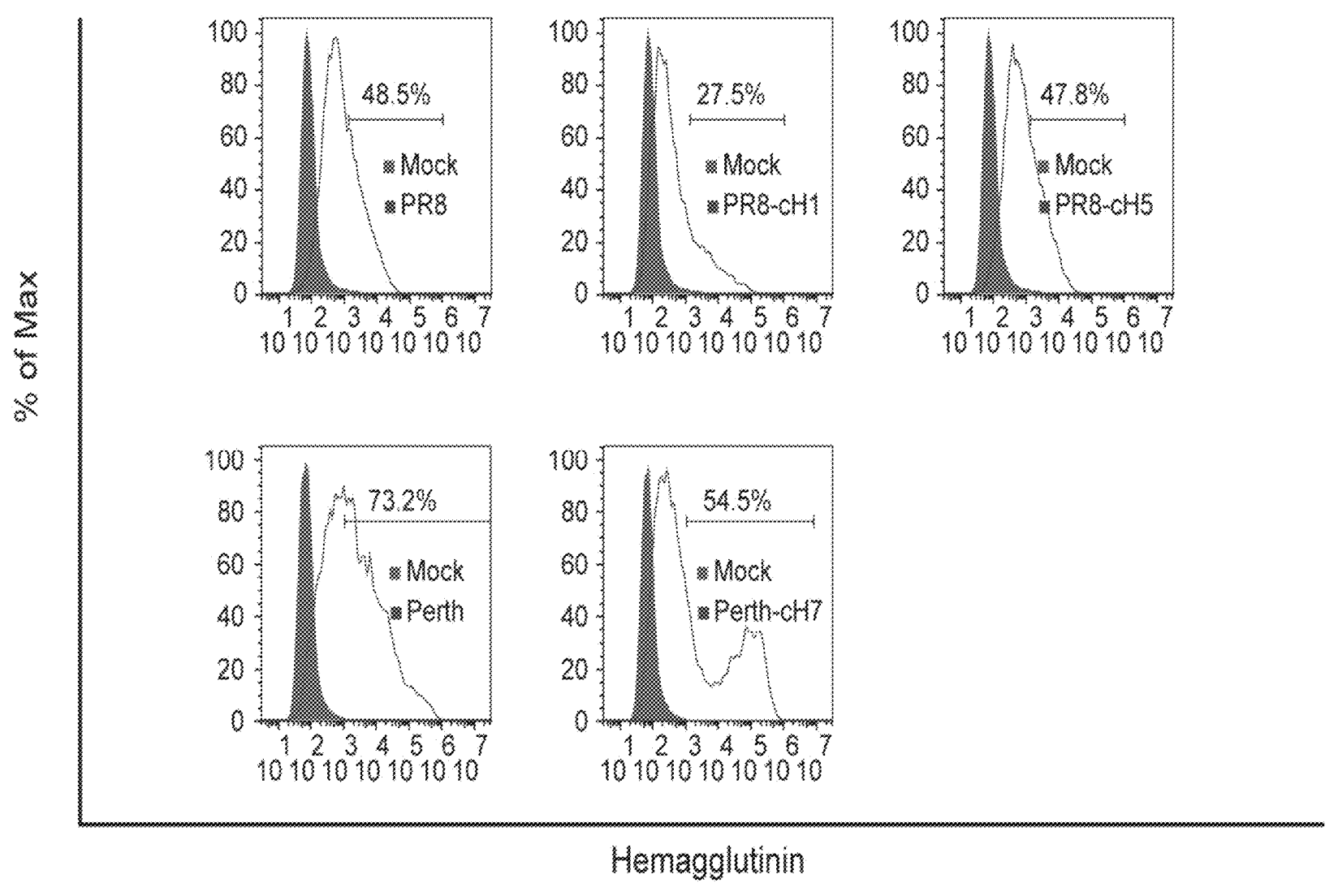

It was next tested whether the different chimeric HA constructs were being expressed and transported to the cell surface. Fluorescence-activated cell sorter (FACS) analysis of transiently transfected 293T cells was performed following surface staining with PR8 and H3 stalk domain specific antibodies, respectively (FIG. 8A). As shown in FIG. 8A, expression of all three chimeric constructs was detected. This detection indicates that the transportation of the chimeric HAs through the Golgi complex to the cell surface is not disrupted.

Figure 8B:
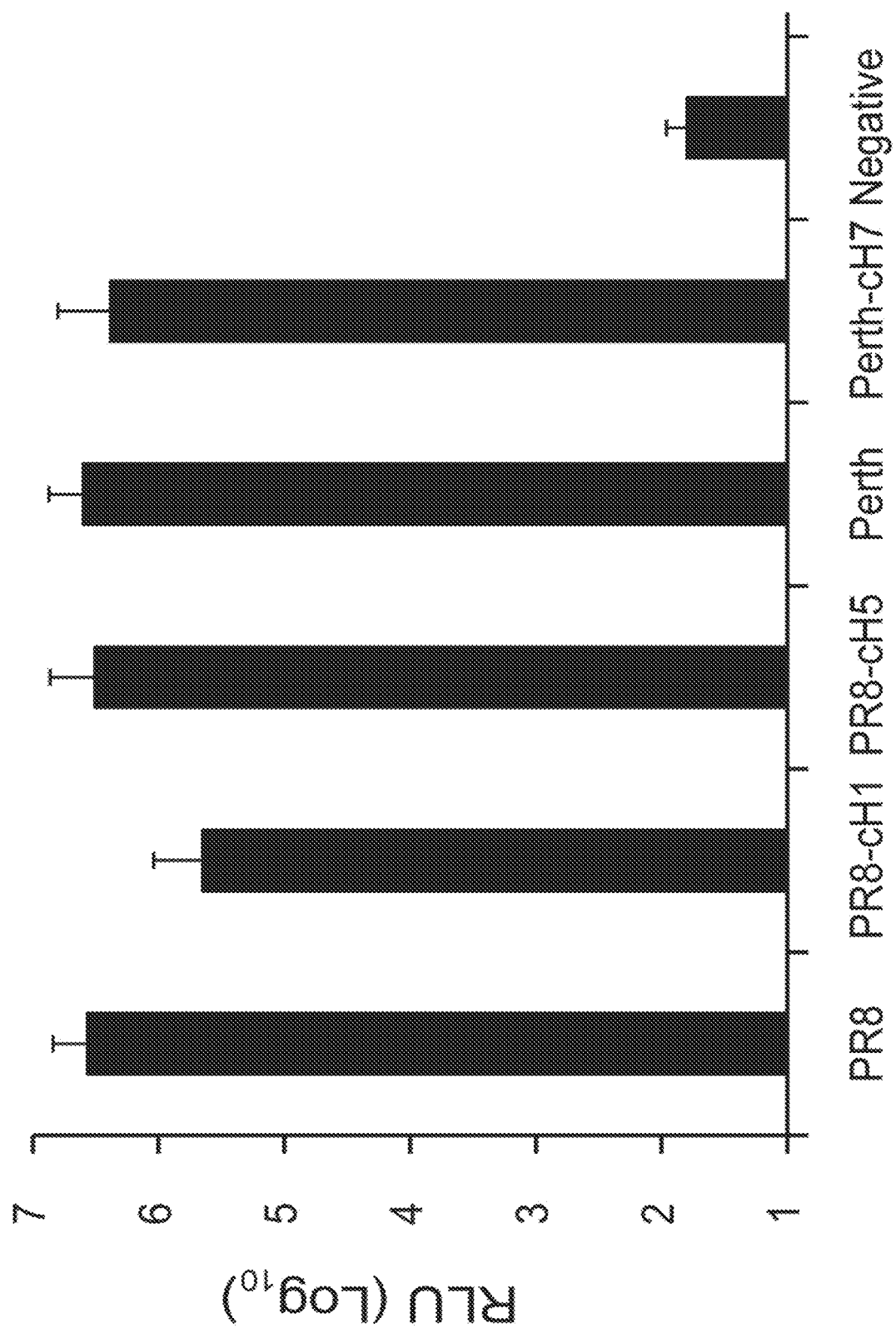

Next the entry characteristics of the different chimeric HAs was examined through infection of MDCK cells with retroviral HA-pseudotyped particles containing the chimeric HA, wild type influenza A PR8 NA and HIV-based luciferase. The entry efficiency mediated by the chimeric HA proteins was detected by luciferase read-out. Comparable levels of pseudotyped particle-mediated luciferase delivery were observed for PR8-cH5 and Perth-cH7 chimeric HAs and the corresponding wild type proteins (FIG. 8B). The PR8-cH1 HA showed a lower luciferase level compared to the other HA constructs.

6.2.3 Generation of Recombinant Influenza Viruses Bearing Chimeric Hemagglutinins.

In light of the above results, whether a chimeric HA is functional in the context of a whole virus particle and ultimately would allow the rescue of a recombinant influenza A virus only expressing a chimeric HA was ascertained. Using previously published protocols (see, e.g., Fodor et al., 1999, J Virol 73:9679-9682; and Hai et al., 2008, J Virol 82:10580-10590), viruses containing all of the different chimeric HAs were successfully generated. The resulting viruses were plaque purified, amplified in 10-Day-old embryonic eggs and the chimeric segments were analyzed by RT-PCR and sequenced. In all cases, the virus was found to have the expected chimeric HA segment and no other HA segments.

Figure 9A:
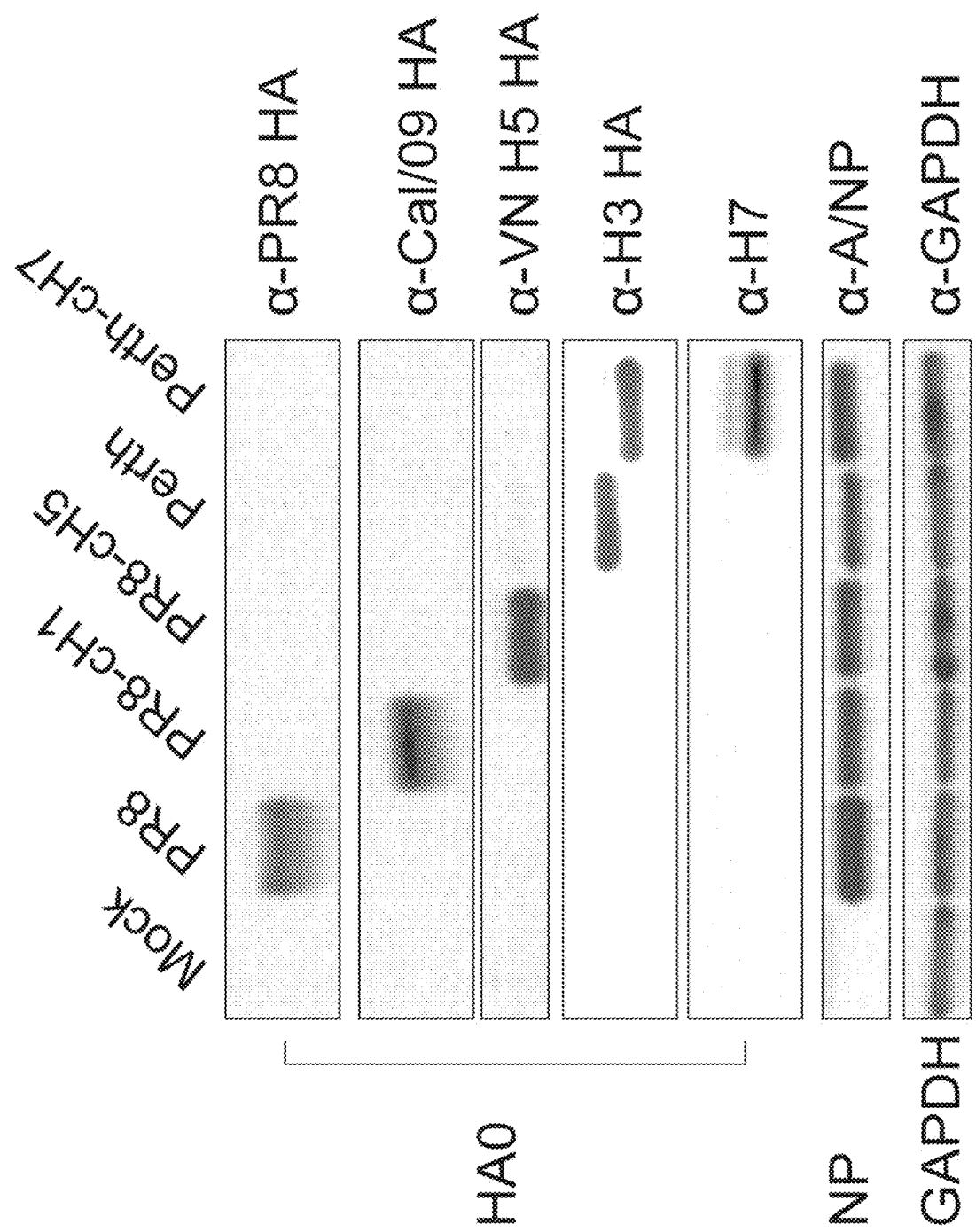
Figure 9B:
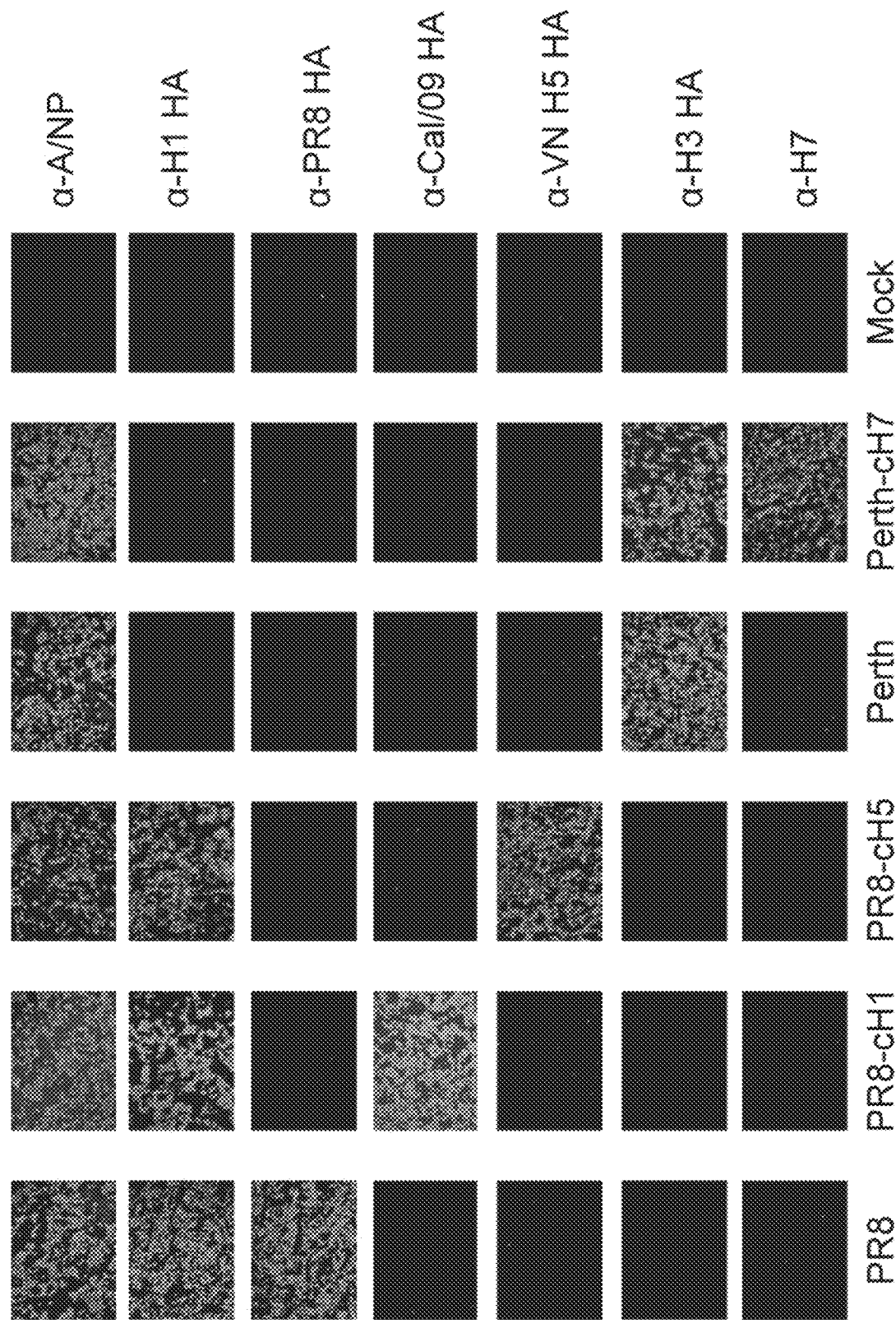
Figure 10A:
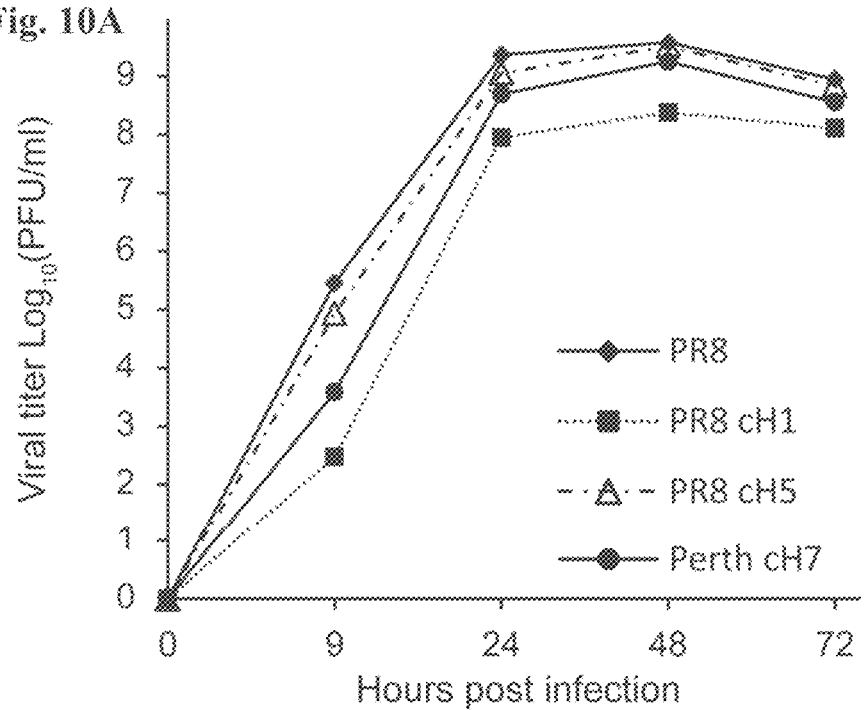
Figure 10B:
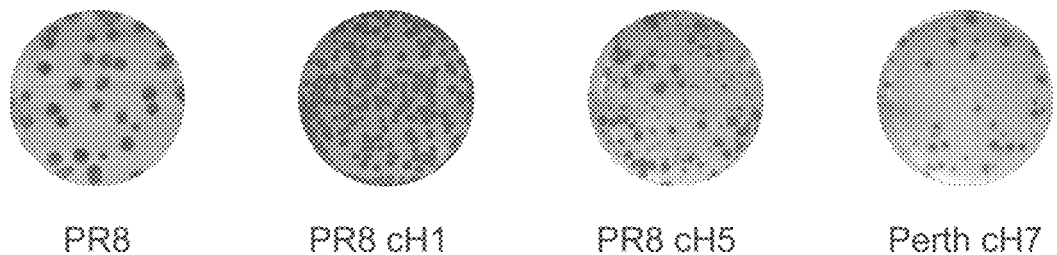

The identity of the chimeric viruses was further demonstrated by Western blotting and indirect immunofluorescence of infected cells (FIGS. 9A and 9B). MDCK cells were infected with rWT A/PR8, wild-type A/Perth, PR8-cH1, PR8-cH5, and Perth-cH7 viruses (FIGS. 9A and 9B). PR8-cH1 and PR8-cH5 chimeric HA proteins were detected in the corresponding samples using antibodies against either Cal/09 HA (29C1) or VN/04 HA (M08) (see Steel et al., 2009, J Virol 83:1742-1753), respectively (FIG. 9A). Using 12D1, a pan H3 stalk mAb (see Wang et al., 2010, PLoS Pathog 6:e1000796), comparable expression levels between the Perth cH7-HA and wild type Perth HA were observed. A positive band was only detected for the Perth-cH7 infection sample when using anti-H7 antibodies (NR-3152).

For the immunofluorescence study, the infection conditions were similar to those for the Western analysis. Infected cells were stained with corresponding antibodies as indicated in FIG. 9B. All the infected cells showed the expected expression of the HAs as well as of the A/NP protein (FIG. 9B).

6.2.4 Replication Characteristics of Recombinant Viruses

The growth properties of the viruses were assessed in 10-day-old embryonated chicken eggs at 37° C. (FIG. 8A). The rWT PR8 virus was included for comparison of the growth kinetics of the recombinant viruses expressing chimeric HAs. Regarding the PR8-cH5 virus, a similar replication pattern as compared to PR8 virus was observed. As for Perth-cH7 virus, there was a 2 fold reduction in viral titer compared to the rWT PR8 virus at 9 hpi. Nevertheless, it reached a similar peak titer as the wild type virus (1X109 PFU/ml) at 48 hpi. The PR8-cH1 virus was attenuated when compared to the rWT PR8 virus, as shown by reduction in titers through all the time points. Nonetheless, even this chimeric virus reached a respectable peak titer of approximately 108 PFU/ml. The plaque phenotype of each of the chimeric viruses was also evaluated in MDCK cells. All viruses formed comparably sized plaques as shown in FIG. 8B. These results confirm that the chimeric HA constructs fold correctly in vivo and are biologically functional.

6.2.5 Conclusion

A novel strategy was developed to generate influenza viruses with chimeric HA proteins bearing different HA globular head domains by taking advantage of the conserved disulfide bond Cys52-Cys277 which demarcates the border between the head and stalk domains. Thus, through substituting the parental head domain with the head domain of another HA, a panel of chimeric HAs with the same stalk but different globular heads was generated. The design was tested across multiple subtypes, including the PR8 stalk domain with Cal/09 and VN H5 globular heads. In addition, an H7 globular head was placed on an H3 stalk domain. These constructs cover both phylogenetic groups of the influenza HA protein. Each construct was expressed on the cell surface and retained fusion activity as shown in FIG. 7. The generation of recombinant viruses bearing the chimeric HAs further validated that the HAs fold correctly and retain biological functions.

6.3 Example 3: Diagnostic Applications of Chimeric Influenza Virus Hemagglutinin Polypeptides and Vaccination of Mice with Chimeric Influenza Virus Hemagglutinin Polypeptides This example demonstrates that chimeric influenza virus hemagglutinin polypeptides can be utilized for diagnostic purposes and that viruses expressing chimeric influenza virus hemagglutinin polypeptides can be utilized in vaccines.

6.3.1 Materials and Methods 6.3.1.1 Cells and Plasmids 293T and MDCK cells were obtained from ATCC and were maintained in Dulbeccos's Modified Eagle's medium (DMEM) and Minimal Essential Medium (both from Gibco), respectively, each supplemented with 10% fetal calf serum (HyClone), and 100 units/ml of penicillin-100 µg/ml of streptomycin (Pen/Strep, Gibco). TNM-FH (Sigma-Aldrich) supplemented with 10% fetal calf serum and Hyclone SFX insect culture media (ThermoScientific) were used for Sf9 and BTI-TN5B 1-4 (High Five) cell culture.

Chimeric hemagglutinin constructs with the stalk of A/Puerto Rico/8/1934 (PR8) containing the globular head domain from either A/Mallard/Sweden/81/02 ("cH6") virus or A/Guinea fowl/Hong Kong/WF 10/99 ("cH9") virus were generated using similar techniques. For the chimeric H6 construct, different components were amplified by PCR and cloned into the pDZ plasmid using a cloning strategy previously described (see, e.g., Fodor et al., 1999, J Virol 73:9679-82; and Hai et al., 2008, Journal of Virology 82:10580-90). Briefly, different components of the chimeric hemagglutinin (cHA) were amplified by PCR with primers containing Sap I sites, digested with Sap I, and cloned into the Sap I sites of the pDZ plasmid. For generation of the baculo-transfer plasmid, cH6 was amplified by PCR, cut with BamHI and NotI, and cloned in frame into a modified pBacPAK8 (Gentech) baculo-transfer vector that harbors a C-terminal T4 phage foldon and a 6-his tag (see Meier et al., 2004, J Mol Biol 344:1051-69). The sequences of all plasmids were confirmed by Sanger sequencing.

6.3.1.2 Rescue of Recombinant cH9 Virus

In order to rescue the recombinant vaccine virus, eight reverse genetics plasmids that encode vRNA and mRNA of the seven wild type viral segments from PR8 and the cH9 were used, as previously described (Fodor et al., 1999, J Virol 73:9679-82; and Pleschka et al., 1996, J Virol 70:4188-92). Briefly, 293T cells were transfected with 1 µg of each of the eight plasmids using Lipofectamine 2000 (Invitrogen). At 12 hours post transfection, the medium was replaced with DMEM containing 0.3% bovine serum albumin, 10 mM HEPES, and 1.5 µg of TPCK (1-1-tosylamide-2-phenylethyl chloromethyl ketone)-treated trypsin/mL. At two days post transfection, virus-containing supernatant was inoculated into 10-day-old embryonated chicken eggs. Allantoic fluid was harvested after 2 days of incubation at 370 C and assayed for the presence of virus by the hemagglutination of chicken red blood cells. The rescued cH9 virus was then propagated in 10-day old eggs following a 48 hour incubation at 37° C. Virus stocks were tittered by plaque assay as previously described (see, e.g., Steel et al., 2009, Journal of Virology 83:1742-53). The sequence of the cH9 was confirmed by sequencing of reverse transcription-PCR products.

6.3.1.3 Recombinant Baculovirus Generation, Protein Expression and Purification

In order to generate recombinant baculoviruses (rBV) carrying the cH6, plasmids and Baculogold DNA (BDBiosciences) were co-transfected into Sf9 cells with Cellfectin II (Invitrogen) according to the manufacturer's instructions. Recombinant baculovirus was amplified in Sf9 cells grown in TNM-FH medium (Gemini Bioproducts, West Sacramento, Calif.) and titers were determined by plaque assay as previously described (see, e.g., Steel et al., 2009, Journal of Virology 83:1742-53).

High Five cells (see Krammer et al., 2010, Mol Biotechnol 45:226-34) grown in HyClone SFX insect cell media (Thermo Fisher Scientific, Waltham, Mass.) were infected with rBV expressing cH6 at a multiplicity of infection (MOI) of 10 and a cell density of $1\times10^6$ cells/ml in 500 ml shaker flasks. Cells were harvested 96 hours post-infection and separated from supernatant by low speed centrifugation for 10 minutes at 2000×g at room temperature. For purification of cH6 protein, the supernatant was collected and incubated with Ni-NTA resin (Qiagen) for 2 hours at 4° C. The slurry was loaded on columns and washed trice with washing buffer (50 mM Na2HCO3, 300 mMNaCl, 20 mM Imidazole, pH 8). Protein was eluted in 0.5 ml steps with elution buffer (50 mM Na2HCO3, 300 mMNaCl, 250 mM Imidazole, pH 8), tested for protein content with Bradford reagent and fractions containing protein were pooled. Protein purity and identity was tested by SDS-PAGE, Coomassie staining and Western blot. Protein concentration was determined with Bradford reagent.

6.3.1.4 Mouse Experiments

For all procedures, mice were anesthetized with intraperitoneal injections of 0.1 mL of ketamine/xylazine mixtures (1.5 mg ketamine and 0.3 mg xylazine).

Mouse 50% lethal doses ($LD_{50}$) were determined in BALB/c mice (Charles River Laboratories) by infecting groups of four mice with 10-fold serial dilutions of influenza virus. Body weights were monitored for a two week period. Mice that lost greater than 25% of their body weight were considered to have reached experimental endpoint and were euthanized. $LD_{50}$ values were calculated by the method of Reed and Meunch (see Reed and Meunch. 1938, Am. J. Hyg. 27:493-497).

For experiments to assess the stem antibodies produced following A/California/04/09 (Cal/09) virus infection, female, 8-10 week old BALB/c mice were first primed with intramuscular administration of 80 µg of an expression plasmid encoding full length HA from PR8 virus, coupled with the application of electrical stimulation as previously described (TriGrid delivery system, Ichor Medical Systems) (see, e.g., Luxemburg et al., 2007, Expert Opinion on Biological Therapy 7:1647-64). Three weeks later, mice were boosted with a sublethal dose of $10^4$ PFU Cal/09 in a 50 µl volume, intranasally. Control animals either received DNA alone or Cal/09 virus alone, or intramuscular injection of the 2009-2010 vaccine (Cal/09 split vaccine). Three weeks post boost, or the equivalent time point for control animals, mice were bled and sera was harvested to test reactivity to cH6 by immunofluorescence as described below.

For experiments testing the efficacy of cH9 virus as a vaccine construct, PR8 full length DNA was administered as described above. Three weeks post prime, mice were inoculated with $10^3$ PFU of cH9 virus instilled intranasally. Control animals either received DNA alone or Cal/09 virus alone or purified inactivated PR8 virus intramuscularly. Three weeks post boost, or the equivalent time point for control animals, mice were challenged with intranasal inoculation of $5 \times 10^4$ $LD_{50}$ of PR8 virus. Mice were weighed for 14 days post challenge. Animals that lost more than 27.5% of their initial body weight were euthanized and scored as dead.

6.3.1.5 Immunofluorescence to Confirm Expression of Chimeric Hemagglutinin

Confluent monolayers of 293T cells were transfected with 1 µg of pDZ cH6 plasmid. At 48 hours post transfection, cells were fixed and blocked with 1% bovine serum albumin in PBS containing 0.1% Tween 20. Cells were then incubated with sera pooled from the animals of each of the four experimental groups described above (PR8 DNA alone, Cal/09 alone, PR8 DNA and Cal/09 infection, or Cal/09 split vaccine alone). After three washes with PBS containing 0.1% Tween 20, cells were incubated for 1 hour with Alexa Fluor 488-conjugated anti-mouse IgG (Invitrogen). Infected cells were analyzed by fluorescence microscopy with an Olympus IX70 microscope.

6.3.1.6 ELISA

Ninety-six well ELISA plates (Nunc, MaxiSorp) were coated with 50 ml of baculovirus-expressed cH6 and incubated overnight at 4° C. Plates were blocked 3% milk/PBS and then washed with PBS/0.1% Tween (PBST). Serum from vaccinated mice was serially diluted in PBS and added to the plate, followed by a 1 hour incubation at 37° C. Plates were then washed with PBST and incubated with 1:2500 dilution of horseradish peroxidase linked anti-mouse IgG (GE Healthcare). Following an additional wash with PBST, SigmafastOPD substrate (Sigma) was added. The reaction was stopped with 3M $H_2SO_4$ and optical density measurements were taken at 490 nm.

6.3.2 Results 6.3.2.1 Chimeric Influenza Virus Hemagglutinin Polypeptides can be Used in Diagnostic Applications A chimeric hemagglutinin construct comprising the globular head domain from the hemagglutinin of an H6 influenza virus subtype and stem/stalk domain from the hemagglutinin of the PR8 virus was generated to serve as analytical tool to assay production of antibodies by the immunized mice against the H6 stem domain. Because the immunized mice were only exposed to the globular head of H1 viruses, antibodies that were generated in the experimental animals would only be reactive to chimeric H6 hemagglutinin (cH6) if they were directed towards its H1 stem.

As shown in FIGS. 11A and 11D, treatment with DNA alone or pandemic split vaccine did not elicit any stem reactive antibodies in the vaccinated mice. Conversely, infection with Cal/09 alone generated stem reactive antibodies (FIG. 11B), though not to the extent elicited by DNA electroporation and infection (FIG. 11C). A cross-reactive H1 stem antibody, C179, was used as a control for the transfection (FIG. 11E). As expected, PY102, an antibody directed against the globular head of PR8, did not react to the transfected cH6 HA (FIG. 11F).

Figure 13:
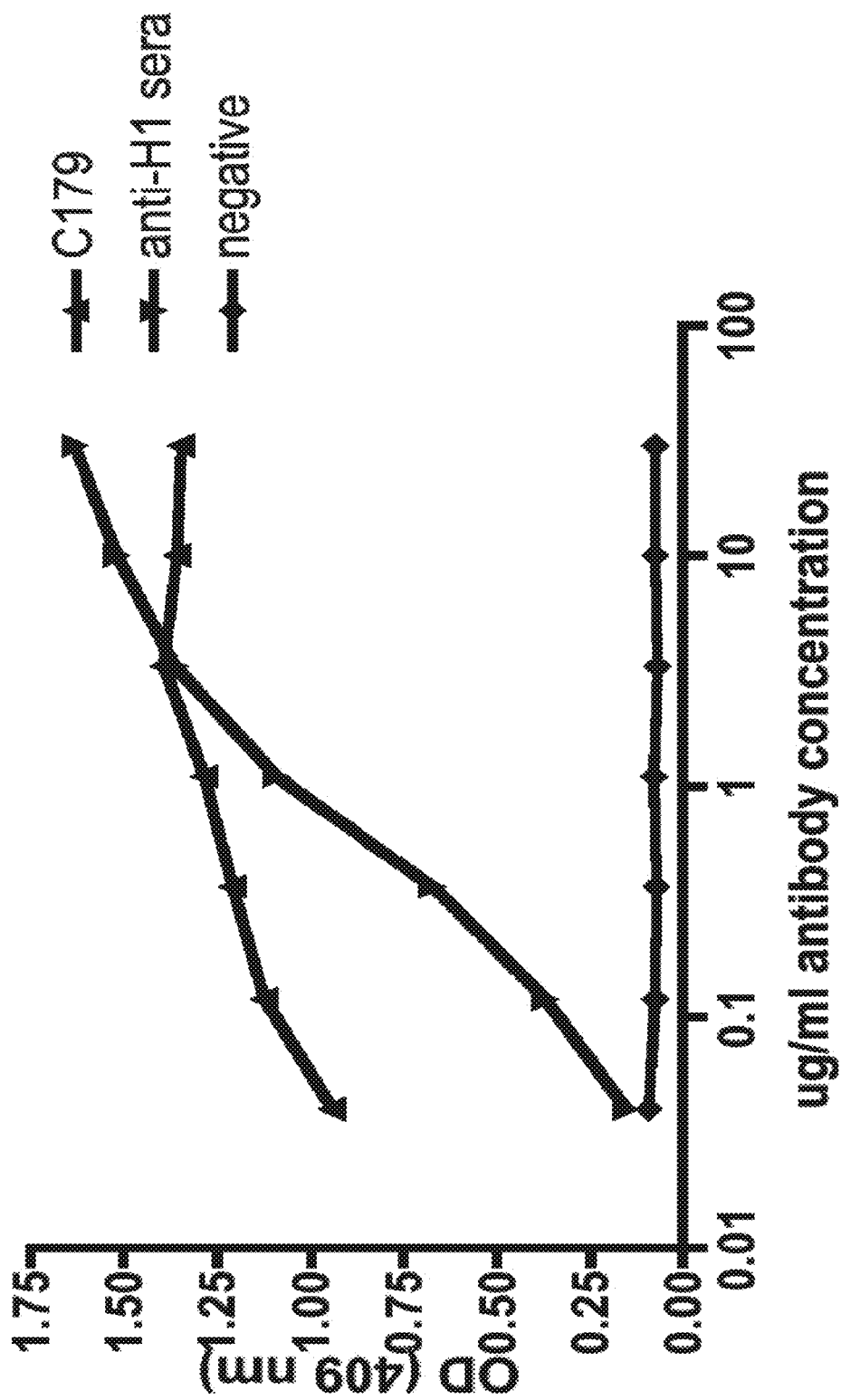

As shown in FIG. 13, the utility of the cH6 chimeric influenza virus hemagglutinin polypeptide as a tool in which to detect stem antibody binding was confirmed by ELISA.

Figure 12:
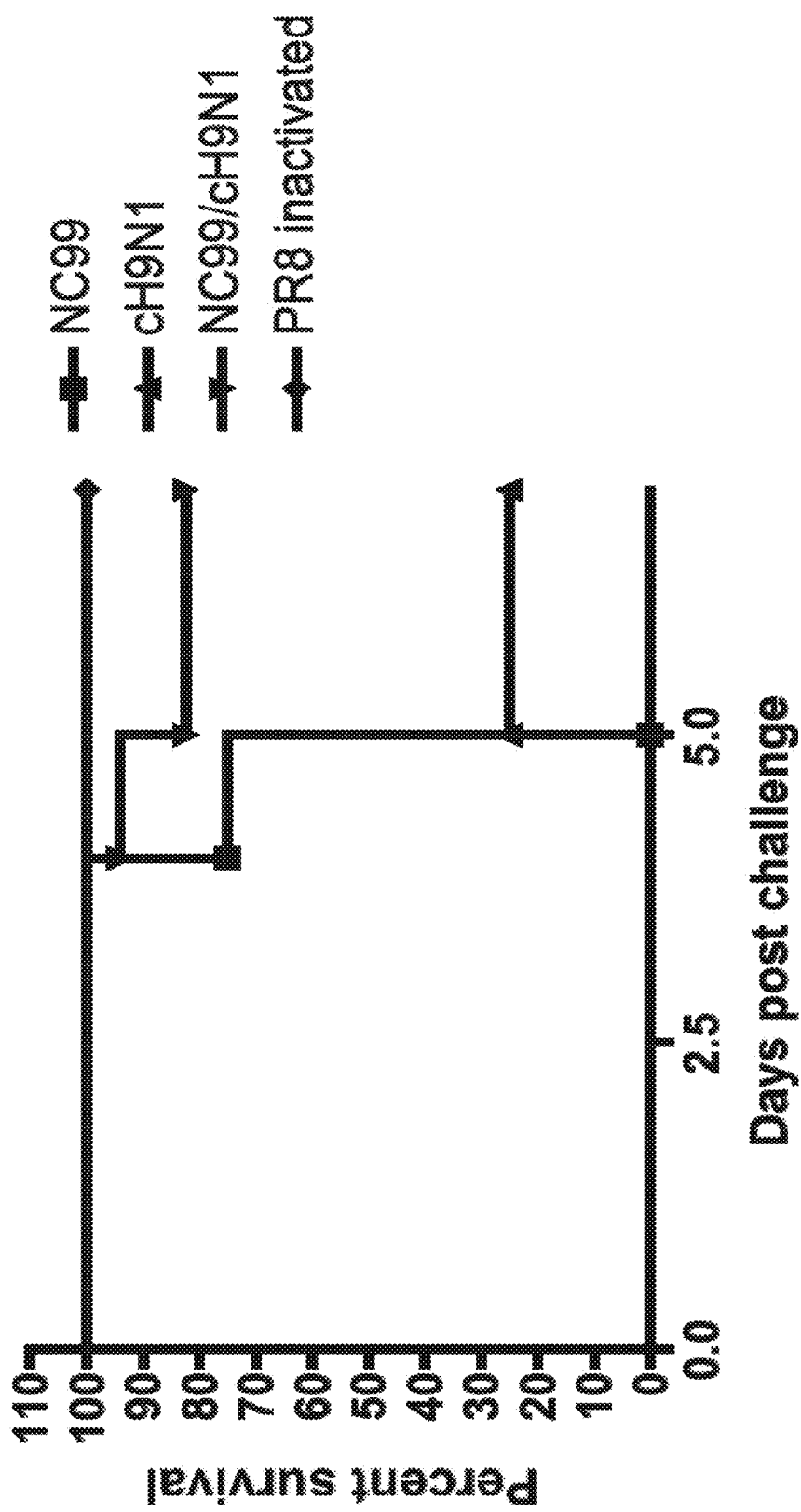

6.3.2.2 Chimeric Influenza Virus Hemagglutinin Polypeptides can be Used in Vaccines As shown in FIG. 12, animals that were vaccinated with inactivated PR8 virus were protected from lethal challenge, while animals that received DNA alone completely succumbed to infection by day 5 post challenge. Animals that received cH9 virus alone also were not protected from infection, with only a 25% survival rate. By contrast, animals that were first primed with DNA and then boosted with cH9 virus were protected from challenge, with a survival rate that was statistically the same as animals vaccinated with the inactivated virus preparation.

6.4 Example 4: Hemagglutinin Stalk Antibodies Elicited by Infection with the 2009 Pandemic H1N1 Influenza Virus This example describes chimeric influenza virus hemagglutinin polypeptides that were used to study stem domain specific antibodies. Using these polypeptides, it was determined that infection with the 2009 pandemic H1N1 virus elicited a boost in titer of virus-neutralizing antibodies directed against the hemagglutinin stem. In addition to the chimeric influenza virus hemagglutinin polypeptides, assays that can be used to measure influenza virus-neutralizing antibodies which are not detected in the traditional hemagglutination-inhibition assay are also described.

6.4.1 Materials and Methods 6.4.1.1 Cells and Plasmids 293T and MDCK cells were obtained from ATCC and were maintained in Dulbeccos's Modified Eagle's medium (DMEM) and Minimal Essential Medium (both from Gibco), respectively, each supplemented with 10% fetal calf serum (HyClone), and 100 units/ml of penicillin-100 µg/ml of streptomycin (Pen/Strep, Gibco). TNM-FH media (Gemini Bioproducts) supplemented with 10% fetal calf serum and Hyclone SFX insect culture media (ThermoScientific) were used for Sf9 and BTI-TN5B 1-4 (High Five) cell culture.

Chimeric hemagglutinin (cHA) constructs with the stalk of A/Puerto Rico/8/1934 (PR8) containing the globular head domain from either A/Mallard/Sweden/81/02 (cH6/1) virus or A/Guinea fowl/Hong Kong/WF10/99 (cH9/1) viruses were generated using methods previously described (Hai et al., 2008, *J Virol* 82, 10580; Fodor et al., 1999, *J Virol* 73, 9679). Briefly, different components of the chimeric hemagglutinin (cHA) were amplified by PCR with primers containing Sap I sites, digested with Sap I, and cloned into the Sap I sites of the pDZ plasmid (Quinlivan et al., 2005, *J Virol* 79, 8431). For generation of the baculo-transfer plasmids, cH6/1 and cH9/1 were amplified by PCR, cut with BamHI and NotI, and cloned in frame into a modified pFastBac (Invitrogen) baculo-transfer vector that harbors a C-terminal T4 phage foldon and a 6-his tag (Meier et al., 2004, *J Mol Biol* 344, 1051). The sequences of all plasmids were confirmed by Sanger sequencing.

6.4.1.2 Recombinant Baculovirus Generation, Protein Expression and Purification

In order to generate recombinant cH6/1 and cH9/1 protein, baculo-transfer vectors were transformed into *E. coli* strain DH10Bac (Invitrogen) according to the manufacturer's instructions. DH10Bac colonies showing the right phenotype were picked, grown up and bacmids were prepared using a Plasmid Midi Kit (Qiagen).

Bacmids carrying the cH6/1 or cH9/1 genes were transfected into Sf9 cells with Cellfectin II (Invitrogen) according to the manufacturer's instructions. Recombinant baculovirus was amplified in Sf9 cells grown in TNM-FH medium (Gemini Bioproducts, West Sacramento, Calif.) and titers were determined by plaque assay (King et al., 2007, *Methods Mol Biol* 388, 77).

High Five cells grown in HyClone SFX insect cell media (Thermo Fisher Scientific) were infected with recombinant baculovirus expressing cH6/1 or cH9/1 at a multiplicity of infection (MOI) of 10 and a cell density of $1\times10^6$ cells/ml in 500 ml shaker flasks (Krammer et al., 2010, *Mol Biotechnol* 45, 226). Cells were harvested 96 hours post infection and separated from supernatant by low speed centrifugation for 10 minutes at 2000 g and room temperature. For purification of cHA proteins, the supernatant was collected and incubated with Ni-NTA resin (Qiagen) for 2 hours at 4° C. The slurry was loaded onto columns and washed 3× with washing buffer (50 mM Na2HCO3, 300 mM NaCl, 20 mM imidazole, pH 8). Protein was eluted in 0.5 ml steps with elution buffer (50 mM Na2HCO3, 300 mM NaCl, 250 mM imidazole, pH 8), tested for protein content with Bradford reagent and fractions containing protein were pooled. Pooled fractions were buffer exchanged in PBS and concentrated using an Amicon Ultra centrifugal filter unit (Millipore) with a 10 kD molecular weight cut-off in a swinging bucket rotor. Protein purity and identity were tested by SDS-PAGE, Coomassie staining and Western blot. The following antibodies were used to confirm expression of cHA: Anti-H6 goat antiserum (BEI, # NR-663), G1-26 (anti-H9, mouse; BEI # NR-9485), 3951 (rabbit, anti-HA2 PR8) (Graves et al., 1983, *Virology* 126, 106), PY102 (anti-PR8 head, mouse), and 12D1 (anti-H3 stalk, mouse) (Wang et al., 2010, *PLoS Pathog* 6, e1000796). Final protein concentrations were determined with Bradford reagent.

6.4.1.3 Rescue of Recombinant cHA Expressing Viruses

In order to rescue the recombinant virus expressing cH9/1, reverse genetics plasmids that encode vRNA and mRNA of the six wild type viral segments from PR8, as well as plasmids encoding the N3 NA from A/mallard/Alberta/24/01 virus and cH9/1 were used, as previously described (Hai et al., 2008, *J Virol* 82, 10580; Fodor et al., 1999, *J Virol* 73, 9679, 27). Briefly, 293T cells were transfected with 1 µg of each of the eight plasmids using Lipofectamine 2000 (Invitrogen) according to the manufacturer's instructions. At 12 hours post transfection, the medium was replaced with DMEM containing 0.3% bovine serum albumin, 10 mM HEPES, and 1.5 µg of TPCK (1-1-tosylamide-2-phenylethyl chloromethyl ketone)-treated trypsin/mL (Sigma T1426). At two days post transfection, virus-containing supernatant was inoculated into 10-day-old embryonated chicken eggs. Allantoic fluid was harvested after 2 days of incubation at 370 C and assayed for the presence of virus by the hemagglutination of chicken red blood cells. The rescued cH9/1 virus was then propagated in 10 day old eggs following a 48 hour incubation at 37° C. Virus stocks were titered by plaque assay as previously described on MDCK cells in the presence of TPCK trypsin (Steel et al., 2009, *J Virol* 83, 1742). The sequence of the cH9/1 RNA was confirmed by sequencing of reverse transcription-PCR products.

6.4.1.4 Immunofluorescence to Confirm Expression of Chimeric Hemagglutinin

Confluent monolayers of MDCK cells were infected with cH9/1N3 virus at an MOI of 2. At 48 hours post infection, cells were fixed and blocked with 1% bovine serum albumin in PBS containing 0.1% Tween 20. Cells were then incubated with mouse mAbs: anti-NP antibody HT103, PY102, anti-H9 (BEI NR #9485), or a pan-H1 stalk-specific antibody (6F12). After three washes with PBS containing 0.1% Tween 20, cells were incubated for 1 hour with Alexa Fluor 488-conjugated anti-mouse IgG (Invitrogen). Infected cells were analyzed by fluorescence microscopy with an Olympus IX70 microscope.

6.4.1.5 Human Serum Samples

Human sera samples were collected and used in accordance with institutional protocols. Sera were collected from three patient cohorts: adults not infected with pH1N1, children not infected with pH1N1, and pH1N1 virus infected adults. Sera were collected from pH1N1 infected patients within the first 3 weeks of symptomatic infection. For experiments using pooled serum, an equal volume of each sample was mixed to generate pool. Confirmation of infection was performed by Wrammert et al. by RT-PCR and by serological assays (Wrammert et al., 2011, *J Exp Med* 208, 181-193).

6.4.1.6 Hemagglutinin Inhibition Assays

Collected sera were first inactivated by trypsin-heat-periodate treatment or by RDE treatment in order to remove non-specific inhibitors of hemagglutination (Coleman, Dowdle, 1969, *Bull World Health Organ* 41, 415 (1969). Hemagglutination inhibition (HI) assays were performed to test reactivity with cH9/1N3 and A/duck/France/MB42/76 (H6 HA) (Desselberger et al., 1978, *Proc Natl Acad Sci USA* 75, 3341 (July, 1978)) viruses as previously described (Lowen et al., 2009, *J Virol* 83, 2803). A sample is considered negative if HI activity is not seen with a 1:10 dilution of the serum.

6.4.1.7 ELISAs

Ninety-six well ELISA plates (Qiagen HisSorb or Nunc Immulon 2) were coated with 50 ul of baculovirus-expressed cH6/1, cH9/1 or full length hemagglutinin (H5 HA, BEI NR #660; H3 HA, BEI NR #15171) proteins or H1 sequence (PR8) long alpha helix (LAH) (Wang et al., 2010, *Proc Natl Acad Sci USA* 107, 18979) diluted in PBS and incubated overnight at 4° C. Plates were blocked with 0.5% milk/2% goat sera/PBS and then washed 3× with PBS/0.1% Tween (PBST). Monoclonal antibodies, sera from human subjects, and mouse sera used as controls were serially diluted in PBS or blocking buffer and then added to the plate, followed by a one hour incubation at room temperature. Plates were then washed 3× with PBST and incubated with 1:5000 dilution of goat anti-Human IgG [Fc] coupled to alkaline phosphatase (AP) (Meridian Life Science) or anti-mouse AP (Invitrogen) for an additional hour. Following washing 3× with PBST, p-nitrophenyl phosphate substrate (Sigma) was added. The reaction was stopped with NaOH after 10 minutes and optical density measurements were taken at 405 nm.

6.4.1.8 Plaque Reduction Assay

Sera from adult infected and naïve (not infected with pH1N1 virus) patients were first pooled and loaded onto a gravity flow column with protein G sepharose (GE Healthcare) for purification of IgG proteins. The column was washed with PBS. The polyclonal antibodies were eluted with a 0.1 M glycine buffer (pH 2.7). A 2 M Tris-HCl buffer (pH 10) was added immediately at a 1:10 ratio to restore the pH. The eluate was buffer exchanged in PBS and concentrated using an Amicon Ultra-15 centrifugal filter unit (Millipore) with a 50 kD MW cut-off in a swinging bucket rotor. Protein concentrations were measured on a NanoDrop 2000 spectrophotometer using the A280 method. Removal of non-specific serum inhibitors was confirmed by HI tests using multiple virus strains that demonstrated an absence of HI activity in the purified IgG preparations (data not shown). Neutralization capability of stalk-reactive antibodies was assessed as previously described (Wang et al., 2010, *PLoS Pathog* 6, e1000796). Virus was first diluted to a concentration that would yield 100 plaque forming units per well. Different concentrations of IgG from pooled sera were then co-incubated with virus at room temperature for an hour. Six-well plates seeded with MDCK cells were washed with PBS and then infected with 200 ul of virus-IgG mixtures. Following a forty-five minute incubation at 37° C., virus and IgG were aspirated from cells and an agar overlay containing appropriate antibody concentration and TPCK trypsin was added to each well. Plates were incubated for 2 days at 37° C. Plaques were visualized by immunostaining (Bouvier et al., 2008, *J Virol* 82, 10052) using anti-H9 antibody G1-26.

6.4.1.9 Pseudotype Particle Neutralization Assay

The procedure for pseudotype particle production was adapted from previous studies (Evans et al., 2007, Nature 446, 801). Briefly, 293-T cells were co-transfected with four plasmids encoding (i) a pro-virus containing the desired reporter (V1-GLuc), (ii) HIV Gag-Pol, (iii) the chimeric cH9/1 hemagglutinin protein and (iv) influenza B/Yamagata/16/88 neuraminidase (NA) (Tscherne et al., 2010, *J Virol Methods* 163, 336). The V1-GLuc plasmid encodes a luciferase protein that is secreted from cells and can be detected in the cell supernatant. Supernatants were collected 48 h post-transfection and subsequently filtered (0.45 μm pore size) in order to purify the cH9/1 particle preparations. Particles were then incubated (at quantity determined to give luciferase activity within the linear range after infection) with different concentrations (50 μg/ml, 10 μg/ml and 2 g/ml) of purified human IgGs and were added to MDCK cells. Infections proceeded for 6 hours before cells were washed and fresh supernatant was placed over cells. All infections using pseudotype particles were performed in the presence of 1 μg/ml polybrene (Sigma, St. Louis, Mo.) (Tscherne et al., 2010, *J Virol Methods* 163, 336). Forty-eight hours post-infection luciferase assays were performed.

6.4.2 Results 6.4.2.1 Development of Chimeric Hemagglutinin-Based Reagents

Chimeric hemagglutinin (cHA) constructs were generated to serve as analytical tools to assess the presence of stalk antibodies in human sera. By taking advantage of a disulfide bond that exists between C52 and C277, and that delineates the boundary between the HA stalk and head, expression plasmids were engineered that encode the globular head domain of an H6 or H9 hemagglutinin atop the stalk domain from the HA of PR8 virus (FIG. 14A). It was hypothesized that human serum samples containing stalk antibodies would likely be negative for hemagglutination inhibition (HI) activity against H6 or H9 viruses (due to lack of prior exposure to these virus subtypes), yet would be reactive with the cH6/1 or cH9/1 constructs due to prior exposure to the H1 hemagglutinin stalk. These tools, recombinantly expressed cHA proteins and viruses expressing the cHAs, could be used to assess relative amounts of stalk antibodies in human serum samples and to measure any neutralizing activity mediated by those stalk-specific antibodies.

In order to generate cH6/1 and cH9/1 protein for analytical assays, plasmids coding for the chimeric HAs were generated and expressed as soluble proteins in a baculovirus expression system. Coomassie staining of 2 μg of total protein suggests a high degree of purity in these preparations (FIG. 17A). The slight delayed migration of cH9/1 is thought to be the result of an increased number of occupied glycosylation sites on the cH9/1 head. The cHA proteins were further characterized by western blot analysis using antibodies reactive with various parts of the HA. As shown in FIG. 17B, only cH6/1, cH9/1 and full length HA from PR8 reacted with a rabbit polyclonal antiserum specific for the PR8 stalk. Monoclonal antibodies against the head domains of H6, H9, and PR8 confirmed that the chimeric constructs were expressing exotic heads atop a PR8 stalk. H3 protein was used as a negative control, and was only detected when using the pan-H3 antibody 12D1 (Wang et al., 2010, *PLoS Pathog* 6, e1000796).

Recombinant viruses expressing the chimeric molecules were also rescued for the purpose of detecting neutralizing stalk antibodies. Because all human influenza viruses over the last century have encoded NA of the N1 or N2 subtype, it was reasoned that the rescue of the cH9/1N3 reassortant virus would allow for the assessment of the neutralizing capability of stalk-specific antibodies, while not measuring any (N1 or N2) neuraminidase antibody activity. The cH9/1N3 virus (expressing the H1 stalk with H9 globular head HA with an N3 subtype neuraminidase) was rescued using reverse genetics and grown to high titers in embryonated chicken eggs. The plaque assay phenotype of this virus was similar to that of PR8 wild type virus (FIG. 17C). To confirm the presence of the H9 head after virus passage, cells were infected with cH9/1N3 virus. Infected cells were then probed with mouse mAb G1-26, an antibody specific for H9 subtype hemagglutinin proteins. A pan-H1 stalk specific antibody, 6F12, was used to detect both wild type PR8 and cH9/1N3 virus infected cells (FIG. 14B).

6.4.2.2 Stalk Specific Antibodies Bind and Neutralize cHA

In order to confirm that cH6/1 and cH9/1 proteins could be used as tools to detect stem antibodies, the use of these cHAs was first validated with an antibody known to react with the HA stalk. Indeed, mouse mAb C179, an antibody reactive with the stalk of H1 HA (Okuno et al., 1993, *J Virol* 67, 2552), bound to baculovirus expressed cH6/1 and cH9/1 protein by ELISA in a dose dependent manner (FIGS. 18A and B).

Next, it was ascertained whether replication of the cH9/1N3 virus could be inhibited by monoclonal antibody 6F12, which has neutralizing activity against H1 influenza viruses (data not shown). Antibody 6F12 was able to bind and neutralize cH9/1N3 virus in a plaque reduction assay (FIGS. 18 C and D), in a dose dependent manner, with one hundred percent inhibition seen at concentrations above 4 μg/ml. These results validated the hypothesis that the chimeric proteins and the recombinant cH9/1N3 virus could be used to detect stalk antibodies with neutralizing activity.

6.4.2.3 Patients Infected with pH1N1 have High Titers of Antibodies that Bind and Neutralize cHA Prior to the use of cH6/1 and cH9/1 soluble proteins to quantitate stalk-reactive antibodies in patient blood samples, the sera for HI activity was tested against viruses expressing these two HA subtypes. Using A/duck/France/MB42/76 (H6) and cH9/1N3 viruses, it was confirmed that all adult and pediatric serum samples collected were HI negative (results not shown).

Next, the reactivity of the sera with cH6/1 and cH9/1 proteins was tested by ELISA. Sera collected from adult and pediatric subjects not infected with pH1N1 viruses showed little reactivity with either protein. However, sera collected from patients infected with pH1N1 influenza virus showed enhanced binding to both cHA constructs, with a greater than 30-fold difference in IgG reactivity (comparing dilutions that yield equivalent optical density readings) when comparing serum pools from pH1N1 infected with those of uninfected adults and children (FIGS. 15 A and B). It was therefore reasoned, by taking the negative HI data into account, that reactivity with cHA proteins is occurring in the stalk domain.

Using pooled samples of human sera, IgG binding to a portion of the HA stem, the long alpha helix (LAH), was also tested. These IgGs had previously been shown to mediate protective immunity in mice (Wang et al., 2010, *Proc Natl Acad Sci USA* 107, 18979). Sera from patients infected with pH1N1 contained antibody reactive with the H1 LAH, whereas patients unexposed to the pandemic virus had minimal LAH-specific serum antibody (FIG. 15C).

The H5 hemagglutinin subtype is within the same phylogenetic group as the H1 HA, and shares a very similar stalk structure (Ekiert et al., 2009, *Science* 324, 246). Interestingly, patients exposed to the pH1N1 had boosted serum antibody specificities reactive with the H5 protein (FIG. 15D), while not having any serum HI activity against the homologous H5 subtype virus (data not shown). This result suggested that exposure to the pH1N1 virus may have conferred a degree of anti-H5 immunity mediated by stalk-specific antibodies.

Importantly, patients infected with pH1N1 did not have boosted serum antibody specific for an H3 hemagglutinin protein (H3 being in a separate phylogenetic group from H1 and H5 HAs) (FIG. 15E). This result demonstrates that the enhanced titer of stalk-specific antibodies in sera from pH1N1-infected patients is not a function of general immune stimulation; rather, the H1 stalk antibody specificities were selectively boosted by infection with the pandemic virus strain.

Next, it was assessed whether these stalk reactive antibodies found in these human samples had neutralizing capability. Serum samples from infected and uninfected adults were pooled and total IgG was purified in order to remove non-specific inhibitors (eg: sialic acid containing molecules and lectins) that would bind to the hemagglutinin head. Using these pure IgG preparations, complete inhibition plaque formation at antibody concentrations above 55.5 µg/mL total serum IgG (FIGS. 16 A and B) was achieved. In accordance with the ELISA data, an approximately 30-fold difference in neutralizing capability was observed when comparing sera from pH1N1 infected with those of uninfected adults. Using mAb 6F12 as a standard, a comparison was able to be made between neutralizing activities mediated by 6F12 and the polyclonal human IgG preparation. By comparing the concentrations of 6F12 and human IgGs that yielded 100% neutralization of cHA virus, it was estimated that 7% of total human IgG from patients infected with pH1N1 during the last 30 days comprised neutralizing stalk antibodies.

Finally, the neutralizing capability of stalk reactive antibodies was evaluated, using a pseudotype particle infection assay that has a read-out of luciferase activity which is generated upon virus entry into host cells. Pseudotyped particles expressing the cH9/1 protein were incubated with purified human IgG and neutralizing activity was measured by inhibition of particle entry resulting in absence of luciferase enzymatic activity in cell supernatants (see methods). Consistent with the plaque reduction assay, the pseudotyped particle assay also showed 100% neutralization of particles at total IgG concentrations of exceeding 10 µg/ml (FIG. 16C).

6.4.3 Conclusion

Novel analytical tools, in the form of chimeric hemagglutinin proteins and viruses expressing those chimeric proteins, were developed that allowed for the selectively detection of stalk-specific antibodies in preparations that also include antibodies that bind the globular head of hemagglutinin proteins. These novel hemagglutinin constructs have a constant H1 subtype stalk, with globular head domains from distinct hemagglutinin subtypes (ex: H1 stalk with H6 head). This was accomplished by taking advantage of a disulfide bond that exists between cysteines 52 and 277 in the hemagglutinin protein (19) to exchange the intervening sequence with that of a different HA subtype.

Using these chimeric hemagglutinin (cHA) constructs, it was demonstrated that a small cohort of humans with confirmed pH1N1 virus infection generated a high titer of stalk specific, neutralizing antibodies compared to uninfected adult and pediatric controls not infected with pH1N1 viruses. These findings support the hypothesis that antibodies reactive with the hemagglutintin stalk, generated in response to pH1N1 infection, likely contributed to the dying out of seasonal H1N1 viruses that were circulating prior to the influenza pandemic of 2009.

6.5 Example 5: Influenza Viruses Expressing Chimeric Hemagglutinins: Globular Head and Stalk Domains Derived from Different Subtypes and Phylogenic Groups This example describes several functional chimeric influenza virus hemagglutinins encompassing a variety of globular head and stalk combinations from different hemagglutinin subtypes and different phylogenic groups as wells as recombinant influenza viruses expressing these chimeric hemagglutinins, which had growth properties similar to those of wild-type influenza viruses. These chimeric recombinant viruses possess growth properties similar to those of wild-type influenza viruses and can be used as reagents to measure domain-specific antibodies in virological and immunological assays.

6.5.1 Materials and Methods 6.5.1.1 Cells and Viruses 293T and MDCK cells were obtained from the American Type Culture Collection (ATCC) and were maintained either in Dulbecco's minimal essential medium (DMEM) or in MEM (Gibco, Invitrogen) supplemented with 10% fetal calf serum (HyClone; Thermo Scientific) and penicillin-streptomycin (Gibco, Invitrogen). The A/Puerto Rico/8/1934 (PR8) and A/Perth/16/2009 (Perth/09) wild type (kindly provided by Alexander Klimov, CDC) and recombinant viruses were grown in 10-day old specific pathogen-free embryonated hen's eggs (Charles River) at 37° C. for 2 days.

6.5.1.2 Construction of Plasmids.

Plasmids encoding the different chimeric hemagglutinins were constructed using a strategy similar to what has been previously described (see, e.g., Fodor et al., 1999, *J Virol* 73:9679-9682; and Hai et al., 2008, *J Virol* 82:10580-10590). Briefly, the different segments of chimeric HA were amplified by PCR with primers containing SapI sites, digested with SapI, and cloned into the SapI sites of the ambisense expression vector pDZ vector in which vRNA transcription is controlled by the human RNA polymerase I promoter and the mouse RNA polymerase I terminator, and mRNA/cRNA transcription is controlled by the chicken beta actin polymerase II promoter (see, e.g., Quinlivan et al., 2005, *J Virol* 79:8431-8439), through multi-segmental ligation. We kindly thank Daniel Perez (University of Maryland) for the H7 HA plasmid (Genbank ID: DQ017504). The plasmids encoding A/Puerto Rico/8/1934 (PR8) genes were used as previously described (Hai et al., 2008, *J Virol* 82:10580-10590).

6.5.1.3 Nucleotide Sequence Accession Number

All constructed cHA genes used in this study have been deposited in the Influenza Research Database under the accession number IRD-RG-684014, IRD-RG-684022, IRD-RG-684030, and IRD-RG-684038. The chimeric cH1/1, cH5/1, cH7/3 and cH5/3 are listed as A/Puerto Rico/8-RGcH1-1/34, A/Puerto Rico/8-RGcH5-1/34, A/Perth/16-RGcH7-3/09, and A/Perth/16-RGcH5-3/09, respectively.

6.5.1.4 Flow Cytometric Analysis

To assess levels of hemagglutinin protein expression at the cell surface, 293T cells were transfected with 1 µg of the appropriate plasmid using Lipofectamine 2000 (Invitrogen) according to the manufacturer's instructions or MDCK cells were infected with cHA-expressing recombinant viruses. At 48 h post-transfection, 293T cells were trypsinized and resuspended in PBS containing 2% FBS prior to staining with the monoclonal antibody (mAb) 6F12 (5 µg/ml), a mAb generated in our laboratory that is broadly reactive to the stalk domain of group 1 HAs (data not shown) or with the mAb 12D1 (5 g/mL) against H3 HAs (see Wang et al., 2010, *PLoS Pathog* 6:e1000796). At 12 h post-infection, MDCK cells were resuspended by trypsinization and stained with the mAb 12D1. Stained cells were analyzed on a Beckman Coulter Cytomics FC 500 flow cytometer, and the results were analyzed using FlowJo software.

6.5.1.5 Pseudoparticle Generation and Entry Assay

The procedure for pseudoparticle production was adapted from previous studies (see, e.g., Evans et al., 2007, *Nature* 446:801-805 and Tscherne et al, 2010, *J Virol Methods* 163:336-43). Briefly, we co-transfected 293T cells with four plasmids encoding (i) a pro-virus containing the desired reporter (V1-*Gaussia* luciferase) (Evans et al., 2007, *Nature* 446:801-805), (ii) HIV Gag-Pol (Evans et al., 2007, *Nature* 446:801-805), (iii) chimeric hemagglutinin protein and (iv) B/Yamagata/16/88 virus neuraminidase (NA). Supernatants were collected 72 h post-transfection and subsequently filtered (0.45 µm pore size). The presence of pseudotype virus like particles (VLPs) was evaluated through hemagglutination assay. Different VLP preparations were adjusted to the same 4 hemagglutination units prior to inoculation of MDCK cells. All of the following assays using pseudoparticles were performed in the presence of 1 µg/mL polybrene (Sigma) to increase the efficiency of transduction (see, e.g., Evans et al., 2007, *Nature* 446:801-805 and Tscherne et al, 2010, *J Virol Methods* 163:336-43).

The entry assay was performed by transducing MDCK cells with pseudoparticles that expressed different chimeric hemagglutinins and contained the *Gaussia* luciferase reporter. Twenty-four hours post-transduction, cells were washed three times with fresh medium to remove any residual *Gaussia* luciferase protein present in the inoculum. Forty-eight hours post-transduction, luciferase assays were performed (Evans et al., 2007, *Nature* 446:801-805).

6.5.1.6 Rescue of Recombinant Chimeric Influenza a Viruses

Rescue of influenza A viruses from plasmid DNA was performed as previously described (see, e.g., Fodor et al., 1999, *J Virol* 73:9679-9682; and Hai et al., 2008, *J Virol* 82:10580-10590). To generate the recombinant wild-type (rWT) PR8 virus, 293T cells were co-transfected with 1 µg of 8 pDZ PR8 rescue plasmids using Lipofectamine 2000 (Invitrogen). The wild type HA plasmid was substituted with a plasmid encoding the desired chimeric HA in order to generate cHA-expressing recombinant viruses. At 6 h post-transfection, the medium was replaced with DMEM containing 0.3% bovine serum albumin (BSA), 10 mM HEPES, and 1.5 μg/ml TPCK (L-1-tosylamide-2-phenylethyl chloromethyl ketone)-treated trypsin (Sigma). After 24 hours post-transfection, 8-day old embryonated chicken eggs were inoculated with virus-containing supernatant. Allantoic fluid was harvested after 2 days of incubation at 37° C. and assayed for the presence of virus by hemagglutination of chicken red blood cells. Virus stocks were titered by plaque assay on MDCK cells as previously described (Fodor et al., 1999, *J Virol* 73:9679-9682, Hai et al., 2008, *J Virol* 82:10580-10590).

6.5.1.7 Virus Growth Kinetics Assay

To analyze the replication characteristics of recombinant viruses, 10-day old embryonated chicken eggs were inoculated with 100 plaque forming units (pfu) of wild-type or cHA-expressing recombinant viruses. Allantoic fluid was harvested and subsequently assayed for viral growth at 0, 9, 24, 48, and 72 h post-infection (hpi). The titers of virus present in allantoic fluid were determined by plaque assay on MDCK cells as referenced above.

6.5.1.8 Immunostaining of Plaques

Plaques were visualized by immunostaining with mAb HT103 against the influenza A nucleoprotein (NP), using a protocol that has been previously described (Bouvier et al., 2008, *Journal of Virology* 82:10052-8; and Steel et a.l, 2009, *J Virol* 83:1742-53).

6.5.1.9 Western Blot and Indirect Immunofluorescence Analysis

Confluent MDCK cells were infected (multiplicity of infection [MOI] of 2) with indicated recombinant influenza viruses or mock infected with phosphate-buffered saline (PBS) for 1 h at 37° C. At 12 hpi, cells were lysed in 1×SDS loading buffer as described previously (see, e.g., Hai et al., 2008, *J Virol* 82:10580-10590). The reduced cell lysates were analyzed by Western blot analysis using monoclonal antibodies (mAbs) against influenza A virus nucleoprotein (NP) (HT103), PR8 HA head domain (PY102), Cal/09 HA head domain (29E3), VN/04 HA head domain (mAb #8) and 12D1, a pan-H3 antibody reactive against the HA stalk. In order to detect H7 head domains, polyclonal goat sera NR-3152 was used (raised against A/FPV/Dutch/27 (H7) virus, BEI Resources). An anti-glyceraldehyde 3-phosphate dehydrogenase (GAPDH) antibody (Abcam) was used for the loading control. Proteins were visualized using an enhanced chemiluminescence protein detection system (PerkinElmer Life Sciences).

For immunofluorescence analysis, confluent monolayers of MDCK cells on 15-mm coverslips were infected with recombinant viruses at an MOI of 2. At 15 hpi, cells were fixed and permeabilized with methanol-acetone (ratio, 1:1) at −20° C. for 20 minutes. After being blocked with 1% bovine serum albumin in PBS containing 0.1% Tween 20, cells were incubated for 1 h with the antibodies described above, as well as mAb 6F12. After three washes with PBS containing 0.1% Tween 20, cells were incubated for 1 h with Alexa Fluor 594-conjugated anti-mouse IgG (Invitrogen) or Alexa Fluor 594-conjugated anti-goat IgG (Invitrogen). Following the final three washes, infected cells were analyzed by fluorescence microscopy with an Olympus IX70 microscope.

6.5.1.10 Plaque Reduction Assay

Plaque reduction assay was performed as previously described (see Wang et al., 2010, *PLoS Pathog* 6:e1000796). Approximately 60 to 80 pfu of recombinant viruses expressing cHA made up of Cal/09 or VN/04 globular head domains atop a PR8 stalk were incubated with or without different concentrations (100, 20, 4, 0.8, 0.16 and 0.032 ug/ml) of mAb KB2, a broadly neutralizing anti-HA stalk antibody generated in our laboratory (data not shown) for 60 minutes in a total volume of 240 uL at room temperature. A confluent layer of MDCK cells in 6-well plates was washed twice with PBS and then incubated with the antibody-virus mixture for 40 minutes at 37° C. A TPCK-trypsin agar overlay supplemented with antibody at the above-described concentrations or no antibody was then added to each well after the inoculum had been aspirated off. Plates were incubated for 2 days at 37° C. Plaques were then visualized by immunostaining (Bouvier et al., 2008, *Journal of Virology* 82:10052-8; and Steel et a.l, 2009, *J Virol* 83:1742-53) with anti-influenza A NP antibody HT103.

6.5.1.11 Pseudotype Particle Neutralization Assay

The procedure for pseudotype particle production was the same as described above, using the cHA construct that is comprised of either a VN/04 (H5) or a Cal/09 (H1) head and a PR8 (H1) stalk with the influenza B/Yamagata/16/88 virus NA. Particles were then incubated with different concentrations of mAb KB2 at 5 fold dilutions from 100 to 0.032 µg/mL. Then, these mixtures were added to MDCK cells. Transductions proceeded for 6 hours before cells were washed and fresh medium was placed over cells. All transductions using pseudotype particles were performed in the presence of 1 µg/mL polybrene (Sigma, St. Louis, Mo.) (Tscherne et al, 2010, *J Virol Methods* 163:336-43). Forty-eight hours post-transduction, luciferase assays were performed in order to assay the degree in which entry was blocked by mAb KB2.

6.5.2 Results:

6.5.2.1 Generation of Chimeric Hemagglutinins

In order to see if the cysteine residues forming the Cys52-Cys277 disulfide bond were conserved, an alignment of influenza A virus HA sequences of the H1, H3, H5 and H7 subtypes were used in this study. Because these cysteine residues are highly conserved across HA subtypes, for both group 1 and group 2 HAs, the Cys52-Cys277 disulfide bond was used as a delineating point between the head and stalk domains. By defining the sequence between Cys52 and Cys277 as the head region, and the remainder of the molecule as the stalk, it was rationalized that constructs could be made that encode novel head and stalk combinations from a variety of HA subtypes (FIGS. 19 A and B).

The degree of amino acid identity that exists between the stalk regions of hemagglutinin subtypes further encouraged us that the swapping of head domains might be possible. Higher percentages of amino acid identity were seen in the stalk domains across all subtypes, compared to the head domains (FIG. 20).

All 16 subtypes of influenza HA are classified into two phylogenetic groups (Palese and Shaw, 2006, Orthomyxoviridae: the viruses and their replication, *Fields virology*, 5th ed., 1647-1690). Because higher percentages of amino acid identity was observed within stalk regions of a particular group (FIG. 20), and because one cHA virus that contained head and stalk domains from group 1 viruses had been successfully generated (Pica et al., 2012, *PNAS* 109:2573-8), an attempt was made to generate intra-group cHAs. For group 1, two chimeric hemagglutinin constructs that encode either the pandemic H1 Cal/09 HA or VN/04 globular head domain with the stalk region from PR8 (H1) HA (cH1/1 and cH5/1, respectively) were generated (FIG. 19B). A similar strategy was applied to generate a chimeric HA that expressed head and stalk domains from different group 2 influenza strains: the head from Alb/01 (H7, group 2) and the stalk region from Perth/09 (H3, group 2) HA (cH7/3) (FIG. 19B). Finally, it was evaluated whether the head and stalk domains could be swapped to make an inter-group chimeric HA containing the head domain of VN/05 HA (H5, group 1) atop a Perth/09 HA (H3, group 2) stalk (cH5/3) (FIG. 19B).

Following the construction of these plasmids, experiments were performed to determine whether the different chimeric HA constructs could be expressed and transported to the cell surface like wild-type HAs. Fluorescence-activated cell sorter (FACS) analysis of transiently transfected 293T cells was performed following surface staining with H1 and H3 stalk domain specific antibodies, respectively. Using this method, cell surface expression of all four chimeric constructs were detected (FIG. 21). However, compared to the wild type PR8 HA less surface protein expression was detected for the cH1/1 construct, which could be attributed to the inherent character associated with the head domain of the Cal/09 HA or a lower transfection efficiency for this chimeric DNA construct. In addition, it is of note that there were differences in the cell surface expression pattern for the cH7/3 and cH5/3 constructs. This "double peak" expression pattern was observed only in transfection conditions, and was reproducible. It was not detected upon infection with either cH7/3 or cH5/3-expressing recombinant viruses (FIG. 21). Therefore, these data indicate that the cHAs can be transported through the Golgi complex to the cell surface.

Next, the entry characteristics of the different cHAs through transduction of MDCK cells were examined using retroviral pseudotype particles that contained a luciferase reporter construct and expressed the cHA and wild-type B/Yamagata/16/88 virus NA on the particle surface. The entry efficiency mediated by the cHA proteins was detected by the luciferase read-out. Comparable levels of pseudotype particle-mediated luciferase expression were observed for cH5/1, cH7/3 and cH5/3 chimeric HAs and the corresponding wild type proteins (FIG. 22). Particles encoding the cH1/1 HA expressed lower luciferase levels compared to the other HA constructs, which could be due to either the lower expression of the cH1/1 in the producer cell line and hence fewer HA trimers per particle or the less efficient entry properties of the cH1/1 HA. It is also possible that when normalizing the pseudotype particles to 4 hemagglutinin units, the actual amount of pseudotype particles may vary due to differences in binding to red blood cells.

6.5.2.2 Generation of Recombinant Influenza Viruses Bearing Chimeric Hemagglutinins Because it had determined that our cHA constructs were efficiently expressed and transported to the cell surface, a study was performed to assess whether a recombinant influenza virus that encodes a cHA could be rescued. Viruses containing the different cHAs were successfully generated using previously published protocols (see, e.g., Fodor et al., 1999, *J Virol* 73:9679-9682; and Hai et al., 2008, *J Virol* 82:10580-10590). The resulting viruses were plaque purified, amplified in 10 day old embryonated eggs and the chimeric segments were analyzed by RT-PCR and sequenced. In all cases, the virus was found to have the expected chimeric HA segment and no other HA segment (data not shown).

The presence of the cHAs in rescued viruses was further confirmed by Western blot (FIG. 23) and indirect immunofluorescence of infected cells (FIG. 24). MDCK cells were infected with rWT PR8, wild-type Perth/09, cH1/1, cH5/1, cH7/3 and cH5/3 viruses. cH1/1 and cH5/1 chimeric HA proteins were detected in the corresponding samples using antibodies reactive against the head domains of Cal/09 (H1) HA (29E3) (Medina et al., 2010, *Nature Communications* 1:28) or VN/04 (H5) HA (mAb #8) (Steel et al., 2009, *J Virol* 83:1742-53) respectively (FIG. 23). Comparable expression levels among the cH7/3, cH5/3 and wild type Perth HA were observed using 12D1, a pan-H3 anti-stalk mAb (see Wang et al., 2010, *PLoS Pathog* 6:e1000796). The wild type Perth HA showed a slower migration on the gel that is likely due to a higher number of glycosylation sites in the globular head domain. It was confirmed that the correct HA head domain was expressed atop an H3 stalk by using anti-H7 polyclonal (NR-3152) or anti-H5 monoclonal antibodies (mAb #8) on cH7/3 or cH5/3 infection samples, respectively. Positive bands were detected in both cases.

For the immunofluorescence study, the infection conditions were similar to those used for Western blot analysis. Infected cells were stained with corresponding antibodies as used in FIG. 23. All infected cells showed the expected expression of the chimeric and wild type HAs, as well as of the influenza A virus NP (FIG. 24).

6.5.2.3 Replication Characteristics of Recombinant Viruses

The growth properties of wild type and recombinant viruses were assessed in 10-day-old embryonated chicken eggs at 37° C. (FIG. 25A). The rWT PR8 virus was included for comparison of the growth kinetics of the recombinant viruses expressing chimeric HAs. cH5/1 and cH5/3 viruses displayed comparable replication kinetics to that of rWT PR8 virus. cH7/3 virus grew to similar peak titers as rWT PR8 at 48 hpi ($1 \times 10^9$ PFU/mL), though there was a 2 log reduction in viral titer compared to the rWT PR8 virus at 9 hpi. The cH1/1 virus was attenuated as compared to the rWT PR8 virus, as shown by reduced viral titers at all time points. Nonetheless, cH1/1 virus reached a respectable peak titer of approximately $10^8$ PFU/mL. The Perth/09 Wild type virus grows to comparable peak titers in embryonated eggs (data not shown).

The plaque phenotype of each of the chimeric viruses was also evaluated in MDCK cells. All viruses formed comparable sized plaques as shown in FIG. 25B. These data together confirm that the chimeric HA constructs fold correctly and are biologically functional.

6.5.2.4 Stalk Specific Antibodies can Neutralize cHA-Expressing Viruses and Pseudoparticles Finally, stalk-specific antibodies were tested for the ability to neutralize our newly generated recombinant viruses expressing cHAs. Plaque reduction assays were performed in the presence of mAb KB2, an HA-stalk specific antibody with broad group 1 reactivity or without antibody. It was shown that mAb KB2 neutralizes all cHA-expressing viruses with similar efficiency and in a dose dependent manner. At 100 ug/mL, mAb KB2 was able to completely neutralize cH1/1 and cH5/1 viruses with 100% efficiency, with some neutralizing activity at concentrations as low as 4 ug/mL (FIG. 26A).

To confirm these results, a pseudotype particle inhibition assay was performed with mAb KB2. Pseudotype particles expressing cH1/1 or cH5/1 and influenza B virus NA were added to MDCK cells in the presence of mAb KB2, or without antibody. Forty-eight hours post-transduction, supernatant was collected and luciferase activity was analyzed. As expected, mAb KB2 blocked the entry of cH1/1 and cH5/1 pseudotype particles in a dose dependent manner at concentrations above 4 ug/mL. While a lower concentration of mAb KB2 was sufficient to inhibit entry of pseudotype particles compared to concentrations used in the plaque reduction assay, this was an expected result due to the assumed lower incorporation of HA trimers on the surface of pseudotype particles (Corti et al., 2010, *The Journal of Clinical Investigation* 120:1663-73). This phenomenon of different neutralizing potencies of mAbs in assays that involve whole virus versus pseudotype particles has been appreciated in other studies (Corti et al., 2010, *The Journal of Clinical IInvestigation* 120:1663-7321; Sui et al., 2009, *Nature Structural & Molecular Biology* 16:265-73).

6.5.3 Conclusion

A novel strategy was developed to generate influenza viruses with chimeric HA proteins bearing different HA globular head domains by taking advantage of the conserved disulfide bond Cys52-Cys277 which demarcates the border between the head and stalk domains. Thus, through substituting the parental head domain with the head domain of another HA, a panel of chimeric HAs with the same stalk but different globular heads was generated. The design was tested across multiple subtypes, including the PR8 stalk domain with Cal/09 and VN H5 globular heads. In addition, an H7 globular head was placed on an H3 stalk domain. These constructs cover both phylogenetic groups of the influenza HA protein. Each construct was expressed on the cell surface and retained fusion activity. The generation of recombinant viruses bearing the chimeric HAs further validated that the HAs fold correctly and retain biological functions.

6.6 Example 6: Chimeric Hemagglutinin Constructs as a Universal Influenza Vaccine This example demonstrates the protective efficacy of a stalk-specific immune response that can be elicited through vaccination with chimeric hemagglutinin (cHA) constructs, proteins that contain unique hemagglutinin head and stalk combinations.

6.6.1 Materials and Methods 6.6.1.1 Cells and Viruses 293T and MDCK cells were obtained from ATCC and were maintained in Dulbeccos's Modified Eagle's medium (DMEM) and Minimal Essential Medium (both from Gibco). Each were supplemented with 10% fetal calf serum (HyClone), and 100 units/ml of penicillin-100 µg/ml of streptomycin (Pen/Strep, Gibco).

Influenza virus A/Fort Monmouth/1/1947 (FM1) and A/Netherlands/602/2009 were passaged in mouse lungs and then grown in 10 day old embryonated chicken eggs for 48 hours. Low pathogenicity A/Vietnam/1203/04 (VN04):PR8 2:6 reassortant virus with the polybasic cleavage site removed (see, e.g., Steel et al., 2009, *J Virol* 83:1742-1753) and B/Yamagata/16/1988 virus were grown in 10-day old embryonated eggs for 48 hours at 37° C. or 72 hours at 33° C., respectively.

Recombinant influenza viruses were produced by reverse genetics system as described above and as previously described (see, e.g., Quinlivan et al., 2005, *J Virol* 79:8431-8439). cH9/1 N1 virus, a virus expressing the HA globular head domain of an H9 virus atop an H1 stalk (from PR8 virus), and cH5/1 (H5 head (VN04), H1 stalk) N1 viruses were rescued in a similar manner as previously described (see, e.g., Pica et al., 2012, *PNAS USA* 109:2573-2578). In order to generate the YAM-HA virus, the extracellular domain of the B/Yamagata/16/1988 (WT YAM) HA was substituted with the corresponding domain of A/Puerto Rico/8/1934 virus HA (see, e.g., Hai et al., 2011, *Journal of virology* 85:6832-6843). The reverse genetic plasmids encoding the other 7 WT YAM viral segments were constructed in a previous study (see, e.g., Hai et al., 2008, *J Virol* 82:10580-10590). Following rescue, cHA-expressing recombinant viruses were propagated in 10 day old embryonated chicken eggs for 48 hours at 37° C. YAM-HA virus was grown in 8-day old embryonated chicken eggs for 72 hours at 33° C.

Recombinant and wild-type viruses were titered on MDCK cells (ATCC) in the presence of TPCK trypsin as described above. cH5/1 N1 virus was partially purified over a 30% sucrose cushion for use in ELISA assays. cH9/1 N1, cH5/1 N1 and FM1 viruses were purified via gradient centrifugation and inactivated with formaldehyde diluted (1:4000) in PBS to be used as positive control vaccines.

6.6.1.2 Generation of cH6/1 and cH9/1 Protein Constructs

Soluble cH6/1 and cH9/1 proteins were generated using a baculovirus expression system as described above and as previously described (see, e.g., Pica et al., 2012, PNAS USA 109:2573-2578). Briefly, baculotransfer vectors were first generated followed by transfection of bacmids into Sf9 cells. Recombinant baculovirus were then used to infect High Five cells at an MOI of 10. Supernatants were harvested 96 h postinfection and then incubated with Ni-NTA resin (Qiagen) for 2 h at 4° C. to purify His-tagged recombinant cHA proteins. The slurry was loaded onto columns, and following washes, was eluted in pH 8 elution buffer (50 mM Na2HCO3, 300 mM NaCl, 250 mM imidazole). Pooled fractions that contained protein were buffer-exchanged in PBS and concentrated using an Amicon Ultra centrifugal filter unit (Millipore) with a 10-kDa molecular mass cutoff in a swinging bucket rotor. Protein purity and identity were tested by SDS/PAGE, Coomassie staining, and Western blot. Final protein concentrations were determined with Bradford reagent.

6.6.1.3 Animals

Animals were allowed access to food and water ad libitum and kept on a 12 hour light/dark cycle. Female 6-8 week old BALB/c mice (Jackson Laboratories) were anesthetized for all intranasal procedures with intraperitoneal (IP) injection of 0.1 ml of ketamine/xylazine (0.15 mg ketamine and 0.03 mg xylazine).

6.6.1.4 Vaccination and Challenge Experiments

Naïve 6-8 week old female BALB/c mice were vaccinated with cH9/1 protein, intranasally (10 ug) in the presence of adjuvant R848 (Invitrogen) and intraperitoneally (10 ug) with Addavax, an MF59-like adjuvant (Invitrogen). Animals were boosted with cH6/1 protein, or BSA (BioRad) three weeks post prime. Booster vaccinations were also administered intranasally (10 ug) and intraperitoneally (10 ug), though with poly I:C as an adjuvant (Invitrogen). Inactivated FM1 virus (1 ug) was administered intramuscularly in a volume of 50 ul as a positive control. Three weeks post boost, animals were bled and sera was harvested, and animals were challenged with 5 LD50 of FM1 virus. Weights were monitored for 14 days post challenge.

In other experiments, animals were primed with cH9/1 encoding plasmid DNA (80 ug, TriGrid delivery system; Ichor Medical Systems) and then boosted three weeks later with cH6/1 or cH9/1 (control) protein administered with polyI:C intranasally (10 ug) and intramuscularly (10 ug). The boost was repeated three weeks later with cH5/1 or cH9/1 (control) protein. Control animals were DNA electroporated with cH9/1 coding DNA as well but were boosted twice with BSA (in a similar way as the treatment group). Positive control animals received either inactivated FM1 or PR8 virus (1 μg) or 1 μg of pH1N1 monovalent split vaccine intramuscularly (BEI). Animals were then challenged 3-5 weeks post boost with 5 LD50 of PR8 or FM1 or 10 LD50 of pH1N1 virus. Animals used for CD8+ T-cell depletion were treated 48 and 24 hours prior to challenge with 300 μg of a anti-CD8+ T-cell antibody (see, e.g., M. L. Salem, 2000, Int. J. Immunopharmacol. 22:707) (from hybridoma line 2.43, purchased from ATCC) and challenged with 5 LD50 of PR8 virus. Weights were monitored for 14 days post challenge. A 20% cutoff was used for all viruses.

For other experiments, mice were inoculated with YAM-HA or WT YAM virus, and then vaccinated with BSA or cH6/1 protein in the presence of poly I:C intramuscularly and intraperitoneally three weeks later. Naïve animals served as an additional control. All animals were bled and challenged 3-5 weeks following vaccination with 250 LD50 cH9/1 N1 virus, or 10LD50 of 2:6 reassortant H5 virus with the polybasic cleavage site removed in the PR8 background (see, e.g., Steel et al., 2009, J Virol 83:1742-1753). Formaldehyde-inactivated cH9/1 N1 virus (1 ug) and cH5/1 N1 virus were administered intramuscularly in a volume of 50 ul as a positive control for the appropriate viral challenge. Animals were euthanized if they lost more than 30% of their initial body weight following challenge, according to institutional guidelines. A 20% cutoff was used for infection with the less pathogenic cH9/1 N1 and A/Netherlands/602/2009 viruses. For challenges using these two viruses, more stringent doses were used in order to appreciate death or substantial weight losses of all controls (250 or 10 LD50).

6.6.1.5 Enzyme Linked Immunosorbant Assay

Immulon 4HBX (Thermo Scientific) plates were coated overnight with partially purified cH5/1 N1 virus diluted to 5 ug/mL in PBS. Plates were blocked for 1 hour with 0.1% Tween 20-PBS (TPBS) containing 3% non-fat milk powder, and then incubated with mouse sera serially diluted in TPBS containing 1% milk powder for 1 hour at room temperature. After three washes, plates were incubated for 1 hour at room temperature with alkaline phosphate (AP) linked anti-mouse IgG (γ-chain specific, Invitrogen). Plates were then washed three times with TPBS, developed with p-nitrophenylphosphate (PNPP) substrate (Zymed), stopped with 0.5M NaOH, and read at the optical density of 405 nm. For all experiments, a Synergy 4 (BioTek) plate reader was used.

Stalk-specific antibody titers were detected by ELISA as described above. PR8 antigens were used to coat ELISA plates in order to quantify stalk-specific reactivity. To detect the neutralization capability of stalk-specific antibodies in vaccinated mice, sera were pooled and total serum IgG was purified.

Pseudoparticles expressing H5 HA were used in a pseudoparticle entry assay as previously described (see, e.g., Hai et al., 2012, J. Virol. 86:5774-5781 and N. Pica et al., 2012, PNAS 109:2573-2578). Upon entry, pseudoparticles express a luciferase reporter. Inhibition of this entry by IgG was quantified as the percentage of expression compared to non-IgG treated controls. Because animals had not been exposed to H5 globular head domains, these assays determined the degree to which stalk-specific antibodies produced by vaccination neutralize virus. Monoclonal antibody CR6261 and purified IgG from influenza B wild type infected mice were used as controls.

6.6.1.6 Plaque Reduction Neutralization Assay (PRNA)

Dilutions of mAbs were first pre-incubated with 60 to 80 plaque-forming units (pfu) of virus (cH9N1 influenza A virus) for 1 hour at RT on a shaker. The virus and purified IgG mixture was then used to infect a monolayer of MDCK cells in duplicate in a 12-well format and incubated at 37° C. for 1 hour with intermittent rocking every 10 minutes. The agar overlay was supplemented with corresponding IgG dilutions. At two days post infection (dpi), the monolayer was fixed with 4% PFA/1×PBS for 30 minutes. Cells were blocked with 5% NF-milk/1×PBS for 30 minutes at RT and were incubated accordingly with either with an H9 specific monoclonal antibody (5 μg/mL) for 1 hour at RT. An anti-mouse secondary conjugated to HRP was used as a secondary at a 1:1000 dilution. Plaques were visualized using TrueBlue peroxidase substrate (KPL Inc.) and the reaction was stopped with tap water. Plaques were counted for each antibody and percent inhibition calculated over the no mAb group.

6.6.1.7 Statistical Tests

Statistical analyses were performed using a one tailed student's T test (Prism4, GraphPad). For FIG. 29C, all values are plotted as averages with standard error of the mean. Differences in survival were calculated with Kaplan Meier survival analysis with log rank significance test.

For analyses with P-values, P-values at or below 0.05 are considered statistically significant. Welch's correction was used if variances were determined to be statistically different. P-values at or below 0.05 are considered statistically significant. When comparing stalk serum reactivity to maximum weight loss in FIG. 29C, one value was detected as an outlier (modified Z-score >3.5 standard deviations above the mean) according to the methods of Iglewicz and Hoaglin (see Iglewicz, B. a. H., D. 1993. Volume 16: How to detect and handle outliers. In E. Mykytka (ed.), The ASQC Basic References in Quality Control: Statistical Techniques. American Society of Quality Control), and was omitted from analyses.

Figure 27A:
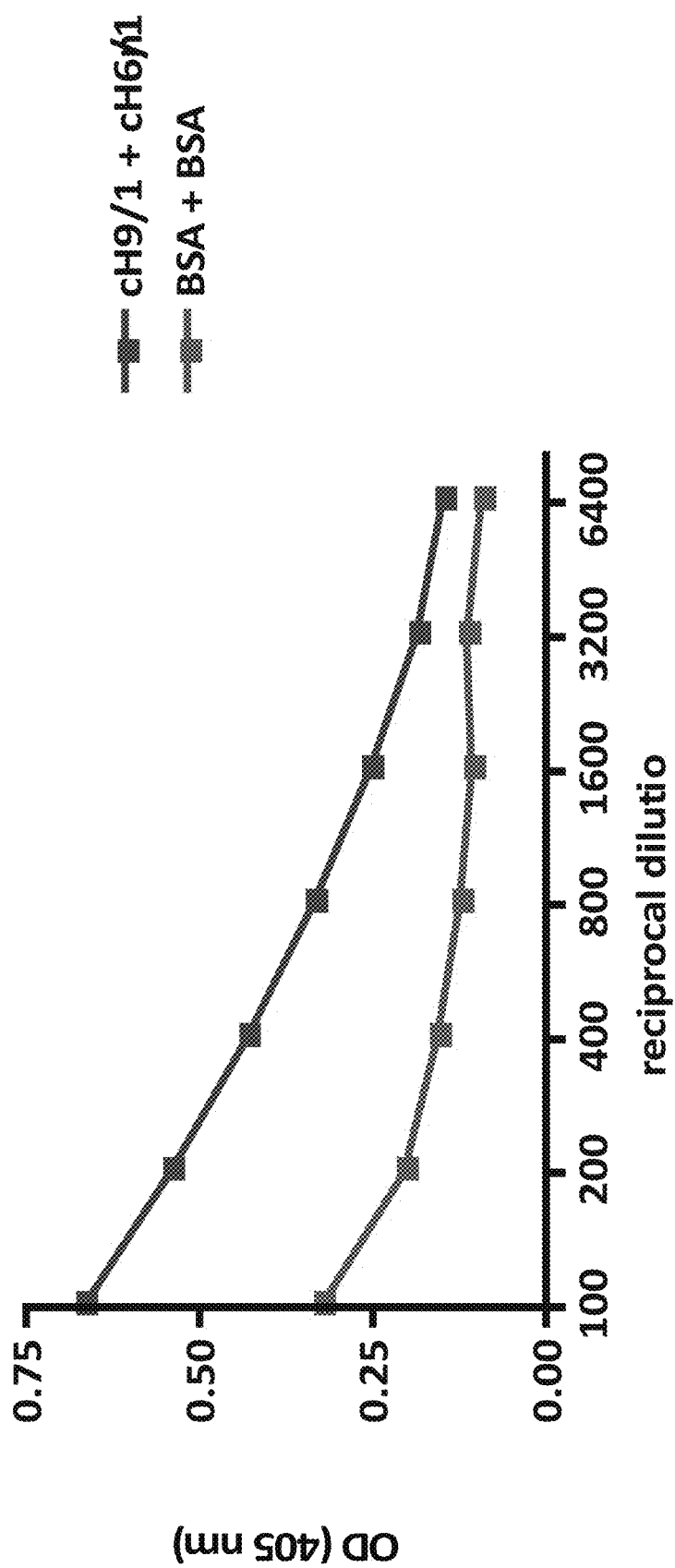
Figure 27B:
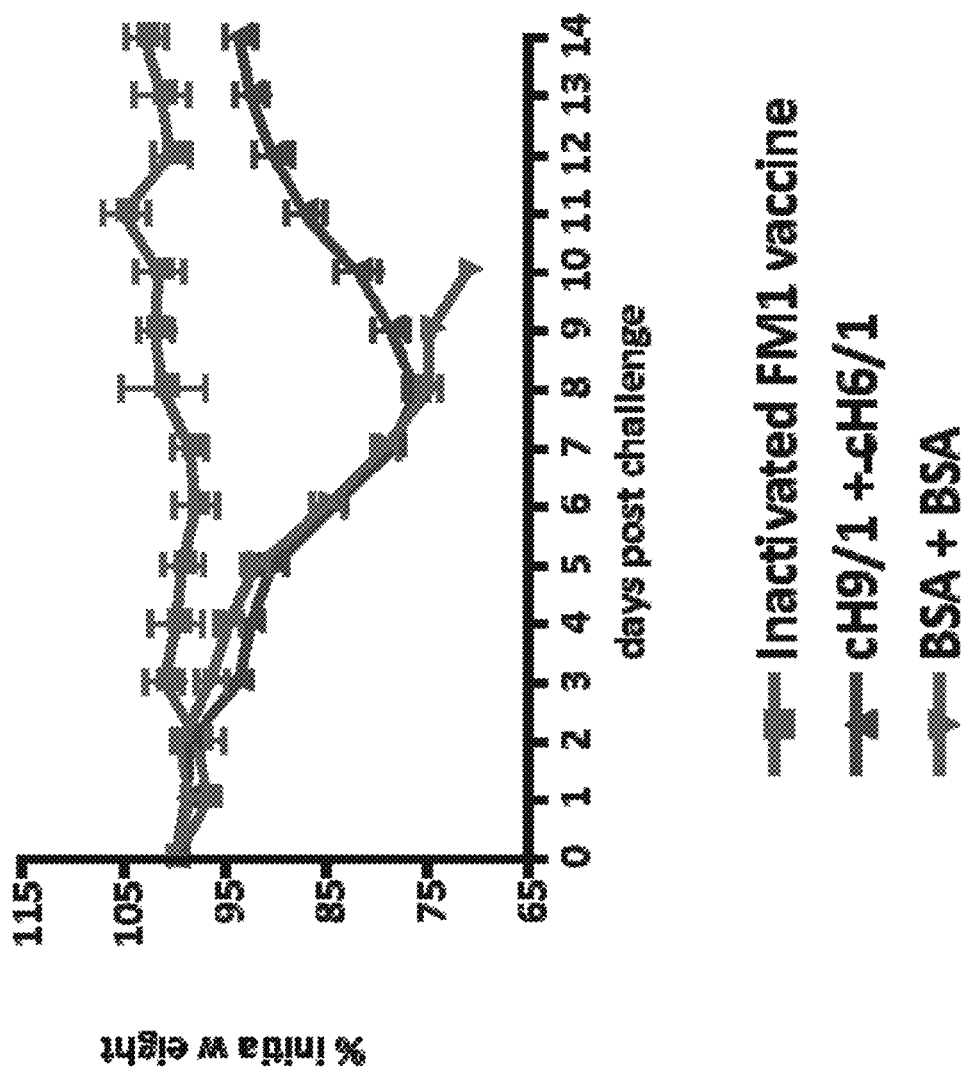
Figure 27C:
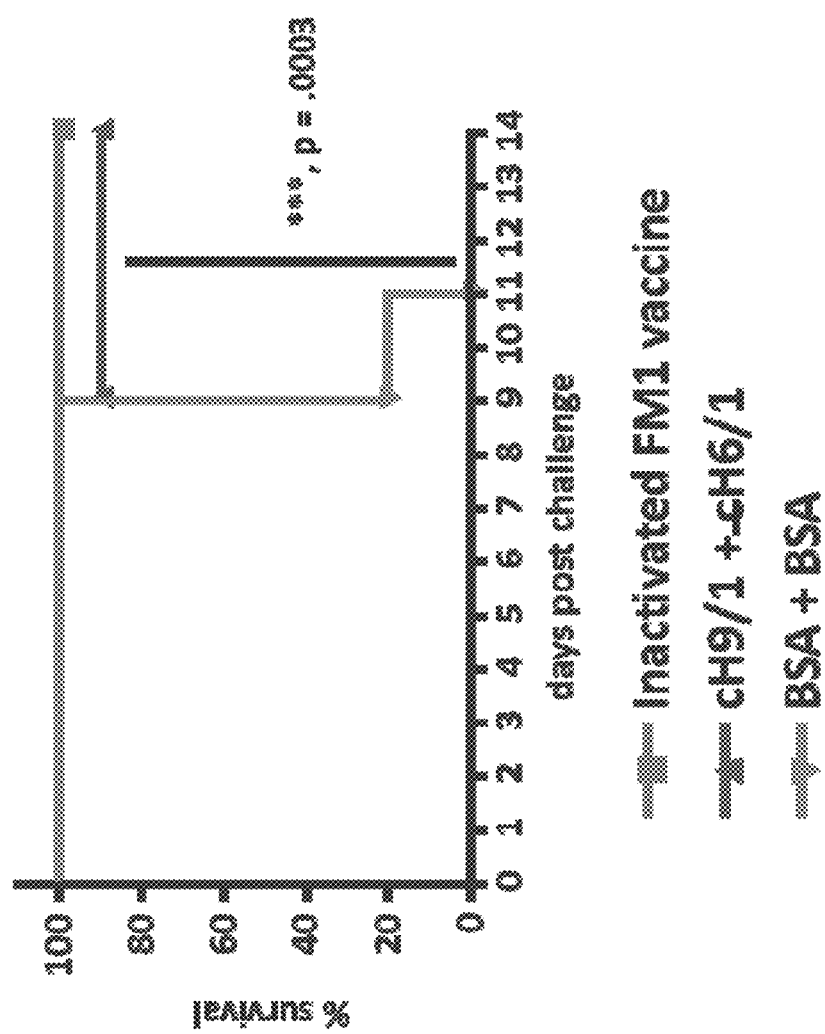

6.6.2 Results 6.6.2.1 Sequential Vaccination with cHA Constructs Elicits HA Stalk-Specific Antibodies and Provides Protection from Lethal Influenza Challenge It was hypothesized that constructs that express globular head domains from viruses with different antigenicities could stimulate polyclonal responses towards the stalk domain of the HA. To test this, mice were first vaccinated with cH9/1 soluble protein with adjuvant, whereby the stalk of the HA is from A/Puerto Rico/8/1934 (PR8) virus and the head from an H9 isolate. Three weeks post prime, mice were boosted with a second soluble cHA, cH6/1 (head from H6 virus, stalk from PR8 virus), with the intent of stimulating humoral responses towards the stalk domain of the molecule. (Mice vaccinated with inactivated FM1 virus served as a positive control). Three weeks post boost, mice were bled to assess serum reactivity to the H1 stalk domain, and then challenged with mouse-adapted A/Fort Mounmoth/1/1947 (FM1) virus. As shown in FIG. 27A, vaccinated mice produced serum antibody responses towards the HA stalk domain. Following challenge with FM1, animals lost a considerable amount of weight (FIG. 27B), though recovered after day 7 for an overall survival rate of 90% (FIG. 27C). Even though mice had only been exposed to the globular head domains of H9 and H6 viruses, it was verified that all mice were HI negative to FM1 virus, and thereby confirmed that the protection elicited from vaccination was the result of an immune response specific to the stalk domain. Therefore, vaccination with PR8-based cHAs provides stalk-specific immunity that is protective in the face of an FM1 virus challenge.

6.6.2.2 Vaccination with cH6/1 Protein Elicits Stalk-Specific Immunity that Mediates Protection from cH9/1 N1 Virus Challenge Although antibody responses were generated towards the stalk by administering two different soluble cHA constructs, a substantial degree of morbidity was seen following FM1 challenge. Because mice are immunologically naïve to influenza virus, it was possible that multiple exposures to influenza virus followed by the introduction of an antigenically distinct head was required in order to induce high serum antibody titers against the HA stalk. Enhanced stimulation of serum antibody titers with specificity to the hemagglutinin stalk may also require infection, and may explain why a robust protection following prime and boost with cHA proteins alone was not observed.

In order to stimulate immune responses towards the viral hemagglutinin, but not generate protective immunity to other viral proteins, a recombinant B/Yamagata/16/1988 virus was constructed that expresses the ectodomain of the HA from PR8 virus (YAM-HA) (see, e.g., Hai et al., 2011, Journal of virology 85:6832-6843). Mice were inoculated with YAM-HA in order to mimic prior exposures to influenza virus, and then vaccinated 3 weeks later with BSA or cH6/1 protein. As an additional control, mice were infected with wild-type B/Yamagata/16/1988 (WT YAM) virus and vaccinated with BSA. An influenza A virus that expressed the cH9/1 (H9 head, H1 stalk) was then used as the challenge virus, in order to definitively demonstrate the protective nature of an immune response directed only towards the HA stalk. Again, because animals were exposed to the globular head domains from H1 and H6 viruses, the protection seen following challenge with a virus that expressed the cH9/1 HA was most likely a result of immunity towards the H1 stalk domain.

As shown in FIG. 28A, animals that received cH6/1 protein vaccine following YAM-HA exposure were completely protected from 250 LD50 challenge with a cH9/1 expressing virus in the PR8 background. Animals vaccinated with cH6/1 soluble protein lost statistically less weight on days 3, 4, and 5 compared to animals that were vaccinated with BSA. This protection from weight loss resulted in increased survival in the group vaccinated with cH6/1, compared to the cohort vaccinated with BSA (p=0.038; FIG. 28B). Naïve animals and those inoculated with WT YAM were not protected from infection, demonstrating that any protection that was seen in the other vaccination groups was not a result of viral replication, but was instead a specific response to the H1 stalk domain. Because animals were exposed to the globular head domains from H1 and H6 viruses, and were HI negative to the cH9/1 challenge virus, it is believed that the protection seen here is a result of immunity towards the H1 stalk domain.

Figure 28C:
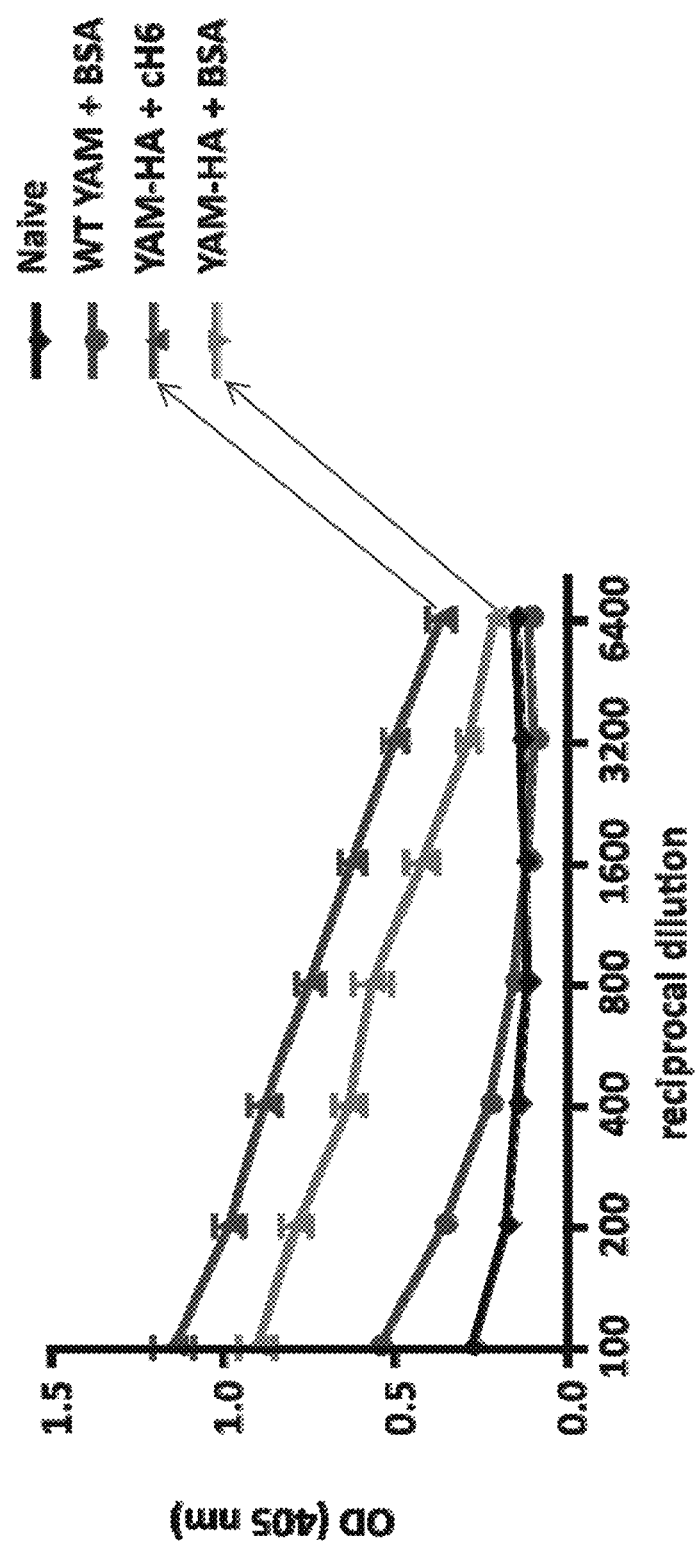
Figure 28D:
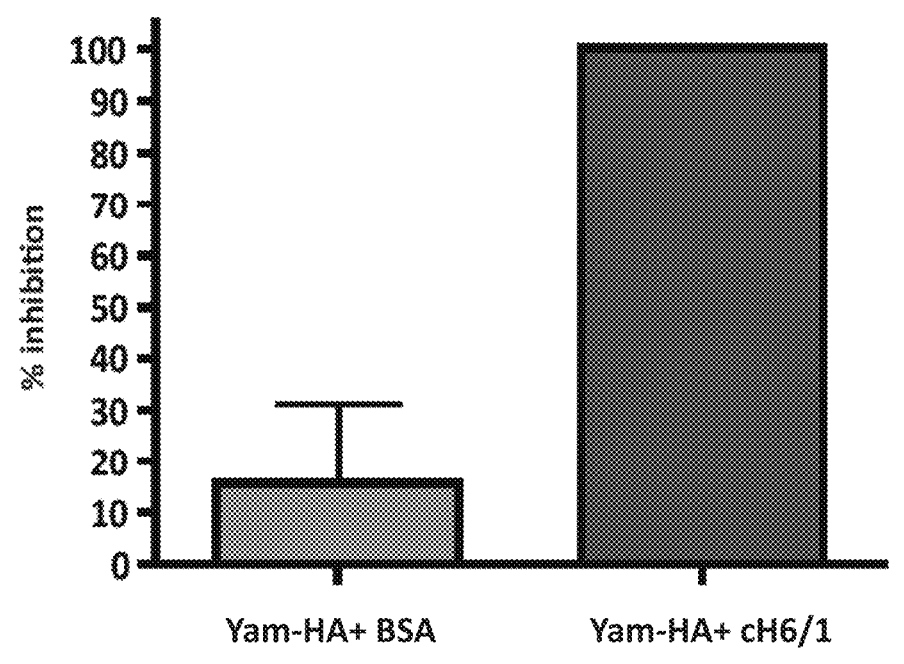

It is of note that monoclonal antibodies with specificities to the HA stalk have been isolated from individuals infected with or vaccinated against seasonal H1N1 viruses (see, e.g., Corti et al., 2010, The Journal of clinical investigation 120:1663-1673; Corti et al., 2011, Science 333:850-856; Ekiert et al., 2011, Science 333:843-850; Sui et al., 2009, Nat Struct Mol Biol 16:265-273; Throsby et al., 2008, PLoS One 3:e3942), and stalk titers have been appreciated in individuals not infected with the pH1N1 virus, although at lower levels (see, e.g., Pica et al., 2012, PNAS USA 109:2573-2578). As such, it is not surprising that YAM-HA inoculated animals were able to generate some degree of stalk titer. Vaccination with the cH6/1 construct, however, increased serum stalk titers by 4 fold (reciprocal dilutions that yielded equivalent OD values) (FIG. 28C, and protected animals from substantial weight loss and death (FIGS. 28A and 28B). Vaccination with the cH6/1 construct elicited the production of stalk-specific IgG that neutralized virus with 100% efficiency (YAM-HA+BSA) (FIG. 28D) whereas serum from prime only animals exhibited neutralizing levels barely above background (YAM-HA+BSA). Indeed, animals inoculated with YAM-HA and then vaccinated with BSA had statistically similar survival rates to those that were inoculated with WT YAM virus and vaccinated with BSA (p=0.058). In contrast, the use of cH6/1 protein as a vaccine yielded 100% survival from challenge, a rate that was highly significant when compared to that of animals inoculated with WT YAM (p<0.0001). Survival was also enhanced when compared to that of mice inoculated with YAM-HA and vaccinated with BSA (p=0.038). These differences were not reflected in the pseudoparticle entry assay, as IgG from YAM-HA+BSA mice and YAM-HA+cH6/1 mice inhibited the entry of pseudoparticles encoding an H5 HA with similar efficiency (FIG. 28E). It is important to note that the latter assay only detects the ability of antibodies to block entry of pseudoparticles. Therefore, the effects of stalk-antibodies downstream of entry and/or their interaction with infected (immune) cells would not be detected in this assay. This might explain why differences in neutralization were not observed between the two groups and did not reflect the in vivo findings. Nonetheless, the antibodies elicited by these infection protocols were stalk specific and were broadly neutralizing. Because the challenge virus only encodes the stalk domain from an H1 virus, it can be concluded that the protection seen was the result of the host immune response to the HA stalk domain that was stimulated through cH6/1 vaccination.

Figure 29A:
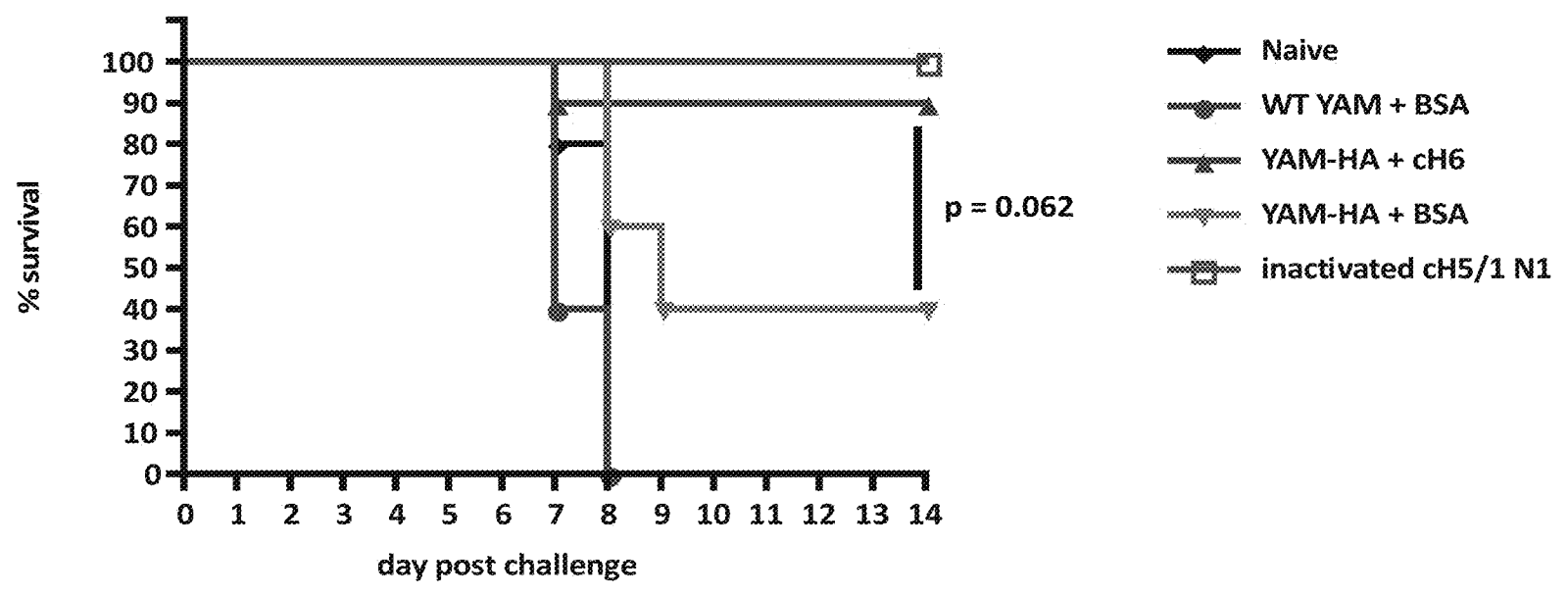
Figure 29B:
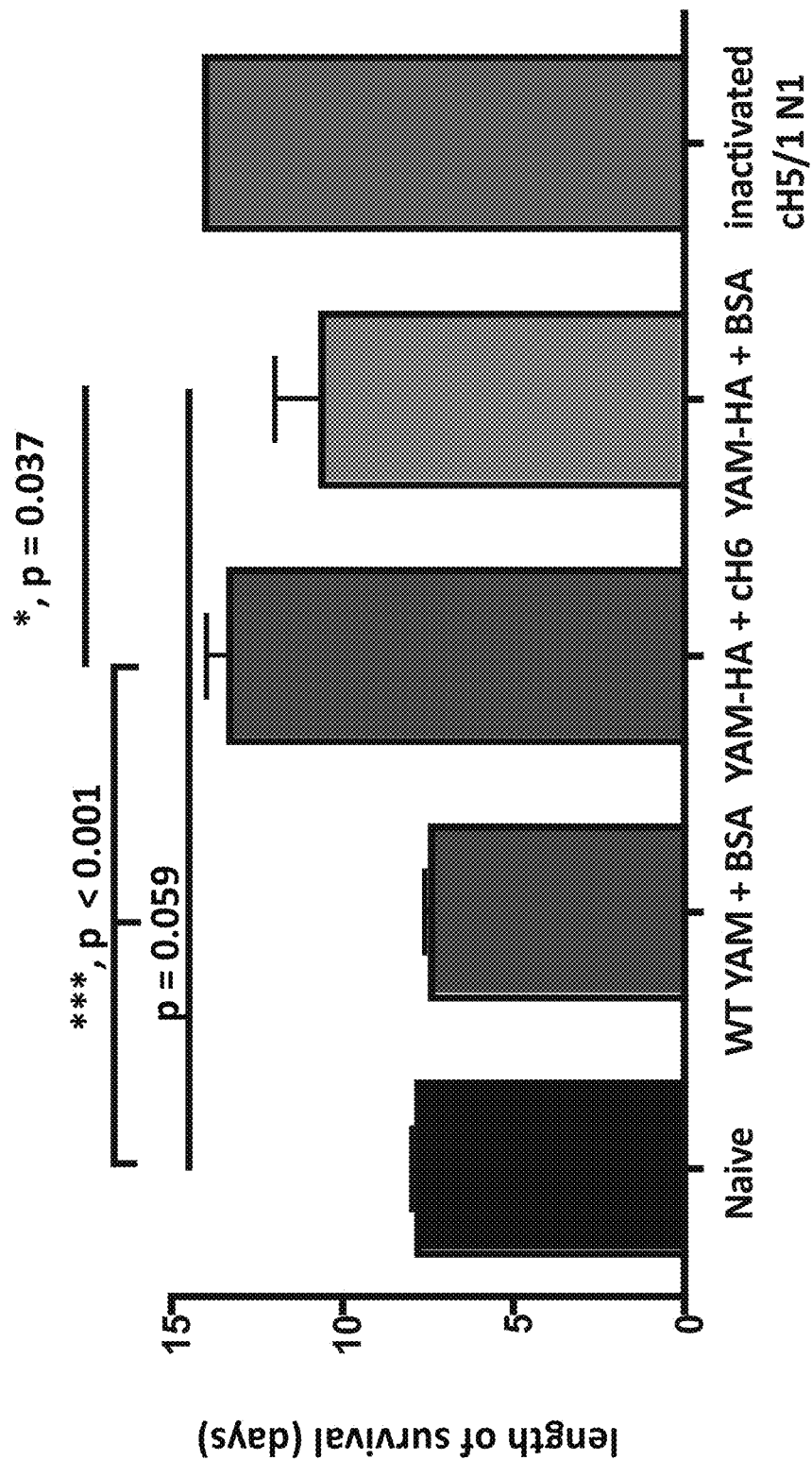
Figure 29C:
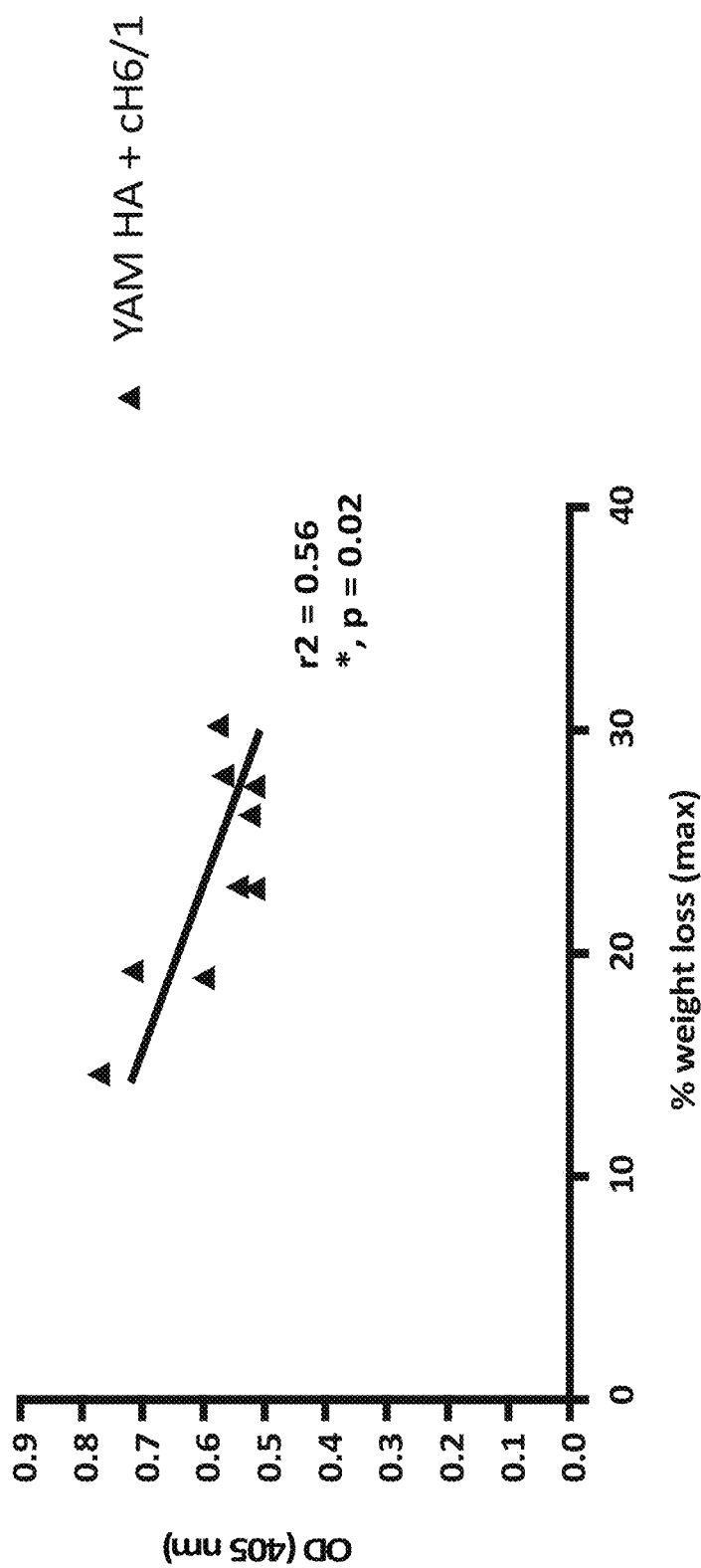

6.6.2.3 Vaccination with cH6/1 Protein Protects Mice from Lethal H5 Influenza Virus Challenge Whether vaccination with cH6/1 protein could protect mice from challenge with an H5 virus was next ascertained. Mice were inoculated and vaccinated as described above, and challenged with 10 LD50 of a 2:6 reassortant virus that expresses the HA and NA from A/Vietnam/1203/2004 virus in the PR8 background (see, e.g., Steel et al., 2009, *J Virol* 83:1742-1753). As expected, naïve animals and those inoculated with WT YAM virus were not protected from challenge and succumbed to infection by day 8. Animals inoculated with YAM-HA virus and vaccinated with BSA were marginally protected from challenge, with a survival rate of 40%. Increased protection was seen when animals were vaccinated with cH6/1 protein, with 90% survival. The difference in survival rates between the two vaccine groups approached statistical significance (p=0.06), although mice vaccinated with cH6/1 protein survived for a statically longer time (p=0.037) (FIGS. 29A and 29B). When comparing reactivity to the HA stalk to the % maximal weight loss over the monitoring period following H5 challenge, an inverse correlation was detected, whereby animals with higher serum stalk titers tended to lose less weight following challenge (FIG. 29C), supporting the notion that cH6/1 can boost HA-stalk based immunity.

Using challenge viruses with HA globular head domains to which vaccinated mice were immunologically naïve and HI negative, the results indicate that protection from challenge following vaccination was solely based on an immune response towards the HA stalk. To exclude the possibility that cross reactive antibodies towards the receptor binding site could be playing a role in the protection seen here, mice were all tested for HI and found to be HI negative to their respective challenge viruses.

Figure 15B:
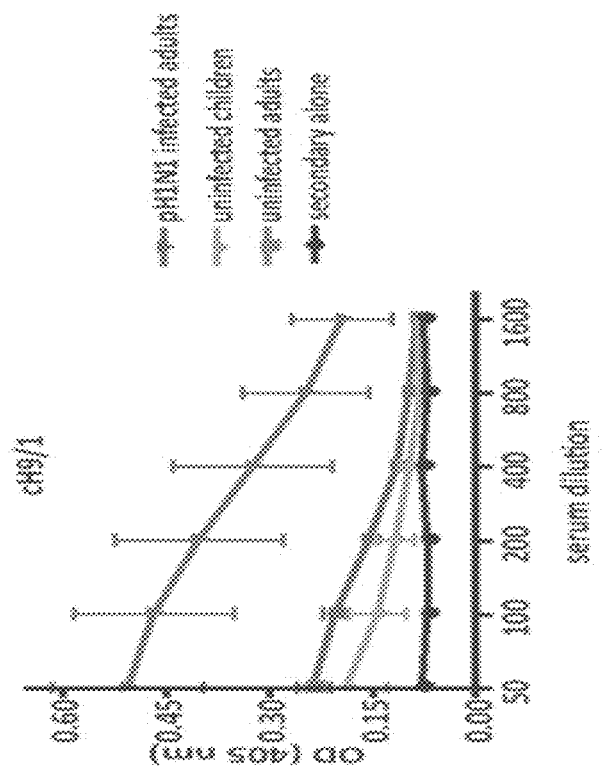
Figure 15A:
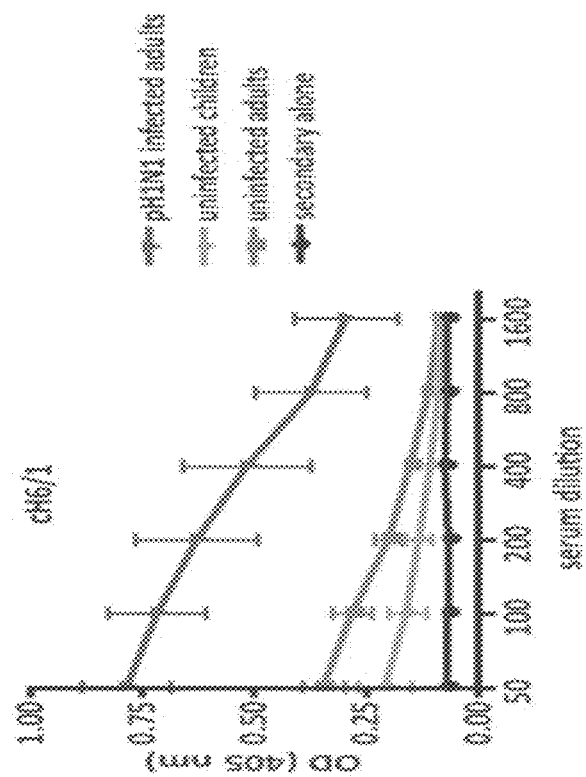
Figure 15D:
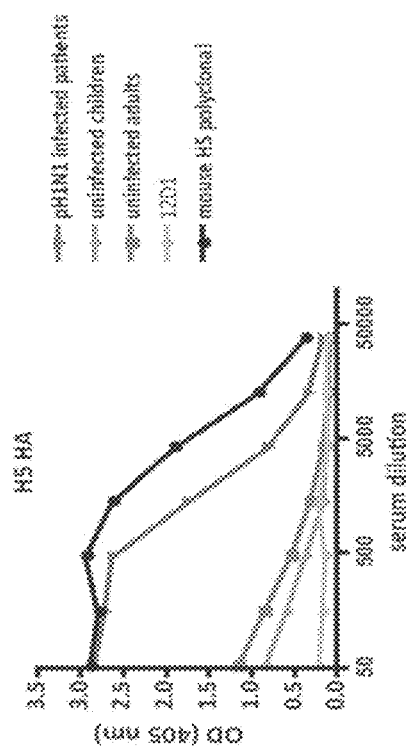
Figure 15C:
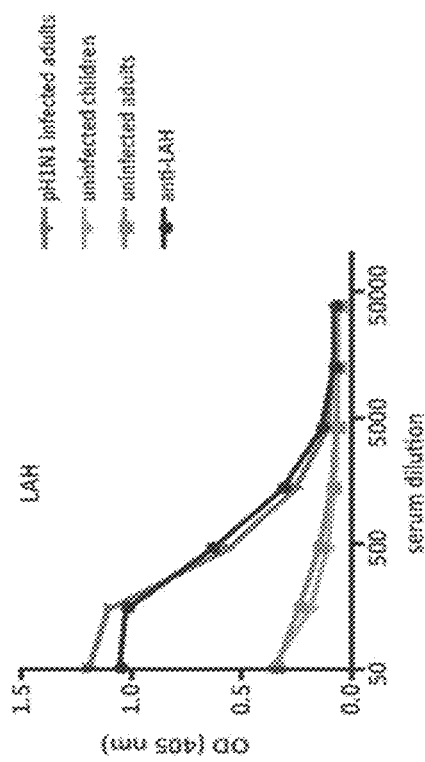
Figure 15E:
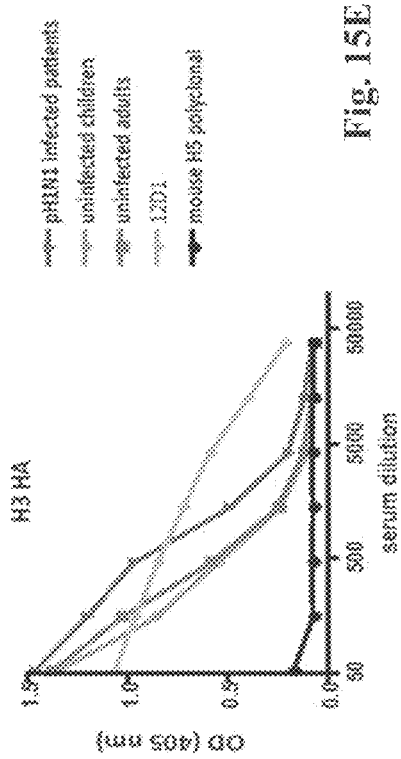
Figure 30A:
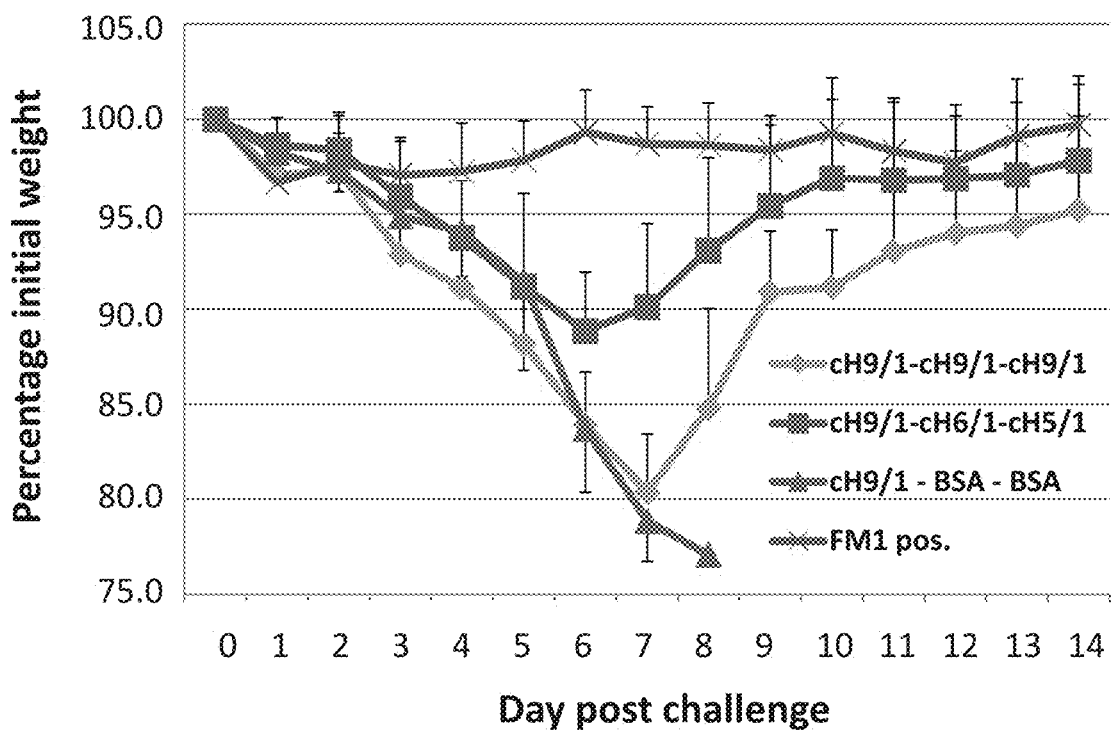
Figure 30B:
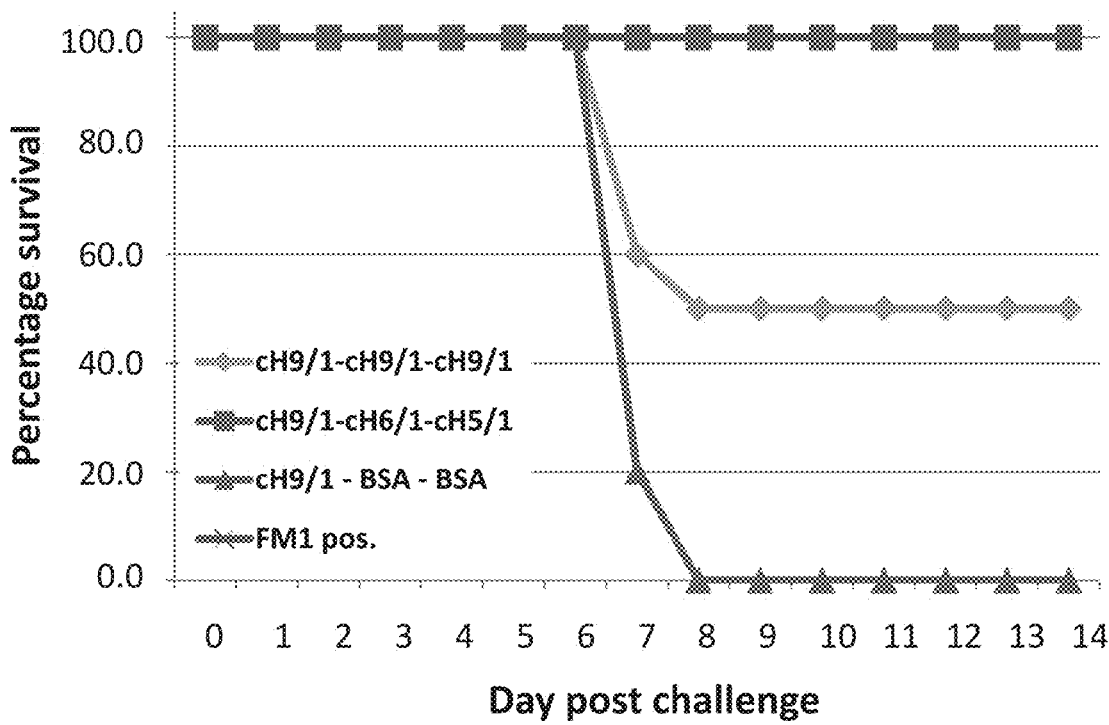
Figure 30C:
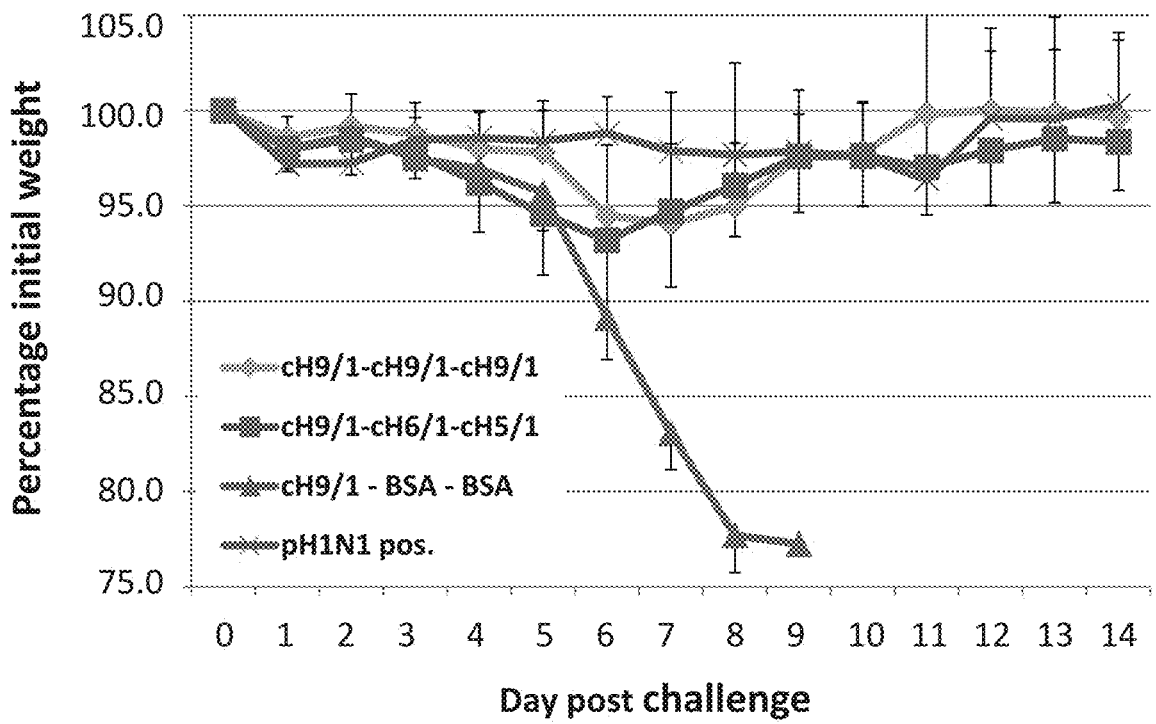
Figure 30D:
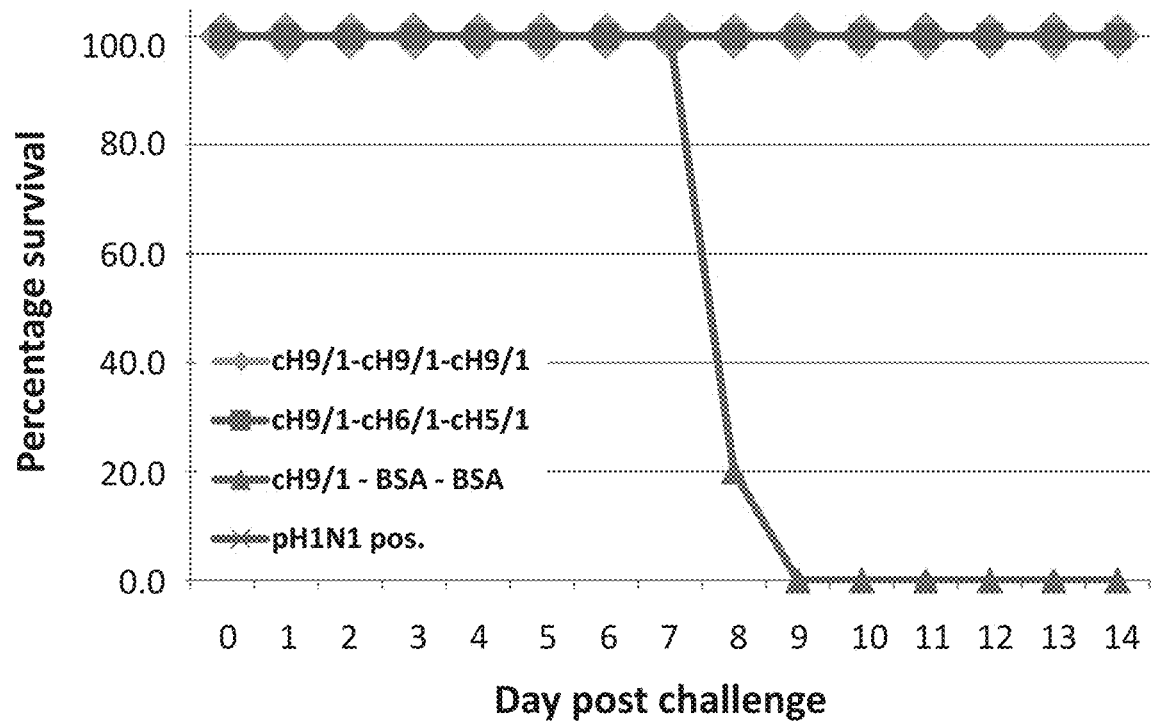
Figure 30E:
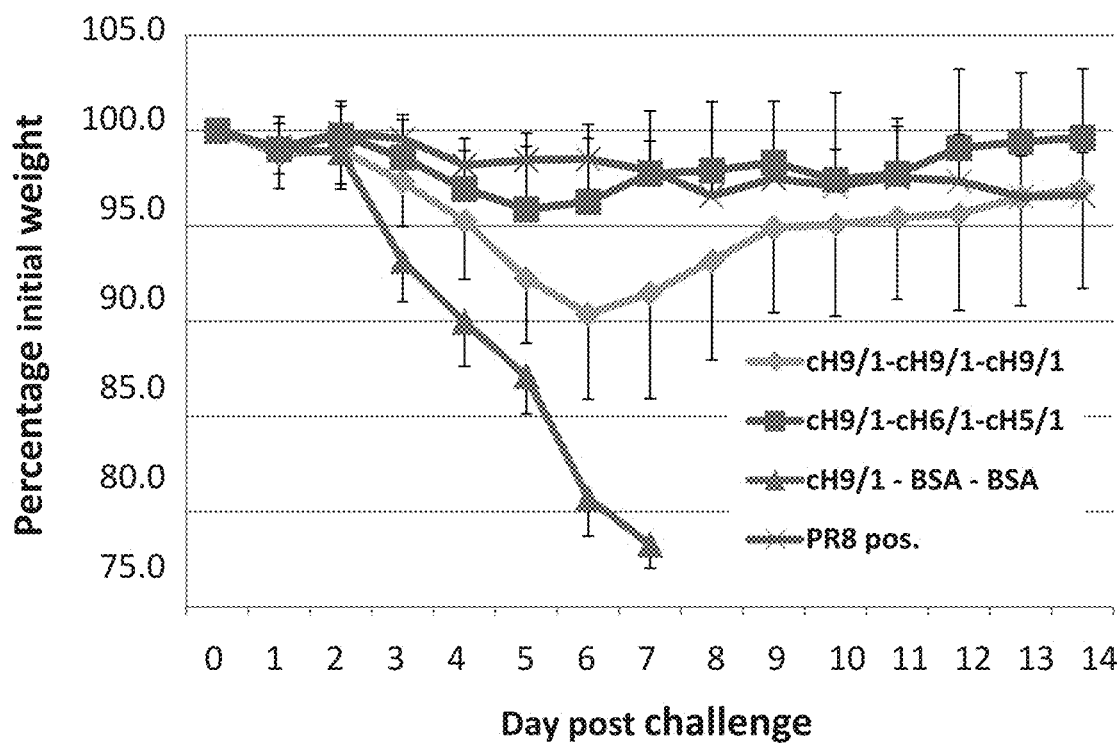
Figure 30F:
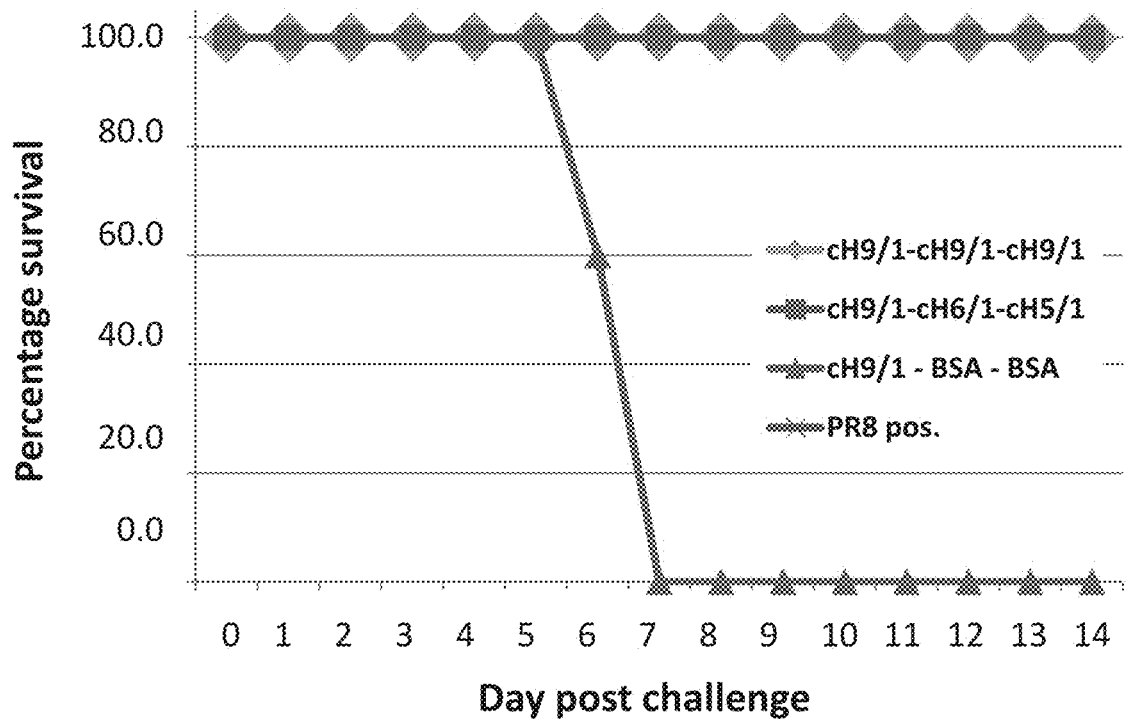
Figure 30G:
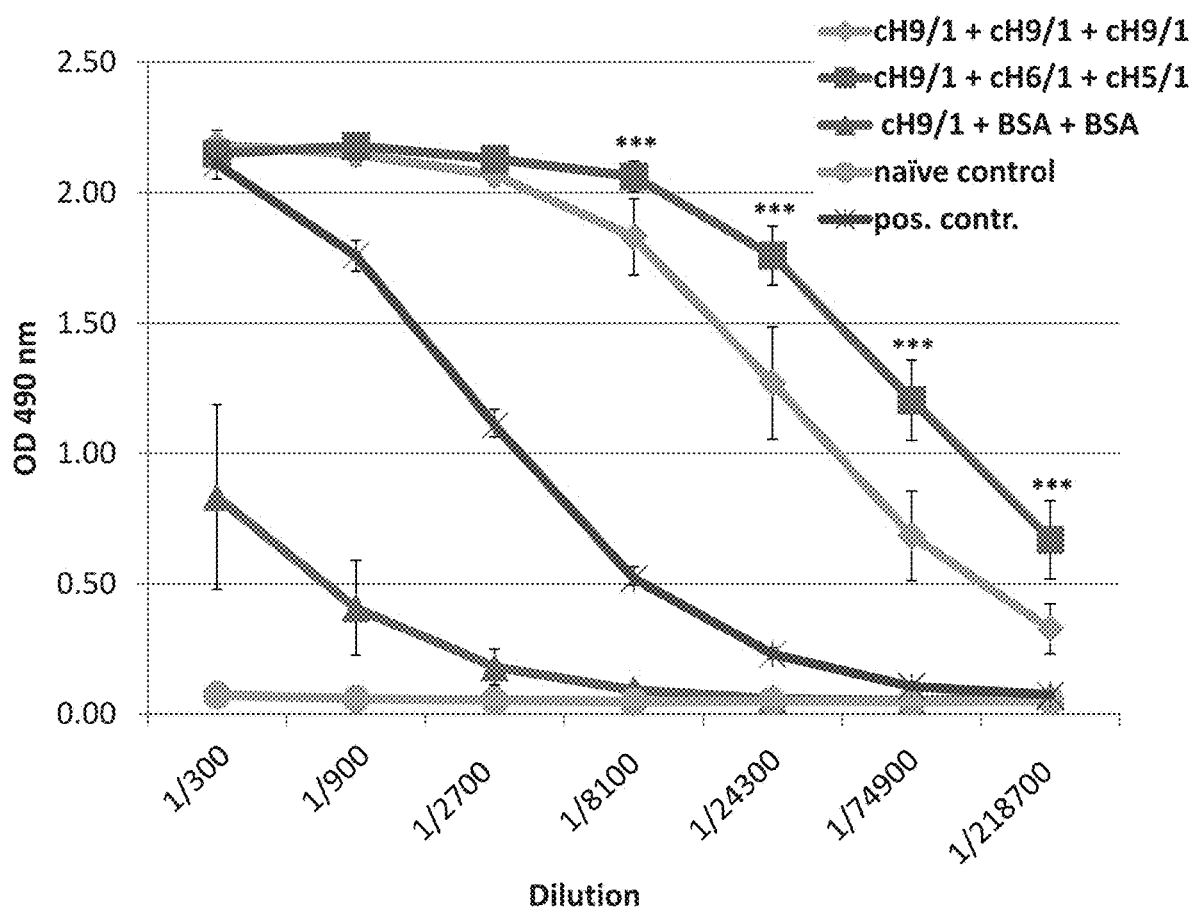
Figure 30H:
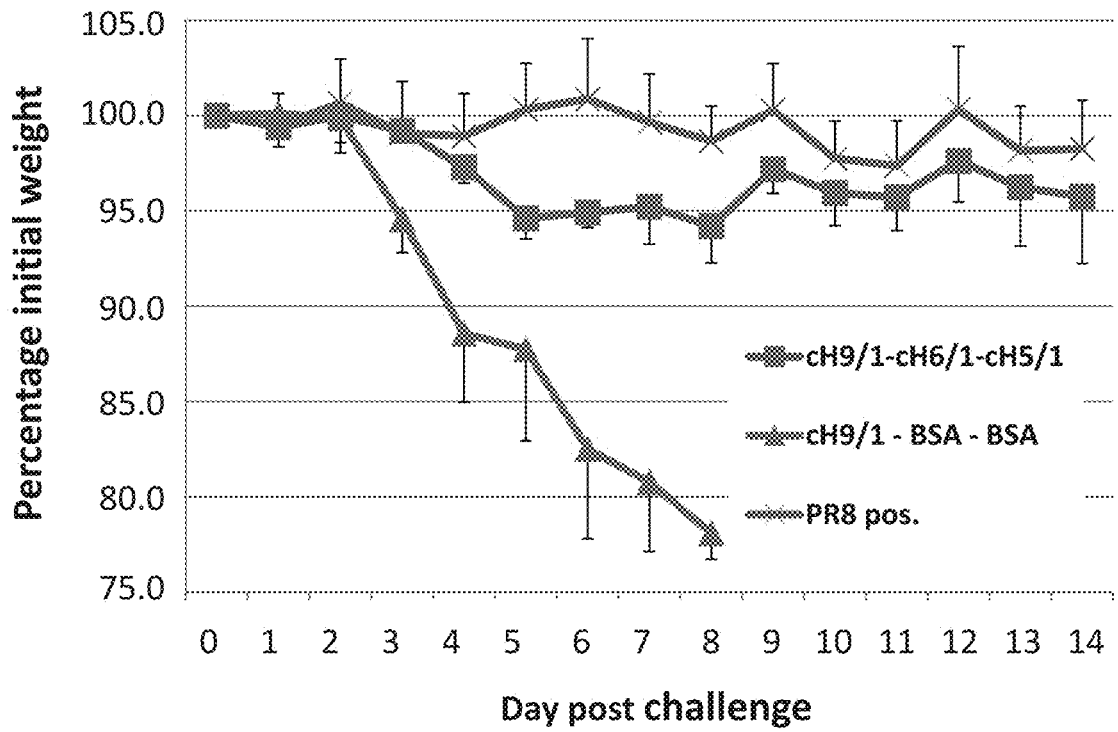
Figure 30I:
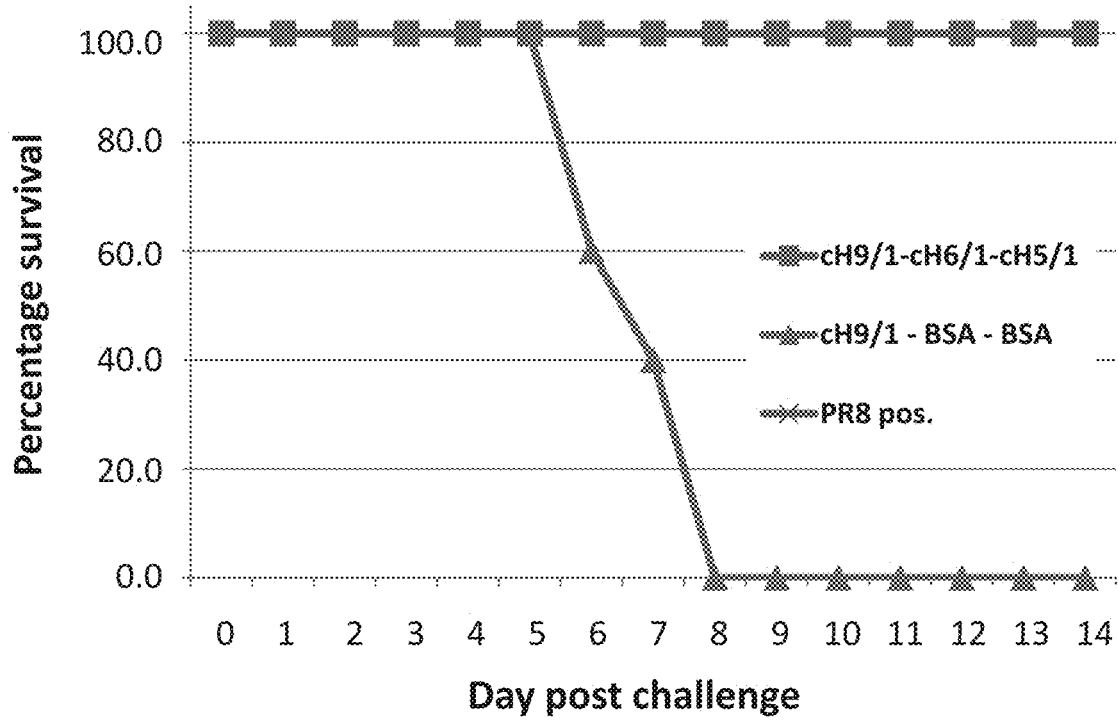

6.6.2.4 Vaccination with cHA Elicits Stalk-Specific Immunity that Mediates Protection from H1N1 Virus Challenges Stalk-specific antibodies have been detected in human sera (see, e.g., FIGS. 15A and 15B; M. Thorsby et al., 2008, PLoS One 3:e3942, D. C. Ekiert et al., 2009, Science 324:246-251, D. C. Ekiert et al., 2011, Science 333:843-850, J. Wrammert et al., 2011, J. Exp. Med. 208:181-193 and N. Pica et al., 2012, PNAS 109:2573-2578). Because it is possible that previous exposure to influenza virus HA is critical to the robust production of a stalk specific immune response, it was ascertained whether preexisting immunity to the influenza virus in mice could be recapitulated. It was hypothesized that this would more effectively protect against morbidity following virus challenge. To achieve this, mice were primed with a DNA expression vector (see, e.g., J. Steel et al, 2010, MBio 1(1), pii:e00018-10) that encodes cH9/1, then were boosted with soluble cH6/1 protein, followed by cH5/1 protein (H5 head, H1 stalk), and finally challenged with a panel of H1N1 viruses (FIGS. 30A-30F). Following infection with FM1 (FIGS. 30A and 30B), A/Netherlands/602/2009 (pH1N1) (FIGS. 30C and 30D) and PR8 viruses (FIGS. 30E and 30F), all cHA-vaccinated animals were protected from challenge and displayed only minimal amounts of weight loss, if any. In contrast, negative control animals that received BSA following priming with cH9/1 DNA lost considerable amounts of weight and, with the exception of one animal, succumbed to infection by day 9 (FIGS. 30A-30F). The survival of the cHA-vaccinated animals in each of the challenge experiments was significantly different from that of controls (FIGS. 30B, 30D and 30F). To confirm that the protection elicited was a result of stalk-specific humoral immunity, all mice were confirmed to be HI negative to each challenge virus though the sera were capable of binding H1 HA by ELISA (FIG. 30G), confirming the production of stalk specific antibodies by our vaccination protocol. Because it is possible that CD8 T cells directed towards epitopes within the HA stalk could be playing a role in the protection seen here (see, e.g., M. Tamura et al., J. Virol. 72:9404-9406), mice were vaccinated and depleted of CD8 T cells by administering monoclonal antibody 2.43 prior to PR8 challenge (M. L. Salem, 2000, Int. J. Immunopharmacol. 22:707-718). Depletion did not affect weight loss nor survival outcomes, implicating a humoral response in the protection elicited by vaccination (FIGS. 30H and 30I). Therefore, an adaptive humoral immune response towards the HA stalk, and not the head, was providing protection against the three different H1N1 viruses.

Figure 30J:
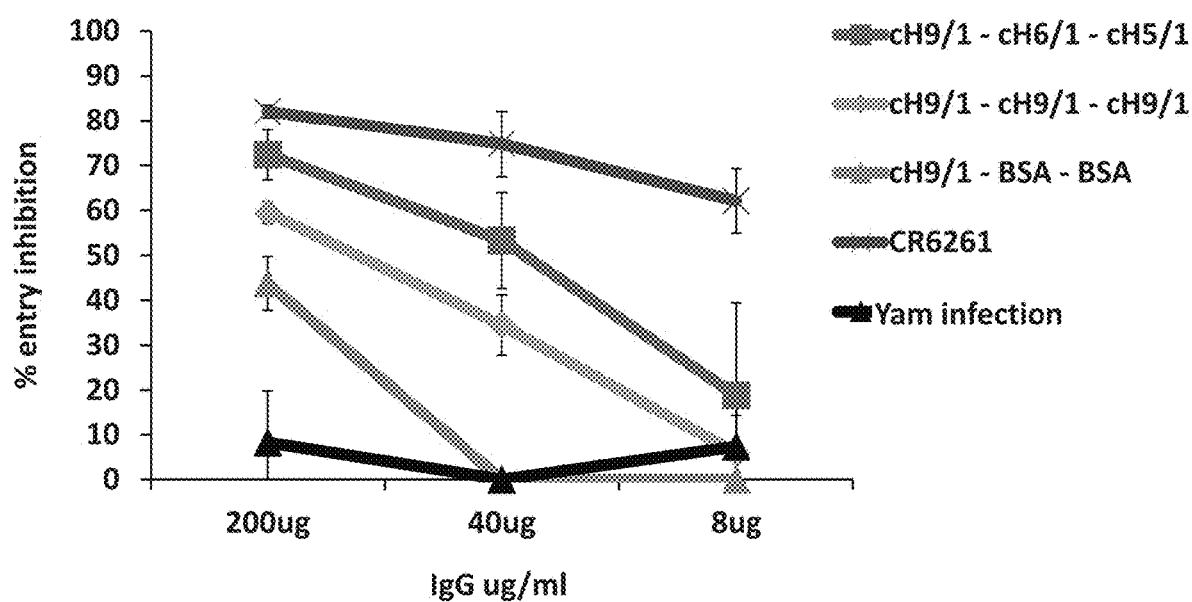

In order to further validate that the cHA-based vaccination protocol induced stalk-specific antibodies with neutralizing capability against other subtypes, the ability of purified IgG from vaccinated mice to block the entry of pseudoparticles that harbor an H2 HA was tested. Because pseudoparticles express a luciferase reporter gene following entry, neutralizing activity was measured by the absence of luciferase enzymatic activity in cell supernatants (R. Hai et al., 2012, *J. Virol.* 86:5774-5781 and N. Pica et al., 2012, *PNAS* 109:2573-2578). Consistent with the protection seen following challenge, IgG purified from vaccinated mice inhibited the entry of pseudoparticles in a dose-dependent manner and with similar efficacy to that of CR6261, a monoclonal antibody with specificity to the HA stalk that was used as the positive control (FIG. 30J). The vaccination protocol, therefore, elicited stalk antibodies with broad specificities, capable of neutralizing other group 1 HAs like H2.

6.6.3 Conclusion

This example demonstrates the protective effect of a stalk-specific immune response that can be elicited through vaccination with chimeric HAs. It was demonstrated that an immune response directed towards the HA stalk was sufficient for protection from viral challenge, and that this vaccination protocol provided heterosubtypic protection. A similar strategy could be developed in humans to provide protection against a broad range of influenza viruses, negating the need for annual vaccination, and enhancing pandemic preparedness.

6.7 Example 7: A Carboxy-Terminal Trimerization Domain Stabilizes Conformational Epitopes on the Stalk Domain of Soluble Recombinant Hemagglutinin Substrates This example demonstrates that a carboxy-terminal trimerization domain is important to the structural integrity of stalk epitopes on recombinant soluble influenza virus hemagglutinin.

6.7.1 Materials and Methods

6.7.1.1 Cells

Sf9 insect cells (ATCC # CRL-1711) were grown in TMN-FH medium (Gemini Bio-Products) supplemented with 10% FBS (Atlanta Biologicals), 0.1% Pluronic F68 (Sigma) and a Penicillin-Streptomycin antibiotic (Gibco) mixture. BTI-TN-5B 1-4 cells (High Five—Vienna Institute of Biotechnology subclone) were grown in HyClone SFX serum free medium (Fisher Scientific) supplemented with Penicillin-Streptomycin antibiotic mixture (Gibco).

6.7.1.2 Cloning and Recombinant Baculovirus Generation

Sequences coding for HAs of H1 strains A/Puerto Rico/8/34 (PR8), A/California/04/09 (Cal09), H2 strain A/Japan/305/57 (JAP57), H3 strains A/Hong Kong/1/68 (HK68), A/Wisconsin/67/05 (Wisc05) and H5 strain A/Viet Nam/1203/04 (VN04—with removed polybasic cleavage site; see Steel et al., 2009, J Virol 83: 1742-1753) were amplified from pCAGGS plasmids by polymerase chain reaction and cloned into a modified pFastBac vector (Invitrogen) using BamHI or StuI and NotI restriction endonucleases (NEB). Two sets of constructs, HA without and with trimerization domain, were cloned: HA constructs without trimerization domain were designed so that the C-terminal transmembrane- and endodomain of the HA were replaced with a hexahistidine-tag (HA sequence ends with 1509 for H1, V509 for H2 and H5 and G508 for H3; H3 numbering); the other set of constructs, HA with a trimerization domain, also lack the C-terminal transmembrane- and endodomains (HA sequence ends with V503-H3 numbering) but include a thrombin cleavage site and a T4 foldon trimerization domain (see, e.g., Meier et al., 2004, J Mol Biol 344: 1051-1069) in addition to the C-terminal hexahistidine-tag (FIG. 31). Generated recombinant pFastBac clones were transformed into DH10Bac bacteria (Invitrogen) according to the manufacturer's instructions and recombinant bacmids were prepared with a PureLink Plasmid Filter Midiprep kit (Invitrogen). Recombinant bacmids were transformed into Sf9 cells using Cellfectin II (Invitrogen) for rescue of recombinant baculovirus. All sequences were confirmed by Sanger sequencing.

6.7.1.3 Protein Expression, Purification and Characterization

Baculovirus was amplified in Sf9 cells to a passage 3 stock and then used to infect BTI-TN-5B 1-4 (High Five) cells at $1 \times 10^6$ cells/ml in HyClone SFX serum free media (Fisher Scientific) at a multiplicity of infection of 10. Expression was carried out in 1000 ml shaker flasks for 96 hours at 28° C. After 96 hours, supernatants were cleared by low speed centrifugation (5000 g, 4° C., 20 min) and incubated with Ni-NTA (Qiagen) resin (3 ml slurry for 250 ml of culture supernatant) for two hours at room temperature (RT). The resin-supernatant mixture was then passed over 10 ml polypropylene columns (Qiagen). The retained resin was washed four times with 15 ml of washing buffer (50 mM Na2HCO3, 300 mM NaCl, 20 mM imidazole, pH 8) and protein was eluted with elution buffer (50 mM Na2HCO3, 300 mM NaCl, 300 mM imidazole, pH 8). The eluate was concentrated using Amicon Ultracell (Millipore) centrifugation units with a cut-off of 30 kDa and buffer was changed to phosphate buffered saline (PBS) of pH 7.4. Protein concentration was quantified using Quickstart Bradford Dye Reagent (Bio-Rad) with a bovine serum albumin standard curve. Protein purity, integrity and identity was assessed by sodium dodecyl sulfate polyacrylamide gel electrophoresis (SDS-PAGE) (4-20% polyacrylamide—Mini PROTEAN TGX gels, Bio-Rad), Coomassie staining and Western blot or enzyme linked immunosorbent assay (ELISA). Extent of trimerization and/or multimerization was tested by cross-linking of HA with bis-[sulfosuccinimidyl]suberate ($BS^3$—Fisher Scientific) according to the manufacturer's recommendations. Briefly, 3 µg of HA were incubated in 30 µl of PBS in the presence of a 25 fold molar excess of $BS^3$ crosslinker. The mixture was incubated at RT for 30 minutes and then $BS^3$ was quenched by adding 1M Tris-HCl buffer (pH 8) to a final concentration of 50 mM. Subsequently SDS-PAGE and/or Western blot analysis with a mouse anti-his primary antibody (Sigma) and anti-mouse horseradish peroxidase (Santa Cruz Biotechnology) or alkaline phosphatase (Santa Cruz Biotechnology) conjugated secondary antibody was performed.

6.7.1.4 Enzyme Linked Immunosorbent Assay

Immunolon 4HBX (Fisher Scientific) plates were coated with recombinant HA with and without trimerization domain at a concentration of 5 µg/ml in coating buffer (0.1 M Na2CO3/NaHCO$_3$, pH 9.2, 50 µl/well) overnight at 4° C. The plates were then blocked for one hour at RT with PBS (pH 7.4) containing 1% Tween 20 (TBPS) and 3% non-fat dry milk powder. After blocking, plates were washed once with TPBS and then incubated with three fold dilutions of monoclonal antibody or sera (100 µl per well in TPBS with 1% milk powder—monoclonal antibody starting concentration 30 µg/ml; 1:100 dilution for sera) for one hour at RT. Plates were then washed trice with 100 µl of TPBS and incubated for another hour at RT with horse radish peroxidase conjugated anti-mouse IgG (Santa Cruz Biotechnology) or anti-human Fab secondary antibody (Sigma) at a dilution of 1:3000 (50 µl per well). After three more washes, plates were developed using SigmaFAST OPD substrate (Sigma) (100 µl/well), stopped with 3M HCl (50 µl/well) and read at an absorption of 490 nm on a Synergy 4 (BioTek) plate reader. The obtained read-out was background subtracted with values from secondary antibody-only incubated wells.

For stability studies, HA from PR8 virus with trimerization domain was stored at 4° C. for 60 days, or at −80° C. and went through one (standard), two, three or four freeze-thaw cycles. Stability of head versus stalk binding antibodies was compared using PY102 and C179 monoclonal antibodies. Antibody-HA combinations in ELISA were done in triplicates except for stability studies where duplicates were used.

6.7.2 Results

6.7.2.1 a C-Terminal Trimerization Domain Stabilizes HAs and Induces Trimer Formation The extracellular domain of various group 1 and group 2 HAs were expressed in soluble form with or without a C-terminal T4 phage trimerization domain (FIG. 31) in the baculoviral expression system. Proteins were harvested 96 hours post infection and purified via a C-terminal hexahistidine-tag using a Ni-NTA column. Purified protein was concentrated using ultrafiltration spin columns, assessed for protein integrity and impurities by SDS-PAGE and Coomassie staining and quantified with Bradford reagent. Based on the amino acid sequence and the fact that baculovirus expressed full length HAs without polybasic cleavage site are usually uncleaved, the extracellular domain of HA would have an expected molecular mass of approximately 60 kDa per monomer (or 180 kDa per trimer) without taking glycosylation into account. Cal09 (H1), JAP57 (H2) and VN04 (H5 without polybasic cleavage site) HA without trimerization domain seemed to be partially cleaved into HA1 and HA2 as indicated by the presence of bands at approximately 40 kDa (HA1) and 25 kDa (HA2) in addition to the uncleaved HA band at 60 kDa (HA0). Based on the exclusive presence of a 60 kDa band for Cal09, JAP57 and VN04 HAs with trimerization domains in the non-reducing, denaturing SDS-PAGE, it can be assumed that these proteins are expressed mostly as an uncleaved HA0 (FIG. 32A). Additionally, preparations of Wisc05 (H3) HA without a trimerization domain showed a degradation product at 40 kDa that was reactive when probed with an anti-stalk antibody (12D1). This species was thus likely a product of non-specific cleavage. Wisc05 HA with trimerization domain appeared only as an HA0 band (FIG. 32A). PR8 and HK68 HA appeared to be very stable (present as HA0) even in the absence of a trimerization domain.

HAs were crosslinked with and without T4 trimerization domain using BS3, a hydrophilic 11 Angstrom chemical crosslinker that was recently used to show trimerization for HAs (see, e.g., Weldon et al., 2010, PLoS One 5). After crosslinking, samples were diluted in a reducing, denaturing loading dye and resolved on a reducing, denaturing SDS-PAGE gel. Group 1 HAs without trimerization domain formed high molecular weight oligomers that barely ran into the running gel and were mostly retained in the stacking gel (FIGS. 32B and 32C). The strongest phenotype was detected for VN04 and JAP57; other group 1 HAs also formed additional trimers (approximately 230 kDa), dimers (130 to 150 kDa) and monomers (60 kDa) (FIGS. 32B and 32C). Group 1 HAs with trimerization domain formed mostly trimers that ran at approximately 230 kD on the SDS-PAGE gel and formed a defined band in the running gel. However, they also formed dimers (approximately 130 to 150 kDa, strongest for Cal09) and monomers (60 kDa). Group 2 HAs behaved differently: HK68 HA formed predominantly trimers and to some degree dimers regardless of the presence of a trimerization domain. Wisc05 HA showed mainly dimerization in the absence of a trimerization domain, while HA with the T4 domain was mostly trimerized.

6.7.2.2 a C-Terminal Trimerization Domain Strongly Enhances Binding of Stalk-Reactive Antibodies to HA Substrates The reactivity of a panel of broadly reactive, neutralizing antibodies to the HA constructs was assessed in order to determine differential binding of these antibodies to HA substrates with and without trimerization domain. Stalk-specific antibodies mAb C179, mouse mAb 6F12, human mAb CR6261 (all group 1 specific); and mouse mAb 12D1 and human mAb CR8020 (both group 2 specific) were used in the experiment. Four other stalk-reactive antibodies, KB2, BD3, GG3 and IB11, that were recently isolated and characterized to have reactivity to both H1 and H5 Has also were used in the experiment. As a control, strain specific antibodies that are known to bind to the globular head domain of HA were used. As additional controls, sera of mice sub-lethally infected with influenza virus strains (PR8, Cal09, H3, VN04) or vaccinated with VLPs (JAP57) was used. Antibodies C179, CR6261 and 6F12 showed a strong binding phenotype to both H1 HAs that were tested (Cal09 and PR8). It is of note that they bound exclusively to HAs that had a trimerization domain (FIGS. 33A and 33B); no binding was observed to HAs without a trimerization domain. Similar binding characteristics were seen with the four other stalk-reactive broadly neutralizing H1-H5 antibodies. In contrast, head-specific antibodies, such as 7B2 (Cal09) and PY102 (PR8), reacted with HAs irrespective of the expression of a trimerization domain and these findings were confirmed using sera from Cal09 or PR8 infected animals (FIGS. 33A and 33B).

This effect is not specific to the H1 subtype—when testing the binding of C179 and CR6261 to JAP57 (H2) and VN04 (H5) HAs with and without a trimerization domain, a similar phenotype was observed, where these antibodies only reacted with trimerized forms of the protein (FIGS. 34A and 34B). The same result was seen when reactivity of the four H1-H5 antibodies was assessed. Head-specific antibodies 8F8 (JAP57) and mAb #8 (VN04) or polyclonal anti-H2 or anti-H5 sera recognized both forms of HA equally well.

For group 2 HA-binding antibodies a different pattern emerged. In order to test the effects of a trimerization domain on reactivity of stalk antibodies with group 2 HAs, broadly reactive antibodies CR8020 and 12D1 were used. CR8020 binds a conformational epitope in group 2 HAs, while 12D1 is thought to bind to a linear epitope within the long alpha helix (LAH) of the HA2 subunit. CR8020 binding to HK68 and Wisc05 HAs with trimerization domains was greatly enhanced over binding to HAs without trimerization domain (FIGS. 35A and 35B). However, lack of the trimerization domain did not completely abolish binding as seen with group 1 HAs. 12D1 did not distinguish between HAs with or without the trimerization domain (FIG. 35).

6.7.3 Conclusion

The T4 trimerization domain allows for successful trimerization of soluble HA molecules and greatly increases the stability of these molecules following baculovirus expression.

6.8 Example 8: Influenza Virus Expressing a Chimeric Ha Comprising the Stem Domain of an H1 Influenza Virus and the Globular Head Domain of an H5 Influenza Virus (cH5/1)

This example demonstrates that the engineering and rescue of an influenza virus expressing a chimeric HA comprising the stem domain of an H1 influenza virus and the globular head domain of an H5 influenza virus (i.e, an influenza virus comprising a genome engineered to express a cH5/1 chimeric influenza hemagglutinin polypeptide).

A plasmid for rescue of influenza virus expressing a cH5/1 chimeric influenza hemagglutinin polypeptide was constructed by substituting codons for the globular head domain (53 to 276, H3 numbering) in a rescue plasmid that carries the HA gene of A/California/04/09 with the globular head domain of A/Vietnam/1203/04 (H5). The sequence of the construct was confirmed by Sanger sequencing and expression in 293T cells was tested using Western blot analysis in accordance with the methods described above.

Generation of recombinant virus for rescue was accomplished using the approaches described in Example 5, above. The plasmid encoding the cH5/1$_{Cal09}$ HA was co-transfected into 293T cells with 7 complementary rescue plasmids that encode for the 7 other genomic segments of the influenza A virus (PR8 backbone). Supernatants were harvested on day one post transfection and were directly inoculated into 10 day old embryonated eggs. 48 hours post-inoculation eggs were chilled to 4° C. and allantoic fluid was harvested. Virus growth was assessed by hemagglutination assay. Supernatants from positive eggs were plaqued on MDCK cells and single plaques were picked and propagated again in embryonated eggs. RNA from plaque purified viruses was isolated, reverse-transcribed and the sequence was confirmed by Sanger sequencing. The identity of the virus clones was proven by staining with a strictly H1 stalk-reactive antibody (6F12) and a strain specific anti-head antibody against A/Vietnam/1203/04 (H5), confirming the generation of and isolation of influenza virus comprising a genome engineered to express a cH5/1 chimeric influenza hemagglutinin polypeptide comprising the HA gene of A/California/04/09 and the globular head domain of A/Vietnam/1203/04 (H5).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A chimeric influenza virus hemagglutinin (HA) polypeptide comprising a stem domain of an HA from influenza virus A/California/4/2009 (H1N1) or A/California/4/2009 (H1N1)-like influenza virus HA and a globular head domain of an HA from an HA from influenza virus A/Vietnam/1203/2004 (H5) or an A/Vietnam/1203/2004 (H5)-like influenza virus HA.

2. The chimeric influenza virus HA polypeptide of claim 1, wherein the stem domain of the HA maintains cysteine residues $A_p$ and $A_q$, wherein $A_p$ is a Cys that corresponds to amino acid position 52 of an HA1 domain using H3 numbering, and wherein $A_q$ is a Cys that corresponds to amino acid position 277 of an HA1 domain using H3 numbering.

3. The chimeric influenza virus HA polypeptide of claim 1, wherein:

(a) the HA stem domain comprises (i) an HA1 N-terminal stem segment, wherein the HA1 N-terminal stem segment consists of amino acid residues $HA1_{N-term}$ through $A_p$; (ii) an HA1 C-terminal stem segment, wherein the HA1 C-terminal stem segment consists of amino acid residues $A_q$ through $HA1_{c\text{-}term}$; and (iii) an HA2 stem domain; and (b) the HA globular head domain comprises the amino acid residues between $A_p$ and $A_q$ of an HA1 domain; wherein $HA1_{N\text{-}term}$ is the N-terminal amino acid of a mature HA0 protein lacking a signal peptide; wherein $HA1_{c\text{-}term}$ is the C-terminal amino acid of an HA1 domain; and wherein $A_p$ is the Cys that corresponds to amino acid position 52 of an HA1 domain using H3 numbering; and wherein $A_q$ is the Cys that corresponds to amino acid position 277 of an HA1 domain using H3 numbering.

4. The chimeric influenza virus HA polypeptide of claim 1, wherein:
(a) the HA stem domain comprises (i) an HA1 N-terminal stem segment, wherein the HA1 N-terminal stem segment consists of amino acid residues $HA1_{N\text{-}term}$ through $A_{p-10}$, $A_{p-9}$, $A_{p-8}$, $A_{p-7}$, $A_{p-6}$, $A_{p-5}$, $A_{p-4}$, $A_{p-3}$, $A_{p-2}$, $A_{p-1}$, $A_p$, $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, or $A_{p+10}$; (ii) an HA1 C-terminal stem segment, wherein the HA1 C-terminal stem segment consists of amino acid residues $A_{q-10}$, $A_{q-9}$, $A_{q-8}$, $A_{q-7}$, $A_{q-6}$, $A_{q-5}$, $A_{q-4}$, $A_{q-3}$, $A_{q-2}$, $A_{q-1}$, $A_q$, $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, or $A_{q+10}$ through $HA1_{c\text{-}term}$; and (iii) an HA2 stem domain; and
(b) the HA globular head domain comprises the amino acid residues between (i) through $A_{p-10}$, $A_{p-9}$, $A_{p-8}$, $A_{p-7}$, $A_{p-6}$, $A_{p-5}$, $A_{p-4}$, $A_{p-3}$, $A_{p-2}$, $A_{p-1}$, $A_p$, $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, or $A_{p+10}$, and (ii) $A_{q-10}$, $A_{q-9}$, $A_{q-8}$, $A_{q-7}$, $A_{q-6}$, $A_{q-5}$, $A_{q-4}$, $A_{q-3}$, $A_{q-2}$, $A_{q-1}$, $A_q$, $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, or $A_{q+10}$ of an HA1 domain;
wherein $HA1_{N\text{-}term}$ is the N-terminal amino acid of a mature HA0 protein lacking a signal peptide; wherein $HA1_{C\text{-}term}$ is the C-terminal amino acid of an HA1 domain; and wherein $A_p$ is the Cys that corresponds to amino acid position 52 of an HA1 domain using H3 numbering; and
wherein $A_q$ is the Cys that corresponds to amino acid position 277 of an HA1 domain using H3 numbering.

5. The chimeric influenza virus hemagglutinin (HA) polypeptide of claim 1, wherein:
(a) the HA stem domain comprises (i) an HA1 N-terminal stem segment, wherein the HA1 N-terminal stem segment consists of amino acid residues $HA1_{N\text{-}term}$ through $A_{p-10}$, $A_{p-9}$, $A_{p-8}$, $A_{p-7}$, $A_{p-6}$, $A_{p-5}$, $A_{p-4}$, $A_{p-3}$, $A_{p-2}$, $A_{p-1}$, $A_p$, $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, or $A_{p+10}$; (ii) an HA1 C-terminal stem segment, wherein the HA1 C-terminal stem segment consists of amino acid residues $A_{q-1}$, $A_{q-2}$, $A_{q-3}$, $A_{q-4}$, $A_q$, $A_{q+1}$, $A_{q+2}$, or $A_{q+3}$ through $HA1_{C\text{-}term}$; and (iii) an HA2 stem domain; and
(b) the HA globular head domain comprises the amino acid residues between (i) $A_{p-10}$, $A_{p-9}$, $A_{p-8}$, $A_{p-7}$, $A_{p-6}$, $A_{p-5}$, $A_{p-4}$, $A_{p-3}$, $A_{p-2}$, $A_{p-1}$, $A_p$, $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, or $A_{p+10}$ and (ii) $A_{q-1}$, $A_{q-2}$, $A_{q-3}$, $A_{q-4}$, $A_q$, $A_{q+1}$, $A_{q+2}$, or $A_{q+3}$ of an HA1 domain; and
wherein $HA1_{N\text{-}term}$ is the N-terminal amino acid of a mature HA0 protein lacking a signal peptide; wherein $HA1_{C\text{-}term}$ is the C-terminal amino acid of an HA1 domain; and wherein Ap is the Cys that corresponds to amino acid position 52 of an HA1 domain using H3 numbering; wherein Aq is the Cys that corresponds to amino acid position 277 of an HA1 domain using H3 numbering.

6. The chimeric influenza HA polypeptide of claim 1, wherein the polypeptide further comprises an HA influenza virus luminal domain, an influenza virus HA transmembrane domain, and an influenza virus HA cytoplasmic domain.

7. The chimeric influenza virus HA polypeptide of claim 6, wherein the luminal domain, the transmembrane domain, and the cytoplasmic domain are from influenza virus A/California/4/2009 HA or influenza virus A/California/4/2009 (H1N1)-like influenza virus HA.

8. The chimeric influenza virus HA polypeptide of claim 3, wherein the polypeptide further comprises a luminal domain, a transmembrane domain, and a cytoplasmic domain from influenza virus A/California/4/2009 HA or influenza virus A/California/4/2009 (H1N1)-like influenza virus HA.

9. The chimeric influenza virus HA polypeptide of claim 1, wherein the polypeptide is soluble.

10. The chimeric influenza virus HA polypeptide of claim 9, wherein the polypeptide comprises a trimerization domain.

11. The chimeric influenza virus HA polypeptide of claim 9, wherein the polypeptide does not comprise a transmembrane domain or an endodomain of an influenza virus HA, and further comprises (i) a thrombin cleavage site and a T4 trimerization domain; (ii) a HIS tag, or both.

12. The chimeric influenza virus HA polypeptide of claim 1, which is expressed and isolated from a mammalian cell or an insect cell.

13. A nucleic acid encoding the chimeric influenza virus hemagglutinin (HA) polypeptide of claim 1.

14. A nucleic acid encoding the chimeric influenza virus hemagglutinin (HA) polypeptide of claim 3.

15. A host cell expressing the nucleic acid of claim 13.

16. A virus comprising: (a) a genome engineered to express a nucleic acid encoding the chimeric influenza virus HA polypeptide of claim 1; or (b) the chimeric influenza virus HA polypeptide of claim 1.

17. The virus of claim 16, which is an influenza A virus.

18. The virus of claim 16, which is a vesicular stomatitis virus (VSV), Newcastle disease virus (NDV), adenovirus, or baculovirus.

19. An embryonated egg or cell line comprising the virus of claim 16.

20. A method for producing the chimeric influenza virus HA polypeptide of claim 1, comprising (a) culturing a cell or cell line expressing the chimeric influenza virus HA polypeptide of claim 1; and (b) isolating the chimeric influenza virus HA polypeptide.

21. A method for producing the virus of claim 16, comprising (a) propagating the virus of claim 16 in an embryonated egg; and (b) isolating the virus from the embryonated egg.

22. An immunogenic composition comprising the chimeric influenza virus HA polypeptide of claim 1.

23. An immunogenic composition comprising the virus of any one of claim 16.

24. The immunogenic composition of claim 22 further comprising an adjuvant.

25. The immunogenic composition of claim 24, wherein the adjuvant is an aluminum salt, 3 De-O-acylated monophosphoryl lipid A, MF59, AS03, AS04, polysorbate 80, an imidazopyridine compound, an imidazoquinoxaline compound, Matrix-M, MVA, ISCOMATRIX, AddaVax, polyI:C, in vitro transcribed RNA hairpin from Sendai virus Cantell strain defective interfering RNA, a saponin, Freund's adjuvant, an oil in water emulsion, CpG, a physical adjuvant, or a Toll-like receptor stimulatory molecule.

26. A method of immunizing a subject against influenza virus comprising administering to the subject an effective amount of the immunogenic composition of claim 22.

27. A method of preventing an influenza virus disease in a subject comprising administering to the subject an effective amount of the immunogenic composition of claim 22.

28. A method of immunizing a subject against influenza virus comprising administering to the subject an effective amount of the immunogenic composition of claim 23.

29. A method of preventing an influenza virus disease in a subject comprising administering to the subject an effective amount of the immunogenic composition of claim 23.

30. The method of claim 26, wherein the subject is human.
31. The method of claim 27, wherein the subject is human.
32. The method of claim 28, wherein the subject is human.
33. The method of claim 29, wherein the subject is human.

* * * * *

SEQUENCE LISTING

```
<160> NUMBER OF SEQ ID NOS: 35

<210> SEQ ID NO 1
<211> LENGTH: 565
<212> TYPE: PRT
<213> ORGANISM: Influenza virus A
<220> FEATURE:
<223> OTHER INFORMATION: influenza virus A hemagglutinin subtype H1

<400> SEQUENCE: 1

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270
```

```
Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
        290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 2
<211> LENGTH: 562
<212> TYPE: PRT
<213> ORGANISM: Influenza virus A
<220> FEATURE:
<223> OTHER INFORMATION: influenza virus A hemagglutinin subtype H2

<400> SEQUENCE: 2

Met Ala Ile Ile Tyr Leu Ile Leu Leu Phe Thr Ala Val Arg Gly Asp
1               5                   10                  15

Gln Ile Cys Ile Gly Tyr His Ser Asn Asn Ser Thr Glu Lys Val Asp
            20                  25                  30

Thr Ile Leu Glu Arg Asn Val Thr Val Thr His Ala Gln Asn Ile Leu
        35                  40                  45

Glu Lys Thr His Asn Gly Lys Leu Cys Lys Leu Asn Gly Ile Pro Pro
    50                  55                  60
```

-continued

```
Leu Glu Leu Gly Asp Cys Ser Ile Ala Gly Trp Leu Leu Gly Asn Pro
 65                  70                  75                  80

Glu Cys Asp Arg Leu Leu Thr Val Pro Glu Trp Ser Tyr Ile Met Glu
                 85                  90                  95

Lys Glu Asn Pro Arg Asn Gly Leu Cys Tyr Pro Gly Ser Phe Asn Asp
            100                 105                 110

Tyr Glu Glu Leu Lys His Leu Leu Ser Ser Val Thr His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Ile Gly Thr Ser Thr Leu Asn Lys Arg Ser Ile
    210                 215                 220

Pro Val Ile Ala Thr Arg Pro Lys Val Asn Gly Gln Gly Gly Arg Met
225                 230                 235                 240

Glu Phe Ser Trp Thr Ile Leu Asp Ile Trp Asp Thr Ile Asn Phe Glu
                245                 250                 255

Ser Thr Gly Asn Leu Ile Ala Pro Glu Tyr Gly Phe Arg Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Ile Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Ile Asp Gly Ile Thr Asn Arg Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Arg Val Arg Met
    450                 455                 460

Gln Leu Arg Asp Asn Ala Lys Glu Leu Gly Asn Gly Cys Phe Glu Phe
465                 470                 475                 480
```

```
Tyr His Lys Cys Asp Asp Glu Cys Met Asn Ser Val Lys Asn Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Asn Met Gly Val Tyr Gln Ile Leu Ala
        515                 520                 525

Ile Tyr Ala Thr Val Ala Gly Ser Leu Ser Leu Ala Ile Met Ile Ala
530                 535                 540

Gly Ile Ser Leu Trp Met Cys Ser Asn Gly Ser Leu Gln Cys Arg Ile
545                 550                 555                 560

Cys Ile

<210> SEQ ID NO 3
<211> LENGTH: 566
<212> TYPE: PRT
<213> ORGANISM: Influenza virus A
<220> FEATURE:
<223> OTHER INFORMATION: influenza virus A hemagglutinin subtype H3

<400> SEQUENCE: 3

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
130                 135                 140

Gly Val Thr Gln Asn Gly Gly Ser Asn Ala Cys Lys Arg Gly Pro Gly
145                 150                 155                 160

Asn Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Glu Ser Gly Arg Val Thr Val Ser Thr Arg Arg
210                 215                 220

Ser Gln Gln Ser Ile Ile Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270
```

```
Tyr Phe Lys Met Arg Thr Gly Lys Ser Ser Ile Met Ser Asp Ala
            275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
            355                 360                 365

Phe Arg His Gln Asn Ser Glu Gly Thr Gly Gln Ala Ala Asp Leu Lys
            370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
435                 440                 445

Asn Gln His Thr Ile Asp Leu Thr Asp Ser Glu Met Asn Lys Leu Phe
            450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 4
<211> LENGTH: 564
<212> TYPE: PRT
<213> ORGANISM: Influenza virus A
<220> FEATURE:
<223> OTHER INFORMATION: influenza virus A hemagglutinin subtype H4

<400> SEQUENCE: 4

Met Leu Ser Ile Val Ile Leu Phe Leu Leu Ile Ala Glu Asn Ser Ser
1               5                   10                  15

Gln Asn Tyr Thr Gly Asn Pro Val Ile Cys Met Gly His His Ala Val
            20                  25                  30

Ala Asn Gly Thr Met Val Lys Thr Leu Ala Asp Asp Gln Val Glu Val
        35                  40                  45

Val Thr Ala Gln Glu Leu Val Glu Ser Gln Asn Leu Pro Glu Leu Cys
50                  55                  60
```

-continued

```
Pro Ser Pro Leu Arg Leu Val Asp Gly Gln Thr Cys Asp Ile Ile Asn
 65                  70                  75                  80

Gly Ala Leu Gly Ser Pro Gly Cys Asp His Leu Asn Gly Ala Glu Trp
                 85                  90                  95

Asp Val Phe Ile Glu Arg Pro Asn Ala Val Asp Thr Cys Tyr Pro Phe
            100                 105                 110

Asp Val Pro Glu Tyr Gln Ser Leu Arg Ser Ile Leu Ala Asn Asn Gly
        115                 120                 125

Lys Phe Glu Phe Ile Ala Glu Glu Phe Gln Trp Asn Thr Val Lys Gln
    130                 135                 140

Asn Gly Lys Ser Gly Ala Cys Lys Arg Ala Asn Val Asp Asp Phe Phe
145                 150                 155                 160

Asn Arg Leu Asn Trp Leu Val Lys Ser Asp Gly Asn Ala Tyr Pro Leu
                165                 170                 175

Gln Asn Leu Thr Lys Ile Asn Asn Gly Asp Tyr Ala Arg Leu Tyr Ile
            180                 185                 190

Trp Gly Val His His Pro Ser Thr Ser Thr Glu Gln Thr Asn Leu Tyr
        195                 200                 205

Lys Asn Asn Pro Gly Arg Val Thr Val Ser Thr Lys Thr Ser Gln Thr
    210                 215                 220

Ser Val Val Pro Asp Ile Gly Ser Arg Pro Leu Val Arg Gly Gln Ser
225                 230                 235                 240

Gly Arg Val Ser Phe Tyr Trp Thr Ile Val Glu Pro Gly Asp Leu Ile
                245                 250                 255

Val Phe Asn Thr Ile Gly Asn Leu Ile Ala Pro Arg Gly His Tyr Lys
            260                 265                 270

Leu Asn Asn Gln Lys Lys Ser Thr Ile Leu Asn Thr Ala Ile Pro Ile
        275                 280                 285

Gly Ser Cys Val Ser Lys Cys His Thr Asp Lys Gly Ser Leu Ser Thr
    290                 295                 300

Thr Lys Pro Phe Gln Asn Ile Ser Arg Ile Ala Val Gly Asp Cys Pro
305                 310                 315                 320

Arg Tyr Val Lys Gln Gly Ser Leu Lys Leu Ala Thr Gly Met Arg Asn
                325                 330                 335

Ile Pro Glu Lys Ala Ser Arg Gly Leu Phe Gly Ala Ile Ala Gly Phe
            340                 345                 350

Ile Glu Asn Gly Trp Gln Gly Leu Ile Asp Gly Trp Tyr Gly Phe Arg
        355                 360                 365

His Gln Asn Ala Glu Gly Thr Gly Thr Ala Ala Asp Leu Lys Ser Thr
    370                 375                 380

Gln Ala Ala Ile Asp Gln Ile Asn Gly Lys Leu Asn Arg Leu Ile Glu
385                 390                 395                 400

Lys Thr Asn Asp Lys Tyr His Gln Ile Glu Lys Glu Phe Glu Gln Val
                405                 410                 415

Glu Gly Arg Ile Gln Asp Leu Glu Asn Tyr Val Glu Asp Thr Lys Ile
            420                 425                 430

Asp Leu Trp Ser Tyr Asn Ala Glu Leu Leu Val Ala Leu Glu Asn Gln
        435                 440                 445

His Thr Ile Asp Val Thr Asp Ser Glu Met Asn Lys Leu Phe Glu Arg
    450                 455                 460

Val Arg Arg Gln Leu Arg Glu Asn Ala Glu Asp Lys Gly Asn Gly Cys
465                 470                 475                 480
```

```
Phe Glu Ile Phe His Lys Cys Asp Asn Asn Cys Ile Glu Ser Ile Arg
                485                 490                 495

Asn Gly Thr Tyr Asp His Asp Ile Tyr Arg Asp Glu Ala Ile Asn Asn
            500                 505                 510

Arg Phe Gln Ile Gln Gly Val Lys Leu Thr Gln Gly Tyr Lys Asp Ile
        515                 520                 525

Ile Leu Trp Ile Ser Phe Ser Ile Ser Cys Phe Leu Leu Val Ala Leu
    530                 535                 540

Leu Leu Ala Phe Ile Leu Trp Ala Cys Gln Asn Gly Asn Ile Arg Cys
545                 550                 555                 560

Gln Ile Cys Ile

<210> SEQ ID NO 5
<211> LENGTH: 564
<212> TYPE: PRT
<213> ORGANISM: Influenza virus A
<220> FEATURE:
<223> OTHER INFORMATION: influenza virus A hemagglutinin subtype H5

<400> SEQUENCE: 5

Met Glu Arg Ile Val Leu Leu Leu Ala Ile Val Ser Leu Val Lys Ser
1               5                   10                  15

Asp Gln Ile Cys Ile Gly Tyr His Ala Asn Lys Ser Thr Lys Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Leu Pro Glu Trp Leu Tyr Ile Val
                85                  90                  95

Glu Lys Asp Asn Pro Ile Asn Ser Leu Cys Tyr Pro Gly Asp Phe Asn
            100                 105                 110

Asp Tyr Glu Glu Leu Lys Tyr Leu Leu Ser Ser Thr Asn His Phe Glu
        115                 120                 125

Lys Ile Arg Ile Ile Pro Arg Ser Ser Trp Ser Asn His Asp Ala Ser
    130                 135                 140

Ser Gly Val Ser Ser Ala Cys Pro Tyr Ile Gly Arg Ser Ser Phe Leu
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Arg Tyr Ala Tyr Lys Ile
            260                 265                 270
```

```
Val Lys Lys Gly Asp Ser Ala Ile Met Lys Ser Gly Leu Ala Tyr Gly
            275                 280                 285

Asn Cys Asp Thr Lys Cys Gln Thr Pro Val Gly Glu Ile Asn Ser Ser
        290                 295                 300

Met Pro Phe His Asn Ile His Pro His Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Lys Lys Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Arg Phe Glu Ala Val Gly Lys Glu Phe Asn Asn Leu Glu
                405                 410                 415

Arg Arg Val Glu Asn Leu Asn Lys Lys Met Glu Asp Gly Phe Leu Asp
            420                 425                 430

Val Trp Thr Tyr Asn Val Glu Leu Leu Val Leu Met Glu Asn Glu Arg
        435                 440                 445

Thr Leu Asp Phe His Asp Ser Asn Val Asn Asn Leu Tyr Asp Lys Val
    450                 455                 460

Arg Leu Gln Leu Lys Asp Asn Ala Arg Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Asn Arg
            500                 505                 510

Glu Glu Ile Ser Gly Val Lys Leu Glu Ser Met Gly Val Tyr Gln Ile
        515                 520                 525

Leu Ser Ile Tyr Ser Thr Val Ala Ser Ser Leu Ala Leu Ala Ile Met
    530                 535                 540

Ile Ala Gly Leu Ser Phe Trp Met Cys Ser Asn Gly Ser Leu Gln Cys
545                 550                 555                 560

Arg Ile Cys Ile

<210> SEQ ID NO 6
<211> LENGTH: 566
<212> TYPE: PRT
<213> ORGANISM: Influenza virus A
<220> FEATURE:
<223> OTHER INFORMATION: influenza virus A hemagglutinin subtype H6

<400> SEQUENCE: 6

Met Ile Ala Ile Ile Val Val Ala Ile Leu Ala Thr Ala Gly Arg Ser
1               5                   10                  15

Asp Lys Ile Cys Ile Gly Tyr His Ala Asn Asn Ser Thr Thr Gln Ile
            20                  25                  30

Asp Thr Ile Leu Glu Lys Asn Val Thr Val Thr His Ser Val Glu Leu
        35                  40                  45

Leu Glu Asn Gln Lys Glu Glu Arg Phe Cys Lys Ile Leu Lys Lys Ala
    50                  55                  60
```

```
Pro Leu Asp Leu Lys Gly Cys Thr Ile Glu Gly Trp Ile Leu Gly Asn
 65                  70                  75                  80

Pro Gln Cys Asp Leu Leu Leu Gly Asp Gln Ser Trp Ser Tyr Ile Val
                 85                  90                  95

Glu Arg Pro Thr Ala Gln Asn Gly Ile Cys Tyr Pro Gly Val Leu Asn
            100                 105                 110

Glu Val Glu Glu Leu Lys Ala Leu Ile Gly Ser Gly Glu Arg Val Glu
        115                 120                 125

Arg Phe Glu Met Phe Pro Lys Ser Thr Trp Thr Gly Val Asp Thr Ser
130                 135                 140

Ser Gly Val Thr Arg Ala Cys Pro Tyr Asn Ser Gly Ser Ser Phe Tyr
145                 150                 155                 160

Arg Asn Leu Leu Trp Ile Ile Lys Thr Lys Ser Ala Ala Tyr Ser Val
                165                 170                 175

Ile Lys Gly Ala Tyr Asn Asn Thr Gly Asn Gln Pro Ile Leu Tyr Phe
            180                 185                 190

Trp Gly Val His His Pro Pro Asp Thr Asn Glu Gln Asn Thr Leu Tyr
        195                 200                 205

Gly Ser Gly Asp Arg Tyr Val Arg Met Gly Thr Glu Ser Met Asn Phe
210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Ile Leu Lys Pro Gly Glu Thr Leu
                245                 250                 255

Asn Val Glu Ser Asn Gly Asn Leu Ile Ala Pro Trp Tyr Ala Phe Arg
            260                 265                 270

Phe Val Ser Thr Ser Asn Lys Gly Ala Val Phe Lys Ser Asn Leu Pro
        275                 280                 285

Ile Glu Asn Cys Asp Ala Thr Cys Gln Thr Val Ala Gly Val Leu Arg
290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

Asn Val Pro Gln Ile Glu Thr Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Glu Asn Ser Gln Gly Ser Gly Tyr Ala Ala Asp Arg Glu Ser
370                 375                 380

Thr Gln Lys Ala Val Asp Gly Ile Thr Asn Lys Val Asn Ser Ile Ile
385                 390                 395                 400

Asp Lys Met Asn Thr Gln Phe Glu Ala Val Asp His Glu Phe Ser Asn
                405                 410                 415

Leu Glu Arg Arg Ile Asp Asn Leu Asn Lys Arg Met Glu Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Leu His Asp Ala Asn Val Lys Asn Leu Tyr Glu
450                 455                 460

Arg Val Lys Ser Gln Leu Arg Asp Asn Ala Met Ile Leu Gly Asn Gly
465                 470                 475                 480
```

```
Cys Phe Glu Phe Trp His Lys Cys Asp Asp Glu Cys Met Glu Ser Val
                485                 490                 495

Lys Asn Gly Thr Tyr Asp Tyr Pro Lys Tyr Gln Asp Glu Ser Lys Leu
            500                 505                 510

Asn Arg Gln Glu Ile Glu Ser Val Lys Leu Glu Ser Leu Gly Val Tyr
            515                 520                 525

Gln Ile Leu Ala Ile Tyr Ser Thr Val Ser Ser Ser Leu Val Leu Val
        530                 535                 540

Gly Leu Ile Ile Ala Val Gly Leu Trp Met Cys Ser Asn Gly Ser Met
545                 550                 555                 560

Gln Cys Arg Ile Cys Ile
                565

<210> SEQ ID NO 7
<211> LENGTH: 563
<212> TYPE: PRT
<213> ORGANISM: Influenza virus A
<220> FEATURE:
<223> OTHER INFORMATION: influenza virus A hemagglutinin subtype H7

<400> SEQUENCE: 7

Met Asn Thr Gln Ile Leu Val Phe Ala Leu Val Ala Val Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Lys Ile Cys Ser Lys Gly Lys
50                  55                  60

Arg Thr Thr Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Asn Asp Val Cys Tyr Pro Gly Lys Phe Val Asn
            100                 105                 110

Glu Glu Ala Leu Arg Gln Ile Leu Arg Gly Ser Gly Ile Asp Lys
        115                 120                 125

Glu Thr Met Gly Phe Thr Tyr Ser Gly Ile Arg Thr Asn Gly Thr Thr
130                 135                 140

Ser Ala Cys Arg Arg Ser Gly Ser Ser Phe Tyr Ala Glu Met Glu Trp
145                 150                 155                 160

Leu Leu Ser Asn Thr Asp Asn Ala Ser Phe Pro Gln Met Thr Lys Ser
                165                 170                 175

Tyr Lys Asn Thr Arg Arg Glu Ser Ala Leu Ile Val Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Lys Tyr His Gln Ser Phe Val Pro
210                 215                 220

Ser Pro Gly Thr Arg Pro Gln Ile Asn Gly Gln Ser Gly Arg Ile Asp
225                 230                 235                 240

Phe His Trp Leu Ile Leu Asp Pro Asn Asp Thr Val Thr Phe Ser Phe
                245                 250                 255

Asn Gly Ala Phe Ile Ala Pro Asn Arg Ala Ser Phe Leu Arg Gly Lys
            260                 265                 270
```

-continued

```
Ser Met Gly Ile Gln Ser Asp Val Gln Val Asp Ala Asn Cys Glu Gly
            275                 280                 285

Glu Cys Tyr His Ser Gly Thr Ile Thr Ser Arg Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Pro Ser
                325                 330                 335

Lys Lys Arg Lys Arg Gly Leu Phe Gly Ala Ile Ala Gly Phe Ile
                340                 345                 350

Glu Asn Gly Trp Glu Gly Leu Val Asp Gly Trp Tyr Gly Phe Arg His
                355                 360                 365

Gln Asn Ala Gln Gly Glu Gly Thr Ala Ala Asp Tyr Lys Ser Thr Gln
    370                 375                 380

Ser Ala Ile Asp Gln Ile Thr Gly Lys Leu Asn Arg Leu Ile Glu Lys
385                 390                 395                 400

Thr Asn Gln Gln Phe Glu Leu Ile Asp Asn Glu Phe Thr Glu Val Glu
                405                 410                 415

Lys Gln Ile Gly Asn Leu Ile Asn Trp Thr Lys Asp Ser Ile Thr Glu
                420                 425                 430

Val Trp Ser Tyr Asn Ala Glu Leu Ile Val Ala Met Glu Asn Gln His
                435                 440                 445

Thr Ile Asp Leu Ala Asp Ser Glu Met Asn Arg Leu Tyr Glu Arg Val
                450                 455                 460

Arg Lys Gln Leu Arg Glu Asn Ala Glu Glu Asp Gly Thr Gly Cys Phe
465                 470                 475                 480

Glu Ile Phe His Lys Cys Asp Asp Cys Met Ala Ser Ile Arg Asn
                485                 490                 495

Asn Thr Tyr Asp His Ser Lys Tyr Arg Glu Glu Ala Met Gln Asn Arg
                500                 505                 510

Ile Gln Ile Asp Pro Val Lys Leu Ser Ser Gly Tyr Lys Asp Val Ile
                515                 520                 525

Leu Trp Phe Ser Phe Gly Ala Ser Cys Phe Leu Leu Leu Ala Ile Ala
                530                 535                 540

Met Gly Leu Val Phe Ile Cys Val Lys Asn Gly Asn Met Arg Cys Thr
545                 550                 555                 560

Ile Cys Ile

<210> SEQ ID NO 8
<211> LENGTH: 565
<212> TYPE: PRT
<213> ORGANISM: Influenza virus A
<220> FEATURE:
<223> OTHER INFORMATION: influenza virus A hemagglutinin subtype H8

<400> SEQUENCE: 8

Met Glu Lys Phe Ile Ala Ile Ala Thr Leu Ala Ser Thr Asn Ala Tyr
1               5                   10                  15

Asp Arg Ile Cys Ile Gly Tyr Gln Ser Asn Asn Ser Thr Asp Thr Val
                20                  25                  30

Asn Thr Leu Ile Glu Gln Asn Val Pro Val Thr Gln Thr Met Glu Leu
            35                  40                  45

Val Glu Thr Glu Lys His Pro Ala Tyr Cys Asn Thr Asp Leu Gly Ala
        50                  55                  60
```

-continued

```
Pro Leu Glu Leu Arg Asp Cys Lys Ile Glu Ala Val Ile Tyr Gly Asn
 65                  70                  75                  80

Pro Lys Cys Asp Ile His Leu Lys Asp Gln Gly Trp Ser Tyr Ile Val
                 85                  90                  95

Glu Arg Pro Ser Ala Pro Glu Gly Met Cys Tyr Pro Gly Ser Val Glu
            100                 105                 110

Asn Leu Glu Glu Leu Arg Phe Val Phe Ser Ser Ala Ala Ser Tyr Lys
        115                 120                 125

Arg Ile Arg Leu Phe Asp Tyr Ser Arg Trp Asn Val Thr Arg Ser Gly
130                 135                 140

Thr Ser Lys Ala Cys Asn Ala Ser Thr Gly Gln Ser Phe Tyr Arg
145                 150                 155                 160

Ser Ile Asn Trp Leu Thr Lys Lys Glu Pro Asp Thr Tyr Asp Phe Asn
                165                 170                 175

Glu Gly Ala Tyr Val Asn Asn Glu Asp Gly Asp Ile Ile Phe Leu Trp
            180                 185                 190

Gly Ile His His Pro Pro Asp Thr Lys Glu Gln Thr Thr Leu Tyr Lys
        195                 200                 205

Asn Ala Asn Thr Leu Ser Ser Val Thr Thr Asn Thr Ile Asn Arg Ser
210                 215                 220

Phe Gln Pro Asn Ile Gly Pro Arg Pro Leu Val Arg Gly Gln Gln Gly
225                 230                 235                 240

Arg Met Asp Tyr Tyr Trp Gly Ile Leu Lys Arg Gly Glu Thr Leu Lys
                245                 250                 255

Ile Arg Thr Asn Gly Asn Leu Ile Ala Pro Glu Phe Gly Tyr Leu Leu
            260                 265                 270

Lys Gly Glu Ser Tyr Gly Arg Ile Ile Gln Asn Glu Asp Ile Pro Ile
        275                 280                 285

Gly Asn Cys Asn Thr Lys Cys Gln Thr Tyr Ala Gly Ala Ile Asn Ser
290                 295                 300

Ser Lys Pro Phe Gln Asn Ala Ser Arg His Tyr Met Gly Glu Cys Pro
305                 310                 315                 320

Lys Tyr Val Lys Lys Ala Ser Leu Arg Leu Ala Val Gly Leu Arg Asn
                325                 330                 335

Thr Pro Ser Val Glu Pro Arg Gly Leu Phe Gly Ala Ile Ala Gly Phe
            340                 345                 350

Ile Glu Gly Gly Trp Ser Gly Met Ile Asp Gly Trp Tyr Gly Phe His
        355                 360                 365

His Ser Asn Ser Glu Gly Thr Gly Met Ala Ala Asp Gln Lys Ser Thr
370                 375                 380

Gln Glu Ala Ile Asp Lys Ile Thr Asn Lys Val Asn Asn Ile Val Asp
385                 390                 395                 400

Lys Met Asn Arg Glu Phe Glu Val Val Asn His Glu Phe Ser Glu Val
                405                 410                 415

Glu Lys Arg Ile Asn Met Ile Asn Asp Lys Ile Asp Asp Gln Ile Glu
            420                 425                 430

Asp Leu Trp Ala Tyr Asn Ala Glu Leu Leu Val Leu Leu Glu Asn Gln
        435                 440                 445

Lys Thr Leu Asp Glu His Asp Ser Asn Val Lys Asn Leu Phe Asp Glu
450                 455                 460

Val Lys Arg Arg Leu Ser Ala Asn Ala Ile Asp Ala Gly Asn Gly Cys
465                 470                 475                 480
```

-continued

Phe Asp Ile Leu His Lys Cys Asp Asn Glu Cys Met Glu Thr Ile Lys
                485                 490                 495

Asn Gly Thr Tyr Asp His Lys Glu Tyr Glu Glu Ala Lys Leu Glu
            500                 505                 510

Arg Ser Lys Ile Asn Gly Val Lys Leu Glu Glu Asn Thr Thr Tyr Lys
            515                 520                 525

Ile Leu Ser Ile Tyr Ser Thr Val Ala Ala Ser Leu Cys Leu Ala Ile
            530                 535                 540

Leu Ile Ala Gly Gly Leu Ile Leu Gly Met Gln Asn Gly Ser Cys Arg
545                 550                 555                 560

Cys Met Phe Cys Ile
                565

<210> SEQ ID NO 9
<211> LENGTH: 560
<212> TYPE: PRT
<213> ORGANISM: Influenza virus A
<220> FEATURE:
<223> OTHER INFORMATION: influenza virus A hemagglutinin subtype H9

<400> SEQUENCE: 9

Met Glu Thr Lys Ala Ile Ile Ala Ala Leu Leu Met Val Thr Ala Ala
1               5                   10                  15

Asn Ala Asp Lys Ile Cys Ile Gly Tyr Gln Ser Thr Asn Ser Thr Glu
                20                  25                  30

Thr Val Asp Thr Leu Thr Glu Ser Asn Val Pro Val Thr His Thr Lys
            35                  40                  45

Glu Leu Leu His Thr Glu His Asn Gly Met Leu Cys Ala Thr Asp Leu
50                  55                  60

Gly His Pro Leu Ile Leu Asp Thr Cys Thr Ile Glu Gly Leu Ile Tyr
65                  70                  75                  80

Gly Asn Pro Ser Cys Asp Ile Leu Leu Gly Gly Lys Glu Trp Ser Tyr
                85                  90                  95

Ile Val Glu Arg Ser Ser Ala Val Asn Gly Met Cys Tyr Pro Gly Asn
                100                 105                 110

Val Glu Asn Leu Glu Glu Leu Arg Ser Leu Phe Ser Ser Ala Lys Ser
            115                 120                 125

Tyr Lys Arg Ile Gln Ile Phe Pro Asp Lys Thr Trp Asn Val Thr Tyr
            130                 135                 140

Ser Gly Thr Ser Arg Ala Cys Ser Asn Ser Phe Tyr Arg Ser Met Arg
145                 150                 155                 160

Trp Leu Thr His Lys Ser Asn Ser Tyr Pro Phe Gln Asn Ala His Tyr
                165                 170                 175

Thr Asn Asn Glu Arg Glu Asn Ile Leu Phe Met Trp Gly Ile His His
                180                 185                 190

Pro Pro Thr Asp Thr Glu Gln Thr Asp Leu Tyr Lys Asn Ala Asp Thr
            195                 200                 205

Thr Thr Ser Val Thr Thr Glu Asp Ile Asn Arg Thr Phe Lys Pro Val
            210                 215                 220

Ile Gly Pro Arg Pro Leu Val Asn Gly Gln Gln Gly Arg Ile Asp Tyr
225                 230                 235                 240

Tyr Trp Ser Val Leu Lys Pro Gly Gln Thr Leu Arg Ile Arg Ser Asn
                245                 250                 255

Gly Asn Leu Ile Ala Pro Trp Tyr Gly His Val Leu Thr Gly Glu Ser
                260                 265                 270

```
His Gly Arg Ile Leu Lys Thr Asp Leu Asn Asn Gly Asn Cys Val Val
            275                 280                 285

Gln Cys Gln Thr Glu Lys Gly Gly Leu Asn Thr Thr Leu Pro Phe His
290                 295                 300

Asn Ile Ser Lys Tyr Ala Phe Gly Asn Cys Pro Lys Tyr Val Gly Val
305                 310                 315                 320

Lys Ser Leu Lys Leu Pro Val Gly Leu Arg Asn Val Pro Ala Val Ser
            325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
            355                 360                 365

Gly Val Gly Met Ala Ala Asp Lys Gly Ser Thr Gln Lys Ala Ile Asp
370                 375                 380

Lys Ile Thr Ser Lys Val Asn Asn Ile Ile Asp Lys Met Asn Lys Gln
385                 390                 395                 400

Tyr Glu Val Ile Asp His Glu Phe Asn Glu Leu Glu Ala Arg Leu Asn
            405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
435                 440                 445

His Asp Ala Asn Val Asn Asn Leu Tyr Asn Lys Val Lys Arg Ala Leu
            450                 455                 460

Gly Ser Asn Ala Val Glu Asp Gly Asn Gly Cys Phe Glu Leu Tyr His
465                 470                 475                 480

Lys Cys Asp Asp Gln Cys Met Glu Thr Ile Arg Asn Gly Thr Tyr Asp
            485                 490                 495

Arg Gln Lys Tyr Gln Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
            515                 520                 525

Ser Thr Val Ala Ser Ser Leu Val Leu Ala Met Gly Phe Ala Ala Phe
530                 535                 540

Leu Phe Trp Ala Met Ser Asn Gly Ser Cys Arg Cys Asn Ile Cys Ile
545                 550                 555                 560

<210> SEQ ID NO 10
<211> LENGTH: 561
<212> TYPE: PRT
<213> ORGANISM: Influenza virus A
<220> FEATURE:
<223> OTHER INFORMATION: influenza virus A hemagglutinin subtype H10

<400> SEQUENCE: 10

Met Tyr Lys Val Val Ile Ile Ala Leu Leu Gly Ala Val Lys Gly
1               5                   10                  15

Leu Asp Arg Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
            35                  40                  45

Thr Val Glu Ser Thr Asn Leu Asn Lys Leu Cys Met Lys Gly Arg Ser
        50                  55                  60

Tyr Lys Asp Leu Gly Asn Cys His Pro Val Gly Met Leu Ile Gly Thr
65                  70                  75                  80
```

```
Pro Val Cys Asp Pro His Leu Thr Gly Thr Trp Asp Thr Leu Ile Glu
             85                  90                  95

Arg Glu Asn Ala Ile Ala His Cys Tyr Pro Gly Ala Thr Ile Asn Glu
            100                 105                 110

Glu Ala Leu Arg Gln Lys Ile Met Glu Ser Gly Gly Ile Ser Lys Met
            115                 120                 125

Ser Thr Gly Phe Thr Tyr Gly Ser Ser Ile Thr Ser Ala Gly Thr Thr
            130                 135                 140

Lys Ala Cys Met Arg Asn Gly Gly Asp Ser Phe Tyr Ala Glu Leu Lys
145                 150                 155                 160

Trp Leu Val Ser Lys Thr Lys Gly Gln Asn Phe Pro Gln Thr Thr Asn
                165                 170                 175

Thr Tyr Arg Asn Thr Asp Thr Ala Glu His Leu Ile Ile Trp Gly Ile
            180                 185                 190

His His Pro Ser Ser Thr Gln Glu Lys Asn Asp Leu Tyr Gly Thr Gln
            195                 200                 205

Ser Leu Ser Ile Ser Val Glu Ser Ser Thr Tyr Gln Asn Asn Phe Val
            210                 215                 220

Pro Val Val Gly Ala Arg Pro Gln Val Asn Gly Gln Ser Gly Arg Ile
225                 230                 235                 240

Asp Phe His Trp Thr Leu Val Gln Pro Gly Asp Asn Ile Thr Phe Ser
                245                 250                 255

Asp Asn Gly Gly Leu Ile Ala Pro Ser Arg Val Ser Lys Leu Thr Gly
                260                 265                 270

Arg Asp Leu Gly Ile Gln Ser Glu Ala Leu Ile Asp Asn Ser Cys Glu
            275                 280                 285

Ser Lys Cys Phe Trp Arg Gly Gly Ser Ile Asn Thr Lys Leu Pro Phe
            290                 295                 300

Gln Asn Leu Ser Pro Arg Thr Val Gly Gln Cys Pro Lys Tyr Val Asn
305                 310                 315                 320

Gln Arg Ser Leu Leu Leu Ala Thr Gly Met Arg Asn Val Pro Glu Val
                325                 330                 335

Val Gln Gly Arg Gly Leu Phe Gly Ala Ile Ala Gly Phe Ile Glu Asn
                340                 345                 350

Gly Trp Glu Gly Met Val Asp Gly Trp Tyr Gly Phe Arg His Gln Asn
            355                 360                 365

Ala Gln Gly Thr Gly Gln Ala Ala Asp Tyr Lys Ser Thr Gln Ala Ala
            370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
                405                 410                 415

Ile Gly Asn Val Ile Asn Trp Thr Lys Asp Ser Ile Thr Asp Ile Trp
                420                 425                 430

Thr Tyr Asn Ala Glu Leu Leu Val Ala Met Glu Asn Gln His Thr Ile
            435                 440                 445

Asp Met Ala Asp Ser Glu Met Leu Asn Leu Tyr Glu Arg Val Arg Lys
450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
                485                 490                 495
```

```
Tyr Asp His Ser Gln Tyr Arg Glu Glu Ala Leu Leu Asn Arg Leu Asn
                500                 505                 510

Ile Asn Pro Val Lys Leu Ser Ser Gly Tyr Lys Asp Ile Ile Leu Trp
        515                 520                 525

Phe Ser Phe Gly Glu Ser Cys Phe Val Leu Leu Ala Val Val Met Gly
    530                 535                 540

Leu Val Phe Phe Cys Leu Lys Asn Gly Asn Met Arg Cys Thr Ile Cys
545                 550                 555                 560

Ile

<210> SEQ ID NO 11
<211> LENGTH: 565
<212> TYPE: PRT
<213> ORGANISM: Influenza virus A
<220> FEATURE:
<223> OTHER INFORMATION: influenza virus A hemagglutinin subtype H11

<400> SEQUENCE: 11

Met Glu Lys Thr Leu Leu Phe Ala Ala Ile Phe Leu Cys Val Lys Ala
1               5                   10                  15

Asp Glu Ile Cys Ile Gly Tyr Leu Ser Asn Asn Ser Thr Asp Lys Val
            20                  25                  30

Asp Thr Ile Ile Glu Asn Asn Val Thr Val Thr Ser Ser Val Glu Leu
        35                  40                  45

Val Glu Thr Glu His Thr Gly Ser Phe Cys Ser Ile Asn Gly Lys Gln
    50                  55                  60

Pro Ile Ser Leu Gly Asp Cys Ser Phe Ala Gly Trp Ile Leu Gly Asn
65                  70                  75                  80

Pro Met Cys Asp Glu Leu Ile Gly Lys Thr Ser Trp Ser Tyr Ile Val
                85                  90                  95

Glu Lys Pro Asn Pro Thr Asn Gly Ile Cys Tyr Pro Gly Thr Leu Glu
            100                 105                 110

Ser Glu Glu Glu Leu Arg Leu Lys Phe Ser Gly Val Leu Glu Phe Asn
        115                 120                 125

Lys Phe Glu Val Phe Thr Ser Asn Gly Trp Gly Ala Val Asn Ser Gly
    130                 135                 140

Val Gly Val Thr Ala Ala Cys Lys Phe Gly Gly Ser Asn Ser Phe Phe
145                 150                 155                 160

Arg Asn Met Val Trp Leu Ile His Gln Ser Gly Thr Tyr Pro Val Ile
                165                 170                 175

Lys Arg Thr Phe Asn Asn Thr Lys Gly Arg Asp Val Leu Ile Val Trp
            180                 185                 190

Gly Ile His His Pro Ala Thr Leu Thr Glu His Gln Asp Leu Tyr Lys
        195                 200                 205

Lys Asp Ser Ser Tyr Val Ala Val Gly Ser Glu Thr Tyr Asn Arg Arg
    210                 215                 220

Phe Thr Pro Glu Ile Asn Thr Arg Pro Arg Val Asn Gly Gln Ala Gly
225                 230                 235                 240

Arg Met Thr Phe Tyr Trp Lys Ile Val Lys Pro Gly Glu Ser Ile Thr
                245                 250                 255

Phe Glu Ser Asn Gly Ala Phe Leu Ala Pro Arg Tyr Ala Phe Glu Ile
            260                 265                 270

Val Ser Val Gly Asn Gly Lys Leu Phe Arg Ser Glu Leu Asn Ile Glu
        275                 280                 285
```

```
Ser Cys Ser Thr Lys Cys Gln Thr Glu Ile Gly Gly Ile Asn Thr Asn
    290                 295                 300

Lys Ser Phe His Asn Val His Arg Asn Thr Ile Gly Asp Cys Pro Lys
305                 310                 315                 320

Tyr Val Asn Val Lys Ser Leu Lys Leu Ala Thr Gly Pro Arg Asn Val
                325                 330                 335

Pro Ala Ile Ala Ser Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Arg Asp Glu Glu Gly Thr Gly Ile Ala Ala Asp Lys Glu Ser Thr Gln
    370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Val Asp
            420                 425                 430

Ile Trp Ser Tyr Asn Ala Gln Leu Leu Val Leu Leu Glu Asn Glu Lys
        435                 440                 445

Thr Leu Asp Leu His Asp Ser Asn Val Arg Asn Leu His Glu Lys Val
    450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Lys Cys Ile Glu Arg Val Arg Asn
                485                 490                 495

Gly Thr Tyr Asp His Lys Glu Phe Glu Glu Glu Ser Lys Ile Asn Arg
            500                 505                 510

Gln Glu Ile Glu Gly Val Lys Leu Asp Ser Ser Gly Asn Val Tyr Lys
        515                 520                 525

Ile Leu Ser Ile Tyr Ser Cys Ile Ala Ser Ser Leu Val Leu Ala Ala
    530                 535                 540

Leu Ile Met Gly Phe Met Phe Trp Ala Cys Ser Asn Gly Ser Cys Arg
545                 550                 555                 560

Cys Thr Ile Cys Ile
                565

<210> SEQ ID NO 12
<211> LENGTH: 564
<212> TYPE: PRT
<213> ORGANISM: Influenza virus A
<220> FEATURE:
<223> OTHER INFORMATION: influenza virus A hemagglutinin subtype H12

<400> SEQUENCE: 12

Met Glu Lys Phe Ile Ile Leu Ser Thr Val Leu Ala Ala Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ser Glu Gln Asn Val Pro Val Thr Gln Val Glu Glu
        35                  40                  45

Leu Val His Arg Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80
```

```
Asn Pro Lys Cys Asp Leu Tyr Leu Asn Gly Arg Glu Trp Ser Tyr Ile
             85                  90                  95

Val Glu Arg Pro Lys Glu Met Glu Gly Val Cys Tyr Pro Gly Ser Ile
        100                 105                 110

Glu Asn Gln Glu Glu Leu Arg Ser Leu Phe Ser Ser Ile Lys Lys Tyr
        115                 120                 125

Glu Arg Val Lys Met Phe Asp Phe Thr Lys Trp Asn Val Thr Tyr Thr
    130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Val Lys Leu Tyr Lys
        195                 200                 205

Asn Pro Asp Thr Leu Ser Ser Val Thr Thr Val Glu Ile Asn Arg Ser
        210                 215                 220

Phe Lys Pro Asn Ile Gly Pro Arg Pro Leu Val Arg Gly Gln Gln Gly
225                 230                 235                 240

Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
            260                 265                 270

Thr Gly Lys Ser His Gly Arg Ile Leu Lys Asn Asn Leu Pro Met Gly
        275                 280                 285

Gln Cys Val Thr Glu Cys Gln Leu Asn Glu Gly Val Met Asn Thr Ser
        290                 295                 300

Lys Pro Phe Gln Asn Thr Ser Lys His Tyr Ile Gly Lys Cys Pro Lys
305                 310                 315                 320

Tyr Ile Pro Ser Gly Ser Leu Lys Leu Ala Ile Gly Leu Arg Asn Val
                325                 330                 335

Pro Gln Val Gln Asp Arg Gly Leu Phe Gly Ala Ile Ala Gly Phe Ile
            340                 345                 350

Glu Gly Gly Trp Pro Gly Leu Val Ala Gly Trp Tyr Gly Phe Gln His
        355                 360                 365

Gln Asn Ala Glu Gly Thr Gly Ile Ala Ala Asp Arg Asp Ser Thr Gln
        370                 375                 380

Arg Ala Ile Asp Asn Met Gln Asn Lys Leu Asn Asn Val Ile Asp Lys
385                 390                 395                 400

Met Asn Lys Gln Phe Glu Val Val Asn His Glu Phe Ser Glu Val Glu
                405                 410                 415

Ser Arg Ile Asn Met Ile Asn Ser Lys Ile Asp Asp Gln Ile Thr Asp
            420                 425                 430

Ile Trp Ala Tyr Asn Ala Glu Leu Leu Val Leu Leu Glu Asn Gln Lys
        435                 440                 445

Thr Leu Asp Glu His Asp Ala Asn Val Arg Asn Leu His Asp Arg Val
        450                 455                 460

Arg Arg Val Leu Arg Glu Asn Ala Ile Asp Thr Gly Asp Gly Cys Phe
465                 470                 475                 480

Glu Ile Leu His Lys Cys Asp Asn Asn Cys Met Asp Thr Ile Arg Asn
                485                 490                 495
```

```
Gly Thr Tyr Asn His Lys Glu Tyr Glu Glu Ser Lys Ile Glu Arg
                500                 505                 510

Gln Lys Val Asn Gly Val Lys Leu Glu Glu Asn Ser Thr Tyr Lys Ile
            515                 520                 525

Leu Ser Ile Tyr Ser Ser Val Ala Ser Ser Leu Val Leu Leu Leu Met
        530                 535                 540

Ile Ile Gly Gly Phe Ile Phe Gly Cys Gln Asn Gly Asn Val Arg Cys
545                 550                 555                 560

Thr Phe Cys Ile

<210> SEQ ID NO 13
<211> LENGTH: 566
<212> TYPE: PRT
<213> ORGANISM: Influenza virus A
<220> FEATURE:
<223> OTHER INFORMATION: influenza virus A hemagglutinin subtype H13

<400> SEQUENCE: 13

Met Ala Leu Asn Val Ile Ala Thr Leu Thr Leu Ile Ser Val Cys Val
1               5                   10                  15

His Ala Asp Arg Ile Cys Val Gly Tyr Leu Ser Thr Asn Ser Ser Glu
            20                  25                  30

Arg Val Asp Thr Leu Leu Glu Asn Gly Val Pro Val Thr Ser Ser Ile
        35                  40                  45

Asp Leu Ile Glu Thr Asn His Thr Gly Thr Tyr Cys Ser Leu Asn Gly
    50                  55                  60

Val Ser Pro Val His Leu Gly Asp Cys Ser Phe Glu Gly Trp Ile Val
65                  70                  75                  80

Gly Asn Pro Ala Cys Thr Ser Asn Phe Gly Ile Arg Glu Trp Ser Tyr
                85                  90                  95

Leu Ile Glu Asp Pro Ala Ala Pro His Gly Leu Cys Tyr Pro Gly Glu
            100                 105                 110

Leu Asn Asn Asn Gly Glu Leu Arg His Leu Phe Ser Gly Ile Arg Ser
        115                 120                 125

Phe Ser Arg Thr Glu Leu Ile Pro Pro Thr Ser Trp Gly Glu Val Leu
    130                 135                 140

Asp Gly Thr Thr Ser Ala Cys Arg Asp Asn Thr Gly Thr Asn Ser Phe
145                 150                 155                 160

Tyr Arg Asn Leu Val Trp Phe Ile Lys Lys Asn Thr Arg Tyr Pro Val
                165                 170                 175

Ile Ser Lys Thr Tyr Asn Asn Thr Thr Gly Arg Asp Val Leu Val Leu
            180                 185                 190

Trp Gly Ile His His Pro Val Ser Val Asp Glu Thr Lys Thr Leu Tyr
        195                 200                 205

Val Asn Ser Asp Pro Tyr Thr Leu Val Ser Thr Lys Ser Trp Ser Glu
    210                 215                 220

Lys Tyr Lys Leu Glu Thr Gly Val Arg Pro Gly Tyr Asn Gly Gln Arg
225                 230                 235                 240

Ser Trp Met Lys Ile Tyr Trp Ser Leu Ile His Pro Gly Glu Met Ile
                245                 250                 255

Thr Phe Glu Ser Asn Gly Gly Phe Leu Ala Pro Arg Tyr Gly Tyr Ile
            260                 265                 270

Ile Glu Glu Tyr Gly Lys Gly Arg Ile Phe Gln Ser Arg Ile Arg Met
        275                 280                 285
```

-continued

```
Ser Arg Cys Asn Thr Lys Cys Gln Thr Ser Val Gly Gly Ile Asn Thr
    290                 295                 300

Asn Arg Thr Phe Gln Asn Ile Asp Lys Asn Ala Leu Gly Asp Cys Pro
305                 310                 315                 320

Lys Tyr Ile Lys Ser Gly Gln Leu Lys Leu Ala Thr Gly Leu Arg Asn
                325                 330                 335

Val Pro Ala Ile Ser Asn Arg Gly Leu Phe Gly Ala Ile Ala Gly Phe
            340                 345                 350

Ile Glu Gly Gly Trp Pro Gly Leu Ile Asn Gly Trp Tyr Gly Phe Gln
        355                 360                 365

His Gln Asn Glu Gln Gly Thr Gly Ile Ala Ala Asp Lys Glu Ser Thr
    370                 375                 380

Gln Lys Ala Ile Asp Gln Ile Thr Thr Lys Ile Asn Asn Ile Ile Asp
385                 390                 395                 400

Lys Met Asn Gly Asn Tyr Asp Ser Ile Arg Gly Glu Phe Asn Gln Val
                405                 410                 415

Glu Lys Arg Ile Asn Met Leu Ala Asp Arg Ile Asp Asp Ala Val Thr
            420                 425                 430

Asp Ile Trp Ser Tyr Asn Ala Lys Leu Leu Val Leu Leu Glu Asn Asp
        435                 440                 445

Lys Thr Leu Asp Met His Asp Ala Asn Val Lys Asn Leu His Glu Gln
    450                 455                 460

Val Arg Arg Glu Leu Lys Asp Asn Ala Ile Asp Glu Gly Asn Gly Cys
465                 470                 475                 480

Phe Glu Leu Leu His Lys Cys Asn Asp Ser Cys Met Glu Thr Ile Arg
                485                 490                 495

Asn Gly Thr Tyr Asp His Thr Glu Tyr Ala Glu Glu Ser Lys Leu Lys
            500                 505                 510

Arg Gln Glu Ile Asp Gly Ile Lys Leu Lys Ser Glu Asp Asn Val Tyr
        515                 520                 525

Lys Ala Leu Ser Ile Tyr Ser Cys Ile Ala Ser Ser Val Val Leu Val
    530                 535                 540

Gly Leu Ile Leu Ser Phe Ile Met Trp Ala Cys Ser Ser Gly Asn Cys
545                 550                 555                 560

Arg Phe Asn Val Cys Ile
                565
```

<210> SEQ ID NO 14
<211> LENGTH: 568
<212> TYPE: PRT
<213> ORGANISM: Influenza virus A
<220> FEATURE:
<223> OTHER INFORMATION: influenza virus A hemagglutinin subtype H14

<400> SEQUENCE: 14

```
Met Ile Ala Leu Ile Leu Val Ala Leu Ala Leu Ser His Thr Ala Tyr
1               5                   10                  15

Ser Gln Ile Thr Asn Gly Thr Thr Gly Asn Pro Ile Ile Cys Leu Gly
            20                  25                  30

His His Ala Val Glu Asn Gly Thr Ser Val Lys Thr Leu Thr Asp Asn
        35                  40                  45

His Val Glu Val Val Ser Ala Lys Glu Leu Val Glu Thr Asn His Thr
    50                  55                  60

Asp Glu Leu Cys Pro Ser Pro Leu Lys Leu Val Asp Gly Gln Asp Cys
65                  70                  75                  80
```

-continued

```
His Leu Ile Asn Gly Ala Leu Gly Ser Pro Gly Cys Asp Arg Leu Gln
                 85                  90                  95
Asp Thr Thr Trp Asp Val Phe Ile Glu Arg Pro Thr Ala Val Asp Thr
            100                 105                 110
Cys Tyr Pro Phe Asp Val Pro Asp Tyr Gln Ser Leu Arg Ser Ile Leu
        115                 120                 125
Ala Ser Ser Gly Ser Leu Glu Phe Ile Ala Glu Gln Phe Thr Trp Asn
    130                 135                 140
Gly Val Lys Val Asp Gly Ser Ser Ala Cys Leu Arg Gly Gly Arg
145                 150                 155                 160
Asn Ser Phe Phe Ser Arg Leu Asn Trp Leu Thr Lys Ala Thr Asn Gly
                165                 170                 175
Asn Tyr Gly Pro Ile Asn Val Thr Lys Glu Asn Thr Gly Ser Tyr Val
            180                 185                 190
Arg Leu Tyr Leu Trp Gly Val His His Pro Ser Ser Asp Asn Glu Gln
        195                 200                 205
Thr Asp Leu Tyr Lys Val Ala Thr Gly Arg Val Thr Val Ser Thr Arg
    210                 215                 220
Ser Asp Gln Ile Ser Ile Val Pro Asn Ile Gly Ser Arg Pro Arg Val
225                 230                 235                 240
Arg Asn Gln Ser Gly Arg Ile Ser Ile Tyr Trp Thr Leu Val Asn Pro
                245                 250                 255
Gly Asp Ser Ile Ile Phe Asn Ser Ile Gly Asn Leu Ile Ala Pro Arg
            260                 265                 270
Gly His Tyr Lys Ile Ser Lys Ser Thr Lys Ser Thr Val Leu Lys Ser
        275                 280                 285
Asp Lys Arg Ile Gly Ser Cys Thr Ser Pro Cys Leu Thr Asp Lys Gly
    290                 295                 300
Ser Ile Gln Ser Asp Lys Pro Phe Gln Asn Val Ser Arg Ile Ala Ile
305                 310                 315                 320
Gly Asn Cys Pro Lys Tyr Val Lys Gln Gly Ser Leu Met Leu Ala Thr
                325                 330                 335
Gly Met Arg Asn Ile Pro Gly Lys Gln Ala Lys Gly Leu Phe Gly Ala
            340                 345                 350
Ile Ala Gly Phe Ile Glu Asn Gly Trp Gln Gly Leu Ile Asp Gly Trp
        355                 360                 365
Tyr Gly Phe Arg His Gln Asn Ala Glu Gly Thr Gly Thr Ala Ala Asp
    370                 375                 380
Leu Lys Ser Thr Gln Ala Ala Ile Asp Gln Ile Asn Gly Lys Leu Asn
385                 390                 395                 400
Arg Leu Ile Glu Lys Thr Asn Glu Lys Tyr His Gln Ile Glu Lys Glu
                405                 410                 415
Phe Glu Gln Val Glu Gly Arg Ile Gln Asp Leu Glu Lys Tyr Val Glu
            420                 425                 430
Asp Thr Lys Ile Asp Leu Trp Ser Tyr Asn Ala Glu Leu Leu Val Ala
        435                 440                 445
Leu Glu Asn Gln His Thr Ile Asp Val Thr Asp Ser Glu Met Asn Lys
    450                 455                 460
Leu Phe Glu Arg Val Arg Arg Gln Leu Arg Glu Asn Ala Glu Asp Gln
465                 470                 475                 480
Gly Asn Gly Cys Phe Glu Ile Phe His Gln Cys Asp Asn Asn Cys Ile
                485                 490                 495
```

```
Glu Ser Ile Arg Asn Gly Thr Tyr Asp His Asn Ile Tyr Arg Asp Glu
                500                 505                 510

Ala Ile Asn Asn Arg Ile Lys Ile Asn Pro Val Thr Leu Thr Met Gly
            515                 520                 525

Tyr Lys Asp Ile Ile Leu Trp Ile Ser Phe Ser Met Ser Cys Phe Val
        530                 535                 540

Phe Val Ala Leu Ile Leu Gly Phe Val Leu Trp Ala Cys Gln Asn Gly
545                 550                 555                 560

Asn Ile Arg Cys Gln Ile Cys Ile
                565

<210> SEQ ID NO 15
<211> LENGTH: 570
<212> TYPE: PRT
<213> ORGANISM: Influenza virus A
<220> FEATURE:
<223> OTHER INFORMATION: influenza virus A hemagglutinin subtype H15

<400> SEQUENCE: 15

Met Asn Thr Gln Ile Ile Val Ile Leu Val Leu Gly Leu Ser Met Val
1               5                   10                  15

Lys Ser Asp Lys Ile Cys Leu Gly His His Ala Val Ala Asn Gly Thr
            20                  25                  30

Lys Val Asn Thr Leu Thr Glu Arg Gly Val Glu Val Val Asn Ala Thr
        35                  40                  45

Glu Thr Val Glu Ile Thr Gly Ile Asp Lys Val Cys Thr Lys Gly Lys
    50                  55                  60

Lys Ala Val Asp Leu Gly Ser Cys Gly Ile Leu Gly Thr Ile Ile Gly
65                  70                  75                  80

Pro Pro Gln Cys Asp Leu His Leu Glu Phe Lys Ala Asp Leu Ile Ile
                85                  90                  95

Glu Arg Arg Asn Ser Ser Asp Ile Cys Tyr Pro Gly Arg Phe Thr Asn
            100                 105                 110

Glu Glu Ala Leu Arg Gln Ile Ile Arg Glu Ser Gly Ile Asp Lys
        115                 120                 125

Glu Ser Met Gly Phe Arg Tyr Ser Gly Ile Arg Thr Asp Gly Ala Thr
    130                 135                 140

Ser Ala Cys Lys Arg Thr Val Ser Ser Phe Tyr Ser Glu Met Lys Trp
145                 150                 155                 160

Leu Ser Ser Ser Met Asn Asn Gln Val Phe Pro Gln Leu Asn Gln Thr
                165                 170                 175

Tyr Arg Asn Thr Arg Lys Glu Pro Ala Leu Ile Val Trp Gly Val His
            180                 185                 190

His Ser Ser Ser Leu Asp Glu Gln Asn Lys Leu Tyr Gly Thr Gly Asn
        195                 200                 205

Lys Leu Ile Thr Val Gly Ser Ser Lys Tyr Gln Gln Ser Phe Ser Pro
    210                 215                 220

Ser Pro Gly Ala Arg Pro Lys Val Asn Gly Gln Ala Gly Arg Ile Asp
225                 230                 235                 240

Phe His Trp Met Leu Leu Asp Pro Gly Asp Thr Val Thr Phe Thr Phe
                245                 250                 255

Asn Gly Ala Phe Ile Ala Pro Asp Arg Ala Thr Phe Leu Arg Ser Asn
            260                 265                 270

Ala Pro Ser Gly Ile Glu Tyr Asn Gly Lys Ser Leu Gly Ile Gln Ser
        275                 280                 285
```

```
Asp Ala Gln Ile Asp Glu Ser Cys Glu Gly Glu Cys Phe Tyr Ser Gly
    290                 295                 300

Gly Thr Ile Asn Ser Pro Leu Pro Phe Gln Asn Ile Asp Ser Arg Ala
305                 310                 315                 320

Val Gly Lys Cys Pro Arg Tyr Val Lys Gln Ser Ser Leu Pro Leu Ala
                325                 330                 335

Leu Gly Met Lys Asn Val Pro Glu Lys Ile Arg Thr Arg Gly Leu Phe
            340                 345                 350

Gly Ala Ile Ala Gly Phe Ile Glu Asn Gly Trp Glu Gly Leu Ile Asp
            355                 360                 365

Gly Trp Tyr Gly Phe Arg His Gln Asn Ala Gln Gly Gln Gly Thr Ala
    370                 375                 380

Ala Asp Tyr Lys Ser Thr Gln Ala Ala Ile Asp Gln Ile Thr Gly Lys
385                 390                 395                 400

Leu Asn Arg Leu Ile Glu Lys Thr Asn Lys Gln Phe Glu Leu Ile Asp
                405                 410                 415

Asn Glu Phe Thr Glu Val Glu Gln Gln Ile Gly Asn Val Ile Asn Trp
            420                 425                 430

Thr Arg Asp Ser Leu Thr Glu Ile Trp Ser Tyr Asn Ala Glu Leu Leu
    435                 440                 445

Val Ala Met Glu Asn Gln His Thr Ile Asp Leu Ala Asp Ser Glu Met
450                 455                 460

Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
                485                 490                 495

Cys Met Glu Ser Ile Arg Asn Asn Thr Tyr Asn His Thr Glu Tyr Arg
            500                 505                 510

Gln Glu Ala Leu Gln Asn Arg Ile Met Ile Asn Pro Val Lys Leu Ser
            515                 520                 525

Ser Gly Tyr Lys Asp Val Ile Leu Trp Phe Ser Phe Gly Ala Ser Cys
    530                 535                 540

Val Met Leu Leu Ala Ile Ala Met Gly Leu Ile Phe Met Cys Val Lys
545                 550                 555                 560

Asn Gly Asn Leu Arg Cys Thr Ile Cys Ile
                565                 570
```

```
<210> SEQ ID NO 16
<211> LENGTH: 565
<212> TYPE: PRT
<213> ORGANISM: Influenza virus A
<220> FEATURE:
<223> OTHER INFORMATION: influenza virus A hemagglutinin subtype H16

<400> SEQUENCE: 16

Met Met Ile Lys Val Leu Tyr Phe Leu Ile Ile Val Leu Gly Arg Tyr
1               5                   10                  15

Ser Lys Ala Asp Lys Ile Cys Ile Gly Tyr Leu Ser Asn Asn Ser Ser
            20                  25                  30

Asp Thr Val Asp Thr Leu Thr Glu Asn Gly Val Pro Thr Ser Ser
            35                  40                  45

Val Asp Leu Val Glu Thr Asn His Thr Gly Thr Tyr Cys Ser Leu Asn
    50                  55                  60

Gly Ile Ser Pro Ile His Leu Gly Asp Cys Ser Phe Glu Gly Trp Ile
65                  70                  75                  80
```

```
Val Gly Asn Pro Ser Cys Ala Thr Asn Ile Asn Ile Arg Glu Trp Ser
             85                  90                  95

Tyr Leu Ile Glu Asp Pro Asn Ala Pro Asn Lys Phe Cys Tyr Pro Gly
            100                 105                 110

Glu Leu Asp Asn Asn Gly Glu Leu Arg His Leu Phe Ser Gly Val Asn
            115                 120                 125

Ser Phe Ser Arg Thr Glu Leu Ile Asn Pro Ser Lys Trp Gly Asn Val
        130                 135                 140

Leu Asp Gly Val Thr Ala Ser Cys Leu Asp Arg Gly Ala Ser Ser Phe
145                 150                 155                 160

Tyr Arg Asn Leu Val Trp Ile Val Lys Lys Asp Glu Lys Tyr Pro Val
                165                 170                 175

Ile Lys Gly Asp Tyr Asn Asn Thr Thr Gly Arg Asp Val Leu Val Leu
            180                 185                 190

Trp Gly Ile His His Pro Asp Thr Glu Thr Thr Ala Thr Asn Leu Tyr
        195                 200                 205

Val Asn Lys Asn Pro Tyr Thr Leu Val Ser Thr Lys Glu Trp Ser Lys
    210                 215                 220

Arg Tyr Glu Leu Glu Ile Gly Thr Arg Ile Gly Asp Gly Gln Arg Ser
225                 230                 235                 240

Trp Met Lys Leu Tyr Trp His Leu Met His Pro Gly Glu Arg Ile Met
                245                 250                 255

Phe Glu Ser Asn Gly Gly Leu Ile Ala Pro Arg Tyr Gly Tyr Ile Ile
            260                 265                 270

Glu Lys Tyr Gly Thr Gly Arg Ile Phe Gln Ser Gly Val Arg Met Ala
        275                 280                 285

Arg Cys Asn Thr Lys Cys Gln Thr Ser Leu Gly Gly Ile Asn Thr Asn
290                 295                 300

Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ser Ile Gly Glu Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Gln Asn Glu Gln Gly Thr Gly Ile Ala Ala Asp Lys Ala Ser Thr Gln
    370                 375                 380

Lys Ala Ile Asn Glu Ile Thr Thr Lys Ile Asn Asn Ile Ile Glu Lys
385                 390                 395                 400

Met Asn Gly Asn Tyr Asp Ser Ile Arg Gly Glu Phe Asn Gln Val Glu
                405                 410                 415

Lys Arg Ile Asn Met Leu Ala Asp Arg Val Asp Asp Ala Val Thr Asp
            420                 425                 430

Ile Trp Ser Tyr Asn Ala Lys Leu Leu Val Leu Leu Glu Asn Asp Arg
        435                 440                 445

Thr Leu Asp Leu His Asp Ala Asn Val Arg Asn Leu His Asp Gln Val
    450                 455                 460

Lys Arg Ala Leu Lys Ser Asn Ala Ile Asp Glu Gly Asp Gly Cys Phe
465                 470                 475                 480

Asn Leu Leu His Lys Cys Asn Asp Ser Cys Met Glu Thr Ile Arg Asn
                485                 490                 495
```

```
Gly Thr Tyr Asn His Glu Asp Tyr Arg Glu Ser Gln Leu Lys Arg
                500                 505                 510

Gln Glu Ile Glu Gly Ile Lys Leu Lys Thr Asp Asn Val Tyr Lys
            515                 520                 525

Val Leu Ser Ile Tyr Ser Cys Ile Ala Ser Ile Val Leu Val Gly
        530                 535                 540

Leu Ile Leu Ala Phe Ile Met Trp Ala Cys Ser Asn Gly Ser Cys Arg
545                 550                 555                 560

Phe Asn Val Cys Ile
                565

<210> SEQ ID NO 17
<211> LENGTH: 6
<212> TYPE: PRT
<213> ORGANISM: Artificial Sequence
<220> FEATURE:
<223> OTHER INFORMATION: synthetic peptide - His tag

<400> SEQUENCE: 17

His His His His His His
1               5

<210> SEQ ID NO 18
<211> LENGTH: 29
<212> TYPE: PRT
<213> ORGANISM: Artificial Sequence
<220> FEATURE:
<223> OTHER INFORMATION: synthetic peptide - an example of folden
      (trimerization) domain

<400> SEQUENCE: 18

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 19
<211> LENGTH: 7
<212> TYPE: PRT
<213> ORGANISM: Artificial Sequence
<220> FEATURE:
<223> OTHER INFORMATION: synthetic peptide - an example of thrombin
      cleavage site

<400> SEQUENCE: 19

Leu Val Pro Arg Gly Ser Pro
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide - cleavage site recognized by
      Tobacco Etch Virus (TEV) protease
<220> FEATURE:
<221> NAME/KEY: misc_feature
<222> LOCATION: (7)..(7)
<223> OTHER INFORMATION: Xaa = Gly or Ser

<400> SEQUENCE: 20

Glu Asn Leu Tyr Phe Gln Xaa
1               5
```

```
<210> SEQ ID NO 21
<211> LENGTH: 568
<212> TYPE: PRT
<213> ORGANISM: Artificial Sequence
<220> FEATURE:
<223> OTHER INFORMATION: exemplary chimeric influenza virus
      hemagglutinin polypeptide

<400> SEQUENCE: 21

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Cys Asp Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Ala Asp Cys Leu His Glu Lys Tyr Gly Gly Leu Asn Lys Ser
    290                 295                 300

Lys Pro Tyr Tyr Thr Gly Glu His Ala Lys Ala Ile Gly Asn Cys Pro
305                 310                 315                 320

Ile Trp Val Lys Thr Pro Leu Lys Leu Ala Asn Gly Thr Lys Tyr Arg
                325                 330                 335

Pro Pro Ala Lys Leu Leu Lys Glu Arg Gly Phe Phe Gly Ala Ile Ala
            340                 345                 350
```

```
Gly Phe Leu Glu Gly Gly Trp Glu Gly Met Ile Ala Gly Trp His Gly
            355                 360                 365

Tyr Thr Ser His Gly Ala His Gly Val Ala Val Ala Ala Asp Leu Lys
370                 375                 380

Ser Thr Gln Glu Ala Ile Asn Lys Ile Thr Lys Asn Leu Asn Ser Leu
385                 390                 395                 400

Ser Glu Leu Glu Val Lys Asn Leu Gln Arg Leu Ser Gly Ala Met Asp
                405                 410                 415

Glu Leu His Asn Glu Ile Leu Glu Leu Asp Glu Lys Val Asp Asp Leu
            420                 425                 430

Arg Ala Asp Thr Ile Ser Ser Gln Ile Glu Leu Ala Val Leu Leu Ser
            435                 440                 445

Asn Glu Gly Ile Ile Asn Ser Glu Asp Glu His Leu Leu Ala Leu Glu
450                 455                 460

Arg Lys Leu Lys Lys Met Leu Gly Pro Ser Ala Val Glu Ile Gly Asn
465                 470                 475                 480

Gly Cys Phe Glu Thr Lys His Lys Cys Asn Gln Thr Cys Leu Asp Arg
                485                 490                 495

Ile Ala Ala Gly Thr Phe Asn Ala Gly Glu Phe Ser Leu Pro Thr Phe
                500                 505                 510

Asp Ser Leu Asn Ile Thr Ala Ala Ser Leu Asn Asp Asp Gly Leu Asp
            515                 520                 525

Asn His Thr Ile Leu Leu Tyr Tyr Ser Thr Ala Ala Ser Ser Leu Ala
            530                 535                 540

Val Thr Leu Met Leu Ala Ile Phe Ile Val Tyr Met Val Ser Arg Asp
545                 550                 555                 560

Asn Val Ser Cys Ser Ile Cys Leu
                565

<210> SEQ ID NO 22
<211> LENGTH: 5
<212> TYPE: PRT
<213> ORGANISM: Artificial Sequence
<220> FEATURE:
<223> OTHER INFORMATION: synthetic peptide - HA1 N-terminal stem segment

<400> SEQUENCE: 22

Asp Arg Ile Cys Thr
1               5

<210> SEQ ID NO 23
<211> LENGTH: 52
<212> TYPE: PRT
<213> ORGANISM: Artificial Sequence
<220> FEATURE:
<223> OTHER INFORMATION: N-terminal sequence of hemagglutinin protein of
      A/Hong Kong/1/1968 (H3)

<400> SEQUENCE: 23

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys
    50
```

```
<210> SEQ ID NO 24
<211> LENGTH: 52
<212> TYPE: PRT
<213> ORGANISM: Artificial Sequence
<220> FEATURE:
<223> OTHER INFORMATION: N-terminal sequence of hemagglutinin protein of
      A/Perth/16/2009 (H3)

<400> SEQUENCE: 24

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Glu Ile Cys
    50

<210> SEQ ID NO 25
<211> LENGTH: 42
<212> TYPE: PRT
<213> ORGANISM: Artificial Sequence
<220> FEATURE:
<223> OTHER INFORMATION: N-terminal sequence of hemagglutinin protein of
      A/PR/8/34 (H1)

<400> SEQUENCE: 25

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys
        35                  40

<210> SEQ ID NO 26
<211> LENGTH: 42
<212> TYPE: PRT
<213> ORGANISM: Artificial Sequence
<220> FEATURE:
<223> OTHER INFORMATION: N-terminal sequence of hemagglutinin protein of
      A/Cal/4/09 (H1)

<400> SEQUENCE: 26

Asp Thr Leu Cys Ile Gly Tyr His Ala Asn Asn Ser Thr Asp Thr Val
1               5                   10                  15

Asp Thr Val Leu Lys Lys Asn Val Thr Val Thr His Ser Val Asn Leu
            20                  25                  30

Leu Glu Asp Lys His Asn Gly Lys Leu Cys
        35                  40

<210> SEQ ID NO 27
<211> LENGTH: 42
<212> TYPE: PRT
<213> ORGANISM: Artificial Sequence
<220> FEATURE:
<223> OTHER INFORMATION: N-terminal sequence of hemagglutinin protein of
      A/Viet Nam/1203/04 (H5)
```

```
<400> SEQUENCE: 27

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys
        35                  40

<210> SEQ ID NO 28
<211> LENGTH: 42
<212> TYPE: PRT
<213> ORGANISM: Artificial Sequence
<220> FEATURE:
<223> OTHER INFORMATION: N-terminal sequence of hemagglutinin protein of
      A/mallard/Alberta/24/01 (H7)

<400> SEQUENCE: 28

Asp Lys Ile Cys Leu Gly His His Ala Val Ala Asn Gly Thr Lys Val
1               5                   10                  15

Asn Thr Leu Thr Glu Lys Gly Ile Glu Val Val Asn Ala Thr Glu Thr
            20                  25                  30

Val Glu Thr Val Asn Ile Lys Lys Ile Cys
        35                  40

<210> SEQ ID NO 29
<211> LENGTH: 274
<212> TYPE: PRT
<213> ORGANISM: Artificial Sequence
<220> FEATURE:
<223> OTHER INFORMATION: C-terminal sequence of hemagglutinin protein of
      A/Hong Kong/1/1968 (H3)

<400> SEQUENCE: 29

Cys Ile Ser Glu Cys Ile Thr Pro Asn Gly Ser Ile Pro Asn Asp Lys
1               5                   10                  15

Pro Phe Gln Asn Val Asn Lys Ile Thr Tyr Gly Ala Cys Pro Lys Tyr
            20                  25                  30

Val Lys Gln Asn Thr Leu Lys Leu Ala Thr Gly Met Arg Asn Val Pro
        35                  40                  45

Glu Lys Gln Thr Arg Gly Leu Phe Gly Ala Ile Ala Gly Phe Ile Glu
    50                  55                  60

Asn Gly Trp Glu Gly Met Ile Asp Gly Trp Tyr Gly Phe Arg His Gln
65                  70                  75                  80

Asn Ser Glu Gly Thr Gly Gln Ala Ala Asp Leu Lys Ser Thr Gln Ala
                85                  90                  95

Ala Ile Asp Gln Ile Asn Gly Lys Leu Asn Arg Val Ile Glu Lys Thr
            100                 105                 110

Asn Glu Lys Phe His Gln Ile Glu Lys Glu Phe Ser Glu Val Glu Gly
        115                 120                 125

Arg Ile Gln Asp Leu Glu Lys Tyr Val Glu Asp Thr Lys Ile Asp Leu
    130                 135                 140

Trp Ser Tyr Asn Ala Glu Leu Leu Val Ala Leu Glu Asn Gln His Thr
145                 150                 155                 160

Ile Asp Leu Thr Asp Ser Glu Met Asn Lys Leu Phe Glu Lys Thr Arg
                165                 170                 175
```

```
Arg Gln Leu Arg Glu Asn Ala Glu Asp Met Gly Asn Gly Cys Phe Lys
            180                 185                 190

Ile Tyr His Lys Cys Asp Asn Ala Cys Ile Glu Ser Ile Arg Asn Gly
            195                 200                 205

Thr Tyr Asp His Asp Val Tyr Arg Asp Glu Ala Leu Asn Asn Arg Phe
        210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Val Leu Leu
                245                 250                 255

Gly Phe Ile Met Trp Ala Cys Gln Arg Gly Asn Ile Arg Cys Asn Ile
            260                 265                 270

Cys Ile

<210> SEQ ID NO 30
<211> LENGTH: 274
<212> TYPE: PRT
<213> ORGANISM: Artificial Sequence
<220> FEATURE:
<223> OTHER INFORMATION: C-terminal sequence of hemagglutinin protein of
      A/Perth/16/2009 (H3)

<400> SEQUENCE: 30

Cys Asn Ser Glu Cys Ile Thr Pro Asn Gly Ser Ile Pro Asn Asp Lys
1               5                   10                  15

Pro Phe Gln Asn Val Asn Arg Ile Thr Tyr Gly Ala Cys Pro Arg Tyr
            20                  25                  30

Val Lys Gln Asn Thr Leu Lys Leu Ala Thr Gly Met Arg Asn Val Pro
        35                  40                  45

Glu Lys Gln Thr Arg Gly Ile Phe Gly Ala Ile Ala Gly Phe Ile Glu
    50                  55                  60

Asn Gly Trp Glu Gly Met Val Asp Gly Trp Tyr Gly Phe Arg His Gln
65                  70                  75                  80

Asn Ser Glu Gly Arg Gly Gln Ala Ala Asp Leu Lys Ser Thr Gln Ala
                85                  90                  95

Ala Ile Asp Gln Ile Asn Gly Lys Leu Asn Arg Leu Ile Gly Lys Thr
            100                 105                 110

Asn Glu Lys Phe His Gln Ile Glu Lys Glu Phe Ser Glu Val Glu Gly
        115                 120                 125

Arg Ile Gln Asp Leu Glu Lys Tyr Val Glu Asp Thr Lys Ile Asp Leu
    130                 135                 140

Trp Ser Tyr Asn Ala Glu Leu Leu Val Ala Leu Glu Asn Gln His Thr
145                 150                 155                 160

Ile Asp Leu Thr Asp Ser Glu Met Asn Lys Leu Phe Glu Lys Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Ala Leu Leu
                245                 250                 255
```

```
Gly Phe Ile Met Trp Ala Cys Gln Lys Gly Asn Ile Arg Cys Asn Ile
            260                 265                 270

Cys Ile
```

<210> SEQ ID NO 31
<211> LENGTH: 275
<212> TYPE: PRT
<213> ORGANISM: Artificial Sequence
<220> FEATURE:
<223> OTHER INFORMATION: C-terminal sequence of hemagglutinin protein of
      A/PR/8/34 (H1)

<400> SEQUENCE: 31

```
Cys Asn Thr Lys Cys Gln Thr Pro Leu Gly Ala Ile Asn Ser Ser Leu
1               5                   10                  15

Pro Tyr Gln Asn Ile His Pro Val Thr Ile Gly Glu Cys Pro Lys Tyr
            20                  25                  30

Val Arg Ser Ala Lys Leu Arg Met Val Thr Gly Leu Arg Asn Thr Pro
        35                  40                  45

Ser Ile Gln Ser Arg Gly Leu Phe Gly Ala Ile Ala Gly Phe Ile Glu
    50                  55                  60

Gly Gly Trp Thr Gly Met Ile Asp Gly Trp Tyr Gly Tyr His His Gln
65                  70                  75                  80

Asn Glu Gln Gly Ser Gly Tyr Ala Ala Asp Gln Lys Ser Thr Gln Asn
                85                  90                  95

Ala Ile Asn Gly Ile Thr Asn Lys Val Asn Thr Val Ile Glu Lys Met
            100                 105                 110

Asn Ile Gln Phe Thr Ala Val Gly Lys Glu Phe Asn Lys Leu Glu Lys
        115                 120                 125

Arg Met Glu Asn Leu Asn Lys Lys Val Asp Asp Gly Phe Leu Asp Ile
    130                 135                 140

Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175

Ser Gln Leu Lys Asn Asn Ala Lys Glu Ile Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Lys Tyr Ser Glu Glu Ser Lys Leu Asn Arg Glu
    210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255

Gly Ala Ile Ser Phe Trp Met Cys Ser Asn Gly Ser Leu Gln Cys Arg
            260                 265                 270

Ile Cys Ile
        275
```

<210> SEQ ID NO 32
<211> LENGTH: 275
<212> TYPE: PRT
<213> ORGANISM: Artificial Sequence
<220> FEATURE:
<223> OTHER INFORMATION: C-terminal sequence of hemagglutinin protein of
      A/Cal/4/09 (H1)

<400> SEQUENCE: 32

Cys Asn Thr Thr Cys Gln Thr Pro Lys Gly Ala Ile Asn Thr Ser Leu
1               5                   10                  15

Pro Phe Gln Asn Ile His Pro Ile Thr Ile Gly Lys Cys Pro Lys Tyr
            20                  25                  30

Val Lys Ser Thr Lys Leu Arg Leu Ala Thr Gly Leu Arg Asn Ile Pro
        35                  40                  45

Ser Ile Gln Ser Arg Gly Leu Phe Gly Ala Ile Ala Gly Phe Ile Glu
    50                  55                  60

Gly Gly Trp Thr Gly Met Val Asp Gly Trp Tyr Gly Tyr His His Gln
65                  70                  75                  80

Asn Glu Gln Gly Ser Gly Tyr Ala Ala Asp Leu Lys Ser Thr Gln Asn
                85                  90                  95

Ala Ile Asp Glu Ile Thr Asn Lys Val Asn Ser Val Ile Glu Lys Met
            100                 105                 110

Asn Thr Gln Phe Thr Ala Val Gly Lys Glu Phe Asn His Leu Glu Lys
        115                 120                 125

Arg Ile Glu Asn Leu Asn Lys Lys Val Asp Asp Gly Phe Leu Asp Ile
    130                 135                 140

Trp Thr Tyr Asn Ala Glu Leu Leu Val Leu Leu Glu Asn Glu Arg Thr
145                 150                 155                 160

Leu Asp Tyr His Asp Ser Asn Val Lys Asn Leu Tyr Glu Lys Val Arg
                165                 170                 175

Ser Gln Leu Lys Asn Asn Ala Lys Glu Ile Gly Asn Gly Cys Phe Glu
            180                 185                 190

Phe Tyr His Lys Cys Asp Asn Thr Cys Met Glu Ser Val Lys Asn Gly
        195                 200                 205

Thr Tyr Asp Tyr Pro Lys Tyr Ser Glu Glu Ala Lys Leu Asn Arg Glu
    210                 215                 220

Glu Ile Asp Gly Val Lys Leu Glu Ser Thr Arg Ile Tyr Gln Ile Leu
225                 230                 235                 240

Ala Ile Tyr Ser Thr Val Ala Ser Ser Leu Val Leu Val Val Ser Leu
                245                 250                 255

Gly Ala Ile Ser Phe Trp Met Cys Ser Asn Gly Ser Leu Gln Cys Arg
            260                 265                 270

Ile Cys Ile
        275

<210> SEQ ID NO 33
<211> LENGTH: 275
<212> TYPE: PRT
<213> ORGANISM: Artificial Sequence
<220> FEATURE:
<223> OTHER INFORMATION: C-terminal sequence of hemagglutinin protein of
      A/Viet Nam/1203/04 (H5)

<400> SEQUENCE: 33

Cys Asn Thr Lys Cys Gln Thr Pro Met Gly Ala Ile Asn Ser Ser Met
1               5                   10                  15

Pro Phe His Asn Ile His Pro Leu Thr Ile Gly Glu Cys Pro Lys Tyr
            20                  25                  30

Val Lys Ser Asn Arg Leu Val Leu Ala Thr Gly Leu Arg Asn Ser Pro
        35                  40                  45

Gln Arg Glu Thr Arg Gly Leu Phe Gly Ala Ile Ala Gly Phe Ile Glu
    50                  55                  60

Gly Gly Trp Gln Gly Met Val Asp Gly Trp Tyr Gly Tyr His His Ser
65                  70                  75                  80

Asn Glu Gln Gly Ser Gly Tyr Ala Ala Asp Lys Glu Ser Thr Gln Lys
                85                  90                  95

Ala Ile Asp Gly Val Thr Asn Lys Val Asn Ser Ile Ile Asp Lys Met
            100                 105                 110

Asn Thr Gln Phe Glu Ala Val Gly Arg Glu Phe Asn Asn Leu Glu Arg
            115                 120                 125

Arg Ile Glu Asn Leu Asn Lys Lys Met Glu Asp Gly Phe Leu Asp Val
        130                 135                 140

Trp Thr Tyr Asn Ala Glu Leu Leu Val Leu Met Glu Asn Glu Arg Thr
145                 150                 155                 160

Leu Asp Phe His Asp Ser Asn Val Lys Asn Leu Tyr Asp Lys Val Arg
                165                 170                 175

Leu Gln Leu Arg Asp Asn Ala Lys Glu Leu Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Gln Tyr Ser Glu Glu Ala Arg Leu Lys Arg Glu
    210                 215                 220

Glu Ile Ser Gly Val Lys Leu Glu Ser Ile Gly Ile Tyr Gln Ile Leu
225                 230                 235                 240

Ser Ile Tyr Ser Thr Val Ala Ser Ser Leu Ala Leu Ala Ile Met Val
                245                 250                 255

Ala Gly Leu Ser Leu Trp Met Cys Ser Asn Gly Ser Leu Gln Cys Arg
            260                 265                 270

Ile Cys Ile
        275

<210> SEQ ID NO 34
<211> LENGTH: 275
<212> TYPE: PRT
<213> ORGANISM: Artificial Sequence
<220> FEATURE:
<223> OTHER INFORMATION: C-terminal sequence of hemagglutinin protein of
      A/mallard/Alberta/24/01 (H7)

<400> SEQUENCE: 34

Cys Glu Gly Asp Cys Phe His Ser Gly Gly Thr Ile Val Ser Ser Leu
1               5                   10                  15

Pro Phe Gln Asn Ile Asn Pro Arg Thr Val Gly Lys Cys Pro Arg Tyr
            20                  25                  30

Val Lys Gln Thr Ser Leu Leu Leu Ala Thr Gly Met Arg Asn Val Pro
        35                  40                  45

Glu Asn Pro Lys Thr Arg Gly Leu Phe Gly Ala Ile Ala Gly Phe Ile
    50                  55                  60

Glu Asn Gly Trp Glu Gly Leu Ile Asp Gly Trp Tyr Gly Phe Arg His
65                  70                  75                  80

Gln Asn Ala Gln Gly Glu Gly Thr Ala Ala Asp Tyr Lys Ser Thr Gln
                85                  90                  95

Ser Ala Ile Asp Gln Ile Thr Gly Lys Leu Asn Arg Leu Ile Asp Lys
            100                 105                 110

Thr Asn Gln Gln Phe Glu Leu Ile Asp Asn Glu Phe Ser Glu Ile Glu
        115                 120                 125

Gln Gln Ile Gly Asn Val Ile Asn Trp Thr Arg Asp Ser Met Thr Glu
    130                 135                 140

```
Val Trp Ser Tyr Asn Ala Glu Leu Leu Val Ala Met Glu Asn Gln His
145                 150                 155                 160

Thr Ile Asp Leu Ala Asn Ser Glu Met Asn Lys Leu Tyr Glu Arg Val
                165                 170                 175

Arg Lys Gln Leu Arg Glu Asn Ala Glu Glu Asp Gly Thr Gly Cys Phe
                180                 185                 190

Glu Ile Phe His Lys Cys Asp Asp Gln Cys Met Glu Ser Ile Arg Asn
            195                 200                 205

Asn Thr Tyr Asp His Thr Gln Tyr Arg Thr Glu Ser Leu Gln Asn Arg
        210                 215                 220

Ile Gln Ile Asp Pro Val Lys Leu Ser Ser Gly Tyr Lys Asp Ile Ile
225                 230                 235                 240

Leu Trp Phe Ser Phe Gly Ala Ser Cys Phe Ile Leu Leu Ala Ile Ala
                245                 250                 255

Met Gly Leu Val Phe Ile Cys Ile Lys Asn Gly Asn Met Arg Cys Thr
                260                 265                 270

Ile Cys Ile
        275

<210> SEQ ID NO 35
<211> LENGTH: 564
<212> TYPE: PRT
<213> ORGANISM: influenza virus A
<220> FEATURE:
<223> OTHER INFORMATION: influenza virus A hemagglutinin

<400> SEQUENCE: 35

Met Glu Leu Ile Val Leu Leu Ile Leu Leu Asn Pro Tyr Thr Phe Val
1               5                   10                  15

Leu Gly Asp Arg Ile Cys Ile Gly Tyr Gln Ala Asn Gln Asn Asn Gln
                20                  25                  30

Thr Val Asn Thr Leu Leu Glu Gln Asn Val Pro Val Thr Gly Ala Gln
            35                  40                  45

Glu Ile Leu Glu Thr Asn His Asn Gly Lys Leu Cys Ser Leu Asn Gly
    50                  55                  60

Val Pro Pro Leu Asp Leu Gln Ser Cys Thr Leu Ala Gly Trp Leu Leu
65                  70                  75                  80

Gly Asn Pro Asn Cys Asp Ser Leu Leu Glu Ala Glu Trp Ser Tyr
                85                  90                  95

Ile Lys Ile Asn Glu Ser Ala Pro Asp Asp Leu Cys Phe Pro Gly Asn
                100                 105                 110

Phe Glu Asn Leu Gln Asp Leu Leu Glu Met Ser Gly Val Gln Asn
            115                 120                 125

Phe Thr Lys Val Lys Leu Phe Asn Pro Gln Ser Met Thr Gly Val Thr
130                 135                 140

Thr Asn Asn Val Asp Gln Thr Cys Pro Phe Glu Gly Lys Pro Ser Phe
145                 150                 155                 160

Tyr Arg Asn Leu Asn Trp Ile Gln Gly Asn Ser Gly Leu Pro Phe Asn
                165                 170                 175

Ile Glu Ile Lys Asn Pro Thr Ser Asn Pro Leu Leu Leu Trp Gly
            180                 185                 190

Ile His Asn Thr Lys Asp Ala Ala Gln Gln Arg Asn Leu Tyr Gly Asn
        195                 200                 205

Asp Tyr Ser Tyr Thr Ile Phe Asn Phe Gly Glu Lys Ser Glu Glu Phe
210                 215                 220
```

```
Arg Pro Glu Ile Gly Gln Arg Asp Glu Val Lys Ala His Gln Asp Arg
225             230                 235                 240

Ile Asp Tyr Tyr Trp Gly Ser Leu Pro Ala Gln Ser Thr Leu Arg Ile
            245                 250                 255

Glu Ser Thr Gly Asn Leu Ile Ala Pro Glu Tyr Gly Phe Tyr Tyr Lys
            260                 265                 270

Arg Lys Glu Gly Lys Gly Leu Met Lys Ser Lys Leu Pro Ile Ser
            275                 280                 285

Asp Cys Ser Thr Lys Cys Gln Thr Pro Leu Gly Ala Leu Asn Ser Thr
    290                 295                 300

Leu Pro Phe Gln Asn Val His Gln Gln Thr Ile Gly Asn Cys Pro Lys
305             310                 315                 320

Tyr Val Lys Ala Thr Ser Leu Met Leu Ala Thr Gly Leu Arg Asn Asn
                325                 330                 335

Pro Gln Met Glu Gly Arg Gly Leu Phe Gly Ala Ile Ala Gly Phe Ile
                340                 345                 350

Glu Gly Gly Trp Gln Gly Met Ile Asp Gly Trp Tyr Gly Tyr His His
            355                 360                 365

Glu Asn Gln Glu Gly Ser Gly Tyr Ala Ala Asp Lys Glu Ala Thr Gln
370                 375                 380

Lys Ala Val Asp Ala Ile Thr Asn Lys Val Asn Ser Ile Ile Asp Lys
385                 390                 395                 400

Met Asn Ser Gln Phe Glu Ser Asn Ile Lys Glu Phe Asn Arg Leu Glu
                405                 410                 415

Leu Arg Ile Gln His Leu Ser Asp Arg Val Asp Asp Ala Leu Leu Asp
                420                 425                 430

Ile Trp Ser Tyr Asn Thr Glu Leu Leu Val Leu Leu Glu Asn Glu Arg
            435                 440                 445

Thr Leu Asp Phe His Asp Ala Asn Val Lys Asn Leu Phe Glu Lys Val
    450                 455                 460

Lys Ala Gln Leu Lys Asp Asn Ala Ile Asp Glu Gly Asn Gly Cys Phe
465             470                 475                 480

Leu Leu Leu His Lys Cys Asn Asn Ser Cys Met Asp Asp Ile Lys Asn
                485                 490                 495

Gly Thr Tyr Lys Tyr Met Asp Tyr Arg Glu Glu Ser His Ile Glu Lys
            500                 505                 510

Gln Lys Ile Asp Gly Val Lys Leu Thr Asp Tyr Ser Arg Tyr Tyr Ile
        515                 520                 525

Met Thr Leu Tyr Ser Thr Ile Ala Ser Ser Val Val Leu Gly Ser Leu
    530                 535                 540

Ile Ile Ala Ala Phe Leu Trp Gly Cys Gln Lys Gly Ser Ile Gln Cys
545                 550                 555                 560

Lys Ile Cys Ile
```